United States Patent
Lindsley et al.

(10) Patent No.: US 11,884,676 B2
(45) Date of Patent: *Jan. 30, 2024

(54) SUBSTITUTED PYRIMIDO[1,2-B]PYRIDAZINES AS POSITIVE ALLOSTERIC MODULATORS OF THE MUSCARINIC ACETYLCHOLINE RECEPTOR $M_4$

(71) Applicant: Vanderbilt University, Nashville, TN (US)

(72) Inventors: Craig W. Lindsley, Brentwood, TN (US); P. Jeffrey Conn, Nashville, TN (US); Darren W. Engers, Brentwood, TN (US); Alison R. Gregro, Mount Juliet, TN (US); Kayla J. Temple, Spring Hill, TN (US); Madeline F. Long, Nashville, TN (US); Anna E. Ringuette, Nashville, TN (US); Logan A. Baker, Thompson's Station, TN (US); Thomas Jensen, Valby (DK)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/187,868

(22) Filed: Mar. 22, 2023

(65) Prior Publication Data
US 2023/0286991 A1 Sep. 14, 2023

Related U.S. Application Data

(63) Continuation of application No. 18/005,301, filed as application No. PCT/US2021/041836 on Jul. 15, 2021.

(60) Provisional application No. 63/052,085, filed on Jul. 15, 2020.

(51) Int. Cl.
 A61K 31/519 (2006.01)
 C07D 487/04 (2006.01)

(52) U.S. Cl.
 CPC .................. *C07D 487/04* (2013.01)

(58) Field of Classification Search
 CPC ............... A61K 31/519; C07D 487/04
 USPC ......................... 514/259.3; 544/282
 See application file for complete search history.

(56) References Cited

FOREIGN PATENT DOCUMENTS

| WO | 2018118734 A1 | 6/2018 |
|---|---|---|
| WO | 2018118735 A1 | 6/2018 |
| WO | 2018118736 A1 | 6/2018 |
| WO | WO-2022015988 A1 * | 1/2022 |

OTHER PUBLICATIONS

Jordan, V. C. Nature Reviews: Drug Discovery, 2, 2003, 205.*
Hackam, et al. JAMA, 296(14), 2006, 1731-1732.*
Ao, W., et al. "Synthesis of deuterium-labeled crizotinib, a potent and selective dual inhibitor of mesenchymal-epithelial transition factor (c-MET) kinase and anaplastic lymphoma kinase (ALK)." Journal of Labelled Compounds and Radiopharmaceuticals 61.14 (2018): 1036-1042.
Bodick, N. C., et al. "Effects of xanomeline, a selective muscarinic receptor agonist, on cognitive function and behavioral symptoms in Alzheimer disease." Archives of neurology 54.4 (1997): 465-473.
Bymaster, F. P., et al. "Potential role of muscarinic receptors in schizophrenia." Life sciences 64.6-7 (1999): 527-534.
Bymaster, F. P., et al. "Unexpected antipsychotic-like activity with the muscarinic receptor ligand (5R, 6R) 6-(3-propylthio-1, 2, 5-thiadiazol-4-yl)-1-azabicyclo [3.2. 1] octane." European journal of pharmacology 356.2-3 (1998): 109-119.
C.T.F.A. Cosmetic Ingredient Handbook, 1992, pp. 587-592.
International Preliminary Report on Patentability for Application No. PCT/US2021/041836 dated Jan. 17, 2023 (6 pages).
International Search Report and Written Opinion for Application No. PCT/US2021/041836 dated Nov. 10, 2021 (14 pages).
IUPAC 1974 Recommendations for Section E, Fundamental Stereochemistry, in Pure Appl. Chem., 1976, 45: 13-30.

(Continued)

*Primary Examiner* — Douglas M Willis
(74) *Attorney, Agent, or Firm* — Michael Best & Friedrich LLP

(57) ABSTRACT

Disclosed herein are analogues of 6-(4-((2,3-dihydrobenzo[b][1,4]dioxin-6-yl)oxy)piperidin-1 -yl)-[1,2,4]triazolo[4,3-b]pyridazine of formula (Ib), which may be useful as positive allosteric modulators of the muscarinic acetylcholine receptor $M_4$ (mAChR $M_4$). Also disclosed herein are methods of making the compounds, pharmaceutical compositions comprising the compounds, and methods of treating neurological and psychiatric disorders associated with muscarinic acetylcholine receptor dysfunction using the compounds and compositions.

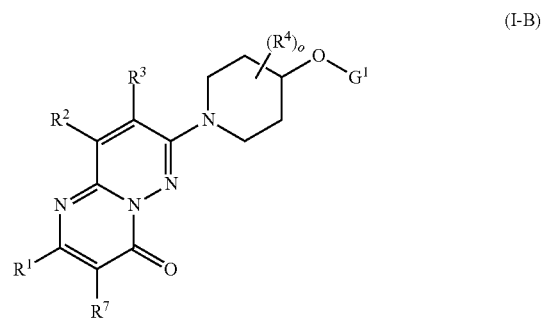

(I-B)

30 Claims, 1 Drawing Sheet

(56) References Cited

OTHER PUBLICATIONS

McCutcheon's vol. 1, Emulsifiers & Detergents, 1994, North American Edition, pp. 236-239.
McGurk, S.R et al. "The role of cognition in vocational functioning in schizophrenia." Schizophrenia research 45.3 (2000): 175-184.
Modern Pharmaceutics, Chapters 9 and 10, Banker & Rhodes, eds. (1979).
Shannon, H. E., et al. "Muscarinic receptor agonists, like dopamine receptor antagonist antipsychotics, inhibit conditioned avoidance response in rats." Journal of Pharmacology and Experimental Therapeutics 290.2 (1999): 901-907.
Shannon, H. E., et al. "Xanomeline, an M1/M4 preferring muscarinic cholinergic receptor agonist, produces antipsychotic-like activity in rats and mice." Schizophrenia research 42.3 (2000): 249-259.
U.S. Appl. No. 18/005,301, filed Jan. 12, 2023.

\* cited by examiner

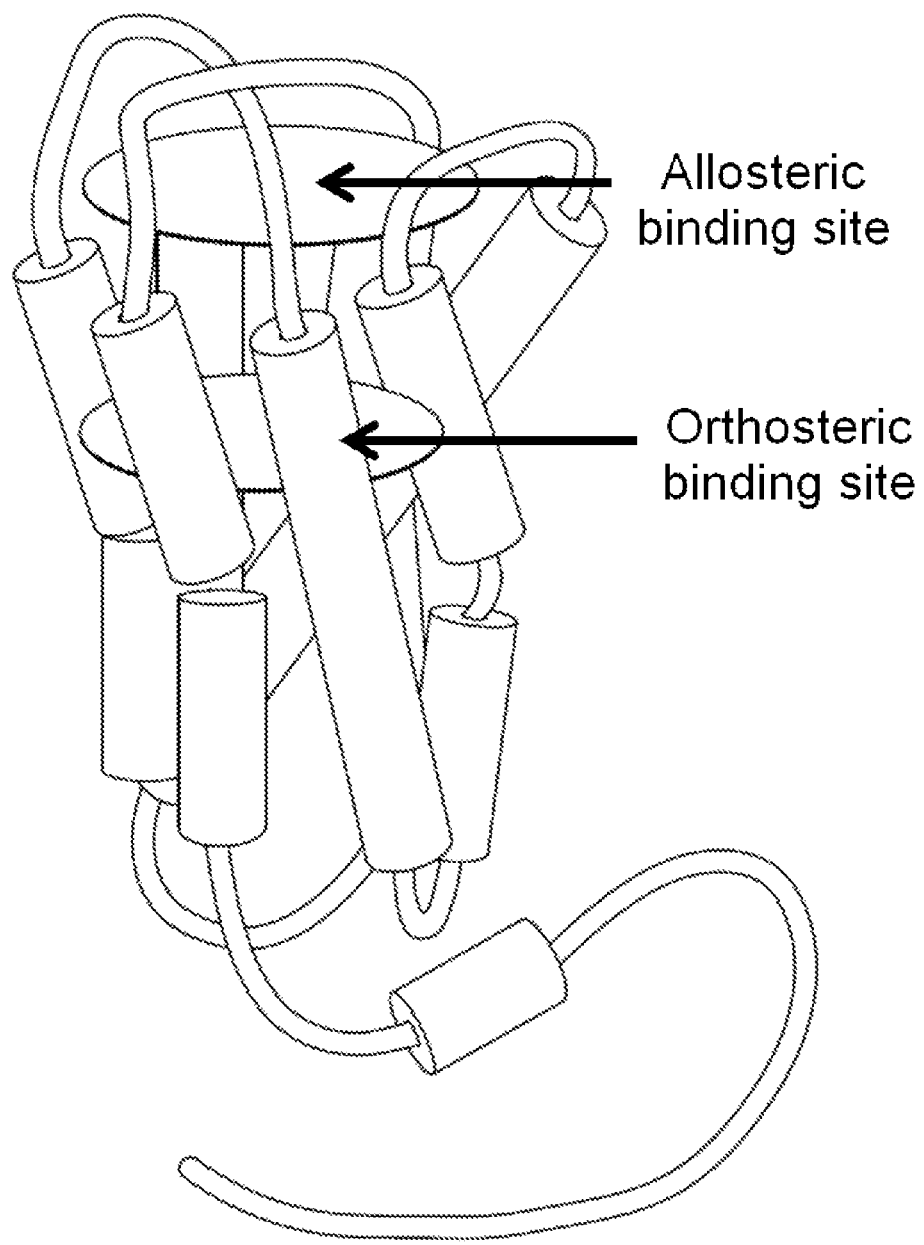

SUBSTITUTED PYRIMIDO[1,2-B]PYRIDAZINES AS POSITIVE ALLOSTERIC MODULATORS OF THE MUSCARINIC ACETYLCHOLINE RECEPTOR $M_4$

RELATED APPLICATIONS

This application is a continuation of U.S. patent application Ser. No. 18/005,301, filed Jan. 12, 2023, which is the U.S. national stage entry, under 35 U.S.C. § 371, of International Application Number PCT/US2021/041836, filed Jul. 15, 2021, which claims priority to U.S. Patent Application No. 63/052,085, filed Jul. 15, 2020, and claims priority to U.S. Patent Application No. 63/052,085, filed Jul. 15, 2020, the entire contents of each of which are hereby incorporated by reference.

TECHNICAL FIELD

The present invention relates to compounds, compositions, and methods for treating neurological and psychiatric disorders associated with muscarinic acetylcholine receptor dysfunction.

BACKGROUND

Cholinergic neurotransmission involves the activation of nicotinic acetylcholine receptors (nAChRs) or the muscarinic acetylcholine receptors (mAChRs) by the binding of the endogenous orthosteric agonist acetylcholine (ACh). Conditions associated with cognitive impairment, such as Alzheimer's disease, are accompanied by a reduction of acetylcholine content in the brain. This is believed to be the result of degeneration of cholinergic neurons of the basal forebrain, which widely innervate multiple areas of the brain, including the association cortices and hippocampus, which are critically involved in higher processes. Clinical data supports that cholinergic hypofunction contributes to the cognitive deficits of patients suffering from schizophrenia. Efforts to increase acetylcholine levels have focused on increasing levels of choline, the precursor for acetylcholine synthesis, and on blocking acetylcholinesterase (AChE), the enzyme that metabolizes acetylcholine. As a result, acetylcholinesterase (AChE) inhibitors, which inhibit the hydrolysis of ACh, have been approved in the United States for use in the palliative, but not disease-modifying, treatment of the cognitive deficits in AD patients.

Attempts to augment central cholinergic function through the administration of choline or phosphatidylcholine have not been successful. AChE inhibitors have shown therapeutic efficacy, but have been found to have frequent cholinergic side effects due to peripheral acetylcholine stimulation, including abdominal cramps, nausea, vomiting, and diarrhea. These gastrointestinal side effects have been observed in about a third of the patients treated. In addition, some AChE inhibitors, such as tacrine, have also been found to cause significant hepatotoxicity with elevated liver transaminases observed in about 30% of patients. The adverse effects of AChE inhibitors have severely limited their clinical utility. An alternative approach to pharmacologically target cholinergic hypofunction is the activation of mAChRs, which are widely expressed throughout the body.

The mAChRs are members of the family A G protein-coupled receptors (GPCRs) and include five subtypes, designated $M_1$-$M_5$. The $M_1$, $M_3$ and $M_5$ subtypes mainly couple to $G_q$ and activate phospholipase C, whereas the $M_2$ and $M_4$ subtypes mainly couple to $G_{i/o}$ and associated effector systems. These five distinct mAChR subtypes have been identified in the mammalian central nervous system where they are prevalent and differentially expressed. $M_1$-$M_5$ have varying roles in cognitive, sensory, motor and autonomic functions. Thus, without wishing to be bound by a particular theory, it is believed that selective agonists of mAChR subtypes that regulate processes involved in cognitive function could prove to be superior therapeutics for treatment of psychosis, schizophrenia and related disorders. The muscarinic $M_4$ receptor has been shown to have a major role in cognitive processing and is believed to have a major role in the pathophysiology of psychotic disorders, including schizophrenia.

Evidence suggests that the most prominent adverse effects of AChE inhibitors and other cholinergic agents are mediated by activation of peripheral $M_2$ and $M_3$ mAChRs and include bradycardia, GI distress, excessive salivation, and sweating. In contrast, $M_4$ has been viewed as the most likely subtype for mediating the effects of muscarinic acetylcholine receptor dysfunction in psychotic disorders, including schizophrenia, cognition disorders, and neuropathic pain. Because of this, considerable effort has been focused on developing selective $M_4$ agonists for treatment of these disorders. Unfortunately, these efforts have been largely unsuccessful because of an inability to develop compounds that are highly selective for the mAChR $M_4$. Because of this, mAChR agonists that have been tested in clinical studies induce a range of adverse effects by activation of peripheral mAChRs. To fully understand the physiological roles of individual mAChR subtypes and to further explore the therapeutic utility of mAChR ligands in psychosis, including schizophrenia, cognition disorders and other disorders, it can be important to develop compounds that are highly selective activators of mAChR $M_4$ and other individual mAChR subtypes.

Previous attempts to develop agonists that are highly selective for individual mAChR subtypes have failed because of the high conservation of the orthosteric ACh binding site. To circumvent problems associated with targeting the highly conserved orthosteric ACh binding site, it is believed that developing compounds that act at allosteric sites on mAChRs that are distinct from the orthosteric site and are less highly conserved. This approach has improved the development of selective ligands for multiple GPCR subtypes. In the case of mAChRs, a major goal has been to develop allosteric ligands that selectively increase activity of mAChR $M_4$ or other mAChR subtypes. Allosteric activators can include allosteric agonists, that act at a site distinct from the orthosteric site to directly activate the receptor in the absence of ACh as well as positive allosteric modulators (PAMs), which do not activate the receptor directly but potentiate activation of the receptor by the endogenous orthosteric agonist ACh. Also, it is possible for a single molecule to have both allosteric potentiator and allosteric agonist activity.

More recently, muscarinic agonists including xanomeline have been shown to be active in animal models with similar profiles to known antipsychotic drugs, but without causing catalepsy (Bymaster et al., *Eur. J. Pharmacol.* 1998, 356, 109, Bymaster et al., *Life Sci.* 1999, 64, 527; Shannon et al., *J. Pharmacol. Exp. Ther.* 1999, 290, 901; Shannon et al., *Schizophrenia Res.* 2000, 42, 249). Further, xanomeline was shown to reduce psychotic behavioral symptoms such as delusions, suspiciousness, vocal outbursts, and hallucinations in Alzheimer's disease patients (Bodick et al., *Arch. Neurol.* 1997, 54, 465), however treatment induced side effects, e.g., gastrointestinal effects, have severely limited the clinical utility of this compound.

WO 2018/118736 discloses 6,5 fused heteroaryl piperidine ether which are allosteric modulators of the M4 muscarinic acetylcholine receptor.

Despite advances in muscarinic acetylcholine receptor research, there is still a scarcity of compounds that are potent, efficacious, and selective activators of the $M_4$ mAChR and also effective in the treatment of neurological and psychiatric disorders associated with cholinergic activity and diseases in which the muscarinic $M_4$ receptor is involved.

SUMMARY

In a first aspect, the invention provides a compound of formula (I),

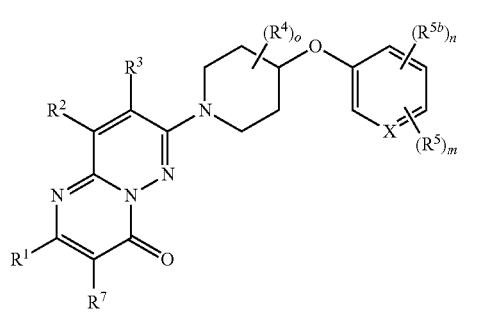

or a pharmaceutically acceptable salt thereof, wherein:
X is $CR^{5a}$ or N;
$R^1$ is selected from hydrogen, $C_1$-$C_4$-alkyl, $C_1$-$C_4$-haloalkyl, $C_1$-$C_4$-hydroxyalkyl, $C_3$-$C_6$-cycloalkyl, -$L^1$-$C_3$-$C_6$-cycloalkyl, halo, -$L^1OR^a$ and $OR^a$;
$R^2$ is selected from hydrogen, $C_1$-$C_4$-alkyl, $C_1$-$C_4$-haloalkyl, $C_3$-$C_6$-cycloalkyl, halo, -$L^2OR^b$, $OR^b$, $NHR^b$, and $N(R^b)_2$;
$R^3$ is selected from hydrogen, $C_1$-$C_4$-alkyl, $C_1$-$C_4$-haloalkyl, $C_3$-$C_6$-cycloalkyl, halo, -$L^3OR^c$, and $OR^c$;
each $R^4$ is independently selected from $C_1$-$C_4$-alkyl, $OR^d$, -$L^4OR^d$, and halo;
each $R^5$ is independently selected from $C_1$-$C_4$-alkyl, $C_1$-$C_4$-haloalkyl, $OR^e$, -$L^5OR^e$, a 5 or 6 membered heteroaryl, a phenyl, $C_3$-$C_6$-cycloalkyl, and halo; or
wherein two $R^5$, taken together with the carbon atoms to which they are attached, form a 5- to 8-membered fused monocyclic heterocycle containing 1-2 heteroatoms independently selected from O, N, and S, the fused monocyclic heterocycle being optionally substituted with 1-4 $R^6$;
$R^{5a}$ is selected from hydrogen, $C_1$-$C_4$-alkyl, $C_1$-$C_4$-haloalkyl, $C_3$-$C_6$-cycloalkyl, $OR^e$, -$L^5OR^e$, and halo;
each $R^{5b}$ is independently selected from $C_1$-$C_2$-alkyl, $C_1$-$C_2$-fluoroalkyl, $C_3$-$C_4$-cycloalkyl, —$OC_1$-$C_2$-alkyl, —$OC_1$-$C_2$-fluoroalkyl, cyano, and halo;
each $R^6$ is independently selected from oxo, $C_1$-$C_4$-alkyl, $OR^f$, -$L^6OR^f$, and halo;
$R^7$ is selected from hydrogen, $C_1$-$C_4$-alkyl, $C_1$-$C_4$-haloalkyl, $C_3$-$C_6$-cycloalkyl, halo, -$L^2OR^b$, $OR^b$, $NHR^b$, and $N(R^b)_2$;
o is 0, 1 or 2;
m is 0, 1 or 2;
n is 0, 1, or 2;

$L^1$, $L^2$, $L^3$, $L^4$, $L^5$, and $L^6$ at each occurrence, are each independently $C_1$-$C_3$-alkylene; and
$R^a$, $R^b$, $R^c$, $R^d$, $R^e$, and $R^f$, at each occurrence, are each independently selected from $C_1$-$C_4$-alkyl, $C_1$-$C_4$-haloalkyl, and $C_3$-$C_6$-cycloalkyl, wherein two $R^b$, together with a nitrogen atom to which they are attached, optionally form a 4- to 7-membered monocyclic heterocyclyl, the heterocyclyl being optionally substituted with 1-4 substituents independently selected from halo, $C_1$-$C_4$-alkyl, and $C_1$-$C_4$-haloalkyl.

In a further aspect, the invention provides a method of treating a neurological and/or psychiatric disorder in a patient, comprising administering to the patient in need thereof a therapeutically effective amount of the compound of formula (I), or a pharmaceutically acceptable salt thereof or a pharmaceutical composition.

In a further aspect, the invention provides a compound of formula (I), or a pharmaceutically acceptable salt thereof, or a pharmaceutical composition, for use in the treatment of a neurological and/or psychiatric disorder.

In a further aspect, the invention provides use of a compound of formula (I), or a pharmaceutically acceptable salt thereof or a pharmaceutical composition, for the preparation of a medicament for the treatment of a neurological and/or psychiatric disorder.

BRIEF DESCRIPTION OF THE DRAWINGS

FIG. 1 shows a schematic illustration of ligand binding sites, including the orthosteric site and an allosteric site, in the muscarinic acetylcholine receptor.

DETAILED DESCRIPTION

Disclosed herein are positive allosteric modulators (i.e. potentiators) of the muscarinic acetylcholine receptor $M_4$ (mAChR $M_4$), methods of making same, pharmaceutical compositions comprising same, and methods of treating neurological and psychiatric disorders associated with muscarinic acetylcholine receptor dysfunction using same. The compounds include analogues of 6-(4-((2,3-dihydrobenzo[b][1,4]dioxin-6-yl)oxy)piperidin-1-yl)-[1,2,4]triazolo[4,3-b]pyridazine.

The human muscarinic acetylcholine receptor $M_4$ (mAChR $M_4$) is a protein of 479 amino acids encoded by the $CHRM_4$ gene. The molecular weight of the unglycosylated protein is about 54 kDa and it is a transmembrane GPCR. As described above, the mAChR $M_4$ is a member of the GPCR Class A family, or the rhodopsin-like GPCRs, which are characterized by structural features similar to rhodopsin such as seven transmembrane segments. The muscarinic acetylcholine receptors have the N-terminus oriented to the extracellular face of the membrane and the C-terminus located on the cytoplasmic face. A schematic of the structure of mAChR $M_4$ is shown in FIG. 1, with the transmembrane segments shown as cylindrical shapes (which span the lipid bilayer of the cell membrane). The orthosteric binding for natural ligand, acetylcholine, for mAChRs is within a pocket located in the transmembrane segments as depicted in FIG. 1.

Previous attempts to develop agonists that are highly selective for individual mAChR subtypes have failed because of the high conservation of the orthosteric ACh binding site. To circumvent problems associated with targeting the highly conserved orthosteric ACh binding site, it is believed that developing compounds that act at allosteric sites on mAChRs that are removed from the orthosteric site and are less highly-conserved. Without wishing to be bound by a particular theory, the compounds of the invention and products of the disclosed methods are believed to bind to an allosteric site distinct from the orthosteric binding site. For example, a disclosed compound can bind at the binding site as illustrated in FIG. 1.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present invention also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context and the understanding of the person skilled in the art.

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, 4,4-dimethylpentan-2-yl, n-heptyl, n-octyl, n-nonyl, and n-decyl.

The term "alkenyl," as used herein, means a straight or branched, hydrocarbon chain containing at least one carbon-carbon double bond and from 2 to 10 carbon atoms.

The term "alkoxyalkyl," as used herein, refers to an alkoxy group, as defined herein, appended to the parent molecular moiety through an alkyl group, as defined herein. The alkoxyalkyl group may be represented by the general formula LOR, wherein L may be a $C_{1-3}$-alkylene such as $CH_2$ and R may be a $C_{1-3}$-alkyl. Representative examples may include but is not limited to —$CH_2OCH_3$, —$CH_2OCH_2CH_3$, —$CH_2OCH_2CH_2CH_3$.

The term "alkoxyfluoroalkyl," as used herein, refers to an alkoxy group, as defined herein, appended to the parent molecular moiety through a fluoroalkyl group, as defined herein.

The term "alkylene," as used herein, refers to a saturated divalent group derived from a straight or branched chain hydrocarbon of 1 to 10 carbon atoms, for example, of 2 to 5 carbon atoms. Representative examples of alkylene include, but are not limited to, —$CH_2$—, —$CH_2CH_2$—, —$CH_2CH_2CH_2$—, —$CH_2CH(CH_3)CH_2$—, —$CH_2CH_2CH_2CH_2$—, —$CH_2CH(CH_3)CH_2CH_2$—, and —$CH_2CH_2CH_2CH_2CH_2$—.

The term "alkylamino," as used herein, means at least one alkyl group, as defined herein, is appended to the parent molecular moiety through an amino group, as defined herein.

The term "aminoalkyl," as used herein, means at least one amino group, as defined herein, is appended to the parent molecular moiety through an alkylene group, as defined herein.

The term "amino," as used herein, means —$NR_xR_y$, wherein $R_x$ and $R_y$ may be hydrogen, alkyl, cycloalkyl, aryl, heteroaryl, heterocycle, alkenyl, or heteroalkyl, or $R_x$ and $R_y$ may together with the N to which they are attached form a heterocycle. In the case of an aminoalkyl group or any other moiety where amino appends together two other moieties, amino may be —$NR_x$—, wherein $R_x$ may be hydrogen, alkyl, cycloalkyl, aryl, heteroaryl, heterocycle, alkenyl, or heteroalkyl.

The term "aryl," as used herein, refers to a phenyl group, or a bicyclic or tricyclic fused ring system. Bicyclic fused ring systems are exemplified by a phenyl group appended to the parent molecular moiety and fused to a phenyl group, a cycloalkyl group as defined herein, a heteroaryl group as defined herein, or a heterocycle as defined herein. Tricyclic fused ring systems are exemplified by a phenyl group appended to the parent molecular moiety and fused to a bicyclic fused ring system as described herein. Representative examples of aryl include, but are not limited to, phenyl, naphthyl, anthracenyl, indolyl (e.g., 1H-indol-4-yl, 1H-indol-5-yl, 1H-indol-6-yl, and 1H-indol-7-yl), benzodioxolyl (e.g., benzo[d][1,3]dioxol-4-yl and benzo[d][1,3]dioxol-5-yl), chromanyl (e.g., chroman-5-yl, chroman-6-yl, chroman-7-yl, and chroman-8-yl), and tetrahydroquinolinyl (e.g., 1,2,3,4-tetrahydroquinolin-5-yl, 1,2,3,4-tetrahydroquinolin-6-yl, 1,2,3,4-tetrahydroquinolin-7-yl, and 1,2,3,4-tetrahydroquinolin-8-yl).

The term "cycloalkoxy," as used herein, refers to a cycloalkyl group, as defined herein, appended to the parent molecular moiety through an oxygen atom.

The term "cycloalkyl," as used herein, refers to a carbocyclic ring system containing three to ten carbon atoms, zero heteroatoms and zero double bonds. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl. "Cycloalkyl" also includes carbocyclic ring systems in which a cycloalkyl group is appended to the parent molecular moiety and is fused to an aryl group as defined herein (e.g., a phenyl group), a heteroaryl group as defined herein, or a heterocycle as defined herein. Representative examples of such cycloalkyl groups include, but are not limited to, 2,3-dihydro-1H-indenyl (e.g., 2,3-dihydro-1H-inden-1-yl and 2,3-dihydro-1H-inden-2-yl), 6,7-dihydro-5H-cyclopenta[b]pyridinyl (e.g., 6,7-dihydro-5H-cyclopenta[b]pyridin-6-yl), oxaspiro[3.3]heptanyl (e.g., 2-oxaspiro[3.3]heptan-6-yl), and 5,6,7,8-tetrahydroquinolinyl (e.g., 5,6,7,8-tetrahydroquinolin-5-yl).

The term "cycloalkenyl," as used herein, means a non-aromatic monocyclic or multicyclic ring system containing at least one carbon-carbon double bond and preferably having from 5-10 carbon atoms per ring. The cycloalkenyl may be monocyclic, bicyclic, bridged, fused, or spirocyclic. Exemplary monocyclic cycloalkenyl rings include cyclopentenyl, cyclohexenyl, cycloheptenyl, and bicyclo[2.2.1]heptenyl.

The term "fluoroalkyl," as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "fluoroalkoxy," as used herein, means at least one fluoroalkyl group, as defined herein, is appended to the parent molecular moiety through an oxygen atom. Representative examples of fluoroalkoxy include, but are not limited to, difluoromethoxy, trifluoromethoxy and 2,2,2-trifluoroethoxy.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "haloalkoxy," as used herein, means at least one haloalkyl group, as defined herein, is appended to the parent molecular moiety through an oxygen atom.

The term "halocycloalkyl," as used herein, means a cycloalkyl group, as defined herein, in which one or more hydrogen atoms are replaced by a halogen.

The term "heteroalkyl," as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, benzimidazolyl, benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl, quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl, naphthyridinyl, pyridoimidazolyl, thiazolo[5,4-b]pyridin-2-yl, thiazolo[5,4-d]pyrimidin-2-yl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), oxabicyclo[2.2.1]heptanyl (including 7-oxabicyclo[2.2.1]heptan-3-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1 3,7]decane), and oxa-adamantane (2-oxatricyclo[3.3.1.1 3,7]decane). The monocyclic, bicyclic, and tricyclic heterocycles are connected to the parent molecular moiety through any carbon atom or any nitrogen atom contained within the rings, and can be unsubstituted or substituted.

The term "hydroxyl" or "hydroxy," as used herein, means an —OH group.

The term "hydroxyalkyl," as used herein, means at least one —OH group, is appended to the parent molecular moiety through an alkylene group, as defined herein.

The term "hydroxyfluoroalkyl," as used herein, means at least one —OH group, is appended to the parent molecular moiety through a fluoroalkyl group, as defined herein.

In some instances, the number of carbon atoms in a hydrocarbyl substituent (e.g., alkyl or cycloalkyl) is indicated by the prefix "C-Cy-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituents" refers to a group (non-hydrogen) "substituted" on a group such as an alkyl, alkenyl, alkynyl, aryl, heteroaryl, cycloalkyl, heteroalkyl, or heterocycle group, at any atom of that group. Any atom can be substituted.

The term "substituted" refers to a group that may be further substituted with one or more non-hydrogen substituent groups. Substituent groups include, but are not limited to, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl. In some embodiments, a group is optionally substituted. In some embodiments, a group is optionally substituted with 1, 2, 3, 4, or 5 substituents. In some embodiments, an aryl, heteroaryl, cycloalkyl, or heterocycle is optionally substituted with 1, 2, 3, 4, or 5 substituents. In some embodiments, an aryl, heteroaryl, cycloalkyl, or heterocycle may be independently unsubstituted or substituted with 1, 2, or 3 substituents.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The term "allosteric site" as used herein refers to a ligand binding site that is topographically distinct from the orthosteric binding site.

The term "modulator" as used herein refers to a molecular entity (e.g., but not limited to, a ligand and a disclosed compound) that modulates the activity of the target receptor protein.

The term "ligand" as used herein refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

The terms "natural ligand" and "endogenous ligand" as used herein are used interchangeably, and refer to a naturally occurring ligand, found in nature, which binds to a receptor.

The term "orthosteric site" as used herein refers to the primary binding site on a receptor that is recognized by the endogenous ligand or agonist for that receptor. For example, the orthosteric site in the mAChR $M_4$ receptor is the site that acetylcholine binds to.

The term "mAChR $M_4$ receptor positive allosteric modulator" as used herein refers to any exogenously administered compound or agent that directly or indirectly augments the activity of the mAChR $M_4$ receptor in the presence or in the absence of acetylcholine, or another agonist, in an animal, in particular a mammal, for example a human. For example, a mAChR $M_4$ receptor positive allosteric modulator can increase the activity of the mAChR $M_4$ receptor in a cell in the presence of extracellular acetylcholine. The cell can be Chinese hamster ovary (CHO-K1) cells transfected with human mAChR $M_4$. The cell can be Chinese hamster ovary (CHO-K1) cells transfected with rat mAChR $M_4$ receptor. The cell can be Chinese hamster ovary (CHO-K1) cells transfected with a mammalian mAChR $M_4$. The term "mAChR $M_4$ receptor positive allosteric modulator" includes a compound that is a "mAChR $M_4$ receptor allosteric potentiator" or a "mAChR $M_4$ receptor allosteric agonist," as well as a compound that has mixed activity comprising pharmacology of both an "mAChR $M_4$ receptor allosteric potentiator" and an "mAChR $M_4$ receptor allosteric agonist." The term "mAChR $M_4$ receptor positive allosteric modulator also includes a compound that is a "mAChR $M_4$ receptor allosteric enhancer."

The term "mAChR $M_4$ receptor allosteric potentiator" as used herein refers to any exogenously administered compound or agent that directly or indirectly augments the response produced by the endogenous ligand (such as acetylcholine) when the endogenous ligand binds to the orthosteric site of the mAChR $M_4$ receptor in an animal, in particular a mammal, for example a human. The mAChR $M_4$ receptor allosteric potentiator binds to a site other than the orthosteric site, that is, an allosteric site, and positively augments the response of the receptor to an agonist or the endogenous ligand. In some embodiments, an allosteric potentiator does not induce desensitization of the receptor, activity of a compound as an mAChR $M_4$ receptor allosteric potentiator may provide advantages over the use of a pure mAChR $M_4$ receptor orthosteric agonist. Such advantages may include, for example, increased safety margin, higher tolerability, diminished potential for abuse, and reduced toxicity.

The term "mAChR $M_4$ receptor allosteric enhancer" as used herein refers to any exogenously administered compound or agent that directly or indirectly augments the response produced by the endogenous ligand (such as acetylcholine) in an animal, in particular a mammal, for example a human. In some embodiments, the allosteric enhancer increases the affinity of the natural ligand or agonist for the orthosteric site. In some embodiments, an allosteric enhancer increases the agonist efficacy. The mAChR $M_4$ receptor allosteric enhancer binds to a site other than the orthosteric site, that is, an allosteric site, and positively augments the response of the receptor to an agonist or the endogenous ligand. An allosteric enhancer has no effect on the receptor by itself and requires the presence of an agonist or the natural ligand to realize a receptor effect.

The term "mAChR $M_4$ receptor allosteric agonist" as used herein refers to any exogenously administered compound or agent that directly activates the activity of the mAChR $M_4$ receptor in the absence of the endogenous ligand (such as acetylcholine) in an animal, in particular a mammal, for example a human. The mAChR $M_4$ receptor allosteric agonist binds to a site that is distinct from the orthosteric acetylcholine site of the mAChR $M_4$ receptor. Because it does not require the presence of the endogenous ligand, activity of a compound as an mAChR $M_4$ receptor allosteric agonist provides advantages if cholinergic tone at a given synapse is low.

The term "mAChR $M_4$ receptor neutral allosteric ligand" as used herein refers to any exogenously administered compound or agent that binds to an allosteric site without affecting the binding or function of agonists or the natural ligand at the orthosteric site in an animal, in particular a mammal, for example a human. However, a neutral allosteric ligand can block the action of other allosteric modulators that act via the same site.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Embodiments of the Invention

In the following, embodiments of the invention are disclosed. The first embodiment is denoted E1, the second embodiment is denoted E2 and so forth.

E1. A compound of formula (I),

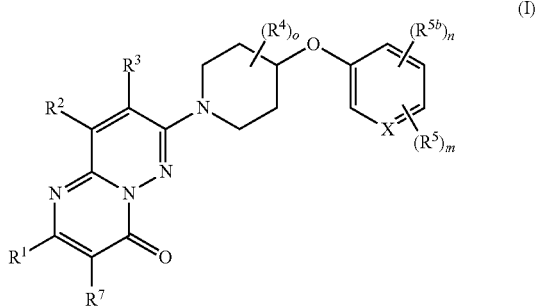

(I)

or a pharmaceutically acceptable salt thereof, wherein:
X is $CR^{5a}$ or N;
$R^1$ is selected from hydrogen, $C_1$-$C_4$-alkyl, $C_1$-$C_4$-haloalkyl, $C_1$-$C_4$-hydroxyalkyl, $C_3$-$C_6$-cycloalkyl, -$L^1$-$C_3$-$C_6$-cycloalkyl, halo, -$L^1OR^a$ and $OR^a$;
$R^2$ is selected from hydrogen, $C_1$-$C_4$-alkyl, $C_1$-$C_4$-haloalkyl, $C_3$-$C_6$-cycloalkyl, halo, -$L^2OR^b$, $OR^b$, $NHR^b$, and $N(R^b)_2$;
$R^3$ is selected from hydrogen, $C_1$-$C_4$-alkyl, $C_1$-$C_4$-haloalkyl, $C_3$-$C_6$-cycloalkyl, halo, -$L^3OR^c$, and $OR^c$;
each $R^4$ is independently selected from $C_1$-$C_4$-alkyl, $OR^d$, -$L^4OR^d$, and halo;

each $R^5$ is independently selected from $C_1$-$C_4$-alkyl, $C_1$-$C_4$-haloalkyl, $OR^e$, -$L^5OR^e$, a 5 or 6 membered heteroaryl, a phenyl, $C_3$-$C_6$-cycloalkyl, and halo; or
wherein two $R^5$, taken together with the carbon atoms to which they are attached, form a 5- to 8-membered fused monocyclic heterocycle containing 1-2 heteroatoms independently selected from O, N, and S, the fused monocyclic heterocycle being optionally substituted with 1-4 $R^6$;
$R^{5a}$ is selected from hydrogen, $C_1$-$C_4$-alkyl, $C_1$-$C_4$-haloalkyl, $C_3$-$C_6$-cycloalkyl, $OR^e$, -$L^5OR^e$, and halo;
each $R^{5b}$ is independently selected from $C_1$-$C_2$-alkyl (e.g., methyl), $C_1$-$C_2$-fluoroalkyl (e.g., trifluoromethyl, difluoromethyl), $C_3$-$C_4$-cycloalkyl (e.g., cyclopropyl), —$OC_1$-$C_2$-alkyl (e.g., methoxy), —$OC_1$-$C_2$-fluoroalkyl (e.g., trifluoromethoxy, difluoromethoxy), cyano, and halo (e.g., fluoro, chloro);
each $R^6$ is independently selected from oxo, $C_1$-$C_4$-alkyl, $OR^f$, -$L^6OR^f$, and halo;
$R^7$ is selected from hydrogen, $C_1$-$C_4$-alkyl, $C_1$-$C_4$-haloalkyl, $C_3$-$C_6$-cycloalkyl, halo, -$L^2OR^b$, $OR^b$, $NHR^b$, and $N(R^b)_2$;
o is 0, 1 or 2;
m is 0, 1 or 2;
n is 0, 1, or 2;
$L^1$, $L^2$, $L^3$, $L^4$, $L^5$, and $L^6$ at each occurrence, are each independently $C_1$-$C_3$-alkylene; and
$R^a$, $R^b$, $R^c$, $R^d$, $R^e$, and $R^f$, at each occurrence, are each independently selected from $C_1$-$C_4$-alkyl, $C_1$-$C_4$-haloalkyl, and $C_3$-$C_6$-cycloalkyl, wherein two $R^b$, together with a nitrogen atom to which they are attached, optionally form a 4- to 7-membered monocyclic heterocyclyl, the heterocyclyl being optionally substituted with 1-4 substituents independently selected from halo, $C_1$-$C_4$-alkyl, and $C_1$-$C_4$-haloalkyl.

E2. The compound of embodiment E1 having the formula (I-A),

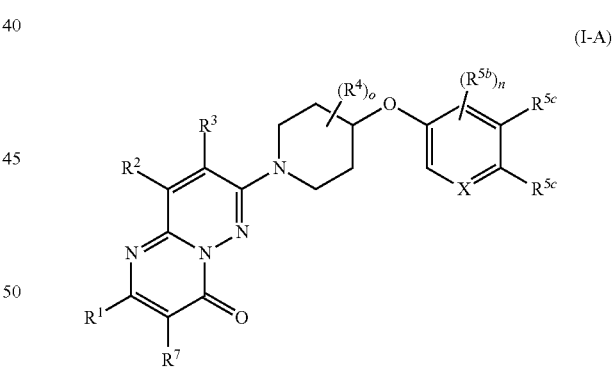

(I-A)

or a pharmaceutically acceptable salt thereof, wherein
each $R^{5c}$ is independently selected from hydrogen, $C_1$-$C_4$-alkyl, $C_1$-$C_4$-haloalkyl, $OR^e$, -$L^5OR^e$, a 5 or 6 membered heteroaryl, a phenyl, $C_3$-$C_6$-cycloalkyl, and halo; or
wherein two $R^{5c}$, taken together with the carbon atoms to which they are attached, form a 5- to 8-membered fused monocyclic heterocycle containing 1-2 heteroatoms independently selected from O, N, and S, the fused monocyclic heterocycle being optionally substituted with 1-4 $R^6$.

E3. The compound of embodiment E1 or E2, or a pharmaceutically acceptable salt thereof, wherein two $R^5$ or $R^{5c}$, taken together with the carbon atoms to which they are attached, form the 5- to 8-membered fused monocyclic heterocycle.

E4. The compound of any of embodiments E1 to E3, or a pharmaceutically acceptable salt thereof, wherein the 5- to 8-membered fused monocyclic heterocycle formed with $R^5$ or $R^{5c}$ contains 1-2 heteroatoms independently selected from O and N and is optionally substituted with 1-2 $R^6$.

E5. The compound of any of embodiments E1 to E3 of formula (I-B),

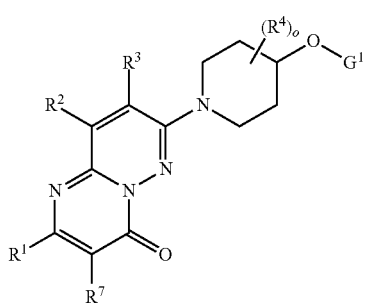

(I-B)

or a pharmaceutically acceptable salt thereof, wherein $G^1$ is

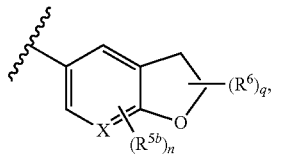

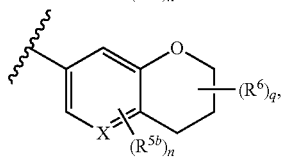

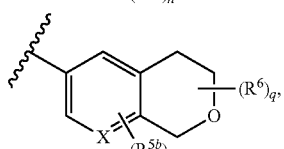

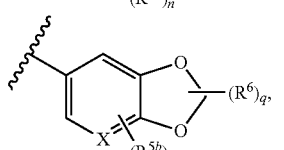

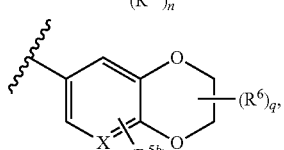

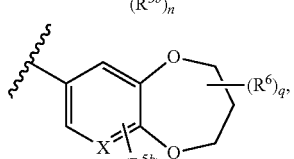

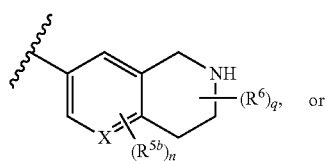

or

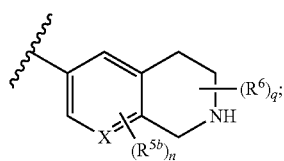

and each q is independently 0, 1, 2, 3, or 4.

E6. The compound of embodiment E5, or a pharmaceutically acceptable salt thereof, wherein $G^1$ is

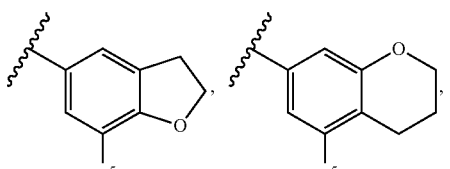

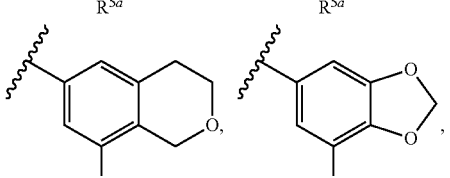

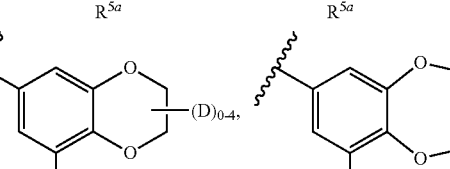

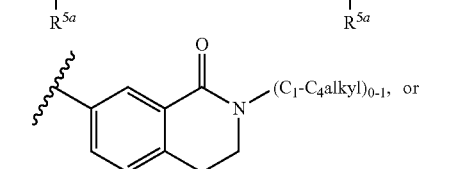

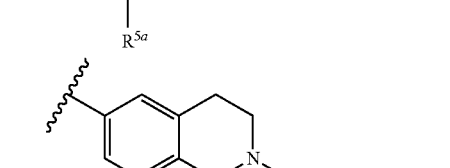

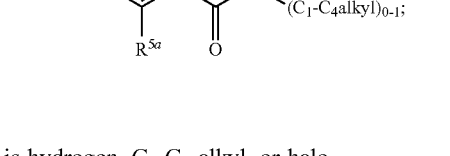

and $R^{5a}$ is hydrogen, $C_1$-$C_4$-alkyl, or halo.

E7. The compound of embodiment E6, or a pharmaceutically acceptable salt thereof, wherein
G$^1$ is

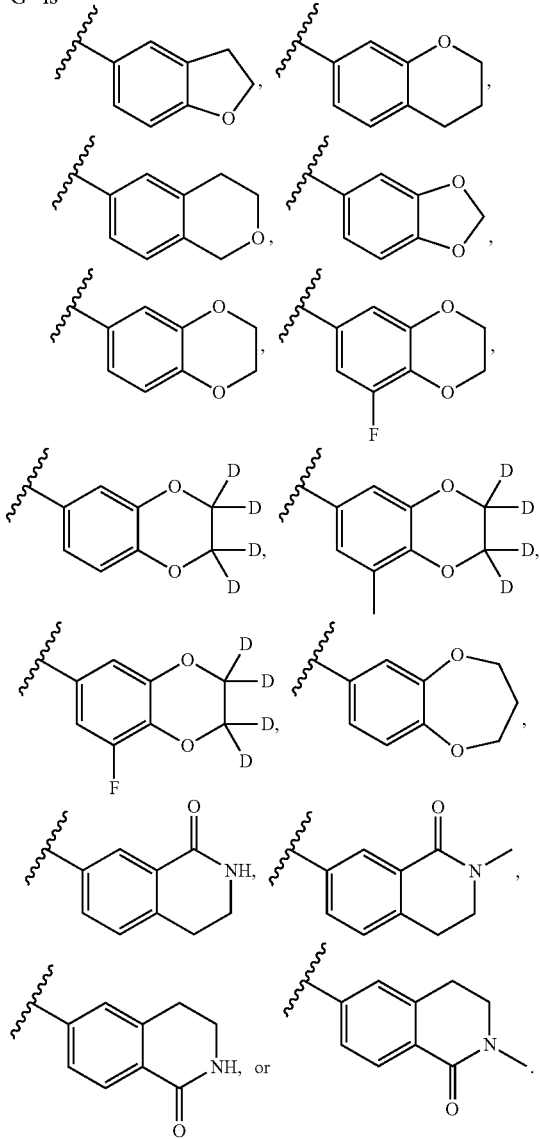

E8. The compound of any one of embodiments E1 to E5 of formula (Ia)

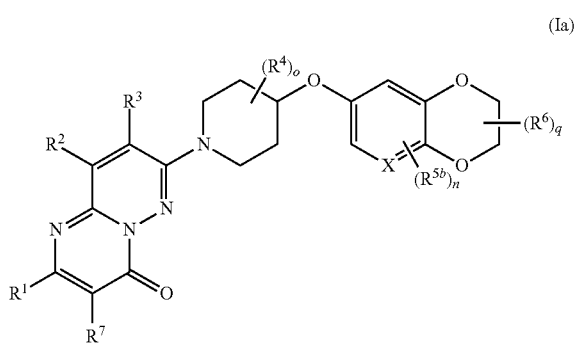

(Ia)

or a pharmaceutically acceptable salt thereof.

E9. The compound of any one of embodiments E1 to E5 of formula (Ib)

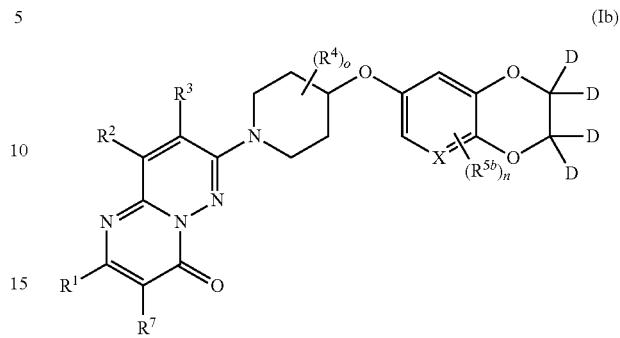

(Ib)

or a pharmaceutically acceptable salt thereof.

E10. The compound of any one of embodiments E1 to E9, or a pharmaceutically acceptable salt thereof, wherein n is 0.

E11. The compound of embodiment E1 or E2, or a pharmaceutically acceptable salt thereof, wherein each R$^5$ or R$^{51}$ is independently selected from hydrogen, C$_1$-C$_4$-alkyl, C$_1$-C$_4$-haloalkyl, OR$^e$, -L$^5$OR$^e$, a 5 or 6 membered heteroaryl, a phenyl, C$_3$-C$_6$-cycloalkyl, and halo.

E12. The compound of embodiment E1, E2, or E11, or a pharmaceutically acceptable salt thereof, wherein each R$^5$ or R$^{5c}$ is independently selected from hydrogen, C$_1$-C$_4$-alkyl, C$_1$-C$_4$-haloalkyl, OR$^e$, -L$^5$OR$^e$, and halo.

E13. The compound of embodiment E12 of formula (I-B)

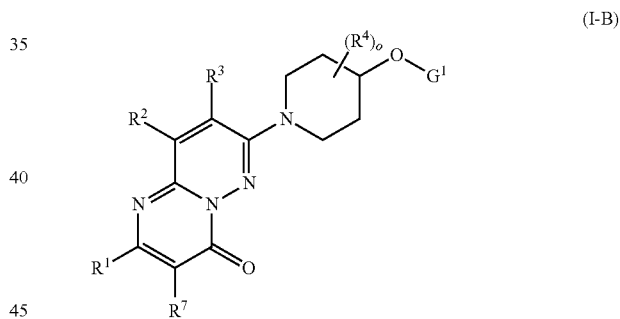

(I-B)

or a pharmaceutically acceptable salt thereof, wherein G$^1$ is

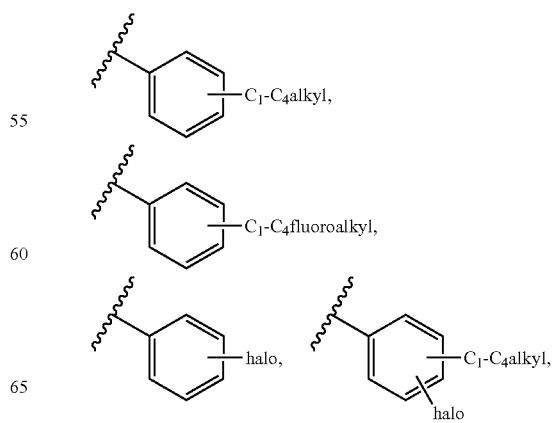

-continued

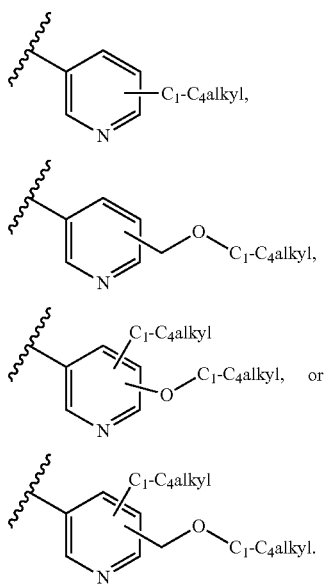

E14. The compound of embodiment E13, or a pharmaceutically acceptable salt thereof, wherein G¹ is

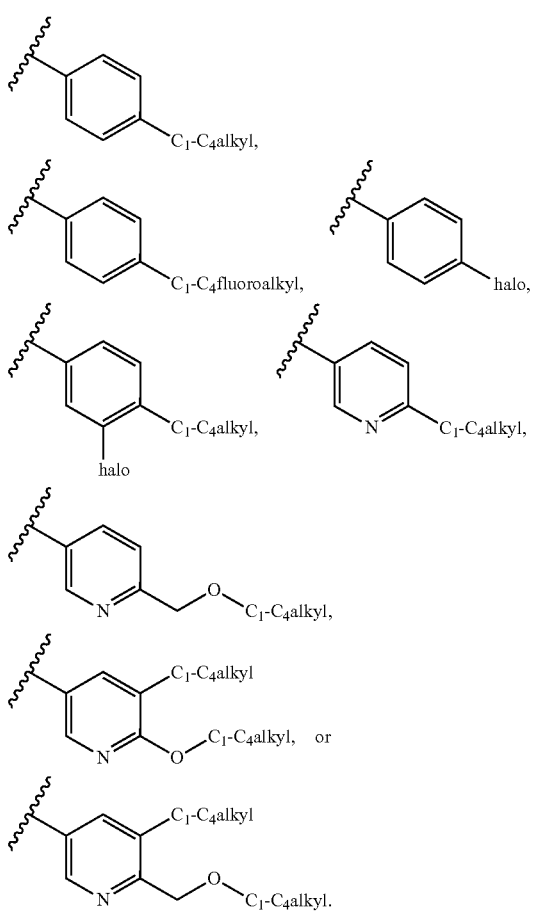

E15. The compound of embodiment E14, or a pharmaceutically acceptable salt thereof, wherein G¹ is

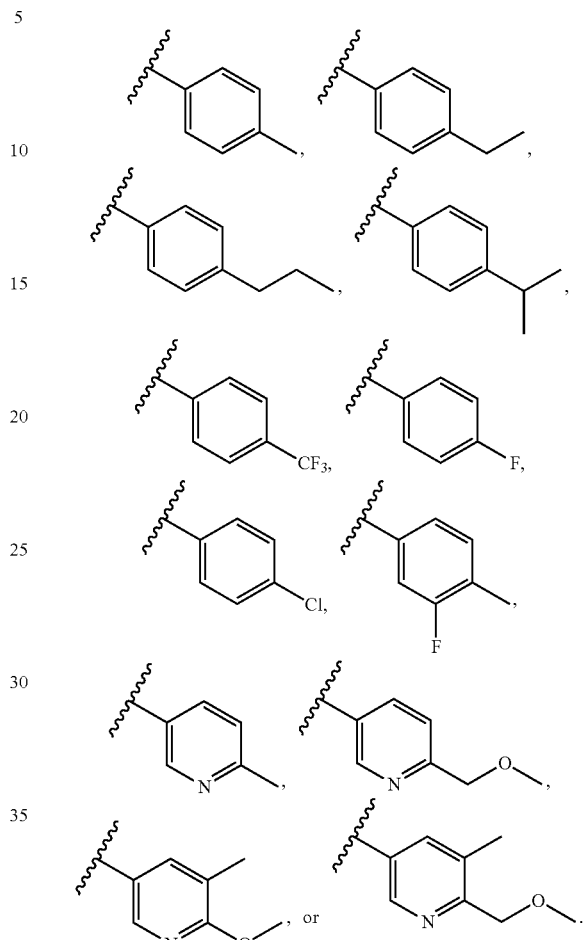

E16. The compound of any one of embodiments E1 to E15, or a pharmaceutically acceptable salt thereof, wherein $R^3$ is hydrogen, $C_1$-$C_4$-alkyl, $C_3$-$C_6$-cycloalkyl, or -$L^3$OR.

E17. The compound of embodiment E16, or a pharmaceutically acceptable salt thereof, wherein $R^3$ is $C_1$-$C_4$-alkyl.

E18. The compound of embodiment E17, or a pharmaceutically acceptable salt thereof, wherein $R^3$ is methyl.

E19. The compound of any of embodiments E1-E18, or a pharmaceutically acceptable salt thereof, wherein $R^1$ is hydrogen, $C_1$-$C_4$-alkyl, $C_1$-$C_4$-haloalkyl, $C_3$-$C_6$-cycloalkyl, -$L^1$-$C_3$-$C_6$-cycloalkyl, or -$L^1$OR$^a$.

E20. The compound of embodiment E19, or a pharmaceutically acceptable salt thereof, wherein $R^1$ is $C_1$-$C_4$-alkyl.

E21. The compound of embodiment E19, or a pharmaceutically acceptable salt thereof, wherein $R^1$ is hydrogen.

E22. The compound of embodiment E19, or a pharmaceutically acceptable salt thereof, wherein $R^1$ is $C_1$-$C_4$-fluoroalkyl.

E23. The compound of embodiment E22, or a pharmaceutically acceptable salt thereof, wherein $R^1$ is trifluoromethyl.

E24. The compound of embodiment E22, or a pharmaceutically acceptable salt thereof, wherein $R^1$ is difluoroethyl.

E25. The compound of any one of embodiments E1 to E24, or a pharmaceutically acceptable salt thereof, wherein R² is selected from hydrogen, $C_1$-$C_4$-alkyl, $C_3$-$C_6$-cycloalkyl, -L²OR$^b$, OR$^b$, NHR$^b$, and N(R$^b$)$_2$.

E26. The compound of embodiment E25, or a pharmaceutically acceptable salt thereof, wherein R² is $C_1$-$C_4$-alkyl.

E27. The compound of embodiment E25, or a pharmaceutically acceptable salt thereof, wherein R² is hydrogen.

E28. The compound of embodiment E25, or a pharmaceutically acceptable salt thereof, wherein R² is methyl.

E29. The compound of any one of embodiments E1 to E28, or a pharmaceutically acceptable salt thereof, wherein R⁴ is $C_1$-$C_4$-alkyl or halo.

E30. The compound of any of embodiments E1 to E29, or a pharmaceutically acceptable salt thereof, wherein o is 0.

E31. The compound of any of embodiments E1 to E29, or a pharmaceutically acceptable salt thereof, wherein o is 1.

E32. The compound of any one of embodiments E1 to E31, or a pharmaceutically acceptable salt thereof, wherein R⁷ is selected from hydrogen, $C_1$-$C_4$-alkyl, $C_3$-$C_6$-cycloalkyl, halo, and N(R$^b$)$_2$.

E33. The compound of embodiment E32, or a pharmaceutically acceptable salt thereof, wherein R⁷ is selected from hydrogen, methyl, cyclopropyl, fluoro, chloro, and azetidin-1-yl.

E34. The compound of embodiment E33, or a pharmaceutically acceptable salt thereof, wherein R⁷ is hydrogen.

E35. The compound of any one of embodiments E1 to E5 or E8 to E34, or a pharmaceutically acceptable salt thereof, wherein X is N.

E36. The compound of any one of embodiments E1 to E34, or a pharmaceutically acceptable salt thereof, wherein X is CR$^{5a}$.

E37. The compound of embodiment E36, or a pharmaceutically acceptable salt thereof, wherein R$^{5a}$ is hydrogen.

E38. The compound of embodiment E1, selected from the group consisting of:

7-(4-((2,3-dihydrobenzo[b][1,4]dioxin-6-yl-2,2,3,3-d4)oxy)piperidin-1-yl)-8-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl)-9-methyl-4H-pyrimido[1,2-b]pyridazin-4-one;

3-chloro-7-(4-((2,3-dihydrobenzo[b][1,4]dioxin-6-yl-2,2,3,3-d4)oxy)piperidin-1-yl)-8-methyl-4H-pyrimido[1,2-b]pyridazin-4-one;

8-methyl-7-(4-((6-methylpyridin-3-yl)oxy)piperidin-1-yl)-4H-pyrimido[1,2-b]pyridazin-4-one;

7-(4-(4-fluorophenoxy)piperidin-1-yl)-8-methyl-4H-pyrimido[1,2-b]pyridazin-4-one;

7-(4-((2,3-dihydrobenzo[b][1,4]dioxin-6-yl)oxy)piperidin-1-yl)-8-methyl-4H-pyrimido[1,2-b]pyridazin-4-one;

3-chloro-8-methyl-7-(4-((8-methyl-2,3-dihydrobenzo[b][1,4]dioxin-6-yl-2,2,3,3-d4)oxy)piperidin-1-yl)-4H-pyrimido[1,2-b]pyridazin-4-one;

8-methyl-7-(4-((8-methyl-2,3-dihydrobenzo[b][1,4]dioxin-6-yl-2,2,3,3-d4)oxy)piperidin-1-yl)-4H-pyrimido[1,2-b]pyridazin-4-one;

7-(4-((2,3-dihydrobenzo[b][1,4]dioxin-6-yl-2,2,3,3-d4)oxy)piperidin-1-yl)-3-fluoro-2,8-dimethyl-4H-pyrimido[1,2-b]pyridazin-4-one;

7-(4-((2,3-dihydrobenzo[b][1,4]dioxin-6-yl-2,2,3,3-d4)oxy)piperidin-1-yl)-3,8-dimethyl-4H-pyrimido[1,2-b]pyridazin-4-one;

3-cyclopropyl-7-(4-((2,3-dihydrobenzo[b][1,4]dioxin-6-yl-2,2,3,3-d4)oxy)piperidin-1-yl)-8-methyl-4H-pyrimido[1,2-b]pyridazin-4-one;

3-chloro-7-(4-((2,3-dihydrobenzo[b][1,4]dioxin-6-yl)oxy)piperidin-1-yl)-8-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl)-2,8-dimethyl-4H-pyrimido[1,2-b]pyridazin-4-one;

7-(4-((2,3-dihydrobenzo[b][1,4]dioxin-6-yl-2,2,3,3-d4)oxy)piperidin-1-yl)-8-methyl-2-(trifluoromethyl)-4H-pyrimido[1,2-b]pyridazin-4-one;

7-((3R,4R)-4-((2,3-dihydrobenzo[b][1,4]dioxin-6-yl)oxy)-3-fluoropiperidin-1-yl)-8-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl)-3-fluoro-2,8,9-trimethyl-4H-pyrimido[1,2-b]pyridazin-4-one;

7-((3S,4R)-4-((2,3-dihydrobenzo[b][1,4]dioxin-6-yl)oxy)-3-fluoropiperidin-1-yl)-2,8-dimethyl-4H-pyrimido[1,2-b]pyridazin-4-one;

7-((3S,4R)-4-((2,3-dihydrobenzo[b][1,4]dioxin-6-yl)oxy)-3-fluoropiperidin-1-yl)-8-methyl-4H-pyrimido[1,2-b]pyridazin-4-one;

3-(azetidin-1-yl)-7-(4-((2,3-dihydrobenzo[b][1,4]dioxin-6-yl-2,2,3,3-d4)oxy)piperidin-1-yl)-8-methyl-4H-pyrimido[1,2-b]pyridazin-4-one;

7-((3R,4R)-4-((2,3-dihydrobenzo[b][1,4]dioxin-6-yl)oxy)-3-fluoropiperidin-1-yl)-3-fluoro-2,8-dimethyl-4H-pyrimido[1,2-b]pyridazin-4-one;

7-((3S,4S)-4-((2,3-dihydrobenzo[b][1,4]dioxin-6-yl)oxy)-3-fluoropiperidin-1-yl)-3-fluoro-2,8-dimethyl-4H-pyrimido[1,2-b]pyridazin-4-one;

7-((3S,4S)-4-((2,3-dihydrobenzo[b][1,4]dioxin-6-yl-2,2,3,3-d4)oxy)-3-fluoropiperidin-1-yl)-3-fluoro-2,8-dimethyl-4H-pyrimido[1,2-b]pyridazin-4-one;

7-(4-((2,3-dihydrobenzo[b][1,4]dioxin-6-yl-2,2,3,3-d4)oxy)piperidin-1-yl-4-d)-8-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl-4-d)-2,8-dimethyl-4H-pyrimido[1,2-b]pyridazin-4-one;

7-((3R,4R)-4-((2,3-dihydrobenzo[b][1,4]dioxin-6-yl-2,2,3,3-d4)oxy)-3-fluoropiperidin-1-yl)-8-methyl-4H-pyrimido[1,2-b]pyridazin-4-one;

7-((3S,4S)-4-((2,3-dihydrobenzo[b][1,4]dioxin-6-yl-2,2,3,3-d4)oxy)-3-fluoropiperidin-1-yl)-8-methyl-4H-pyrimido[1,2-b]pyridazin-4-one;

7-((3R,4S)-4-((2,3-dihydrobenzo[b][1,4]dioxin-6-yl)oxy)-3-fluoropiperidin-1-yl)-8-methyl-4H-pyrimido[1,2-b]pyridazin-4-one;

7-((3R,4S)-4-((2,3-dihydrobenzo[b][1,4]dioxin-6-yl)oxy)-3-fluoropiperidin-1-yl)-2,8-dimethyl-4H-pyrimido[1,2-b]pyridazin-4-one;

7-(4-((2,3-dihydrobenzo[b][1,4]dioxin-6-yl-2,2,3,3-d4)oxy)piperidin-1-yl)-2,3,8-trimethyl-4H-pyrimido[1,2-b]pyridazin-4-one;

2-(difluoromethyl)-7-(4-((2,3-dihydrobenzo[b][1,4]dioxin-6-yl-2,2,3,3-d4)oxy)piperidin-1-yl)-8-methyl-4H-pyrimido[1,2-b]pyridazin-4-one;

2-cyclopropyl-7-(4-((2,3-dihydrobenzo[b][1,4]dioxin-6-yl-2,2,3,3-d4)oxy)piperidin-1-yl)-8-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl-4-d)-8-methyl-2-(trifluoromethyl)-4H-pyrimido[1,2-b]pyridazin-4-one;

7-(4-((2,3-dihydrobenzo[b][1,4]dioxin-6-yl-2,2,3,3-d4)oxy)piperidin-1-yl-4-d)-3-fluoro-2,8-dimethyl-4H-pyrimido[1,2-b]pyridazin-4-one;

7-(4-((2,3-dihydrobenzo[b][1,4]dioxin-6-yl-2,2,3,3-d4)oxy)
piperidin-1-yl-4-d)-2,3,8-trimethyl-4H-pyrimido[1,2-b]
pyridazin-4-one;

3-chloro-7-(4-((2,3-dihydrobenzo[b][1,4]dioxin-6-yl-2,2,3,
3-d4)oxy)piperidin-1-yl)-2,8-dimethyl-4H-pyrimido[1,2-
b]pyridazin-4-one;

7-(4-((2,3-dihydrobenzo[b][1,4]dioxin-6-yl)oxy)piperidin-
1-yl-4-d)-8-methyl-4H-pyrimido[1,2-b]pyridazin-4-one;

7-(4-((2,3-dihydrobenzo[b][1,4]dioxin-6-yl)oxy)piperidin-
1-yl-4-d)-8-methyl-2-(trifluoromethyl)-4H-pyrimido[1,2-
b]pyridazin-4-one;

7-(4-((2,3-dihydrobenzo[b][1,4]dioxin-6-yl)oxy)piperidin-
1-yl-4-d)-3-fluoro-2,8-dimethyl-4H-pyrimido[1,2-b]
pyridazin-4-one;

7-((3R,4R)-4-((2,3-dihydrobenzo[b][1,4]dioxin-6-yl-2,2,
3-d4)oxy)-3-fluoropiperidin-1-yl)-2,8-dimethyl-4H-py-
rimido[1,2-b]pyridazin-4-one;

2,8-dimethyl-7-(4-((6-methylpyridin-3-yl)oxy)piperidin-1-
yl)-4H-pyrimido[1,2-b]pyridazin-4-one;

7-((3R,4R)-4-(benzo[d][1,3]dioxol-5-yloxy)-3-fluoropiperi-
din-1-yl)-8-methyl-4H-pyrimido[1,2-b]pyridazin-4-one;

7-((3R,4R)-3-fluoro-4-(isochroman-6-yloxy)piperidin-1-
yl)-8-methyl-4H-pyrimido[1,2-b]pyridazin-4-one;

7-((3R,4R)-4-((3,4-dihydro-2H-benzo[b][1,4]dioxepin-7-
yl)oxy)-3-fluoropiperidin-1-yl)-8-methyl-4H-pyrimido
[1,2-b]pyridazin-4-one;

7-((3R,4R)-4-((2,3-dihydrobenzofuran-5-yl)oxy)-3-fluo-
ropiperidin-1-yl)-8-methyl-4H-pyrimido[1,2-b]
pyridazin-4-one;

7-((3R,4R)-4-(chroman-7-yloxy)-3-fluoropiperidin-1-yl)-8-
methyl-4H-pyrimido[1,2-b]pyridazin-4-one;

7-(4-((2,3-dihydrobenzo[b][1,4]dioxin-6-yl-2,2,3,3-d4)oxy)
piperidin-1-yl)-2,8,9-trimethyl-4H-pyrimido[1,2-b]
pyridazin-4-one;

7-(4-(benzo[d][1,3]dioxol-5-yloxy)piperidin-1-yl-4-d)-2,8-
dimethyl-4H-pyrimido[1,2-b]pyridazin-4-one;

7-(4-((3,4-dihydro-2H-benzo[b][1,4]dioxepin-7-yl)oxy)pip-
eridin-1-yl-4-d)-2,8-dimethyl-4H-pyrimido[1,2-b]
pyridazin-4-one;

7-(4-((2,3-dihydrobenzo[b][1,4]dioxin-6-yl)oxy)piperidin-
1-yl-4-d)-2,3,8-trimethyl-4H-pyrimido[1,2-b]pyridazin-
4-one;

2-(difluoromethyl)-7-(4-((2,3-dihydrobenzo[b][1,4]dioxin-
6-yl)oxy)piperidin-1-yl-4-d)-8-methyl-4H-pyrimido[1,2-
b]pyridazin-4-one;

7-(4-((2,3-dihydrobenzo[b][1,4]dioxin-6-yl)oxy)piperidin-
1-yl-4-d)-2,8-dimethyl-4H-pyrimido[1,2-b]pyridazin-4-
one;

7-(4-(benzo[d][1,3]dioxol-5-yloxy)piperidin-1-yl-4-d)-8-
methyl-2-(trifluoromethyl)-4H-pyrimido[1,2-b]
pyridazin-4-one;

7-(4-((3,4-dihydro-2H-benzo[b][1,4]dioxepin-7-yl)oxy)pip-
eridin-1-yl-4-d)-8-methyl-2-(trifluoromethyl)-4H-py-
rimido[1,2-b]pyridazin-4-one;

2-(difluoromethyl)-7-(4-((2,3-dihydrobenzo[b][1,4]dioxin-
6-yl-2,2,3,3-d4)oxy)piperidin-1-yl-4-d)-8-methyl-4H-py-
rimido[1,2-b]pyridazin-4-one;

7-(4-(benzo[d][1,3]dioxol-5-yloxy)piperidin-1-yl-4-d)-2-
(difluoromethyl)-8-methyl-4H-pyrimido[1,2-b]
pyridazin-4-one;

2-(difluoromethyl)-7-(4-((3,4-dihydro-2H-benzo[b][1,4]di-
oxepin-7-yl)oxy)piperidin-1-yl-4-d)-8-methyl-4H-py-
rimido[1,2-b]pyridazin-4-one;

7-(4-((2,3-dihydrobenzo[b][1,4]dioxin-6-yl-2,2,3,3-d4)oxy)
piperidin-1-yl)-8,9-dimethyl-2-(trifluoromethyl)-4H-py-
rimido[1,2-b]pyridazin-4-one;

2-(difluoromethyl)-7-(4-((2,3-dihydrobenzo[b][1,4]dioxin-
6-yl-2,2,3,3-d4)oxy)piperidin-1-yl)-8,9-dimethyl-4H-py-
rimido[1,2-b]pyridazin-4-one;

7-(4-(benzo[d][1,3]dioxol-5-yloxy)piperidin-1-yl-4-d)-8-
methyl-4H-pyrimido[1,2-b]pyridazin-4-one;

7-(4-((2,3-dihydrobenzo[b][1,4]dioxin-6-yl-2,2,3,3-d4)oxy)
piperidin-1-yl-4-d)-8,9-dimethyl-4H-pyrimido[1,2-b]
pyridazin-4-one;

7-(4-((2,3-dihydrobenzo[b][1,4]dioxin-6-yl)oxy)piperidin-
1-yl-4-d)-8,9-dimethyl-4H-pyrimido[1,2-b]pyridazin-4-
one;

7-(4-((2,3-dihydrobenzo[b][1,4]dioxin-6-yl)oxy)piperidin-
1-yl)-8,9-dimethyl-4H-pyrimido[1,2-b]pyridazin-4-one;

7-(4-((2,3-dihydrobenzo[b][1,4]dioxin-6-yl-2,2,3,3-d4)oxy)
piperidin-1-yl)-8,9-dimethyl-4H-pyrimido[1,2-b]
pyridazin-4-one;

2,8-dimethyl-7-(4-((1-oxo-1,2,3,4-tetrahydroisoquinolin-7-
yl)oxy)piperidin-1-yl)-4H-pyrimido[1,2-b]pyridazin-4-
one;

2,8-dimethyl-7-(4-((2-methyl-1-oxo-1,2,3,4-tetrahydroiso-
quinolin-7-yl)oxy)piperidin-1-yl)-4H-pyrimido[1,2-b]
pyridazin-4-one;

2,8-dimethyl-7-(4-((2-methyl-1-oxo-1,2,3,4-tetrahydroiso-
quinolin-6-yl)oxy)piperidin-1-yl)-4H-pyrimido[1,2-b]
pyridazin-4-one;

7-(4-((6-methoxy-5-methylpyridin-3-yl)oxy)piperidin-1-
yl)-8-methyl-4H-pyrimido[1,2-b]pyridazin-4-one;

7-(4-((6-(methoxymethyl)pyridin-3-yl)oxy)piperidin-1-yl)-
8-methyl-4H-pyrimido[1,2-b]pyridazin-4-one;

8,9-dimethyl-7-(4-(p-tolyloxy)piperidin-1-yl)-4H-pyrimido
[1,2-b]pyridazin-4-one;

2-(difluoromethyl)-8,9-dimethyl-7-(4-((6-methylpyridin-3-
yl)oxy)piperidin-1-yl)-4H-pyrimido[1,2-b]pyridazin-4-
one;

7-(4-(4-chlorophenoxy)piperidin-1-yl)-2-(difluoromethyl)-
8,9-dimethyl-4H-pyrimido[1,2-b]pyridazin-4-one;

8,9-dimethyl-7-(4-(4-(trifluoromethyl)phenoxy)piperidin-1-
yl)-4H-pyrimido[1,2-b]pyridazin-4-one;

2-(difluoromethyl)-8,9-dimethyl-7-(4-(4-(trifluoromethyl)
phenoxy)piperidin-1-yl)-4H-pyrimido[1,2-b]pyridazin-4-
one;

2,8-dimethyl-7-(4-((1-oxo-1,2,3,4-tetrahydroisoquinolin-6-
yl)oxy)piperidin-1-yl)-4H-pyrimido[1,2-b]pyridazin-4-
one;

7-(4-(4-fluorophenoxy)piperidin-1-yl)-8,9-dimethyl-4H-py-
rimido[1,2-b]pyridazin-4-one;

2-(difluoromethyl)-7-(4-(4-fluorophenoxy)piperidin-1-yl)-
8,9-dimethyl-4H-pyrimido[1,2-b]pyridazin-4-one;

2-(difluoromethyl)-8,9-dimethyl-7-(4-(p-tolyloxy)piperi-
din-1-yl)-4H-pyrimido[1,2-b]pyridazin-4-one;

8,9-dimethyl-7-(4-((6-methylpyridin-3-yl)oxy)piperidin-1-
yl)-4H-pyrimido[1,2-b]pyridazin-4-one;

8,9-dimethyl-7-(4-((6-methylpyridin-3-yl)oxy)piperidin-1-
yl)-4H-pyrimido[1,2-b]pyridazin-4-one;

7-(4-(3-fluoro-4-methylphenoxy)piperidin-1-yl)-8-methyl-
4H-pyrimido[1,2-b]pyridazin-4-one;

7-(4-(4-ethylphenoxy)piperidin-1-yl)-8-methyl-4H-py-
rimido[1,2-b]pyridazin-4-one;

7-(4-(4-isopropylphenoxy)piperidin-1-yl)-8-methyl-4H-py-
rimido[1,2-b]pyridazin-4-one;

8-methyl-7-(4-(4-propylphenoxy)piperidin-1-yl)-4H-py-
rimido[1,2-b]pyridazin-4-one;

8-methyl-7-(4-(p-tolyloxy)piperidin-1-yl-4-d)-4H-pyrimido
[1,2-b]pyridazin-4-one;

7-(4-((6-(methoxymethyl)-5-methylpyridin-3-yl)oxy)pip-
eridin-1-yl)-8-methyl-4H-pyrimido[1,2-b]pyridazin-4-
one;

7-(4-((2,3-dihydrobenzo[b][1,4]dioxin-6-yl)oxy)piperidin-1-yl)-2-ethyl-8,9-dimethyl-4H-pyrimido[1,2-b]pyridazin-4-one;

7-(4-((2,3-dihydrobenzo[b][1,4]dioxin-6-yl)oxy)piperidin-1-yl)-2-isopropyl-8,9-dimethyl-4H-pyrimido[1,2-b]pyridazin-4-one;

7-(4-((2,3-dihydrobenzo[b][1,4]dioxin-6-yl)oxy)piperidin-1-yl)-2-(methoxymethyl)-8,9-dimethyl-4H-pyrimido[1,2-b]pyridazin-4-one;

8-cyclopropyl-7-(4-((2,3-dihydrobenzo[b][1,4]dioxin-6-yl)oxy)piperidin-1-yl)-9-methyl-4H-pyrimido[1,2-b]pyridazin-4-one;

9-cyclopropyl-7-(4-((2,3-dihydrobenzo[b][1,4]dioxin-6-yl)oxy)piperidin-1-yl)-8-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl-4-d)-2,8,9-trimethyl-4H-pyrimido[1,2-b]pyridazin-4-one;

7-(4-((2,3-dihydrobenzo[b][1,4]dioxin-6-yl-2,2,3,3-d4)oxy)piperidin-1-yl-4-d)-8,9-dimethyl-2-(trifluoromethyl)-4H-pyrimido[1,2-b]pyridazin-4-one;

7-(4-((2,3-dihydrobenzo[b][1,4]dioxin-6-yl-2,2,3,3-d4)oxy)piperidin-1-yl-4-d)-2-isopropyl-8,9-dimethyl-4H-pyrimido[1,2-b]pyridazin-4-one;

9-cyclopropyl-7-(4-((2,3-dihydrobenzo[b][1,4]dioxin-6-yl-2,2,3,3-d4)oxy)piperidin-1-yl-4-d)-8-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl-4-d)-2-ethyl-8,9-dimethyl-4H-pyrimido[1,2-b]pyridazin-4-one;

7-(4-((2,3-dihydrobenzo[b][1,4]dioxin-6-yl-2,2,3,3-d4)oxy)piperidin-1-yl)-2-isopropyl-8,9-dimethyl-4H-pyrimido[1,2-b]pyridazin-4-one;

7-(4-((2,3-dihydrobenzo[b][1,4]dioxin-6-yl-2,2,3,3-d4)oxy)piperidin-1-yl)-2-ethyl-8,9-dimethyl-4H-pyrimido[1,2-b]pyridazin-4-one;

2-(cyclopentylmethyl)-7-(4-((2,3-dihydrobenzo[b][1,4]dioxin-6-yl-2,2,3,3-d4)oxy)piperidin-1-yl-4-d)-8,9-dimethyl-4H-pyrimido[1,2-b]pyridazin-4-one;

7-(4-((2,3-dihydrobenzo[b][1,4]dioxin-6-yl-2,2,3,3-d4)oxy)piperidin-1-yl-4-d)-8-(methoxymethyl)-9-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl)-8-(methoxymethyl)-9-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl-4-d)-9-(methoxymethyl)-8-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl)-9-(methoxymethyl)-8-methyl-4H-pyrimido[1,2-b]pyridazin-4-one;

8-cyclopropyl-7-(4-((2,3-dihydrobenzo[b][1,4]dioxin-6-yl-2,2,3,3-d4)oxy)piperidin-1-yl-4-d)-9-methyl-4H-pyrimido[1,2-b]pyridazin-4-one;

8-cyclopropyl-7-(4-((2,3-dihydrobenzo[b][1,4]dioxin-6-yl-2,2,3,3-d4)oxy)piperidin-1-yl)-9-methyl-4H-pyrimido[1,2-b]pyridazin-4-one;

7-((2R,4R)-4-((2,3-dihydrobenzo[b][1,4]dioxin-6-yl)oxy)-2-methylpiperidin-1-yl)-8-methyl-4H-pyrimido[1,2-b]pyridazin-4-one;

7-((2R,4S)-4-((2,3-dihydrobenzo[b][1,4]dioxin-6-yl)oxy)-2-methylpiperidin-1-yl)-8-methyl-4H-pyrimido[1,2-b]pyridazin-4-one;

7-((2R,4S)-4-((2,3-dihydrobenzo[b][1,4]dioxin-6-yl)oxy)-2-methylpiperidin-1-yl)-8-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl-4-d)-2-(methoxymethyl)-8-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl)-2-(methoxymethyl)-8-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl-4-d)-2-(methoxymethyl)-8,9-dimethyl-4H-pyrimido[1,2-b]pyridazin-4-one;

7-((3S,4R)-4-((2,3-dihydrobenzo[b][1,4]dioxin-6-yl-2,2,3,3-d4)oxy)-3-fluoropiperidin-1-yl)-8-methyl-4H-pyrimido[1,2-b]pyridazin-4-one;

7-((3R,4S)-4-((2,3-dihydrobenzo[b][1,4]dioxin-6-yl-2,2,3,3-d4)oxy)-3-fluoropiperidin-1-yl)-8-methyl-4H-pyrimido[1,2-b]pyridazin-4-one;

7-((3R,4S)-4-((2,3-dihydrobenzo[b][1,4]dioxin-6-yl)oxy)-3-methylpiperidin-1-yl)-8-methyl-4H-pyrimido[1,2-b]pyridazin-4-one;

7-((3R,4R)-4-((2,3-dihydrobenzo[b][1,4]dioxin-6-yl)oxy)-3-methylpiperidin-1-yl)-8-methyl-4H-pyrimido[1,2-b]pyridazin-4-one;

7-((3R,4R)-4-((2,3-dihydrobenzo[b][1,4]dioxin-6-yl)oxy)-3-methylpiperidin-1-yl)-8-methyl-4H-pyrimido[1,2-b]pyridazin-4-one;

7-((2R,4R)-4-((2,3-dihydrobenzo[b][1,4]dioxin-6-yl)oxy)-2-methylpiperidin-1-yl)-8-methyl-4H-pyrimido[1,2-b]pyridazin-4-one;

7-((3S,4S)-4-((2,3-dihydrobenzo[b][1,4]dioxin-6-yl-2,2,3-d4)oxy)-3-fluoropiperidin-1-yl)-8,9-dimethyl-4H-pyrimido[1,2-b]pyridazin-4-one;

7-((3S,4R)-4-((2,3-dihydrobenzo[b][1,4]dioxin-6-yl-2,2,3-d4)oxy)-3-fluoropiperidin-1-yl)-8,9-dimethyl-4H-pyrimido[1,2-b]pyridazin-4-one;

7-((3R,4S)-4-((2,3-dihydrobenzo[b][1,4]dioxin-6-yl-2,2,3-d4)oxy)-3-fluoropiperidin-1-yl)-8,9-dimethyl-4H-pyrimido[1,2-b]pyridazin-4-one;

7-((3S,4S)-4-((2,3-dihydrobenzo[b][1,4]dioxin-6-yl-2,2,3-d4)oxy)-3-fluoropiperidin-1-yl)-2-(methoxymethyl)-8,9-dimethyl-4H-pyrimido[1,2-b]pyridazin-4-one;

7-((3S,4R)-4-((2,3-dihydrobenzo[b][1,4]dioxin-6-yl-2,2,3-d4)oxy)-3-fluoropiperidin-1-yl)-2-(methoxymethyl)-8,9-dimethyl-4H-pyrimido[1,2-b]pyridazin-4-one;

7-((3R,4S)-4-((2,3-dihydrobenzo[b][1,4]dioxin-6-yl-2,2,3-d4)oxy)-3-fluoropiperidin-1-yl)-2-(methoxymethyl)-8,9-dimethyl-4H-pyrimido[1,2-b]pyridazin-4-one;

7-(4-((2,3-dihydrobenzo[b][1,4]dioxin-6-yl)oxy)piperidin-1-yl)-8-methyl-9-(methylamino)-4H-pyrimido[1,2-b]pyridazin-4-one;

7-((3R,4R)-4-((2,3-dihydrobenzo[b][1,4]dioxin-6-yl-2,2,3-d4)oxy)-3-fluoropiperidin-1-yl)-2-(methoxymethyl)-8,9-dimethyl-4H-pyrimido[1,2-b]pyridazin-4-one;

7-((3R,4R)-4-((2,3-dihydrobenzo[b][1,4]dioxin-6-yl-2,2,3-d4)oxy)-3-fluoropiperidin-1-yl)-2-(methoxymethyl)-8-methyl-4H-pyrimido[1,2-b]pyridazin-4-one;

7-(4-((2,3-dihydrobenzo[b][1,4]dioxin-6-yl)oxy)piperidin-1-yl)-9-methoxy-8-methyl-4H-pyrimido[1,2-b]pyridazin-4-one;

9-(azetidin-1-yl)-7-(4-((2,3-dihydrobenzo[b][1,4]dioxin-6-yl)oxy)piperidin-1-yl)-8-methyl-4H-pyrimido[1,2-b]pyridazin-4-one;

7-((3R,4R)-4-((2,3-dihydrobenzo[b][1,4]dioxin-6-yl-2,2,3-d4)oxy)-3-fluoropiperidin-1-yl)-8,9-dimethyl-4H-pyrimido[1,2-b]pyridazin-4-one;

7-((2R,4S)-4-((2,3-dihydrobenzo[b][1,4]dioxin-6-yl-2,2,3-d4)oxy)-2-methylpiperidin-1-yl)-8-methyl-4H-pyrimido[1,2-b]pyridazin-4-one;

7-((2R,4S)-4-((8-fluoro-2,3-dihydrobenzo[b][1,4]dioxin-6-yl-2,2,3,3-d4)oxy)-2-methylpiperidin-1-yl)-8-methyl-4H-pyrimido[1,2-b]pyridazin-4-one;

7-((2R,4S)-4-((8-fluoro-2,3-dihydrobenzo[b][1,4]dioxin-6-yl)oxy)-2-methylpiperidin-1-yl)-8-methyl-4H-pyrimido[1,2-b]pyridazin-4-one;

7-((2R,4S)-4-((2,3-dihydrobenzo[b][1,4]dioxin-6-yl-2,2,3,3-d4)oxy)-2-methylpiperidin-1-yl)-8,9-dimethyl-4H-pyrimido[1,2-b]pyridazin-4-one;

7-((2R,4S)-4-((2,3-dihydrobenzo[b][1,4]dioxin-6-yl-2,2,3,3-d4)oxy)-2-methylpiperidin-1-yl)-2-(methoxymethyl)-8,9-dimethyl-4H-pyrimido[1,2-b]pyridazin-4-one;

7-((2R,4S)-4-((2,3-dihydrobenzo[b][1,4]dioxin-6-yl)oxy)-2-methylpiperidin-1-yl)-8,9-dimethyl-4H-pyrimido[1,2-b]pyridazin-4-one;

7-(4-((8-fluoro-2,3-dihydrobenzo[b][1,4]dioxin-6-yl)oxy)piperidin-1-yl)-8-methyl-4H-pyrimido[1,2-b]pyridazin-4-one;

7-(4-((8-fluoro-2,3-dihydrobenzo[b][1,4]dioxin-6-yl-2,2,3,3-d4)oxy)piperidin-1-yl)-8-methyl-4H-pyrimido[1,2-b]pyridazin-4-one;

7-(4-((2,3-dihydrobenzo[b][1,4]dioxin-6-yl-2,2,3,3-d4)oxy)piperidin-1-yl-2,2,6,6-d4)-8-methyl-4H-pyrimido[1,2-b]pyridazin-4-one; or a pharmaceutically acceptable salt thereof.

E39. A pharmaceutical composition comprising a compound of any one of embodiments E1 to E38 and a pharmaceutically acceptable carrier.

E40. A method for treating a neurological and/or psychiatric disorder in a patient in need thereof, comprising administering to the patient a therapeutically effective amount of a compound, or a pharmaceutically acceptable salt thereof, or a pharmaceutical composition according to any one of embodiments E1 to E39.

E41. The method of embodiment E40, wherein the disorder is selected from Alzheimer's disease, schizophrenia, a sleep disorder, borderline personality disorder, Tourette's syndrome, bipolar disorder, tardive dyskinesia, Huntington's disease, a pain disorder, and a cognitive disorder.

E42. The method of embodiment E40, wherein the disorder is selected from psychosis, schizophrenia, conduct disorder, disruptive behavior disorder, bipolar disorder, psychotic episodes of anxiety, anxiety associated with psychosis, mood disorders associated with psychotic disorders, acute mania, depression associated with bipolar disorder, mood disorders associated with schizophrenia, behavioral manifestations of mental retardation, autistic disorder, movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

E43. The method of any one of embodiments E40 to E42, wherein the disorder is associated with muscarinic acetylcholine receptor M4 dysfunction.

E44. A compound, or a pharmaceutically acceptable salt thereof, according to any one of embodiments E1 to E38 for use in therapy.

E45. A compound, or a pharmaceutically acceptable salt thereof, or a pharmaceutical composition according to any one of embodiments E1 to E39 for use in the treatment of a disorder selected from Alzheimer's disease, schizophrenia, a sleep disorder, borderline personality disorder, Tourette's syndrome, bipolar disorder, tardive dyskinesia, Huntington's disease, a pain disorder, and a cognitive disorder.

E46. A compound, or a pharmaceutically acceptable salt thereof, or a pharmaceutical composition according to any one of embodiments E1 to E39 for use in the treatment of a disorder selected from psychosis, schizophrenia, conduct disorder, disruptive behavior disorder, bipolar disorder, psychotic episodes of anxiety, anxiety associated with psychosis, mood disorders associated with psychotic disorders, acute mania, depression associated with bipolar disorder, mood disorders associated with schizophrenia, behavioral manifestations of mental retardation, autistic disorder, movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

E47. Use of a compound or a pharmaceutical composition according to any one of embodiments E1 to E39, or a pharmaceutically acceptable salt thereof, in the manufacture of a medicament for the treatment of a disorder selected from Alzheimer's disease, schizophrenia, borderline personality disorder, Tourette's syndrome, bipolar disorder, tardive dyskinesia, Huntington's disease, a sleep disorder, a pain disorder, and a cognitive disorder.

E48. Use of a compound or a pharmaceutical composition according to any one of embodiments E1 to E39, or a pharmaceutically acceptable salt thereof, in the manufacture of a medicament for the treatment of a disorder selected from psychosis, schizophrenia, conduct disorder, disruptive behavior disorder, bipolar disorder, psychotic episodes of anxiety, anxiety associated with psychosis, mood disorders associated with psychotic disorders, acute mania, depression associated with bipolar disorder, mood disorders associated with schizophrenia, behavioral manifestations of mental retardation, autistic disorder, movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

Compound names can be assigned by using the Struct=Name naming algorithm as part of CHEMDRAW® version 18.0.

The compound may exist as a stereoisomer wherein asymmetric or chiral centers are present. The stereoisomer is "R" or "5" depending on the configuration of substituents around the chiral carbon atom. The terms "R" and "5" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds of the invention may possess tautomeric forms, stereoisomers, geometric isomers, solvates, hydrates as well as polymorphs, and that these also constitute embodiments of the invention.

In the compounds of formula (I), and any subformulas, any "hydrogen" or "H," whether explicitly recited or implicit in the structure, encompasses hydrogen isotopes $^1$H (protium) and $^2$H (deuterium).

The present invention also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

a. Pharmaceutically Acceptable Salts

The compounds of the invention may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the compounds of the invention by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

b. General Synthesis

Compounds of formula (I) or salts thereof may be prepared by synthetic processes or by metabolic processes. Preparation of the compounds by metabolic processes includes those occurring in the human or animal body (in vivo) or processes occurring in vitro. The schemes are representative of methods useful in synthesizing the compounds of the present invention. They are not to constrain the scope of the invention in any way.

Abbreviations used in the schemes that follow include the following: DCE is 1,2-dichloroethane; DCM is dichloromethane; DMF is N,N-dimethylformamide; DMP or Dess-Martin periodinane is 1,1,1-tris(acetyloxy)-1,1-dihydro-1,2-benziodoxol-3-(1H)-one; DtBAD is di-tert-butyl azodicarboxylate; LAH is lithium aluminum hydride; mCPBA is meta-chloroperoxy benzoic acid; MeOH is methanol; MW is microwave (referring to a microwave reactor); Pd(OAc)$_2$ is palladium(II) acetate; PPA is polyphosphoric acid; Rxn is reaction; TBAC is tetrabutylammonium chloride; t-BuXPhos is 2-Di-tert-butylphosphino-2',4',6'-triisopropylbiphenyl; and THF is tetrahydrofuran.

Compounds of formula (I) may be synthesized as shown in Schemes 1-7.

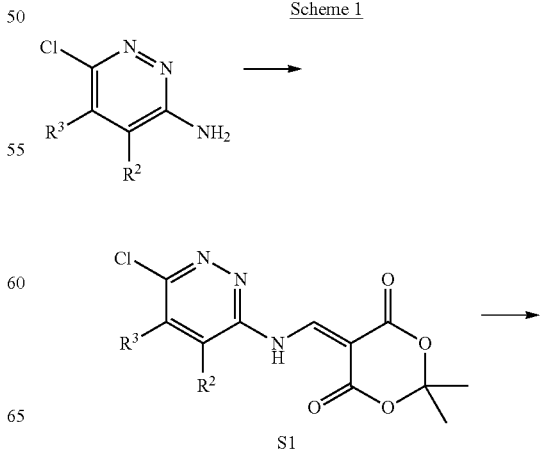

Scheme 1

-continued

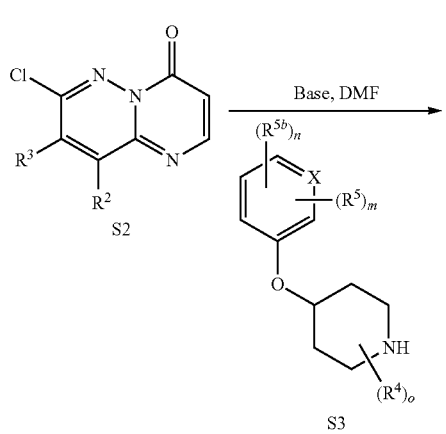

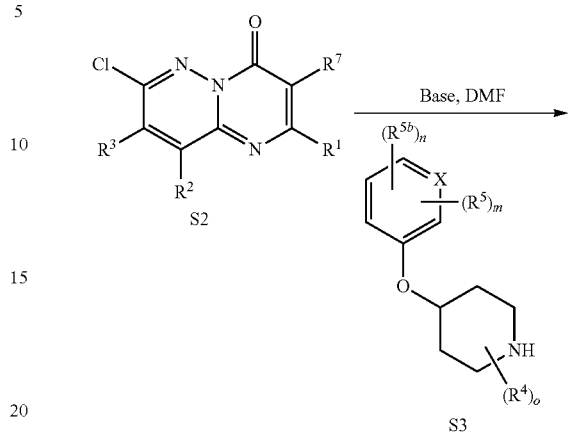

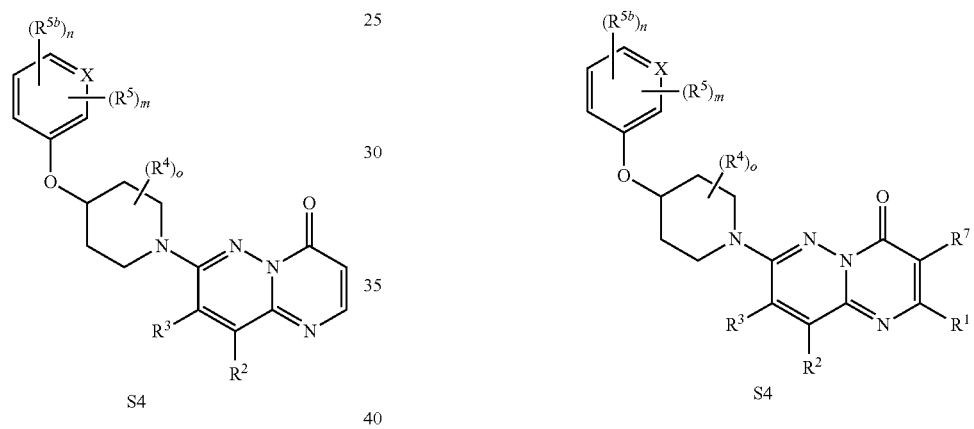

As shown in Scheme 1, reaction of analogues of 6-chloropyridazin-3-amine with triethyl orthoformate and isopropylidene malonate may provide compounds of type S1, which may be cyclized to provide compounds of type S2. Reaction of compounds S2 with an appropriate substituted 4-piperidine ether of type S3 in the presence of a base may provide compounds S4.

As shown in Scheme 2, reaction of analogues of 6-chloropyridazin-3-amine with beta-ketoacids may be cyclized using acid (i.e. PPA) to provide compounds of type S2. Reaction of compounds S2 with an appropriate substituted 4-((2,3-dihydrobenzo[b][1,4]dioxin-6-yl)oxy)piperidine of type S3 in the presence of a base may provide compounds S4.

Scheme 2

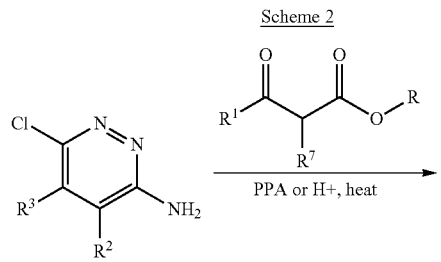

Scheme 3

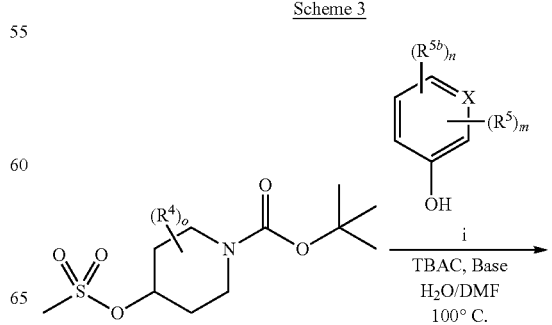

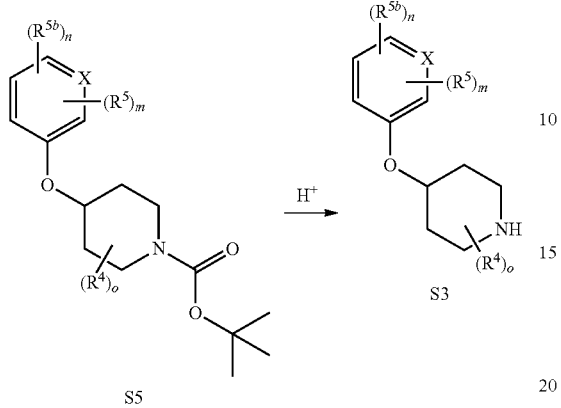

As shown in Scheme 3, intermediates like compound S3 may be prepared via displacement of tert-butyl 4-((methylsulfonyl)oxy)piperidine-1-carboxylate with appropriate alcohols (i.e. compound i) to provide intermediates 5S, which can be deprotected under acidic conditions to provide intermediates S3.

Scheme 4

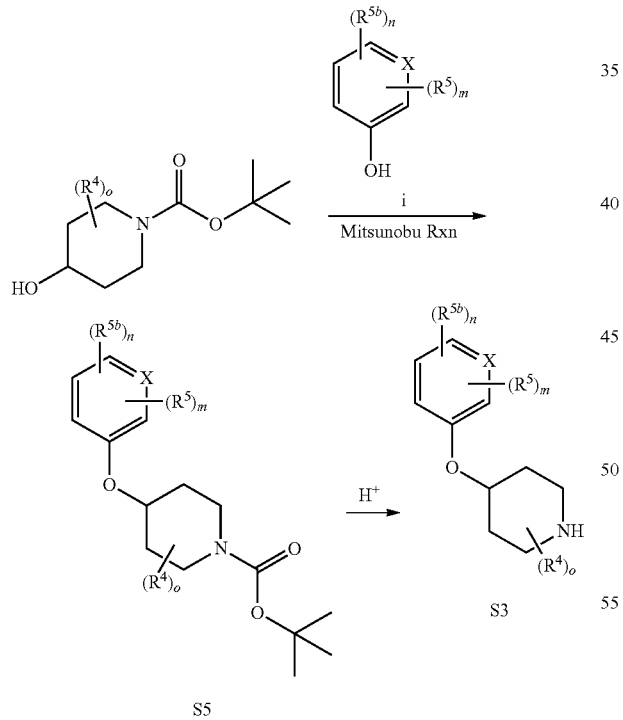

As shown in Scheme 4, intermediates like compound S3 may be prepared via Mitsunobu reaction between analogues of tert-butyl 4-hydroxypiperidine-1-carboxylate with appropriate alcohols (i.e. compound i) to provide intermediates 5S, which may be deprotected under acidic conditions to provide intermediates S3.

Scheme 5

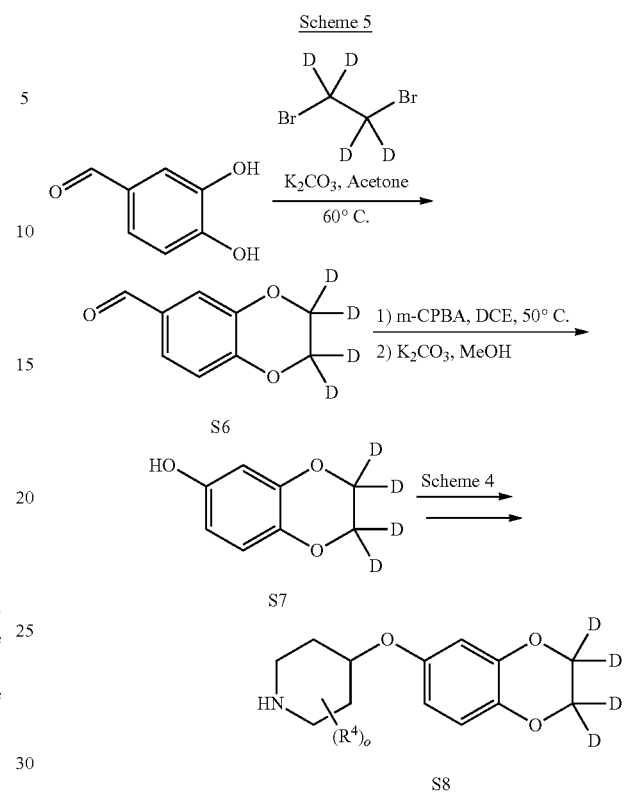

As shown in Scheme 5, reaction of 3,4-dihydroxybenzaldehyde and 1,2-dibromoethane-1,1,2,2-d4 in the presence of base (i.e. $K_2CO_3$) affords intermediate S6. In a 2 step procedure, intermediate S6 is treated with m-CPBA, followed by base and methanol to provide alcohol S7, which may be carried forward as shown in Scheme 4 to provide intermediate S8.

Scheme 6

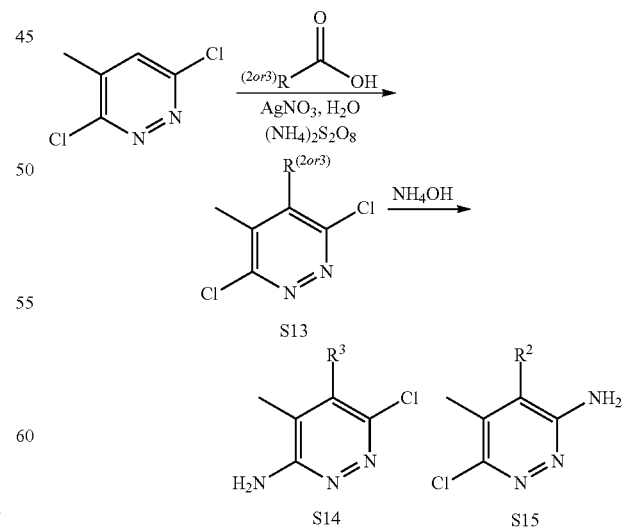

As Shown in Scheme 6, analogues of 6-chloropyridazin-3-amine S14 and S15 may be prepared by a radical based addition of an appropriate carboxylic acid to provide intermediate S13, which may be transformed to the desired intermediate S14 and S15.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, Greene's Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

c. Muscarinic Acetylcholine Receptor $M_4$ Activity

In an embodiment, a compound of the invention potentiates the agonist response (e.g., acetylcholine) of mAChR M4. In some embodiments, a compound of the invention increases mAChR M4 response to non-maximal concentrations of an agonist in the presence of compound of the invention compared to the response to an agonist in the absence of compound of the invention. The potentiation of mAChR M4 activity can be demonstrated by methodology known in the art. For example, activation of mAChR M4 activity can be determined by measurement of calcium flux in response to an agonist, e.g. acetylcholine, in cells loaded with a $Ca^{2+}$-sensitive fluorescent dye (e.g., Fluo-4) and co-expression of a chimeric or promiscuous G protein. In an embodiment, the calcium flux was measured as an increase in fluorescent static ratio. In an embodiment, positive allosteric modulator activity was analyzed as a concentration-dependent increase in the $EC_{20}$ acetylcholine response (i.e. the response of mAChR M4 at a concentration of acetylcholine that yields 20% of the maximal response).

In an embodiment, a compound of the invention activates mAChR M4 response as an increase in calcium fluorescence in mAChR $M_4$-transfected CHO-K1 cells in the presence of a compound of the invention, compared to the response of equivalent CHO-K1 cells in the absence of a compound of the invention.

The compounds of the invention may exhibit positive allosteric modulation of mAChR $M_4$ response to acetylcholine as an increase in response to non-maximal concentrations of acetylcholine in CHO-K1 cells transfected with a mAChR $M_4$ in the presence of the compound, compared to the response to acetylcholine in the absence of the compound.

In vivo efficacy for compounds of the invention may be measured in a number of preclinical rat behavioral models where known, clinically useful antipsychotics display similar positive responses. For example, compounds of the invention may reverse amphetamine-induced hyperlocomotion in male Sprague-Dawley rats at doses ranging from 1 to 100 mg/kg p.o.

3. Pharmaceutical Compositions

The compounds of the invention may be incorporated into pharmaceutical compositions suitable for administration to a subject (such as a patient, which may be a human or non-human). The compounds of the invention may also be provided as formulations, such as spray-dried dispersion formulations.

The pharmaceutical compositions may include a "therapeutically effective amount" or a "prophylactically effective amount" of the agent. A "therapeutically effective amount" refers to an amount effective, at single or multiple dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I) or a pharmaceutically acceptable salt thereof) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount may be less than the therapeutically effective amount.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds of the invention may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the compounds of the invention are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90 weight % of the total composition weight.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10% of the total composition weight.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50% of the total composition weight.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10% of the total composition weight.

Suitable colorants include a colorant such as an FD&C dye. When used, the amount of colorant in a systemic or topical composition is typically about 0.005 to about 0.1% of the total composition weight.

Suitable flavors include menthol, peppermint, and fruit flavors. The amount of flavor(s), when used, in a systemic or topical composition is typically about 0.1 to about 1.0% of the total composition weight.

Suitable sweeteners include aspartame and saccharin. The amount of sweetener(s) in a systemic or topical composition is typically about 0.001 to about 1% of the total composition weight.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5% of the total composition weight.

Suitable preservatives include benzalkonium chloride, methyl paraben and sodium benzoate. The amount of preservative(s) in a systemic or topical composition is typically about 0.01 to about 5% of the total composition weight.

Suitable glidants include silicon dioxide. The amount of glidant(s) in a systemic or topical composition is typically about 1 to about 5% of the total composition weight.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100% of the total composition weight.

Suitable suspending agents include AVICEL RC-591 (from FMC Corporation of Philadelphia, PA) and sodium alginate. The amount of suspending agent(s) in a systemic or topical composition is typically about 1 to about 8% of the total composition weight.

Suitable surfactants include lecithin, Polysorbate 80, and sodium lauryl sulfate, and the TWEENS from Atlas Powder Company of Wilmington, Delaware. Suitable surfactants include those disclosed in the C.T.F.A. Cosmetic Ingredient Handbook, 1992, pp. 587-592; Remington's Pharmaceutical Sciences, 22th Ed. 2013; and McCutcheon's Volume 1, Emulsifiers & Detergents, 1994, North American Edition, pp. 236-239. The amount of surfactant(s) in the systemic or topical composition is typically about 0.1% to about 5% of the total composition weight.

Although the amounts of components in the systemic compositions may vary depending on the type of systemic composition prepared, in general, systemic compositions include 0.01 to 50 weight % of the total composition weight of an active compound (e.g., a compound of formula (I) or a pharmaceutically acceptable salt thereof) and 50 to 99.99 weight % of the total composition weight of one or more carriers. Compositions for parenteral administration typically include 0.1 to 10 weight % of the total composition weight of actives and 90 to 99.9 weight % of the total composition weight of a carrier including a diluent and a solvent.

Compositions for oral administration can have various dosage forms. For example, solid forms include tablets, capsules, granules, and bulk powders. These oral dosage forms include a safe and effective amount, usually at least about 5 weight % of the total composition weight, and more particularly from about 25 to about 50 weight % of the total composition weight of actives. The oral dosage compositions include about 50 to about 95 weight % of carriers of the total composition weight, and more particularly, from about 50 to about 75 weight % of the total composition weight.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I) or a), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The compounds of the invention can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I) or a pharmaceutically acceptable salt thereof), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5 to about 95 weight % of the total composition weight.

Suitable propellants include propane, butane, isobutane, dimethyl ether, carbon dioxide, nitrous oxide, and combinations thereof. The amount of propellant(s) in a topical composition is typically about 0 to about 95 weight % of the total composition weight.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0 to about 95 weight % of the total composition weight.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0 to 95 weight % of the total composition weight.

The amount of thickener(s) in a topical composition is typically about 0 to about 95 weight % of the total composition weight.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0 to 95 weight % of the total composition weight.

The amount of fragrance in a topical composition is typically about 0 to about 0.5 weight %, particularly, about 0.001 to about 0.1 weight % of the total composition weight.

Suitable pH adjusting additives include HCl or NaOH in amounts sufficient to adjust the pH of a topical pharmaceutical composition.

4. Methods of Use

The compounds of the invention and pharmaceutical compositions may be used in methods for treatment of disorders, such as neurological and/or psychiatric disorders, associated with muscarinic acetylcholine receptor dysfunction. The compounds of the invention and pharmaceutical compositions may also be used in methods for the potentiation of muscarinic acetylcholine receptor activity in patient, and in methods for enhancing cognition in a patient. The methods further include cotherapeutic methods for improving treatment outcomes in the context of cognitive or behavioral therapy. In the methods of use described herein, additional therapeutic agent(s) may be administered simultaneously or sequentially with the compounds of the invention and compositions.

a. Treating Disorders

The compounds of the invention, pharmaceutical compositions and formulations may be used in methods for treatment of disorders, such as neurological and/or psychiatric disorders, associated with muscarinic acetylcholine receptor dysfunction. The methods of treatment may comprise administering to a subject in need of such treatment a therapeutically effective amount of the compound of formula (I), a pharmaceutically acceptable salt thereof, or a pharmaceutical composition comprising a therapeutically effective amount of a compound of formula (I), or a pharmaceutically acceptable salt thereof.

In some embodiments, the invention provides to a method for enhancing cognition in a patient comprising the step of administering to the patient a therapeutically effective amount of the compound of formula (I), a pharmaceutically acceptable salt thereof, or a pharmaceutical composition comprising a therapeutically effective amount of a compound of formula (I), or a pharmaceutically acceptable salt thereof.

The compounds of the invention and compositions disclosed herein may be useful for treating, preventing, ameliorating, controlling or reducing the risk of a variety of disorders associated with selective mAChR M4 receptor activation. For example, a treatment can include selective mAChR M4 receptor activation to an extent effective to affect cholinergic activity. A disorder can be associated with cholinergic activity, for example cholinergic hypofunction. Thus, provided is a method of treating or preventing a disorder in a subject comprising the step of administering to the subject at least one compound of the invention or at least one disclosed pharmaceutical composition, in an amount effective to treat the disorder in the subject.

Also provided is a method for the treatment of one or more disorders associated with mAChR M4 receptor activity in a subject comprising the step of administering to the subject a therapeutically effective amount of the compound of formula (I), a pharmaceutically acceptable salt thereof, or a pharmaceutical composition comprising a therapeutically effective amount of a compound of formula (I), or a pharmaceutically acceptable salt thereof.

In some embodiments, the invention provides a compound of formula (I), or a pharmaceutically acceptable salt thereof, for use in a method for the treatment of a disorder associated with the mAChR $M_4$ receptor. In some embodiments, the invention provides a pharmaceutical composition comprising a compound of formula (I), or a pharmaceutically acceptable salt thereof, for use in a method for the treatment of a disorder associated with the mAChR $M_4$ receptor.

In some embodiments, the invention provides a compound of formula (I), or a pharmaceutically acceptable salt thereof, for use in the manufacture of a medicament for the treatment of a disorder associated with the mAChR $M_4$ receptor.

In some embodiments, the invention provides a method for the treatment of a disorder associated with muscarinic acetylcholine receptor dysfunction in a patient, comprising the step of administering to the patient an effective amount of at least one disclosed compound or a pharmaceutically acceptable salt thereof, or a pharmaceutical composition comprising at least one disclosed compound or pharmaceutically acceptable salt thereof.

In some embodiments, the compounds of the invention and compositions have utility in treating a variety of neurological, psychiatric and cognitive disorders associated with the mAChR M4 receptor, including one or more of the following conditions or diseases: schizophrenia, psychotic disorder NOS, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder. In some embodiments, the psychotic disorder is a psychosis associated with an illness selected from major depressive disorder, affective disorder, bipolar disorder, electrolyte disorder, Alzheimer's disease, neurological disorder, hypoglycemia, AIDS, lupus, and post-traumatic stress disorder.

In some embodiments, the disorder is schizophrenia.

In some embodiments, the disorder is psychotic depression.

In some embodiments, the disorder is agitation and psychosis in Alzheimer's disease.

In some embodiment, the disorder is a bipolar disorder.

In some embodiments, the disorder is a neurological disorder is selected from brain tumor, dementia with Lewy bodies, multiple sclerosis, sarcoidosis, Lyme disease, syphilis, Alzheimer's disease, Parkinson's disease, and anti-NMDA receptor encephalitis.

In some embodiments, the disorder is a psychotic disorder is selected from schizophrenia, brief psychotic disorder, schizophreniform disorder, schizoaffective disorder, delusional disorder, and shared psychotic disorder. In some embodiments, the schizophrenia is selected from catastrophic schizophrenia, catatonic schizophrenia, paranoid schizophrenia, residual schizophrenia, disorganized schizophrenia, and undifferentiated schizophrenia. In some embodiments, the disorder is selected from schizoid personality disorder, schizotypal personality disorder, and paranoid personality disorder. In some embodiments, the psychotic disorder is due to a general medical condition and is substance-induced or drug-induced (phencyclidine, ketamine and other dissociative anesthetics, amphetamine and other psychostimulants, and cocaine).

In some embodiments, the present invention provides a method for treating a neurodevelopmental disorder, comprising administering to a patient in need thereof an effective amount of a compound, or a pharmaceutically acceptable salt, or a pharmaceutical composition of the present invention. In some embodiments, the neurodevelopmental disorder is fragile X syndrome.

In some embodiments, the present invention provides a method for treating a cognitive disorder, comprising administering to a patient in need thereof an effective amount of a compound, or a pharmaceutically acceptable salt, or a pharmaceutical composition of the present invention. In some embodiments, cognitive disorders include dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse), delirium, amnestic disorder, substance-induced persisting delirium, dementia due to HIV disease, dementia due to Huntington's disease, dementia due to Parkinson's disease, Parkinsonian-ALS demential complex, dementia of the Alzheimer's type, age-related cognitive decline, and mild cognitive impairment.

In some embodiments, the cognitive disorder is Huntington's disease.

The text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. The fifth edition of the Diagnostic and Statistical Manual of Mental Disorders (DSM-5) (2013, American Psychiatric Association, Washington D.C.) provides a diagnostic tool for neurocognitive disorders (NCDs) that include delirium, followed by the syndromes of major NCD, mild NCD, and their etiological subtypes. The major or mild NCD subtypes include NCD due to Alzheimer's disease, vascular NCD, NCD with Lewy bodies, NCD due to Parkinson's disease, frontotemporal NCD, NCD due to traumatic brain injury, NCD due to HIV infection, substance/medication-induced NCD, NCD due to Huntington's disease, NCD due to prion disease, NCD due to another medical condition, NCD due to multiple etiologies, and unspecified NCD. The NCD category in DSM-5 encompasses the group of disorders in which the primary clinical deficit is in cognitive function, and that are acquired rather than developmental. As used herein, the term "cognitive disorders" includes treatment of those cognitive disorders and neurocognitive disorders as described in DSM-IV-TR or DSM-5. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

In some embodiments, the present invention provides a method for treating sleep disorder, comprising administering to a patient in need thereof an effective amount of a compound, or a pharmaceutically acceptable salt thereof, or a pharmaceutical composition of the present invention.

In some embodiments, the sleep disorder is associated with sleep disturbance in a patient having schizophrenia.

In some embodiments, the present invention provides a method for treating schizophrenia or psychosis, comprising administering to a patient in need thereof an effective amount of a compound, or a pharmaceutically acceptable salt, or a pharmaceutical composition of the present invention. Particular schizophrenia or psychosis pathologies are paranoid, disorganized, catatonic or undifferentiated schizophrenia and substance-induced psychotic disorder. DSM-IV-TR provides a diagnostic tool that includes paranoid, disorganized, catatonic, undifferentiated or residual schizophrenia, and substance-induced psychotic disorder. DSM-5 eliminated the subtypes of schizophrenia, and instead includes a dimensional approach to rating severity for the core symptoms of schizophrenia, to capture the heterogeneity in symptom type and severity expressed across individuals with psychotic disorders. As used herein, the term "schizophrenia or psychosis" includes treatment of those mental disorders as described in DSM-IV-TR or DSM-5. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In some embodiments, the present invention provides a method for treating pain, comprising administering to a patient in need thereof a therapeutically effective amount of a compound or composition of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

The compounds and compositions may be further useful in a method for the prevention, treatment, control, amelioration, or reduction of risk of the diseases, disorders and conditions noted herein. The compounds of the invention and compositions may be further useful in a method for the prevention, treatment, control, amelioration, or reduction of risk of the aforementioned diseases, disorders and conditions, in combination with other agents.

In the treatment of conditions which require activation of mAChR M4, an appropriate dosage level may be about 0.001 mg/kg to about 100 mg/kg patient body weight per day, which can be administered in single or multiple doses. In particular, daily dosages may be in the range of 0.01 mg/kg body weight to about 50 mg/kg body weight per day. The dosage level may be about 0.1 to about 30 mg/kg per day, or more particular about 1 to about 10 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, or 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in some embodiments, the present invention relates to a method for activating mAChR M4 receptor activity in at least one cell, comprising the step of contacting the at least one cell with at least one compound of the invention or pharmaceutical composition in an amount effective to activate mAChR M4 in the at least one cell. In some embodiments, the cell is mammalian, for example, human. In some embodiments, the cell has been isolated from a subject prior to the contacting step. In some embodiments, contacting is via administration to a subject.

In some embodiments, the invention relates to a method for activating mAChR M4 activity in a subject, comprising the step of administering to the subject at least one compound of the invention or at least one product of a disclosed method in a dosage and amount effective to activating mAChR M4 activity in the subject. In some embodiments, the subject is patient. In some embodiments, the patient has been diagnosed with a need for mAChR M4 agonism prior to the administering step. In some embodiments, the patient has been diagnosed with a need for mAChR M4 activation prior to the administering step. In some embodiments, the method further comprises the step of identifying a subject in need of mAChR M4 agonism.

In some embodiments, the invention relates to a method for the treatment of a disorder associated with selective mAChR M4 activation, for example, a disorder associated with cholinergic activity, in a patient comprising the step of administering to the patient at least one compound of the invention or at least one product of a disclosed method in a dosage and amount effective to treat the disorder in the patient. In some embodiments, the patient is a human. In some embodiments, the patient has been diagnosed with a need for treatment for the disorder prior to the administering step. In some embodiments, the method further comprises the step of identifying a subject in need of treatment for the disorder.

In some embodiments, the disorder can be selected from psychosis, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, autistic disorder, movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, obsessive-compulsive disorder, cognitive disorders, dementias, and memory disorders.

In some embodiments, the disorder is Alzheimer's disease.

In some embodiments, the disorder is Tourette's syndrome

In some embodiments, the disorder is tardive dyskinesia.

In some embodiments, the disorder is obsessive-compulsive disorder.

In some embodiments, the disorder is bipolar disorder.

b. Potentiation of Muscarinic Acetylcholine Receptor Activity

In some embodiments, the invention relates to a method for potentiation of muscarinic acetylcholine receptor activity in a patient comprising the step of administering to the patient an effective amount of at least one disclosed compound or a pharmaceutically acceptable salt thereof, or a pharmaceutical composition comprising at least one disclosed compound or pharmaceutically acceptable salt thereof.

In some embodiments, the invention provides a compound of formula (I), or a pharmaceutically acceptable salt thereof, for use in a method for the potentiation of muscarinic acetylcholine receptor activity in patient. In some embodiments, the invention provides a pharmaceutical composition comprising a compound of formula (I), or a pharmaceutically acceptable salt thereof, for use in a method for the potentiation of muscarinic acetylcholine receptor activity in a patient.

In some embodiments, the invention provides a compound of formula (I), or a pharmaceutically acceptable salt thereof, for use in the manufacture of a medicament for the potentiation of muscarinic acetylcholine receptor activity in a patient.

In some embodiments, potentiation of muscarinic acetylcholine receptor activity increases muscarinic acetylcholine receptor activity. In some embodiments, potentiation of muscarinic acetylcholine receptor activity is partial agonism of the muscarinic acetylcholine receptor. In some embodiments, potentiation of muscarinic acetylcholine receptor activity is positive allosteric modulation of the muscarinic acetylcholine receptor.

In some embodiments, potentiation of muscarinic acetylcholine receptor activity in a patient is associated with the treatment of a neurological and/or psychiatric disorder associated with a muscarinic receptor dysfunction, such as a neurological or psychiatric disorder disclosed herein. In some embodiments, the muscarinic receptor is mAChR $M_4$.

c. Enhancing Cognition

In some embodiments, the invention relates to a method for enhancing cognition in a patient comprising the step of administering to the patient an effective amount of least one disclosed compound of the invention.

In some embodiments, the invention provides a compound of formula (I), or a pharmaceutically acceptable salt thereof, for use in a method for the enhancement of cognition in a patient. In some embodiments, the invention provides a pharmaceutical composition comprising a compound of formula (I), or a pharmaceutically acceptable salt thereof, for use in a method for the enhancement of cognition in a patient.

In some embodiments, the invention provides a compound of formula (I), or a pharmaceutically acceptable salt thereof, for use in the manufacture of a medicament for the enhancement of cognition in a patient.

In some embodiments, the patient has been diagnosed with a need for cognition enhancement prior to the administering step. In some embodiments, the method further comprises the step of identifying a patient in need of cognition enhancement. In some embodiments, the need for cognition enhancement is associated with a muscarinic receptor dysfunction. In some embodiments, the muscarinic receptor is mAChR $M_4$.

Cognitive deficits or cognitive impairment include a decline in cognitive functions or cognitive domains, e.g. working memory, attention and vigilance, verbal learning and memory, visual learning and memory, reasoning and problem solving e.g. executive function, speed of processing and/or social cognition. In particular, cognitive deficits or cognitive impairment may indicate deficits in attention, disorganized thinking, slow thinking, difficulty in understanding, poor concentration, impairment of problem solving, poor memory, difficulties in expressing thoughts and/or difficulties in integrating thoughts, feelings and behaviour, or difficulties in extinction of irrelevant thoughts. The terms "cognitive deficits" and "cognitive impairment" are intended to indicate the same and are used interchangeably.

Cognitive functions are, as mentioned above, often impaired in schizophrenic patients. Studies have also concluded that cognitive functioning is associated with vocational functioning in schizophrenia [Schizophrenia Res., 45, 175-184, 2000]. In one embodiment, the patient to be treated for cognitive impairment is schizophrenic.

The skilled person is familiar with various test for measuring the enhancement of cognition. Examples of test for measuring the enhancement of cognition are but not limited to the Novel Object Recognition and the Wisconsin Card Sorting Test d. Cotherapeutic Methods The present invention is further directed to administration of a selective mAChR $M_4$ activator for improving treatment outcomes in the context of cognitive or behavioral therapy. That is, in some embodiments, the invention relates to a cotherapeutic method comprising a step of administering to a patient an effective amount and dosage of a compound of the invention.

In some embodiments, the invention provides a compound of formula (I), or a pharmaceutically acceptable salt thereof, for use in a cotherapeutic method with cognitive or behavioral therapy in a patient. In some embodiments, the invention provides a pharmaceutical composition comprising a compound of formula (I), or a pharmaceutically acceptable salt thereof, for use in a cotherapeutic method with cognitive or behavioral therapy in a patient.

In some embodiments, the invention provides a compound of formula (I), or a pharmaceutically acceptable salt thereof, for use in the manufacture of a medicament for a cotherapeutic method with cognitive or behavioral therapy in a patient.

In some embodiments, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, 7 days before or after administration of the compound. As a further example, cognitive or behavioral therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

It is understood that the disclosed cotherapeutic methods can be used in connection with the compounds of the inventions, compositions, kits, and uses.

e. Combination Therapies

In the methods of use described herein, additional therapeutic agent(s) may be administered simultaneously or sequentially with the compounds of the invention and compositions. Sequential administration includes administration before or after the compounds of the invention and compositions. In some embodiments, the additional therapeutic agent or agents may be administered in the same composition as the compounds of the invention. In other embodiments, there may be an interval of time between administration of the additional therapeutic agent and the compounds of the invention. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I) or a pharmaceutically acceptable salt thereof. The above combinations include combinations of a compound of the present invention not only with one other active compound, but also with two or more other active compounds.

The compounds of the invention can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefor, contemporaneously or sequentially with a disclosed compound. When a compound of the invention is used contemporaneously with one or more other drugs, a pharmaceutical composition in unit dosage form containing such drugs and a compound of the invention may be used. However, the combination therapy can also be administered on overlapping schedules. It is also envisioned that the combination of one or more active ingredients and a compound of the invention may be more efficacious than either as a single agent. Thus, when used in combination with one or more other active ingredients, the compounds of the invention and the other active ingredients may be used in lower doses than when each is used singly.

The pharmaceutical compositions and methods of the present invention can further comprise other therapeutically active compounds as noted herein which are usually applied in the treatment of the above mentioned pathological conditions.

The above combinations include combinations of a disclosed compound not only with one other active compound, but also with two or more other active compounds. Likewise, compounds of the invention can be used in combination with other drugs that are used in the prevention, treatment, control, amelioration, or reduction of risk of the diseases or conditions for which compounds of the invention are useful. Such other drugs can be administered, by a route and in an amount commonly used therefor, contemporaneously or sequentially with a compound of the present invention. Hence, in an embodiment, the pharmaceutical compositions contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from 200:1 to about 1:200. Combinations of a compound of the present invention and other active ingredients will generally also be within the aforementioned range, but in each case, an effective dose of each active ingredient should be used.

In such combinations a compound of the invention and other active agents can be administered separately or in conjunction. In addition, the administration of one element can be prior to, concurrent to, or subsequent to the administration of other agent(s).

Accordingly, the compounds of the invention can be used alone or in combination with other agents which are known to be beneficial in the subject indications or other drugs that affect receptors or enzymes that either increase the efficacy, safety, convenience, or reduce unwanted side effects of the compounds of the invention. The compounds of the invention and the other agent can be coadministered, either in concomitant therapy or in a fixed combination.

In some embodiments, the compound can be employed in combination anti-Alzheimer's agents, beta-secretase inhibitors, cholinergic agents, gamma-secretase inhibitors, HMG-CoA reductase inhibitors, M1 allosteric agonists, M1 positive allosteric modulators, NSAIDs including ibuprofen, vitamin E, and anti-amyloid antibodies. In another embodiment, the subject compound can be employed in combination with sedatives, hypnotics, anxiolytics, antipsychotics (typical and atypical), antianxiety agents, cyclopyrrolones, imidazopyridines, pyrazolopyrimidines, minor tranquilizers, melatonin agonists and antagonists, melatonergic agents, benzodiazepines, barbiturates, 5HT$_2$ antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, brexpiprazole, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, donepezil, memantine, galantamine, doxepin, estazolam, ethchlorvynol, etomidate, fenobam, flunitrazepam, zuflupentixol, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, zaleplon, ziprasidone, zolazepam, zolpidem, and salts thereof, and combinations thereof, and the like, or the subject compound can be administered in conjunction with the use of physical methods such as with light therapy or electrical stimulation.

In some embodiments, the compounds of the invention can be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors such as azilect, antioxidants, A2a adenosine receptor antagonists such as istradefylline, cholinergic agonists, NMDA receptor antagonists such as ketamine, serotonin receptor antagonists and dopamine receptor agonists such as alentemol, bromocriptine, fenoldopam, lisuride, naxagolide, pergolide and pramipexole. It will be appreciated that the dopamine agonist can be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In some embodiments, the compounds of the invention can be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound can be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound can be employed in combination with acetophenazine, alentemol, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, deutetrabenazine, trihexyphenidyl, thioridazine, thiothixene, trifluoperazine, or ziprasidone.

In some embodiments, the compounds of the invention can be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical antidepressants, benzodiazepines, 5-$HT_{1A}$ agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, vortioxetine, fluvoxamine, paroxetine and sertraline; isocarboxazid, phenelzine, escitalopram, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In some embodiments, the compounds of the invention can be coadministered with orthosteric muscarinic agonists, muscarinic potentiators, or cholinesterase inhibitors. In some embodiments, the compounds can be coadministered with GlyT1 inhibitors and the like such as, but not limited to: risperidone, quetiapine, clozapine, haloperidol, fluoxetine, prazepam, xanomeline, lithium, phenobarbitol, and salts thereof and combinations thereof.

f. Modes of Administration

Methods of treatment may include any number of modes of administering a compound of the invention or composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

The compounds and processes of the invention will be better understood by reference to the following examples, which are intended as an illustration of and not a limitation upon the scope of the invention.

5. Examples

All NMR spectra were recorded on a 400 MHz AMX Bruker NMR spectrometer a 400 MHz Bruker Avance AV-III-400 spectrometer or a Varian MR400 spectrometer. $^1$H chemical shifts are reported in δ values in ppm relative to residual protio solvent as the internal standard. Data are reported as follows: chemical shift, multiplicity (s=singlet, bs=broad singlet, d=doublet, t=triplet, q=quartet, dd=doublet of doublets, m=multiplet, ABq=AB quartet), coupling constant, integration. Reversed-phase LCMS analysis was performed using an Agilent 1200 system comprised of a binary pump with degasser, high-performance autosampler, thermostatted column compartment, C18 column, diode-array detector (DAD) and an Agilent 6150 MSD with the following parameters. The gradient conditions were 5% to 95% acetonitrile with the aqueous phase 0.1% TFA in water over 1.4 minutes, hold at 95% acetonitrile for 0.1 min, 0.5 mL/min, 55° C. ("90 sec method"). Samples were separated on a Waters Acquity UPLC BEH C18 column (1.7 µm, 1.0×50 mm) at 0.5 mL/min, with column and solvent temperatures maintained at 55° C. The DAD was set to scan from 190 to 300 nm, and the signals used were 220 nm and 254 nm (both with a band width of 4 nm). The MS detector was configured with an electrospray ionization source, and the low-resolution mass spectra were acquired by scanning from 140 to 700 AMU with a step size of 0.2 AMU at 0.13 cycles/second, and peak width of 0.008 minutes. The drying gas flow was set to 13 liters per minute at 300° C. and the nebulizer pressure was set to 30 psi. The capillary needle voltage was set at 3000 V, and the fragmentor voltage was set at 100V. Data acquisition was performed with Agilent Chemstation and Analytical Studio Reviewer software.

Abbreviations used in the examples and reaction schemes that follow include the following: aq is aqueous; Boc is tert-butoxycarbonyl; BrettPhos is 2-(dicyclohexylphosphino)3,6-dimethoxy-2',4',6'-triisopropyl-1,1'-biphenyl; BrettPhos Pd G3 is [(2-di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate; t-BuOH is tert-butanol; DCE is 1,2-dichloroethane; DCM is dichloromethane; DEA is diethylamine; DMF is N,N-dimethylformamide; DMP or Dess-Martin periodinane is 1,1,1-tris(acetyloxy)-1,1-dihydro-1,2-benziodoxol-3-(1H)-one; DIAD is diisopropyl azodicarboxylate; DIPEA or DIEA is diisopropylethylamine; DMAP is 4-dimethylaminopyridine; DMSO is dimethyl sulfoxide; Dowtherm A is a eutectic mixture of 26.5% diphenyl+73.5% diphenyl oxide; DtBAD is di-tert-butyl-azodicarboxylate; eq or eq. is equivalent(s); EtOAC is ethyl acetate; EtOH is ethanol; h is hour(s); Hex is hexane(s); IPA is isopropyl alcohol; KOAc is potassium acetate; LAH is lithium aluminum hydride; mCPBA is meta-chloroperoxy benzoic acid; MeCN or ACN is acetonitrile; MeOH is methanol; min is minute(s); NaOAc is sodium acetate; NaOMe is sodium methoxide; NCS is N-chlorosuccinimide; NMP is N-methyl-2-pyrrolidone; Pd(dppf)$Cl_2$ is [1,1'-bis(diphenylphosphino)ferrocene]dichloropalladium(II);

Pd(OAc)$_2$ is palladium(II)acetate; PPA is polyphosphoric acid; PPh$_3$ is triphenylphosphine; PPTS is pyridinium p-toluenesulfonate; rt is room temperature; sat. is saturated; sec is second(s); SCX cartridge or HF SCX cartridge is a strong cation exchanger cartridge (i.e. Agilent part #14256027); SFC is supercritical fluid chromatography; TBAC or TBACl is tetrabutylammonium chloride; t-BuX-Phos is 2-Di-tert-butylphosphino-2',4',6'-triisopropylbiphenyl; TEA is triethyamine; TFA is trifluoroacetic acid; THF is tetrahydrofuran; TosCl is para-toluenesulfonyl chloride; and tosyl is para-toluenesulfonyl.

a. Preparation of Intermediates

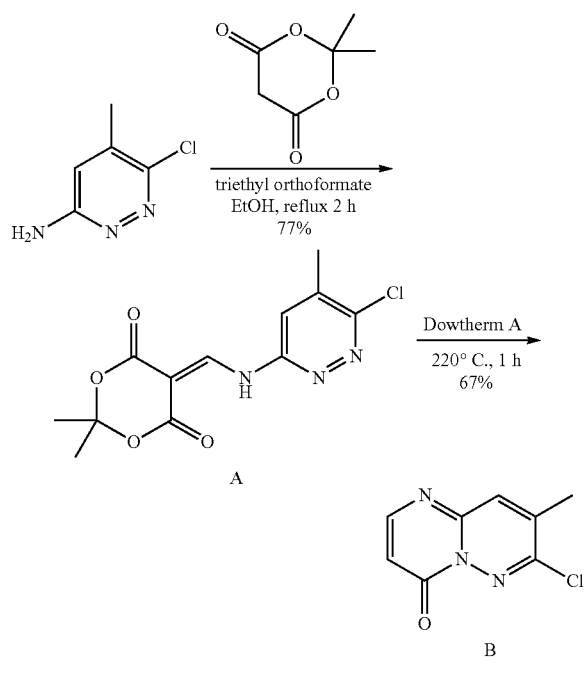

5-(((6-Chloro-5-methylpyridazin-3-yl)amino)methylene)-2,2-dimethyl-1,3-dioxane-4,6-dione (Intermediate A): To a solution of 6-chloro-5-methylpyridazin-3-amine (1 g) in ethanol (12 mL) were added triethyl orthoformate (1.16 mL) and isopropylidene malonate (1.04 g) at ambient temperature. The mixture was then heated to 60° C. for 18 hours. The mixture was filtered and the cake was washed with ethanol (5 mL×3) to afford the intermediate 5-[[(6-chloro-5-methyl-pyridazin-3-yl)amino]methylene]-2,2-dimethyl-1,3-dioxane-4,6-dione (1.59 g, 77% yield). ES-MS [M+1]$^+$: 298.2

7-Chloro-8-methyl-4H-pyrimido[1,2-b]pyridazin-4-one (Intermediate B): A solution of 5-[[(6-chloro-5-methyl-pyridazin-3-yl)amino]methylene]-2,2-dimethyl-1,3-dioxane-4,6-dione (1.59 g) in Dowtherm A (8 mL) was stirred at 220° C. for 1 hour. After cooling, the mixture was added to water and acidified using 1M HCl. The aqueous layer was extracted with hexanes (3×125 mL) to remove Dowtherm A. The aqueous layer was neutralized with aq. NaHCO$_3$ and the mixture was extracted with chloroform/IPA (4:1) (3×). The combined organic layers were dried over magnesium sulfate, concentrated to give the title compound (908 mg, 67% yield). $^1$H NMR (400 MHz, DMSO) δ 8.23 (d, J=6.5 Hz, 1H), 8.03 (q, J=1.3 Hz, 1H), 6.54 (d, J=6.4 Hz, 1H), 2.44 (d, J=1.3 Hz, 3H). ES-MS [M+1]$^+$: 196.

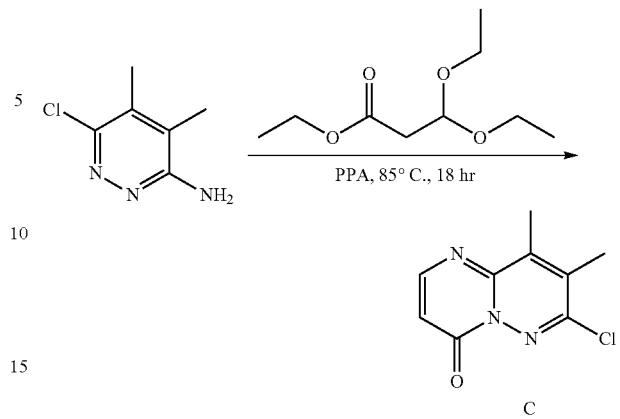

7-Chloro-8,9-dimethyl-pyrimido[1,2-b]pyridazin-4-one (Intermediate C): A mixture of 6-chloro-3-amino-4,5-dimethylpyridazine (550 mg), ethyl 3,3-diethoxypropionate (1.02 mL), and polyphosphoric acid (5 mL) was added to a sealed tube. The mixture was stirred at 85° C. for 5 hours then cooled to room temperature where additional ethyl 3,3-diethoxypropionate (1.02 mL) was added to the reaction mixture. The vial was sealed and the mixture heated to 85° C. for 18 hours. The reaction mixture was then slowly added to a stirred solution of 150 mL of saturated aqueous NaHCO$_3$ and 100 mL of DCM. After complete addition, the mixture was allowed to stir for 20 minutes, the organic layer was separated, and the aqueous layer was further extracted with chloroform/IPA (4:1) (×3). The organic layers were pooled, dried over MgSO$_4$, filtered, and concentrated. The crude product was purified using Teledyne ISCO Combi-Flash system (liquid loading with DCM, 40G column, 0-70% EtOAc/Hex, 35 min run) to give the title compound as a solid (366 mg, 50% yield). $^1$H NMR (400 MHz, CDCl$_3$) δ 8.22-8.20 (d, J=6.5 Hz, 1H), 6.64-6.62 (d, J=6.5 Hz, 1H), 2.62 (d, J=0.6 Hz, 3H), 2.51 (d, J=0.6 Hz, 3H). ES-MS [M+1]$^+$: 210.

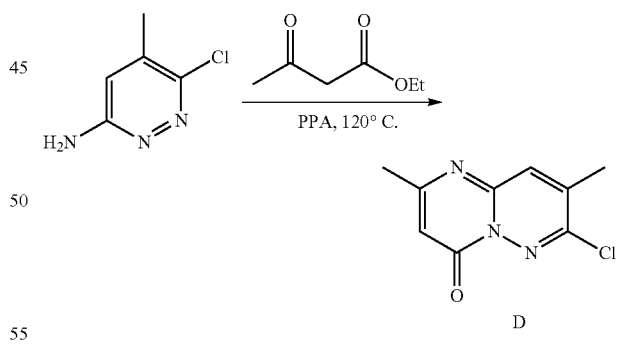

7-Chloro-2,8-dimethyl-4H-pyrimido[1,2-b]pyridazin-4-one (Intermediate D): To a solution of 6-chloro-3-amino-5-methylpyridazine (1 g) in polyphosphoric acid (5 mL) was added ethyl acetoacetate (1.76 mL). The mixture was heated to 120° C. for 18 hours. While still hot, the mixture was slowly added to a stirred solution of 150 mL saturated NaHCO$_3$. The aqueous layer was extracted with chloroform:IPA (4:1) thrice. The organic layers were dried over magnesium sulfate, filtered, and concentrated under vacuum. The crude product was purified using a Teledyne ISCO Combi-Flash system (liquid loading with DCM, 80G column, 0-70% EtOAc/DCM, 42 min run). Fractions containing desired product were concentrated to afford the title compound as a solid (1.34 g, 92% yield). ¹H NMR (400 MHz, CDCl₃) δ 7.59 (q, J=1.3 Hz, 1H), 6.50 (s, 1H), 2.50 (d, J=1.3 Hz, 3H), 2.43 (d, J=0.7 Hz, 3H). ES-MS [M+1]⁺: 210.

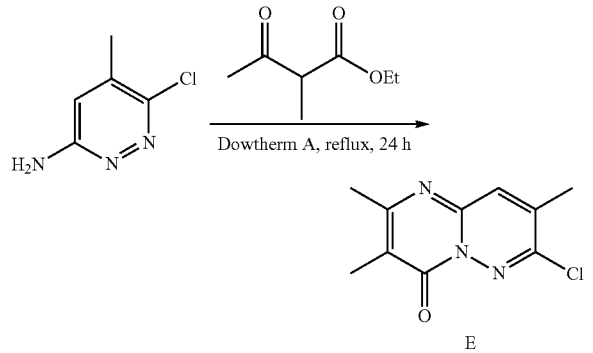

7-Chloro-2,3,8-trimethyl-4H-pyrimido[1,2-b]pyridazin-4-one (Intermediate E): To a solution of 6-chloro-3-amino-5-methylpyridazine (500 mg) in Dowtherm A (2 mL) was added ethyl 2-methyl-3-oxo-butanoate (591 μL) and the reaction was heated to 150° C. for 18 h. Additional ethyl 2-methyl-3-oxo-butanoate (591 μL) was added and the reaction microwave irradiated at 180° C. for 15 minutes. The solution was directly loaded onto a Teledyne ISCO CombiFlash system (120G column, 100% Hex, 6 min; then 0-80% EtOAc/DCM, 15 min run) to afford the title compound as a solid (442 mg, 57% yield). ¹H NMR (400 MHz, CDCl₃) δ 7.53 (q, J=1.3 Hz, 1H), 2.47 (d, J=1.3 Hz, 3H), 2.45 (s, 3H), 2.26 (s, 3H). ES-MS [M+1]⁺: 224.

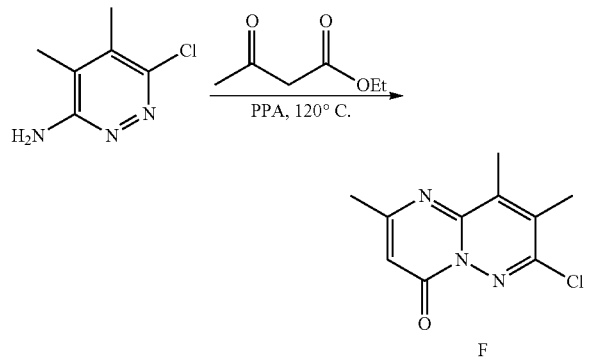

7-Chloro-2,8,9-trimethyl-4H-pyrimido[1,2-b]pyridazin-4-one (Intermediate F): To a solution of 6-chloro-3-amino-4,5-dimethylpyridazine (500 mg) in polyphosphoric acid (4.5 mL) was added ethyl acetoacetate (803 μL). The mixture was heated to 120° C. for 1 hour. While hot, the mixture was slowly added to 125 mL of saturated NaHCO₃ and 50 mL chloroform/IPA (4:1). Upon complete addition, the mixture was allowed to stir for 15 minutes and the organic layer was isolated. The aqueous layer was further extracted with chloroform:IPA (4:1) (×3). The organic layers were dried over magnesium sulfate, filtered, and concentrated under vacuum. The crude product was taken up in 5 mL MeOH, sonicated, and the precipitate was collected by vacuum filtration and washed with hexanes. The solid was dried under nitrogen to yield the title compound as a solid (472 mg, 67% yield). ¹H NMR (400 MHz, CDCl₃) δ 6.49 (s, 1H), 2.60 (d, J=0.8 Hz, 3H), 2.48 (q, J=0.7 Hz, 3H), 2.44 (q, J=0.5 Hz, 3H). ES-MS [M+1]⁺: 224.

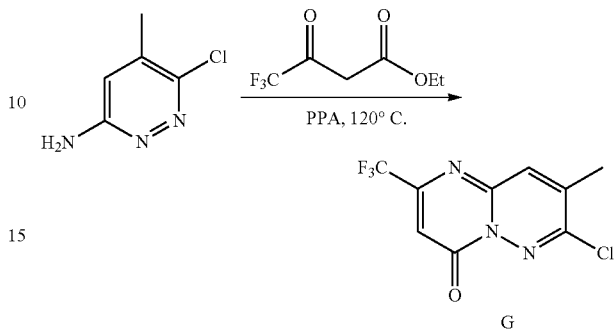

7-Chloro-8-methyl-2-(trifluoromethyl)-4H-pyrimido[1,2-b]pyridazin-4-one (Intermediate G): To a solution of 6-chloro-3-amino-5-methylpyridazine (500 mg) in polyphosphoric acid (5 mL) was added ethyl 4,4,4-trifluoroacetoacetate (1.02 mL). The mixture was heated to 120° C. for 18 hours. While hot, the mixture was slowly added to a beaker containing 125 mL of saturated NaHCO₃ and 50 mL chloroform/IPA (4:1) while maintaining a pH⁻7. Upon complete addition, the mixture was allowed to stir for 15 minutes and the organic layer was isolated. The aqueous layer was further extracted with chloroform:IPA (4:1) thrice. The organic layers were dried over magnesium sulfate, filtered, and concentrated under vacuum. The crude product was dissolved in 15 mL of DMSO (any solids that precipitated were collected to give pure desired product) and the filtrate was purified by reverse-phase chromatography using Gilson HPLC (50×250 mm column, 5-45% ACN/0.05% aqueous NH₄OH, 16 min run). Fractions containing product were concentrated and combined with the previous solid to give the title compound as a solid (393 mg, 43% yield). ¹H NMR (400 MHz, CDCl₃) δ 7.79 (q, J=1.3 Hz, 1H), 6.98 (s, 1H), 2.56 (d, J=1.3 Hz, 3H). ES-MS [M+1]⁺: 264.

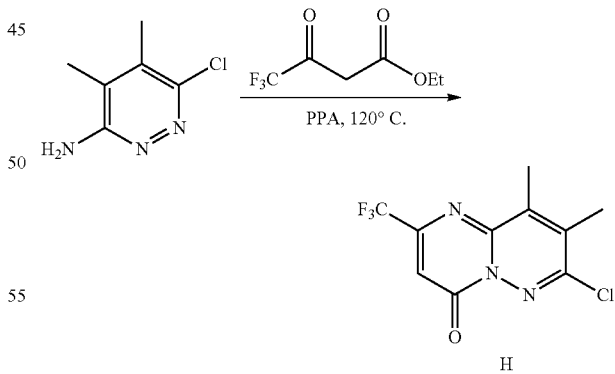

7-Chloro-8,9-dimethyl-2-(trifluoromethyl)-4H-pyrimido[1,2-b]pyridazin-4-one (Intermediate H): To a solution of 6-chloro-3-amino-4,5-dimethylpyridazine (550 mg) in polyphosphoric acid (5 mL) was added ethyl 4,4,4-trifluoroacetoacetate (1.02 mL). The mixture was heated to 120° C. for 18 hours. Additional ethyl 4,4,4-trifluoroacetoacetate (1.02 mL) was added and the mixture was stirred for an additional 7 hours at 120° C. While hot, the mixture was slowly added to a beaker containing 125 mL of saturated NaHCO₃ and 50 mL chloroform/IPA (4:1) while maintaining a pH ~7. Upon complete addition, the mixture was allowed to stir for 15 minutes and the organic layer was isolated. The aqueous layer was further extracted with chloroform:IPA (4:1) thrice. The organic layers were dried over magnesium sulfate, filtered, and concentrated under vacuum. The crude product was dissolved in DMSO (16 mL) and purified by reverse-phase chromatography using Gilson HPLC (50×250 mm column, 5-50% ACN/0.05% aqueous NH₄OH, 16 min run). Fractions containing product were concentrated to afford the title compound (264 mg, 27% yield) as a solid. ¹H NMR (400 MHz, CDCl₃) δ 6.96 (s, 1H), 2.57 (q, J=0.9 Hz, 3H), 2.48 (q, J=0.9 Hz, 3H). ES-MS [M+1]⁺: 278.

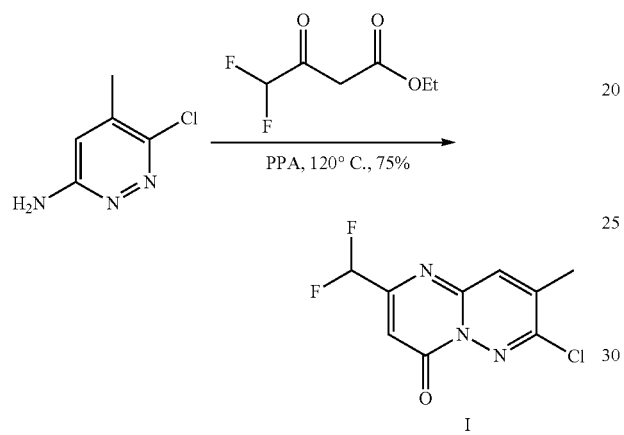

7-Chloro-2-(difluoromethyl)-8-methyl-4H-pyrimido[1,2-b]pyridazin-4-one (Intermediate I): To a solution of 6-chloro-3-amino-5-methylpyridazine (500 mg) in polyphosphoric acid (5 mL) was added ethyl 4,4-difluoroacetoacetate (912 μL). The mixture was heated to 120° C. for 2 hours. While hot, the mixture was slowly added to a beaker containing 125 mL of saturated NaHCO₃ and 50 mL chloroform/IPA (4:1) while maintaining a pH~7. Upon complete addition, the mixture was allowed to stir for 15 minutes and the organic layer was isolated. The aqueous layer was further extracted with chloroform:IPA (4:1) thrice. The organic layers were dried over magnesium sulfate, filtered, and concentrated under vacuum. The crude product was dissolved in DMSO (15 mL) and purified by reverse-phase chromatography using Gilson HPLC (50×250 mm column, 0-45% ACN/0.05% aqueous NH₄OH, 16 min run). Fractions containing product were concentrated to afford the title compound as a solid (640 mg, 75% yield). ¹H NMR (400 MHz, CDCl₃) δ 7.73 (q, J=1.3 Hz, 1H), 6.90 (s, 1H), 6.46 (t, J=54.8 Hz, 1H), 2.55 (d, J=1.3 Hz, 3H). ES-MS [M+1]⁺: 246.

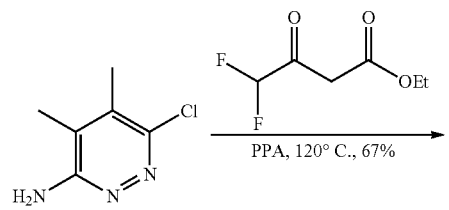

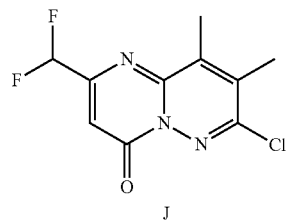

7-Chloro-2-(difluoromethyl)-8,9-dimethyl-4H-pyrimido[1,2-b]pyridazin-4-one (Intermediate J): To a solution of 6-chloro-3-amino-4,5-dimethylpyridazine (1.65 g) in polyphosphoric acid (10 mL) was added ethyl 4,4-difluoroacetoacetate (2.74 mL). The mixture was heated to 120° C. for 6 hours. While hot, the reaction mixture was then slowly added into a stirred saturated NaHCO₃ solution (200 mL). Once the pH~7, the aqueous layer was extracted with chloroform:IPA (4:1). The organic layers were dried over magnesium sulfate, filtered, and concentrated under vacuum. The crude product was purified using aTeledyne ISCO Combi-Flash system (liquid loading with DCM, 120G column, 0-40% EtOAc/DCM, 15 min run) to afford the title compound (1.05 g, 39% yield) as a solid. ¹H NMR (400 MHz, CDCl₃) δ 6.90 (s, 1H), 6.48 (t, J=54.9 Hz, 1H), 2.64 (s, 3H), 2.53 (s, 3H). ES-MS [M+1]⁺: 260.

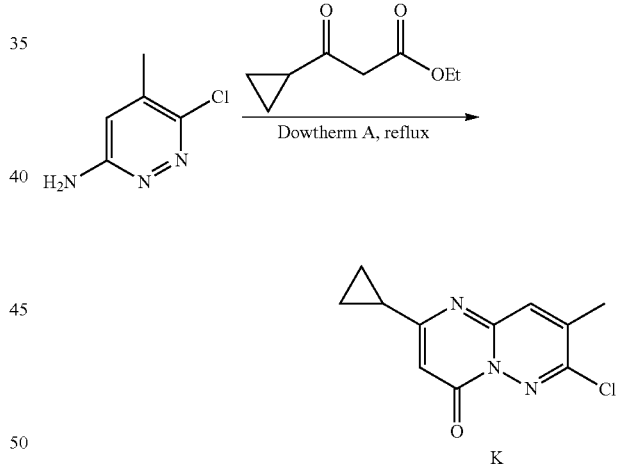

7-Chloro-2-cyclopropyl-8-methyl-4H-pyrimido[1,2-b]pyridazin-4-one (Intermediate K): In a sealed vial was added a solution of 6-chloro-3-amino-5-methylpyridazine (500 mg) and ethyl 3-cyclopropyl-3-oxopropanoate (617 μL) in DOWTHERM A (5 mL). The vial was sealed and the reaction was heated to 150° C. for 18 h. Additional ethyl 3-cyclopropyl-3-oxopropanoate (617 μL) was added and the reaction heated to 220° C. for 3 h. Material was loaded directly onto a Teledyne ISCO Combi-Flash system (liquid loading, 120G column, 100% Hex, 6 min run; then 0-40% EtOAc/DCM, 15 min run) to afford the title compound (44 mg; 5% yield) as a solid. ¹H NMR (400 MHz, CDCl₃) δ 7.52 (q, J=1.3 Hz, 1H), 6.51 (s, 1H), 2.47 (d, J=1.4 Hz, 3H), 1.97-1.86 (m, 1H), 1.18-1.10 (m, 2H), 1.08-0.97 (m, 2H). ES-MS [M+1]⁺: 236.

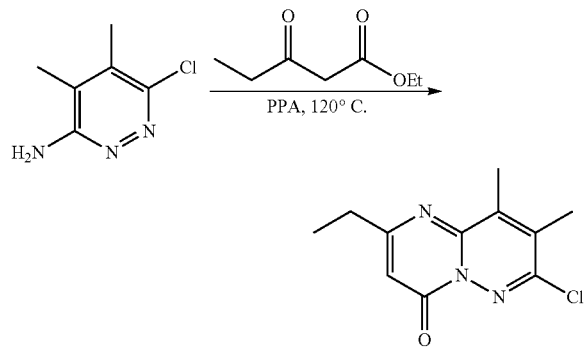

7-Chloro-2-ethyl-8,9-dimethyl-4H-pyrimido[1,2-b]pyridazin-4-one (Intermediate L): To a solution of 6-chloro-3-amino-4,5-dimethylpyridazine (550 mg) in polyphosphoric acid (4 mL) was added ethyl 3-oxopentanoate (913 μL). The mixture was heated to 85° C. for 1 hour, then 120° C. for 1 hour. While hot, the mixture was slowly transferred to a stirred solution of saturated aqueous NaHCO₃ (~150 mL) and chloroform/IPA (4:1) (50 mL). Upon complete addition, the mixture was stirred for 10 minutes then the organic layer was isolated. The aqueous layers was further extracted with chloroform/IPA (4:1) (×3) and the organic layers were pooled, dried over MgSO₄, filtered, and concentrated under vacuum. Upon cooling, a solid precipitate was observed. Hexanes was added, the suspension was sonicated, the solid was collected by vacuum filtration, and washed with hexanes to provide the title compound (469 mg, 57% yield) >95% clean by LCMS. ¹H NMR (400 MHz, CDCl₃) δ 6.50 (s, 1H), 2.70 (q, J=7.6 Hz, 2H), 2.61 (s, 3H), 2.48 (s, 3H), 1.30 (t, J=7.6 Hz, 3H). ES-MS [M+1]⁺: 238.

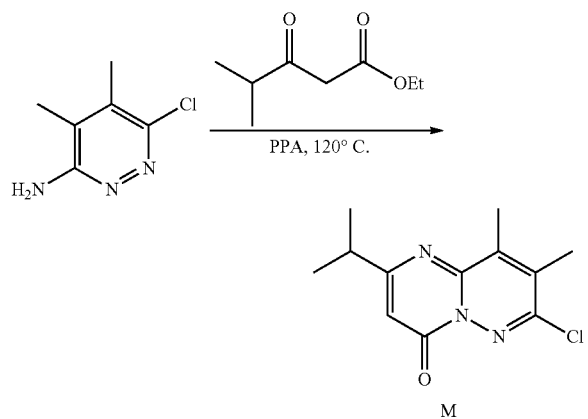

7-Chloro-2-isopropyl-8,9-dimethyl-4H-pyrimido[1,2-b]pyridazin-4-one (Intermediate M): To a solution of 6-chloro-3-amino-4,5-dimethylpyridazine (550 mg) in polyphosphoric acid (5 mL) was added ethyl 4-methyl-3-oxopentanoate (1.13 mL). The mixture was heated to 85° C. for 1 hour, then 120° C. for 1 hour. While still hot, the mixture was slowly added to a stirred solution of saturated aqueous NaHCO₃ (150 mL) and chloroform/IPA (4:1) (50 mL). Upon complete addition, the mixture was stirred for 10 minutes and the organic layer was isolated. The aqueous layer was further extracted with chloroform/IPA (4:1) (3×50 mL) and the organic layers were pooled, dried over MgSO₄, filtered, and concentrated. The crude product was purified using a Teledyne ISCO Combi-Flash system (liquid loading with DCM, 80G column, 0-65% EtOAc/Hex, 20 min run). The column was then flushed with hexanes followed by 0-2% MeOH/DCM, 10 min to give the title compound (204 mg; 23% yield) as a solid. ¹H NMR (400 MHz, CDCl₃) δ 6.47 (s, 1H), 3.63 (hept, J=6.8 Hz, 1H), 2.56 (d, J=1.0 Hz, 3H), 2.44 (d, J=1.0 Hz, 3H), 1.32 (s, 3H), 1.30 (s, 3H). ES-MS [M+1]⁺: 252.

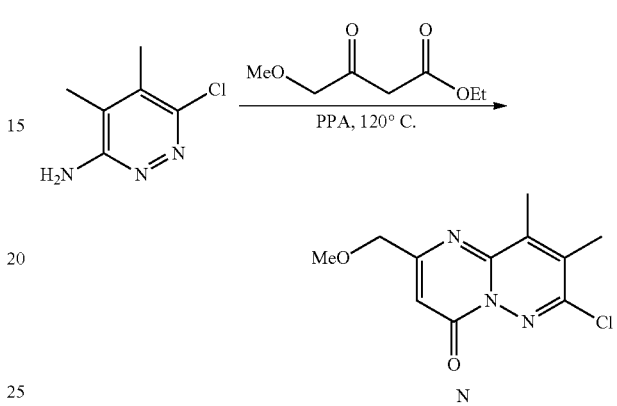

7-Chloro-2-(methoxymethyl)-8,9-dimethyl-4H-pyrimido[1,2-b]pyridazin-4-one (Intermediate N): To a solution of 6-chloro-3-amino-4,5-dimethylpyridazine (1 g) in polyphosphoric acid (9 mL) was added methyl 4-methoxy-3-oxobutanoate (1.23 mL). The mixture was heated to 85° C. for 1 hour, then 120° C. for 30 minutes. The mixture was then quenched by slow addition to a solution of saturated sodium bicarbonate (~150 mL) and 4:1 chloroform/IPA (~50 mL). The organic layer was isolated and the aqueous layer further extracted (×3). The organic layers were pooled, dried over magnesium sulfate, filtered, and concentrated. The crude product was dissolved in DMSO (9 mL) and solid was filtered off. The filtrate was purified using the Gilson (Basic, 50×250 mm column, 5-55% ACN/0.05% aqueous NH₄OH, 16 min run). Fractions containing product were concentrated to give the title compound (219 mg) as a solid. The solid was washed with hexanes then dissolved in DCM and purified using a Teledyne ISCO Combi-Flash system (liquid loading with DCM, 80G column, 0-2% MeOH/DCM/NH₄OH, 10 min run). Fractions containing product were concentrated to give the title compound (682 mg; 43% yield) as a solid. ¹H NMR (400 MHz, CDCl₃) δ 6.77 (t, J=1.0 Hz, 1H), 4.45 (d, J=1.0 Hz, 2H), 3.51 (s, 3H), 2.59 (d, J=0.9 Hz, 3H), 2.49 (d, J=1.0 Hz, 3H). ES-MS [M+1]⁺: 254.

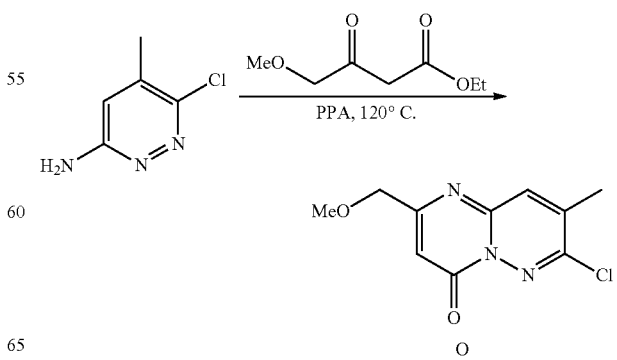

7-Chloro-2-(methoxymethyl)-8-methyl-4H-pyrimido[1,2-b]pyridazin-4-one (Intermediate O): To a solution of 6-chloro-3-amino-5-methylpyridazine (500 mg) in polyphosphoric acid (5 mL) was added methyl 4-methoxy-3-oxo-butanoate (673 μL, 5.22 mmol). The mixture was heated to 85° C. for 1 hour, then 120° C. for 30 minutes. The mixture was then quenched by slow addition to a solution of saturated sodium bicarbonate (~150 mL) and 4:1 chloroform/IPA (~50 mL). The organic layer was isolated and the aqueous layer further extracted (×3). The organic layers were pooled, dried over magnesium sulfate, filtered, and concentrated. The crude product was dissolved in DMSO (12 mL) and purified by reverse-phase chromatography using Gilson HPLC (50×250 mm column, 0-45% ACN/0.05% aqueous NH$_4$OH, 16 min run). Fractions containing product were concentrated to give the title compound as a solid (690 mg, 83% yield). $^1$H NMR (400 MHz, CDCl$_3$) δ 7.61 (q, J=1.3 Hz, 1H), 6.76 (d, J=1.1 Hz, 1H), 4.42 (s, 2H), 3.50 (s, 3H), 2.50 (d, J=1.2 Hz, 3H). ES-MS [M+1]$^+$: 240.

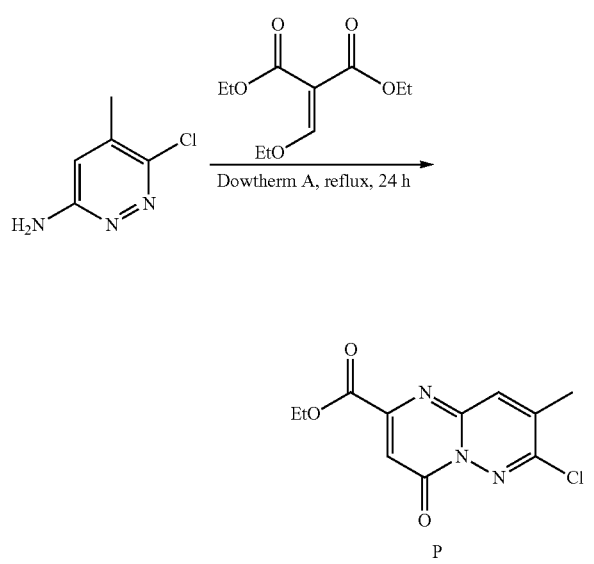

Ethyl 7-chloro-8-methyl-4-oxo-4H-pyrimido[1,2-b]pyridazine-2-carboxylate (Intermediate P): A mixture of diethyl ethoxymethylenemalonate (641 μL) and 6-chloro-3-amino-4,5-dimethylpyridazine (500 mg) in Dowtherm A (6 mL) was heated to 200° C. for 18 hours. The reaction mixture was cooled to room temperature and loaded directly onto a Teledyne ISCO Combi-Flash system (liquid loading, 80G column, 0-55% EtOAc/DCM, 25 min run). Fractions containing desired product were concentrated and determined to be impure by LCMS. Material was dissolved in DMSO (9 mL) and purified by reverse-phase chromatography using Gilson HPLC (50×250 mm column, 5-50% ACN/0.05% aqueous NH$_4$OH, 16 min run). Fractions containing product were concentrated to give the title compound as a solid (250 mg; 28% yield $^1$H NMR (400 MHz, CDCl$_3$) δ 8.93 (s, 1H), 7.75 (s, 1H), 4.42 (q, J=7.1 Hz, 2H), 2.57 (d, J=0.9 Hz, 3H), 1.41 (t, J=7.1 Hz, 3H). ES-MS [M+1]$^+$: 268.2.

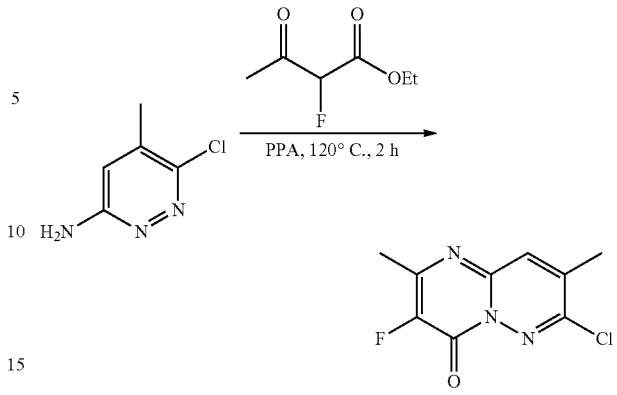

7-Chloro-3-fluoro-2,8-dimethyl-4H-pyrimido[1,2-b]pyridazin-4-one (Intermediate Q): To a solution of 6-chloro-3-amino-5-methylpyridazine (550 mg) in polyphosphoric acid (5.5 mL) was added ethyl 2-fluoroacetoacetate (961 μL). The mixture was heated to 120° C. for 2 hours. The mixture was then quenched by slow addition to a solution of saturated sodium bicarbonate (~150 mL) and 4:1 chloroform/IPA (~50 mL). The organic layer was isolated and the aqueous layer further extracted (×3). The organic layers were pooled, dried over magnesium sulfate, filtered, and concentrated. The mixture was then quenched by slowly adding to a solution of saturated sodium bicarbonate (~150 mL) and 4:1 chloroform/IPA (~50 mL). The organic layer was isolated and the aqueous layer further extracted (×3). The organic layers were pooled, dried over magnesium sulfate, filtered, and concentrated. The crude product was dissolved in DMSO (12 mL) and purified by reverse-phase chromatography using Gilson HPLC (50×250 mm column, 0-45% ACN/0.05% aqueous NH$_4$OH, 16 min run). Fractions containing product were concentrated to give the title compound (627 mg; 72% yield) as a solid. $^1$H NMR (400 MHz, CDCl$_3$) δ 7.60 (q, J=1.3 Hz, 1H), 2.52-2.47 (m, 6H). ES-MS [M+H]$^+$=228.

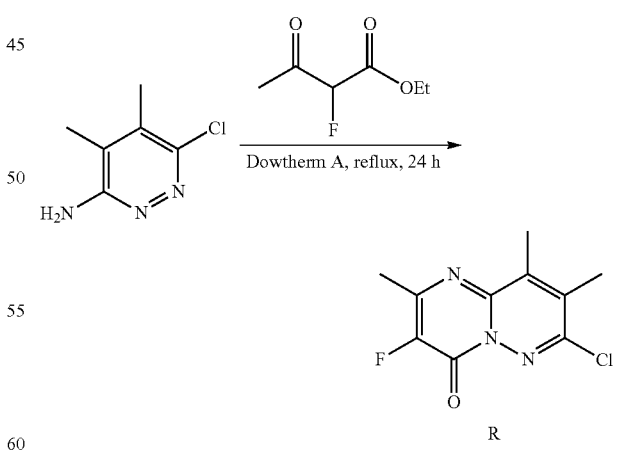

7-Chloro-3-fluoro-2,8,9-trimethyl-4H-pyrimido[1,2-b]pyridazin-4-one (Intermediate R): To a solution of 6-chloro-3-amino-4,5-dimethylpyridazine (550 mg) in Dowtherm A (4 mL) was added ethyl 2-fluoro-3-oxo-butanoate (525 μL) and the reaction was heated to 150° C. for 18 hours. Additional ethyl 2-fluoro-3-oxo-butanoate (525 μL) was added and the reaction stirred for an additional 18 hours at 150° C. The reaction mixture was loaded directly onto a Teledyne ISCO Combi-Flash system (liquid loading with DCM, 120G column, 0-20% Hex/EtOAc, 6 min run; then 0-30% EtOAc/DCM, 10 min run) to afford the title compound (243 mg; 29% yield $^1$H NMR (400 MHz, CDCl$_3$) δ 2.62 (d, J=0.9 Hz, 3H), 2.51 (d, J=3.6 Hz, 3H), 2.48 (t, J=0.9 Hz, 3H). ES-MS [M+1]$^+$: 268.

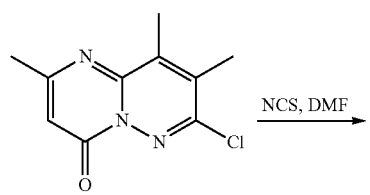

3,7-Dichloro-2,8-dimethyl-4H-pyrimido[1,2-b]pyridazin-4-one (Intermediate S): To a solution of 7-chloro-2,8-dimethyl-pyrimido[1,2-b]pyridazin-4-one (50 mg) in DMF (0.66 mL) was added N-chlorosuccinimide (33 mg). The mixture was stirred at room temperature for 18 h. Additional N-chlorosuccinimide (8 mg) was added and the mixture stirred for 48 h. The mixture was poured into water and extracted with DCM, passed through a phase separator, and concentrated. The crude product was purified using a Teledyne ISCO Combi-Flash system (liquid loading with DCM, 12G column, 0-30% EtOAc/DCM, 10 min run). $^1$H NMR (400 MHz, CDCl$_3$) δ 7.65 (q, J=1.3 Hz, 1H), 2.60 (s, 3H), 2.51 (d, J=1.3 Hz, 3H). ES-MS [M+1]$^+$: 244

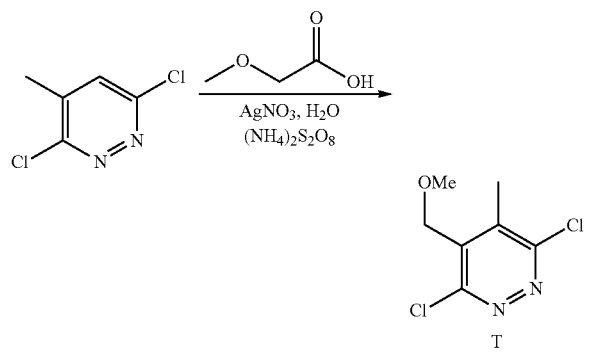

3,6-Dichloro-4-(methoxymethyl)-5-methylpyridazine (Intermediate T): A stirred solution of 3,6-dichloro-4-methylpyridazine (2 g), methoxyacetic acid (2.82 mL) and silver nitrate (1.04 g) in water (100 mL) was heated to 72° C. where ammonium persulfate (4.2 g) was added slowly in several portions. The mixture was heated for 30 minutes at 72° C., then 1 h at 90° C. Additional ammonium persulfate was added portionwise (2.4 g) and the reaction was allowed to stir for another 1 h at 90° C. The mixture was cooled to room temperature and slowly poured into a solution of saturated aqueous bicarbonate (~150 mL) and chloroform/ IPA (4:1) and stirred for 20 minutes then extracted (×3). The organic layers were pooled, dried over magnesium sulfate, filtered, and concentrated. The crude product was dissolved in DMSO (15 mL) and purified by reverse-phase chromatography using Gilson HPLC (20×250 mm column, 15-60% ACN/0.1% aqueous TFA, 16 min run). Fractions containing product were basified with sat. NaHCO$_3$, extracted with 3:1 chloroform/IPA, dried over magnesium sulfate, filtered, and concentrated to give the title compound (1.6 g; 62% yield). $^1$H NMR (400 MHz, CDCl$_3$) δ 4.64 (s, 2H) 3.44 s 3H), 2.52 (s, 3H). ES-MS [M+1]$^+$: 208.

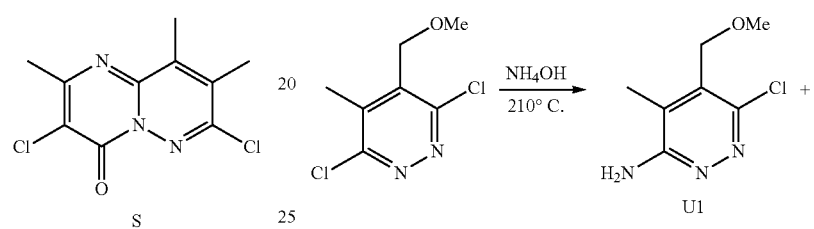

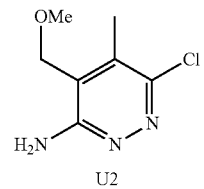

6-Chloro-5-(methoxymethyl)-4-methylpyridazin-3-amine (Intermediate U1): 3,6-Dichloro-4-(methoxymethyl)-5-methyl-pyridazine (1.59 g) was mixed with ammonium hydroxide (78 mL) solution and heated to 210° C. for 24 hours in a stainless steel pressure vessel. The reaction was cooled to room temperature and the reaction mixture was transferred to a round bottom flask with DCM/MeOH and concentrated. The crude product was dissolved in DMSO (12 mL) and purified by reverse-phase chromatography using Gilson HPLC (50×250 mm column, 0-35% ACN/0.05% aqueous NH$_4$OH, 16 min run) to afford the title compound (364 mg; 26% yield). $^1$H NMR (400 MHz, CDCl$_3$) δ 4.72 (s, 2H), 4.59 (s, 2H), 3.42 (s, 3H), 2.23 (s, 3H). ES-MS [M+1]$^+$: 188.

6-Chloro-4-(methoxymethyl)-5-methylpyridazin-3-amine (Intermediate U2): The intermediate was synthesized and isolated as described in the previous step (554 mg; 39% yield). $^1$H NMR (400 MHz, CDCl$_3$) δ 5.27 (s, 2H), 4.52 (s, 2H), 3.38 (s, 3H), 2.36 (s, 3H). ES-MS [M+1]$^+$: 188.

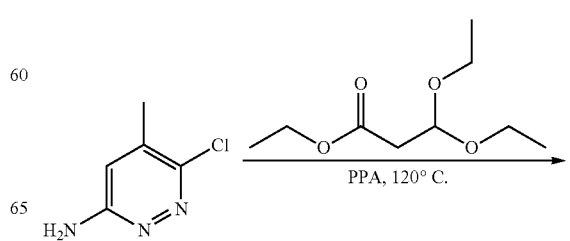

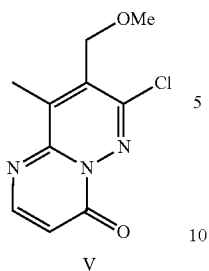

V

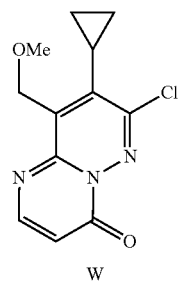

W

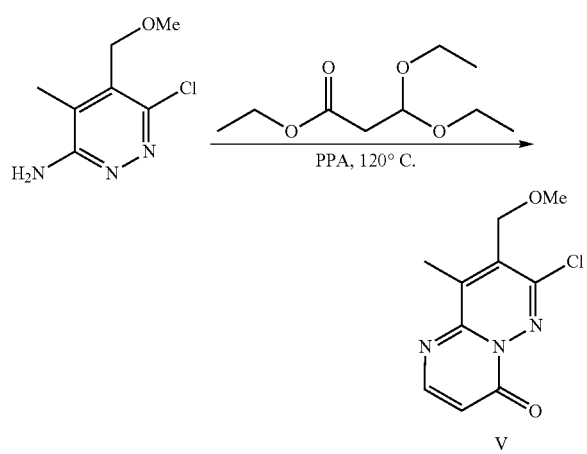

7-Chloro-8-(methoxymethyl)-9-methyl-4H-pyrimido[1,2-b]pyridazin-4-one (Intermediate V): To a mixture of ethyl 3,3-diethoxypropionate (755 µL) and 6-chloro-5-(methoxymethyl)-4-methyl-pyridazin-3-amine (364 mg) was added polyphosphoric acid (3 mL). The mixture was stirred at 120° C. for 5 hours. More ethyl 3,3-diethoxypropionate (755 µL) was added and the mixture stirred at 120° C. for an additional 1 hour. The reaction mixture was then slowly added to a stirred solution of 100 mL of saturated aqueous NaHCO$_3$ and 50 mL of DCM. After complete addition, the mixture was allowed to stir for 20 minutes and the organic layer was separated. The aqueous layer was further extracted with chloroform/IPA (4:1) (×3). The organic layers were combined, dried over MgSO$_4$, filtered, and concentrated. The crude product was dissolved in DMSO (12 mL) and purified by reverse-phase chromatography using Gilson HPLC (50×250 mm column, 0-55% ACN/0.05% aqueous NH$_4$OH, 16 min run). Fractions containing product were concentrated to give the title compound (108 mg; 23% yield) as a solid. $^1$H NMR (400 MHz, CDCl$_3$) δ 8.23 (d, J=6.4 Hz, 1H), 6.68 (d, J=6.4 Hz, 1H), 4.65 (s, 2H), 3.49 (s, 3H), 2.71 (s, 3H). ES-MS [M+1]$^+$: 240.

7-Chloro-9-(methoxymethyl)-8-methyl-4H-pyrimido[1,2-b]pyridazin-4-one (Intermediate W): To a mixture of ethyl 3,3-diethoxypropionate (1.15 mL) and 6-chloro-5-(methoxymethyl)-4-methyl-pyridazin-3-amine (554 mg,) was added polyphosphoric acid (5 mL). The mixture was stirred at 120° C. for 1 hour. More ethyl 3,3-diethoxypropionate (1.15 mL) was added and the mixture stirred at 120° C. for an additional 1 hour. The reaction mixture was then slowly added to a stirred solution of 150 mL of saturated aqueous NaHCO$_3$ and 100 mL of DCM. After complete addition, the mixture was allowed to stir for 20 minutes and the organic layer was separated. The aqueous layer was further extracted with chloroform/IPA (4:1) (×3). The organic layers were combined, dried over MgSO$_4$, filtered, and concentrated. The crude product was dissolved in DMSO (12 mL) and purified by reverse-phase chromatography using Gilson HPLC (50×250 mm column, 0-40% ACN/0.05% aqueous NH$_4$OH, 16 min run). Fractions containing product were concentrated to give the title compound as a solid. $^1$H NMR (400 MHz, CDCl$_3$) δ 8.22 (d, J=6.4 Hz, 1H), 6.64 (d, J=6.4 Hz, 1H), 4.95 (s, 2H), 3.48 (s, 3H), 2.58 (s, 3H). ES-MS [M+1]$^+$: 240.

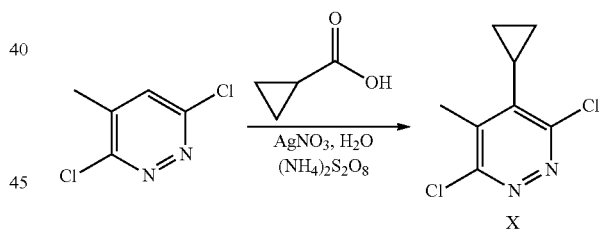

X 3,6-Dichloro-4-cyclopropyl-5-methylpyridazine (Intermediate X): A stirred solution of 3,6-dichloro-4-methylpyridazine (2.5 g), cyclopropanecarboxylic acid (3.66 mL) and silver nitrate (1.3 g) in water (125 mL) was heated to 72° C. where ammonium persulfate (5.25 g) was added slowly in several portions. The mixture was heated for 20 minutes at 72° C. Sulfuric acid (1.23 mL) was added and the mixture was heated to 90° C. for 1 hour. The mixture was cooled to ambient temperature and slowly poured into a solution of saturated aqueous bicarbonate (~150 mL) and chloroform/IPA (4:1) (~75 mL) and stirred for 20 minutes then extracted with chloroform/IPA (4:1) (×3). The organic layers were combined, dried over magnesium sulfate, filtered, and concentrated. The crude product was purified using a Teledyne ISCO Combi-Flash system (liquid loading with DCM, 80G column, 0-25% EtOAc/Hex, 15 min run) to afford the title compound (1.95 g; 63% yield). $^1$H NMR (400 MHz, CDCl$_3$) δ 2.54 (d, J=0.9 Hz, 3H), 1.88-1.75 (m, 1H), 1.34-1.19 (m, 2H), 0.81-0.67 (m, 2H). ES-MS [M+1]$^+$: 203.

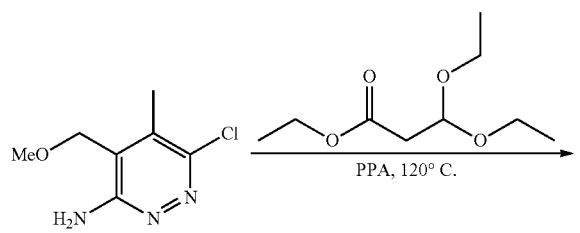

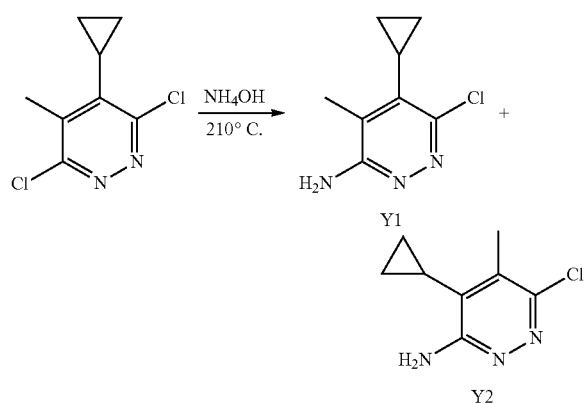

6-Chloro-4-cyclopropyl-5-methylpyridazin-3-amine (Intermediate Y1) and 6-chloro-5-cyclopropyl-4-methylpyridazin-3-amine (Intermediate Y2): 3,6-Dichloro-4-cyclopropyl-5-methyl-pyridazine (1.0 g) was mixed with ammonium hydroxide (15 mL; 28% NH$_3$ in water) solution and 1,4-dioxane (2 mL). The solution was heated to 210° C. for 24 hours (140 psi). The reaction was cooled to room temperature and the reaction mixture was transferred to a round bottom flask with DCM/MeOH and concentrated. The crude product was purified using a Teledyne ISCO Combi-Flash system (solid loading, 80G column, 0-90% EtOAc/DCM, 25 min run; then 0-10% MeOH/DCM/NH$_4$OH, 10 min) to give a mixture of the title compounds. $^1$H NMR (400 MHz, CDCl$_3$) δ 2.46 (d, J=1.2 Hz, 3H), 1.90-1.79 (m, 1H), 1.42-1.29 (m, 2H), 0.86-0.73 (m, 2H). $^1$H NMR (400 MHz, CDCl$_3$) δ 2.60 (d, J=1.3 Hz, 3H), 1.80-1.55 (m, 1H), 1.44-1.32 (m, 2H), 0.81-0.72 (m, 2H). ES-MS [M+1]$^+$: 184.

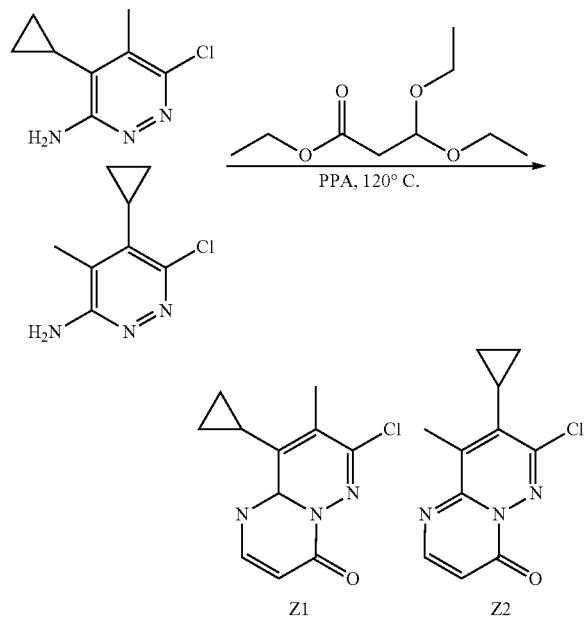

7-Chloro-9-cyclopropyl-8-methyl-4H-pyrimido[1,2-b]pyridazin-4-one (Intermediate Z1): To a mixture of isomers 6-chloro-5-cyclopropyl-4-methyl-pyridazin-3-amine and 6-chloro-4-cyclopropyl-5-methyl-pyridazin-3-amine (928 mg) was added ethyl 3,3-diethoxypropionate (1.97 mL) and polyphosphoric acid (7 mL). The mixture was stirred at 120° C. for 1 hour. More ethyl 3,3-diethoxypropionate (1.97 mL) was added and the mixture stirred an additional 1 hour at 120° C. The reaction mixture was then slowly added to a stirred solution of 150 mL of saturated aqueous NaHCO$_3$ and 100 mL of DCM. After complete addition, the mixture was allowed to stir for 20 minutes and the organic layer was separated. The aqueous layer was further extracted with chloroform/IPA (4:1) (×3). The organic layers were combined, dried over MgSO$_4$, filtered, and concentrated. The crude product was dissolved in DMSO (15 mL) and purified by reverse-phase chromatography using Gilson HPLC (50× 250 mm column, 0-45% ACN/0.1% aqueous TFA, 20 min run). Fractions containing product were neutralized with sat. NaHCO$_3$, and extracted with 3:1 chloroform/IPA. The organic layers were concentrated to give the title compound as a solid (73 mg; 6% yield). ES-MS [M+1]$^+$: 236.

7-Chloro-8-cyclopropyl-9-methyl-4H-pyrimido[1,2-b]pyridazin-4-one (Intermediate Z2): Intermediate Z2 was synthesized and isolated as described in the previous step to give the title compound as a solid (473 mg; 40% yield). ES-MS [M+1]$^+$: 236.

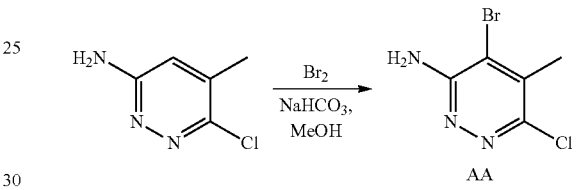

4-Bromo-6-chloro-5-methylpyridazin-3-amine (Intermediate AA): A mixture of 6-chloro-5-methylpyridazin-3-amine (4 g) and NaHCO$_3$ (4.68 g) were suspended in MeOH (40 mL) and treated with Br$_2$ (6.68 g). The mixture was stirred at 20° C. for 4 hours. The mixture was filtered and the cake was washed with a mixture of DCM/MeOH (10:1) (100 mL). The filtrate was concentrated. The residue was diluted with saturated Na$_2$SO$_3$ aqueous solution (50 mL), then extracted by DCM (100 mL×5). The combined organic layers was dried over Na$_2$SO$_4$, and concentrated to give 4-bromo-6-chloro-5-methylpyridazin-3-amine (6.07 g). $^1$H NMR (400 MHz, CDCl$_3$) δ 5.86 (br s, 2H), 2.52 (s, 3H).

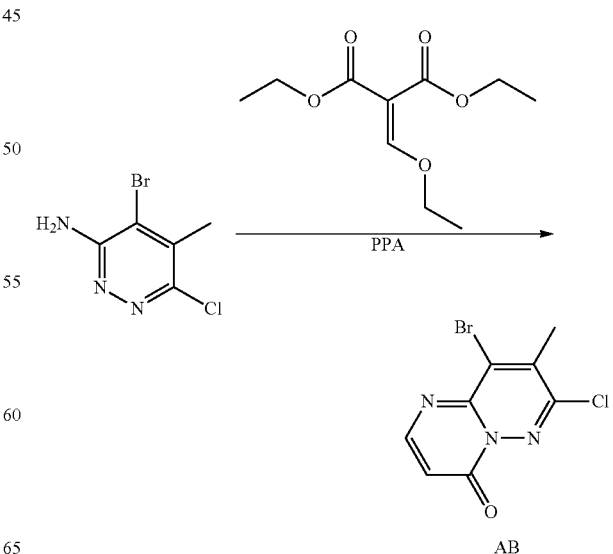

9-Bromo-7-chloro-8-methyl-4H-pyrimido[1,2-b]pyridazin-4-one (Intermediate AB): A mixture of 4-bromo-6-chloro-5-methylpyridazin-3-amine (6 g) and diethyl 2-(ethoxymethylene)malonate (11.66 g) in PPA (100 mL) was stirred at 120° C. for 2 hours. The mixture was added to sat. aq.Na$_2$CO$_3$ while maintaining pH about 8 and extracted with EtOAc (50 mL×4). The combined organic layers were washed with brine (20 mL×2), dried over Na$_2$SO$_4$, filtered and concentrated. The residue was purified by Combi Flash (silica gel, from 0 to 70%, Ethyl acetate in petroleum ether) to give 9-bromo-7-chloro-8-methyl-4H-pyrimido[1,2-b]pyridazin-4-one (4.1 g). $^1$H NMR (400 MHz, CDCl$_3$) δ 8.28 (d, J=6.8 Hz, 1H), 6.68 (d, J=6.4 Hz, 1H), 2.73 (s, 3H).

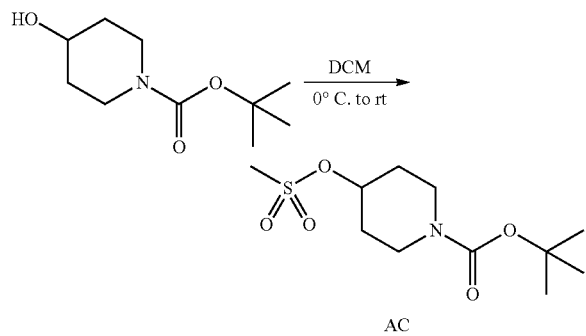

AC tert-Butyl 4-methylsulfonyloxypiperidine-1-carboxylate (Intermediate AC): To a solution of tert-butyl-4-hydroxypiperidine-1-carboxylate (2.5 g) in DCM (40 mL) at 0° C. was added triethylamine (2.42 mL) followed by dropwise addition of methanesulfonyl chloride (1.35 mL). The ice bath was removed and the reaction was stirred for 18 h at room temperature. The reaction mixture was diluted with 3:1 CHCl$_3$/IPA and water. The layers were separated and the aqueous layer was extracted with 3:1 CHCl$_3$/IPA (2×). The combined organic layers were washed with brine, dried over MgSO$_4$, filtered, and concentrated to afford the title compound 3.4 g. $^1$H NMR (400 MHz, CDCl$_3$) δ 4.91-4.85 (m, 1H), 3.73-3.67 (m, 2H), 3.33-3.26 (m, 2H), 3.03 (s, 3H), 1.99-1.93 (m, 2H), 1.85-1.77 (m, 2H), 1.45 (s, 9H).

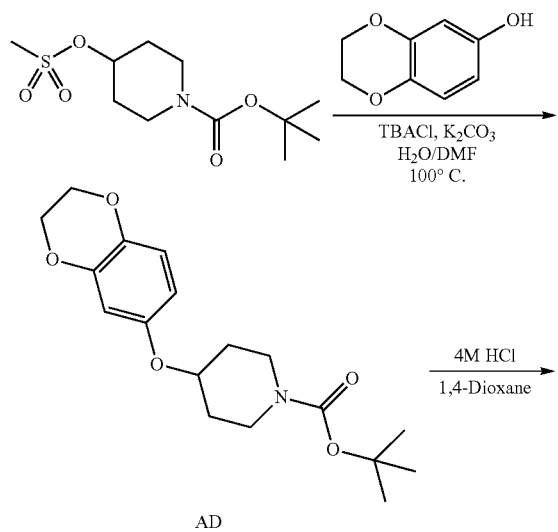

AD

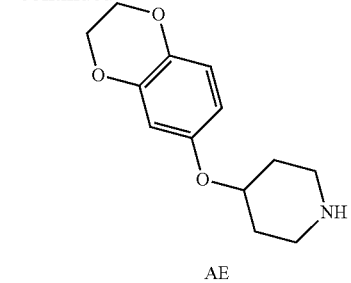

AE tert-Butyl 4-((2,3-dihydrobenzo[b][1,4]dioxin-6-yl)oxy)piperidine-1-carboxylate (Intermediate AD): To a flask was added tert-butyl 4-((methylsulfonyl)oxy)piperidine-1-carboxylate (1.5 g), 6-hydroxy-4-oxachroman (565 mg), tetrabutylammonium chloride (207 mg), and potassium carbonate (1.6 g). After the addition of water (17.5 mL) and DMF (1 mL), the reaction was heated to 100° C. for four hours. The reaction was allowed to cool to room temperature and was extracted with DCM (2×). The combined extracts were washed with water and 2N NaOH before being dried (Na$_2$SO$_4$), filtered, and concentrated in vacuo. Purification by flash chromatography on silica gel (20-70% EtOAc/Hexanes) afforded the title compound (472 mg): 1H-NMR (400 MHz, CDCl$_3$) δ 6.76 (d, J=8.7 Hz, 1H), 6.46 (d, J=2.8 Hz, 1H), 6.42 (dd, J=8.7, 2.8 Hz, 1H), 4.35-4.28 (m, 1H), 4.25-4.18 (m, 4H), 3.69 (ddd, J=12.9, 7.3, 3.5 Hz, 2H), 3.29 (ddd, J=12.5, 7.9, 3.8 Hz, 2H), 1.90-1.85 (m, 2H), 1.74-1.66 (m, 2H), 1.46 (s, 9H). ES-MS [M-C(CH$_3$)$_3$+H]$^+$: 280.4.

4-((2,3-dihydrobenzo[b][1,4]dioxin-6-yl)oxy)piperidine (Intermediate AE): Tert-butyl 4-((2,3-dihydrobenzo[b][1,4]dioxin-6-yl)oxy)piperidine-1-carboxylate (315 mg) was dissolved in 4 M HCl solution in 1,4-dioxane (14 mL). After five hours at room temperature, the reaction was concentrated in vacuo. The crude material was taken up in MeOH and purified by HF SCX cartridge and NH$_3$ solution (2N in MeOH) to afford the title compound (68 mg): $^1$H NMR (400 MHz, DMSO-d$_6$) δ 6.77 (d, J=8.8 Hz, 1H), 6.44-6.39 (m, 2H), 4.48-4.46 (m, 1H), 4.24-4.19 (m, 4H), 3.31 (ddd, J=12.8, 12.8, 3.7 Hz, 2H), 3.16 (ddd, J=8.2, 8.2, 3.9 Hz, 2H), 2.20-2.05 (m, 4H); ES-MS [M+1]$^+$: 236.2.

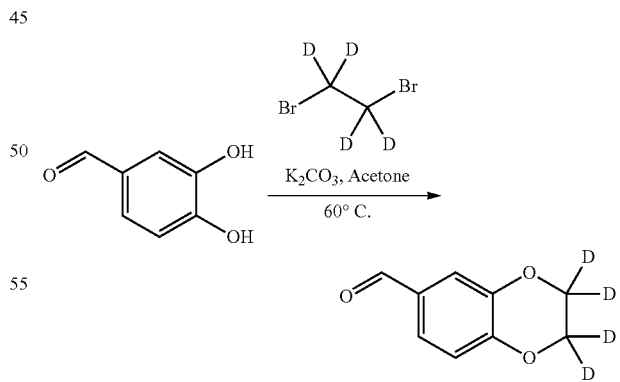

AG 2,2,3,3-Tetradeuterio-1,4-benzodioxine-6-carbaldehyde (Intermediate AG): In a 500 mL round bottom flask were combined 3,4-dihydroxybenzaldehyde (21.3 g), 1,2-dibromoethane-D4 (14.1 mL), and potassium carbonate (65.0 g) in acetone (515 mL). The reaction was heated to reflux for 18 h. The reaction was diluted with EtOAc, filtered through celite, and the filtrate was concentrated in vacuo. The crude sample was purified by flash chromatography on silica gel (0-40% EtOAc/Hexanes) to afford the title compound (15.4 g). $^1$H NMR (400 MHz, CDCl$_3$) δ 9.82 (s, 1H), 7.41-7.38 (m, 2H), 6.97 (d, J=8.8 Hz, 1H). ES-MS [M+1]$^+$: 169.

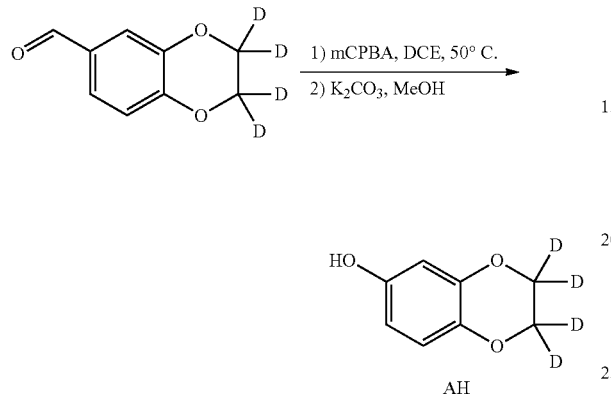

AH 2,2,3,3-Tetradeuterio-1,4-benzodioxin-6-ol (Intermediate AH): Step 1. To a solution of 2,2,3,3-tetradeuterio-1,4-benzodioxine-6-carbaldehyde (15.4 g) in DCE (250 mL) was added 3-chloroperoxybenzoic acid (47.6 g, <77% CAS #937-14-4; Sigma-Aldrich). The reaction mixture was heated to 50° C. for 18 h. The reaction was diluted with DCM and saturated NaHCO$_3$ solution. The layers were separated. The aqueous layer was extracted with DCM (2×) and the combined organic layers were washed with brine, dried (MgSO$_4$), filtered, and concentrated to afford 2,3-dihydrobenzo[b][1,4]dioxin-6-yl-2,2,3,3-d4 formate (15.1 g). ES-MS [M+1]$^+$: 185.

Step 2. 2,3-Dihydrobenzo[b][1,4]dioxin-6-yl-2,2,3,3-d4 formate (15.1 g) was dissolved in methanol (250 mL) and potassium carbonate (15.5 g) was added. After 3 h, the solvent was removed and water/DCM (1:1) were added. The aqueous layer was slowly acidified by dropwise addition of 6 N aqueous HCl to pH<4. The layers were separated, and the aqueous layer was extracted with DCM (2×) and the combined organic layers were washed with brine, dried (MgSO$_4$), filtered, and concentrated. The filtrate was purified by flash chromatography on silica gel (0-40% EtOAc/Hexanes). The desired fractions were concentrated and co-evaporated (2× with toluene) to afford the title compound (12.3 g). $^1$H NMR (400 MHz, CDCl$_3$) δ 6.72 (d, J=8.8 Hz, 1H), 6.39 (d, J=2.9 Hz, 1H), 6.34-6.31 (dd, J=8.7, 2.9 Hz, 1H), 4.64 (s, 1H). ES-MS [M+1]$^+$: 157.

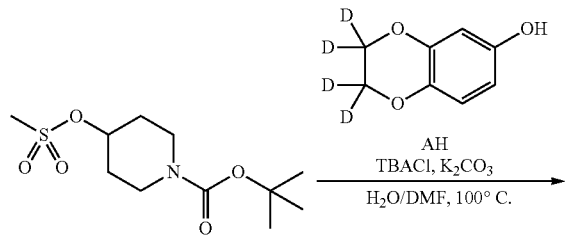

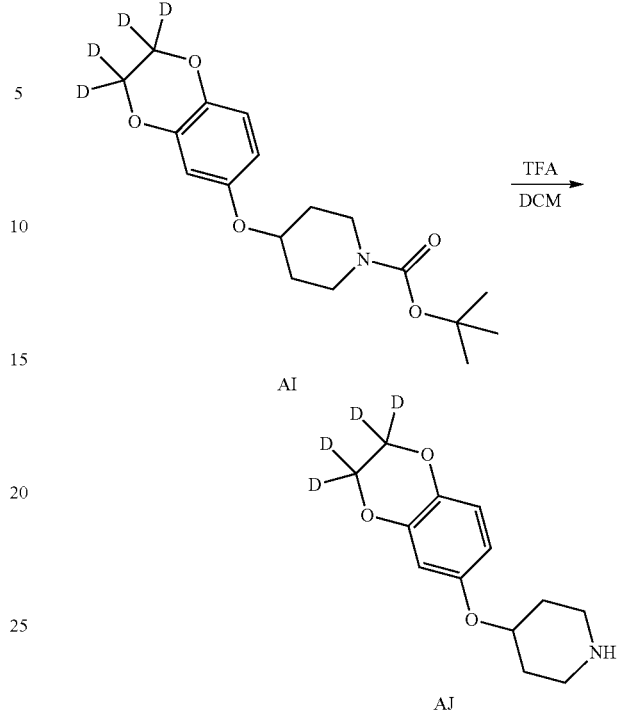

tert-Butyl 4-[(2,2,3,3-tetradeuterio-1,4-benzodioxin-6-yl)oxy]piperidine-1-carboxylate (Intermediate AI): To a 1000 mL round bottom flask were added tert-butyl 4-methylsulfonyloxypiperidine-1-carboxylate (18 g), 2,2,3,3-tetradeuterio-1,4-benzodioxin-6-ol (6.0 g), potassium carbonate (16.2 g), and tetrabutylammonium chloride (2.1 g) in water (360 mL) and DMF (18 mL). The reaction was heated to reflux. After 24 h, the reaction was cooled to room temperature, diluted with EtOAc and washed with water (3×), brine (2×). The organic layer was dried (MgSO$_4$), filtered, and concentrated in vacuo. The crude oil was purified by flash chromatography on silica gel (0-40% EtOAc/Hexanes) to afford the title compound (3.1 g). $^1$H NMR (400 MHz, CDCl$_3$) δ 6.76 (d, J=8.7 Hz, 1H), 6.46 (d, J=2.8 Hz, 1H), 6.44-6.41 (dd, J=8.7, 2.8 Hz, 1H), 4.32-4.27 (m, 1H), 3.72-3.66 (m, 2H), 3.31-3.25 (m, 2H), 1.90-1.85 (m, 2H), 1.74-1.66 (m, 2H), 1.46 (s, 9H). ES-MS [M+1]$^+$: 340.

4-[(2,2,3,3-Tetradeuterio-1,4-benzodioxin-6-yl)oxy]piperidine (Intermediate AJ) as TFA-salt: To a round bottom flask containing tert-butyl 4-[(2,2,3,3-tetradeuterio-1,4-benzodioxin-6-yl)oxy]piperidine-1-carboxylate (760 mg) in DCM (6 mL) was added trifluoroacetic acid (2 mL). After 2 h at room temperature, the solvents were removed and the crude residue was dissolved in DCM and concentrated in vacuo (3×) to afford the title compound (802 mg). $^1$H NMR (400 MHz, CDCl$_3$) δ 6.78 (d, J=8.9 Hz, 1H), 6.45 (d, J=2.8 Hz, 1H), 6.43-6.40 (dd, J=8.8, 2.9 Hz, 1H), 4.51-4.50 (m, 1H), 3.44-3.37 (m, 2H), 3.28-3.25 (m, 2H), 2.16-2.07 (m, 4H). ES-MS [M+1]$^+$: 240.

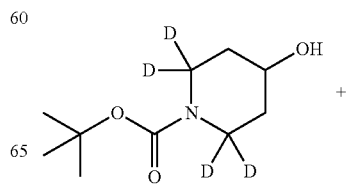

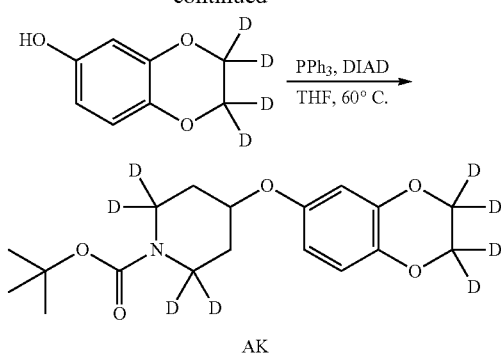

tert-Butyl 2,2,6,6-tetradeuterio-4-[(2,2,3,3-tetradeuterio-1,4-benzodioxin-6-yl)oxy]piperidine-1-carboxylate (Intermediate AK): In a vial were combined tert-butyl 2,2,6,6-tetradeuterio-4-hydroxy-piperidine-1-carboxylate (100 mg, 0.49 mmol)[Reference: J. of Labelled Compounds and Radiopharmaceuticals 2018, 61, 1036-1042], triphenylphosphine (180 mg, 0.68 mmol), and 2,2,3,3-tetradeuterio-1,4-benzodioxin-6-ol (107 mg, 0.68 mmol) in THF (2 mL). The vessel was degassed followed by addition of diisopropyl azodicarboxylate (0.13 mL, 0.68 mmol). The reaction was heated at 60° C. for 18 h. The reaction was dissolved in 3:1 CHCl$_3$:IPA and concentrated with celite. The solid was dry loaded for purification on silica gel (0-25% EtOAc/Hexanes). The desired fractions were concentrated to afford the title compound (123 mg). $^1$H NMR (400 MHz, CDCl$_3$) δ 6.75 (d, J=8.7 Hz, 1H), 6.45 (d, J=2.8 Hz, 1H), 6.42 (dd, J=8.8, 2.9 Hz, 1H), 4.31-4.26 (m, 1H), 1.87-1.83 (m, 2H), 1.71-1.66 (m, 2H), 1.45 (s, 9H). ES-MS [M+1]$^+$: 344.

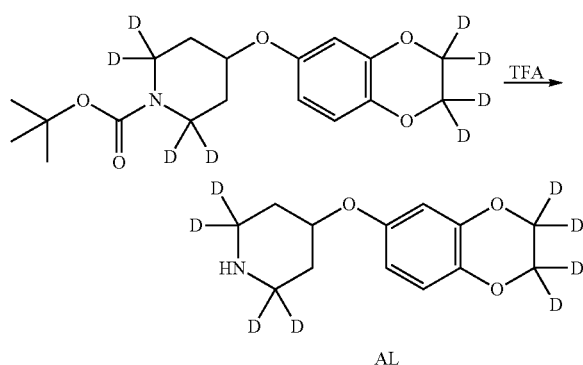

2,2,6,6-Tetradeuterio-4-[(2,2,3,3-tetradeuterio-1,4-benzodioxin-6-yl)oxy]piperidine (Intermediate AL): In a vial were combined tert-butyl 2,2,6,6-tetradeuterio-4-[(2,2,3,3-tetradeuterio-1,4-benzodioxin-6-yl)oxy]piperidine-1-carboxylate (123 mg, 0.36 mmol) and trifluoroacetic acid (0.5 mL) in dichloromethane (2 mL). The reaction stirred for 1 h and was concentrated. The oil was purified by SCX Cartridge (5G), washed with MeOH, and eluted with 7N NH$_3$/MeOH solution. The solvents were removed to afford the title compound (55 mg). $^1$H NMR (400 MHz, CDCl$_3$) δ 6.75 (d, J=8.8 Hz, 1H), 6.46 (d, J=2.8 Hz, 1H), 6.43 (dd, J=8.8, 2.8 Hz, 1H), 4.24-4.18 (m, 1H), 1.99 (d, J=3.8 Hz, 1H), 1.96 (d, J=3.7 Hz, 1H), 1.63 (d, J=8.4 Hz, 1H) 1.60 (d, J=8.6 Hz, 1H). ES-MS [M+1]$^+$: 244.

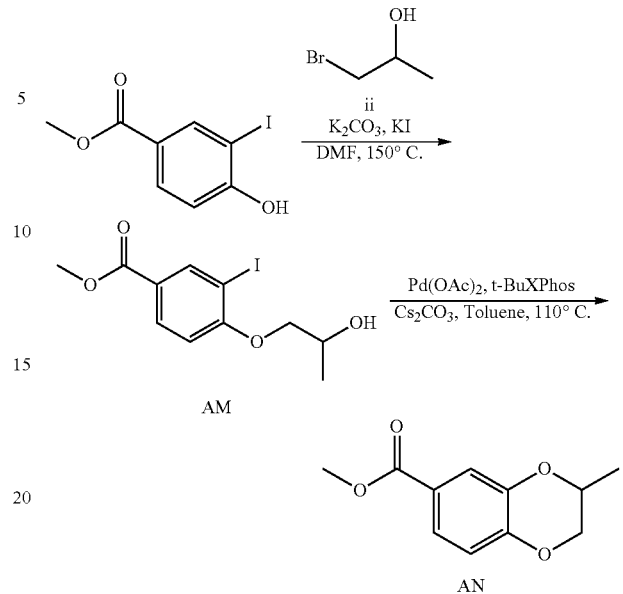

Methyl 4-(2-hydroxypropoxy)-3-iodo-benzoate (Intermediate AM): To a 0° C. solution of 1-bromo-2-propanol (1.04 mL) in DMF (22 mL) was added potassium carbonate (2.69 mL) and potassium iodide (0.59 g). After 15 min, methyl 4-hydroxy-3-iodobenzoate (2.44 g) was added and the reaction was heated to reflux. After 12 h, the reaction was cooled to room temperature and diluted with EtOAc and water. The layers were separated and the organic layer was washed with water (3×), brine (2×), dried (MgSO$_4$), and concentrated to afford the title compound (2.5 g). ES-MS [M+1]$^+$: 337.

Methyl 3-methyl-2,3-dihydro-1,4-benzodioxine-6-carboxylate (Intermediate AN): In a 250 mL round bottom flask were combined methyl 4-(2-hydroxypropoxy)-3-iodo-benzoate (2.5 g), cesium carbonate (4.88 g), palladium (II) acetate (0.14 g) and 2-di-tert-butylphosphino-2',4',6'-triisopropylbiphenyl (0.47 g). The flask was evacuated and purged with anhydrous nitrogen (3×) followed by addition of degassed toluene (18 mL). The reaction was sealed and heated to 110° C. After 5 h, the reaction was cooled to room temperature and the toluene was concentrated in vacuo. The crude oil was diluted with EtOAc and water. The layers were separated, and the organic layer was washed with water (3×), brine (2×), dried over MgSO$_4$, and concentrated. The crude oil was purified by flash chromatography on silica gel (0-20% EtOAc/Hexanes) to afford the title compound (0.34 g). $^1$H NMR (400 MHz, CDCl$_3$) δ 7.56-7.53 (m, 2H), 6.92-6.86 (m, 1H), 4.36-4.22 (m, 2H) 3.89-3.82 (m, 1H) 3.86 (s, 3H), 1.37 (d, J=6.5 Hz, 3H). ES-MS [M+1]$^+$: 209.

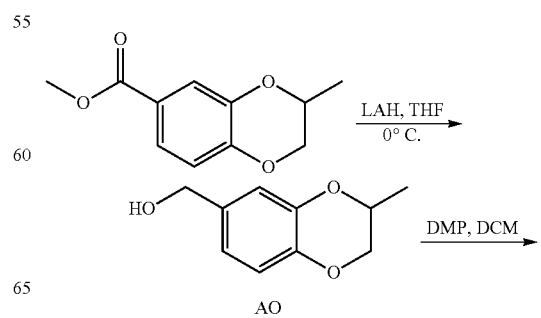

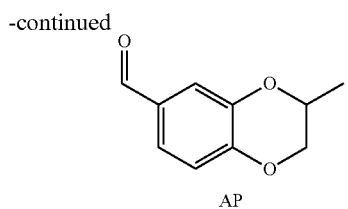

AP (3-methyl-2,3-dihydro-1,4-benzodioxin-6-yl)methanol (Intermediate AO): To a 0° C. suspension of lithium aluminum hydride (1.01 mL, 1 M) in THF (1.2 mL) was added methyl 3-methyl-2,3-dihydro-1,4-benzodioxine-6-carboxylate (200 mg) in THF (1.2 mL). The ice bath was removed and after 1 h at room temperature, the reaction was cooled to 0° C. and quenched with water (40 µL) and 10% NaOH aqueous solution (0.37 mL). After 10 min at 0° C., the suspension was filtered, and the filtrate was concentrated in vacuo. The crude residue was purified by flash chromatography on silica gel (0-50% EtOAc/Hexanes) and the desired fractions were concentrated to afford the title compound 148 mg. ES-MS [M+1]$^+$: 182.

3-methyl-2,3-dihydro-1,4-benzodioxine-6-carbaldehyde (Intermediate AP): To a vial containing (3-methyl-2,3-dihydro-1,4-benzodioxin-6-yl)methanol (148 mg) in DCM (2.7 mL) at 0° C. was added Dess-Martin Periodinane (418 mg). The ice bath was removed and after 18 h, the reaction was diluted with DCM and celite was added. The suspension was concentrated and then dry loaded for flash chromatography on silica gel (0-40% EtOAc/Hexanes). The desired fractions were concentrated to afford the title compound (129 mg). $^1$H NMR (400 MHz, CDCl$_3$) δ 9.82 (s, 1H), 7.41-7.38 (m, 2H), 6.99-6.95 (dd, J=9.1, 5.0 Hz, 1H), 4.38-4.15 (m, 2H) 3.92-3.82 (m, 1H) 1.37 (d, J=6.4 Hz, 3H). ES-MS [M+1]$^+$: 179.

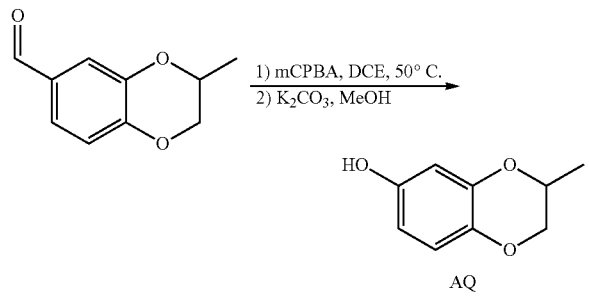

AQ 3-methyl-2,3-dihydro-1,4-benzodioxin-6-ol (Intermediate AQ): Step 1. To a solution of 3-methyl-2,3-dihydro-1,4-benzodioxine-6-carbaldehyde (129 mg) in DCE (1.4 mL) was added 3-chloroperoxybenzoic acid (187 mg, <77% CAS #937-14-4; Sigma-Aldrich). The reaction was heated to 50° C. After 3 h, the reaction was concentrated in vacuo, EtOAc was added to the residue followed by addition of saturated aqueous NaHCO$_3$ (1.5 mL). The organic layer was separated, washed with brine, dried over MgSO$_4$, filtered, and concentrated in vacuo. The crude sample was purified by flash chromatography on silica gel (0-30% EtOAc/Hexanes) to afford 3-methyl-2,3-dihydrobenzo[b][1,4]dioxin-6-yl formate (91 mg). ES-MS [M+1]$^+$: 195.

Step 2. 3-Methyl-2,3-dihydrobenzo[b][1,4]dioxin-6-yl formate (78 mg) was dissolved in methanol (1.4 mL) and potassium carbonate (121 mg) was added. After 45 min, the methanol was concentrated in vacuo. The residue was diluted with DCM and water. The layers were separated and the aqueous layer was extracted with DCM (2×) and the combined organic layers were washed with brine, dried over MgSO$_4$, filtered, and concentrated to afford the title compound (71 mg). $^1$H NMR (400 MHz, CDCl$_3$) δ 6.71 (d, J=8.7 Hz, 1H), 6.39-6.37 (m, 1H), 6.34-3.30 (m, 1H), 4.87 (s, 1H), 4.29-4.21 (m, 1H), 4.15 (dd, J=11.2, 2.2 Hz, 1H), 3.81-3.74 (m, 1H), 1.33 (d, J=6.5 Hz, 3H); ES-MS [M+1]$^+$: 167.

Analytical Separation Example

Chiral SFC separation was performed on a Thar (Waters) Investigator. Column: Chiral Technologies CHIRALPAK IE, 4.6×250 mm, 5 µm. Gradient conditions: 5% to 50% MeOH (MeOH modified with 0.1% DEA) in CO$_2$ over 5 min, hold at 50% CO$_2$ for 5 min. Flow rate: 3.5 mL/min. Column temperature: 40° C. System backpressure: 100 bar. Enantiomer N1: Enantiomer N2 (1:1)

Preparative Separation Example

Chiral SFC separation was performed on a PIC Solution SFC-PICLab PREP 100. Column: Chiral Technologies CHIRALPAK IE, 20×250 mm, 5 µm. Conditions: 10% MeOH in CO$_2$. Flow rate: 80 mL/min. Column temperature: 40° C. System backpressure: 100 bar.

Intermediate AS1 (first eluted peak):
Rt=5.06 min (preparative method); ES-MS [M+Na]$^+$=372.0; 100% ee.

Intermediate AS2 (second eluted peak):
Rt=6.02 min (preparative method; ES-MS [M+Na]$^+$=372.0; 97.3% ee.

tert-Butyl 4-((2,3-dihydrobenzo[b][1,4]dioxin-6-yl)oxy)-3-methylpiperidine-1-carboxylate (Intermediate AT): To a solution of 2,3-dihydrobenzo[b][1,4]dioxin-6-ol (0.2 g, 1.31 mmol) in THF (10 mL) was added tert-butyl 4-hydroxy-3-methylpiperidine-1-carboxylate (340 mg, 1.58 mmol) and PPh$_3$ (641 mg, 2.45 mmol) with stirring at 20° C. under N$_2$ atmosphere. Then DIAD (399 mg, 1.97 mmol) was added dropwise at 20° C. The mixture was stirred at 20° C. for 16 hours. The reaction mixture was concentrated to give a residue. The residue was purified by flash silica gel chromatography (ISCO; 12 g SepaFlash Silica Flash Colun, eluent of 0-10% Ethyl acetate/petroleum ether gradient @ 35 mL/min) to afford the desired product (102 mg). $^1$H NMR (400 MHz, CDCl3) δ 6.77 (d, J=8.8 Hz, 1H), 6.47 (d, J=2.4 Hz, 1H), 6.44 (dd, J=2.8 Hz, 8.8 Hz, 1H), 4.25-4.21 (m, 4H), 3.63-3.58 (m, 2H), 3.32-3.17 (m, 2H), 1.97-1.92 (m, 2H), 1.47 (s, 9H), 1.29-1.23 (m, 2H), 1.00 (d, J=7.2 Hz, 3H).

4-((2,3-dihydrobenzo[b][1,4]dioxin-6-yl)oxy)-3-methylpiperidine (Intermediate AT1): To a solution of tert-butyl 4-((2,3-dihydrobenzo[b][1,4]dioxin-6-yl)oxy)-3-methylpiperidine-1-carboxylate (102 mg, 0.29 mmol) in DCM (10 mL) was added TFA (3.08 g, 27.01 mmol). The mixture was stirred at 20° C. for 16 hours. The reaction mixture was concentrated to afford 4-((2,3-dihydrobenzo[b][1,4]dioxin-6-yl)oxy)-3-methylpiperidine as the 2,2,2-trifluoro acetate salt (98 mg).

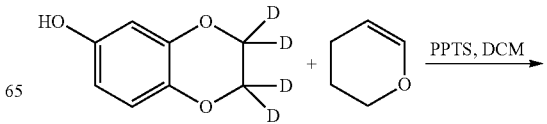

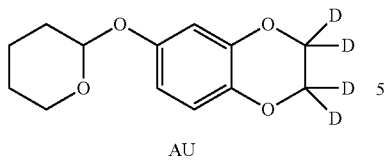

AU 2,2,3,3-Tetradeuterio-6-tetrahydropyran-2-yloxy-1,4-benzodioxine (Intermediate AU): To a solution of 2,2,3,3-tetradeuterio-1,4-benzodioxin-6-ol (2.0 g) and pyridinium tosylate (48 mg) in DCM (32 mL) was added 3,4-dihydro-2H-pyran (1.8 mL). The reaction stirred at room temperature for 3 h. The reaction was diluted with DCM and washed with 5% NaOH solution. The organic layer was dried (MgSO$_4$), filtered, and concentrated. The crude oil was purified by flash chromatography on silica gel (0-30% EtOAc/Hexanes) to afford the title compound (2.61 g). $^1$H NMR (400 MHz, CDCl$_3$) δ 6.75 (d, J=8.9 Hz, 1H), 6.62 (d, J=2.8 Hz, 1H), 6.54 (dd, J=8.8, 2.8, 1H), 5.26 (t, J=3.4, 1H), 3.95-3.89 (m, 1H), 3.60-3.55 (m, 1H), 2.01-1.91 (m, 1H), 1.84-1.80 (m, 2H), 1.67-1.57 (m, 3H); ES-MS [M+1]$^+$: 241.

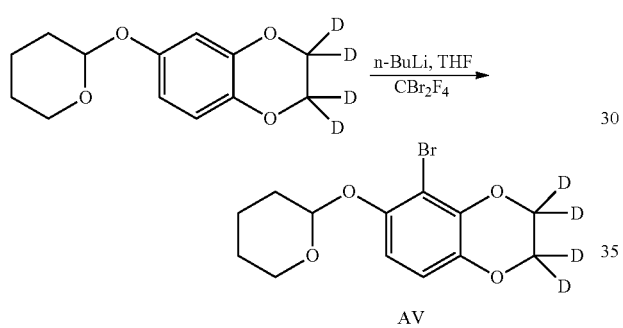

AV

5-Bromo-2,2,3,3-tetradeuterio-6-tetrahydropyran-2-yloxy-1,4-benzodioxine (Intermediate AV): To a solution of 2,2,3,3-tetradeuterio-6-tetrahydropyran-2-yloxy-1,4-benzodioxine (1500 mg) in THF (62 mL) at −50° C. was added dropwise n-butyllithium (7.49 mL, 2.5M in hexanes) and the reaction stirred at −50° C. for 2 h followed by slow addition of 1,2-dibromotetrafluoroethane (3.72 mL). The mixture stirred for 1 h and then the cooling bath was removed. At room temperature, the reaction was quenched with water and extracted with ethyl acetate (3×). The combined organic layers were dried (MgSO$_4$), filtered, and concentrated. The crude oil was purified by flash chromatography on silica gel (0-15% EtOAc/Hexanes) to afford the title compound (1.63 g); $^1$H NMR (400 MHz, CDCl$_3$) δ 6.77 (d, J=9.1 Hz, 1H), 6.69 (d, J=9.1 Hz, 1H), 5.37 (t, J=2.9 Hz, 1H), 3.98-3.92 (m, 1H), 3.62-3.57 (m, 1H), 2.13-1.97 (m, 1H), 1.95-1.86 (m, 1H), 1.85-1.82 (m, 1H), 1.71-1.59 (m, 3H); ES-MS [M+Na]$^+$: 341.

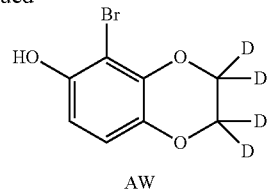

AW

5-Bromo-2,2,3,3-tetradeuterio-1,4-benzodioxin-6-ol (Intermediate AW): In a vial were combined 5-bromo-2,2,3,3-tetradeuterio-6-tetrahydropyran-2-yloxy-1,4-benzodioxine (1632 mg), THF (50 mL), and 1N hydrochloric acid (30 mL). The reaction stirred at room temperature for 1 h. The reaction was diluted with EtOAc and the layers were separated. The aqueous layer was extracted with EtOAc (2×), and the combined organic layers were washed with brine, dried (MgSO$_4$), filtered, and concentrated. The crude oil was purified by flash chromatography on silica gel (0-20% EtOAc/Hexanes) to afford the title compound (1.10 g). $^1$H NMR (400 MHz, CDCl$_3$) δ 6.77 (d, J=8.9 Hz, 1H), 6.55 (d, J=8.9 Hz, 1H), 5.19 (s, 1H); ES-MS [M+1]$^+$: 235.

AX tert-Butyl 4-[(5-bromo-2,2,3,3-tetradeuterio-1,4-benzodioxin-6-yl)oxy]piperidine-1-carboxylate (Intermediate AX): In a round bottom flask were combined tert-butyl 4-methylsulfonyloxypiperidine-1-carboxylate (2.6 g), 5-bromo-2,2,3,3-tetradeuterio-1,4-benzodioxin-6-ol (1.1 g), potassium carbonate (1.97 g), and tetrabutylammonium chloride (0.26 g) in water (17 mL) and DMF (0.9 mL). The reaction was heated to 100° C. After 18 h, the reaction was cooled, diluted with EtOAc and washed with water (3×), brine (2×) and the organic layer was dried (MgSO$_4$), filtered and concentrated. The crude oil was purified by flash chromatography on silica gel (0-40% EtOAc/Hexanes) to afford the title compound (1.18 g). $^1$H NMR (400 MHz, CDCl$_3$) δ 6.76 (d, J=9.1 Hz, 1H), 6.47 (d, J=8.9 Hz, 1H), 4.40-4.39 (m, 1H), 3.68-3.62 (m, 2H), 3.41-3.38 (m, 2H), 1.82-1.81 (m, 4H), 1.45 (s, 9H).

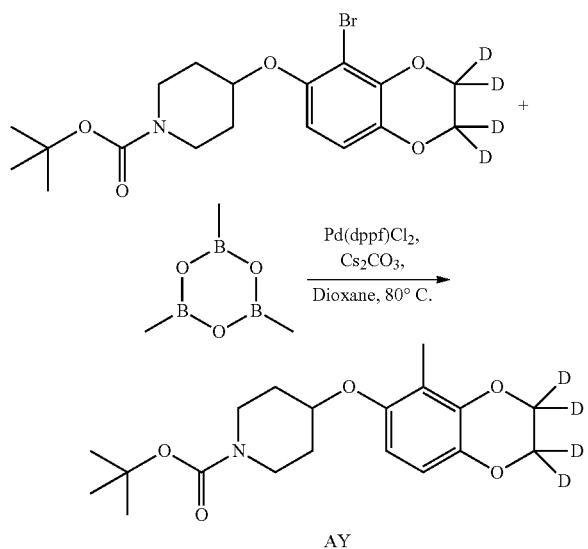

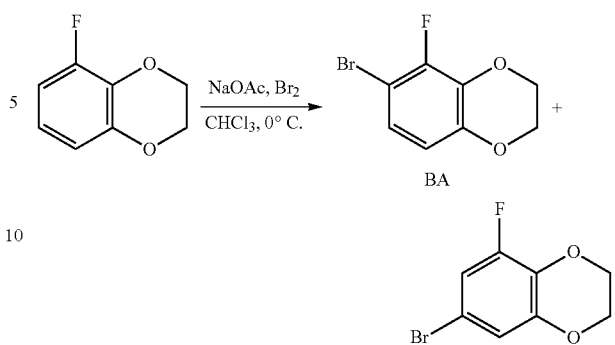

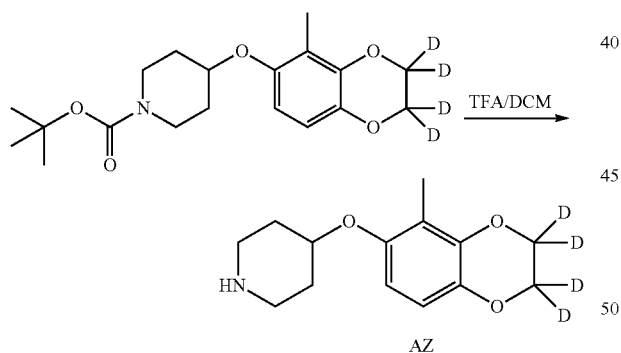

tert-Butyl 4-[(2,2,3,3-tetradeuterio-5-methyl-1,4-benzo-dioxin-6-yl)oxy]piperidine-1-carboxylate (Intermediate AY): In a vial were combined tert-butyl 4-[(5-bromo-2,2,3,3-tetradeuterio-1,4-benzodioxin-6-yl)oxy]piperidine-1-carboxylate (100 mg), cesium carbonate (233 mg), [1,1'-bis(diphenyl)phosphino)ferrocene]dichloropalladium(II) (26 mg), and 2,4,6-trimethylboroxine (0.2 mL; 50% w/w solution in THF) and the solids were degassed (3×) followed by addition of 1,4-dioxane (2.3 mL). The reaction was heated to 80° C. After 2 h, the reaction was filtered through a pad of Celite and rinsed thoroughly with EtOAc/DCM. The filtrate was concentrated and purified by flash chromatography on silica gel (0-40% EtOAc/Hexanes) to afford the title compound (46 mg). ES-MS [M+1]$^+$: 354.

4-[(2,2,3,3-Tetradeuterio-5-methyl-1,4-benzodioxin-6-yl)oxy]piperidine (Intermediate AZ): In a vial were combined tert-butyl 4-[(2,2,3,3-tetradeuterio-5-methyl-1,4-benzodioxin-6-yl)oxy]piperidine-1-carboxylate (46 mg), trifluoroacetic acid (0.2 mL), and DCM (2 mL). The reaction stirred 1 h at rt and was concentrated. The crude residue was loaded onto an SCX cartridge (strong cation exchanger; Agilent part #14256027) in MeOH and washed with MeOH, then eluted with 7N NH$_3$/MeOH solution. Solvents were removed in vacuo to afford the title compound (28 mg). $^1$H NMR (400 MHz, CDCl$_3$) δ 6.62 (d, J=8.9 Hz, 1H), 6.41 (d, J=8.9 Hz, 1H), 4.21-4.15 (m, 1H), 3.15-3.09 (m, 2H), 2.73-2.66 (m, 2H), 2.09 (s, 3H), 1.99-1.94 (m, 2H), 1.71-1.62 (m, 2H); ES-MS [M+1]$^+$: 254.

6-Bromo-5-fluoro-2,3-dihydro-1,4-benzodioxine (Intermediate BA): To a 0° C. solution of 5-fluoro-2,3-dihydro-1,4-benzodioxine (900 mg) and sodium acetate (727 mg) in chloroform (9.7 mL) was added bromine (0.3 mL). The ice bath was removed and after 2 h at rt, the reaction was treated with aqueous saturated NaS$_2$O$_5$ solution, extracted with DCM (3×), passed through a phase separator and concentrated. The crude oil was purified by flash chromatography on silica gel (0-35% EtOAc/Hexanes) to afford the title compound as a 3:1 mixture of regioisomers (1.16 g). Major regioisomer (Intermediate BA): $^1$H NMR (400 MHz, CDCl$_3$) δ, 6.95 (dd, J=8.9, 6.9 Hz, 1H), 6.58 (dd, J=8.9, 2.0 Hz, 1H), 4.32-4.30 (m, 2H), 4.28-4.26 (m, 2H).

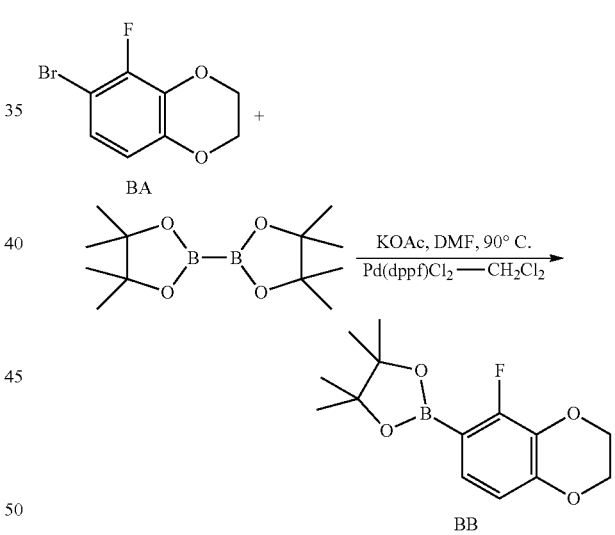

2-(5-Fluoro-2,3-dihydro-1,4-benzodioxin-6-yl)-4,4,5,5-tetramethyl-1,3,2-dioxaborolane (Intermediate BB): To a vial were added 6-bromo-5-fluoro-2,3-dihydro-1,4-benzodioxine (715 mg), dichloro[1,1'-bis(diphenylphosphino)ferrocene]palladium(II) dichloromethane adduct (126 mg), potassium acetate (903 mg), and bis(pinacolato)diboron (935 mg) in DMF (21 mL). After the reaction was degassed (3×), the reaction was heated to 90° C. for 18 h. The reaction was cooled, diluted with EtOAc, filtered through Celite and the filtrate was washed with water (3×), brine (2×), dried (MgSO$_4$), filtered, and concentrated. The crude oil was purified by flash chromatography on silica gel (0-40% EtOAc/Hexanes) to afford the title compound (575 mg); ES-MS [M+1]$^+$: 281.

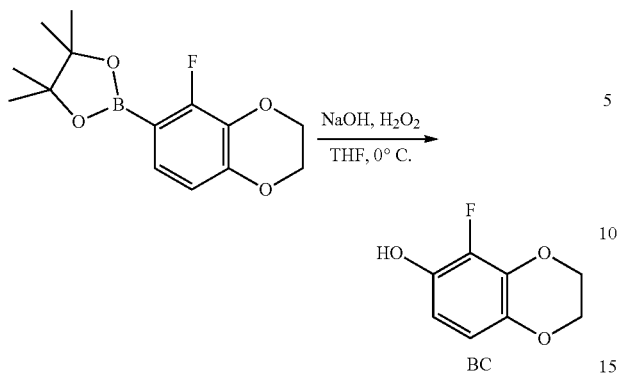

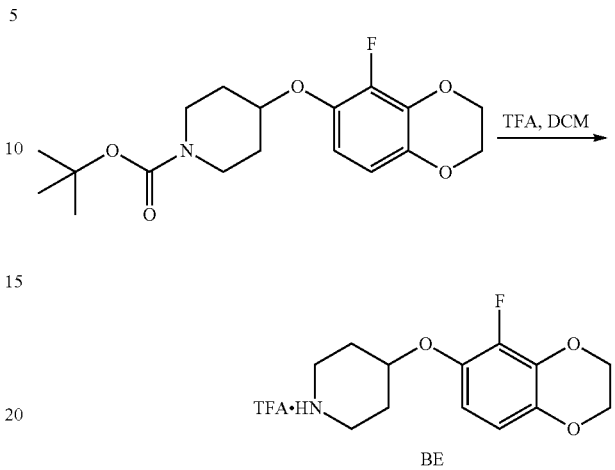

4.31-4.29 (m, 2H), 4.26-4.23 (m, 2H), 3.77-3.71 (m, 2H), 3.29-3.23 (m, 2H), 1.91-1.85 (m, 2H), 1.77-1.69 (m, 2H), 1.46 (s, 9H); ES-MS [M+1]$^+$: 354.

5-Fluoro-2,3-dihydro-1,4-benzodioxin-6-ol (Intermediate BC): To a solution of 2-(5-fluoro-2,3-dihydro-1,4-benzodioxin-6-yl)-4,4,5,5-tetramethyl-1,3,2-dioxaborolane (575 mg) in a mixture of 1N sodium hydroxide solution (6.1 mL) and THF (7.9 mL) at 0° C. was added hydrogen peroxide (0.19 mL, 30% w/w). The reaction stirred at room temperature for 1 h. The pH was adjusted to 3 with 1M HCl solution. The aqueous layer was extracted with EtOAc (3×) and the organic layers were washed with water, brine, dried (MgSO$_4$), filtered and concentrated. The crude residue was purified by flash chromatography on silica gel (0-40% EtOAc/Hexanes) to afford the title compound (124 mg); ES-MS [M+1]$^+$: 171.

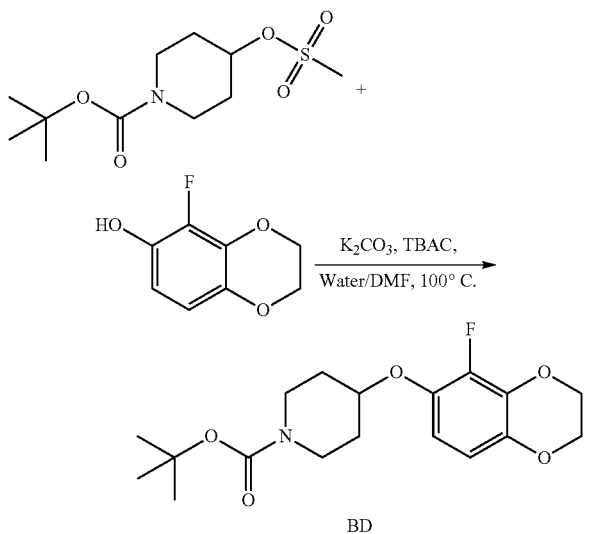

tert-Butyl 4-[(5-fluoro-2,3-dihydro-1,4-benzodioxin-6-yl)oxy]piperidine-1-carboxylate (Intermediate BD): To a vial were added tert-butyl 4-methylsulfonyloxy-piperidine-1-carboxylate (407 mg), 5-fluoro-2,3-dihydro-1,4-benzodioxin-6-ol (124 mg), potassium carbonate (306 mg) and tetrabutylammonium chloride (41 mg) in water (2.3 mL) and DMF (0.1 mL). The vial was sealed and heated to 100° C. for 18 h. The reaction was cooled, diluted with EtOAc and washed with water, saturated NaHCO$_3$ (2×), brine (2×) and the organic layer was dried (MgSO$_4$), filtered and concentrated. The crude oil was purified by flash chromatography on silica gel (0-40% EtOAc/Hexanes) to afford the title compound (176 mg). $^1$H NMR (400 MHz, CDCl$_3$) δ 6.56 (dd, J=9.1, 1.9 Hz, 1H), 6.49 (dd, J=9.1, 7.8 Hz, 1H), 4-((5-fluoro-2,3-dihydrobenzo[b][1,4]dioxin-6-yl)oxy) piperidin-1-ium 2,2,2-trifluoroacetate (Intermediate BE): To a vial were added tert-butyl 4-[(5-fluoro-2,3-dihydro-1,4-benzodioxin-6-yl)oxy]piperidine-1-carboxylate (176 mg), trifluoroacetic acid (0.5 mL), and DCM (2.5 mL). After 1 h at rt, the reaction was concentrated in vacuo, and co-evaporated with DCM (2×) to afford the title compound (202 mg). $^1$H NMR (400 MHz, MeOD) δ 6.63 (dd, J=9.1, 7.8 Hz, 1H), 6.58 (dd, J=9.2, 1.6 Hz, 1H), 4.48-4.44 (m, 1H), 4.28-4.26 (m, 2H), 4.23-4.21 (m, 2H), 3.44-3.37 (m, 2H), 3.22-3.17 (m, 2H), 2.14-2.05 (m, 2H), 2.04-1.97 (m, 2H); ES-MS [M+1]$^+$: 254.

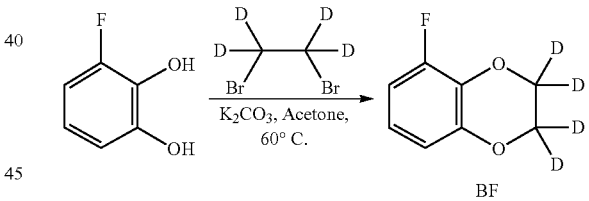

2,2,3,3-Tetradeuterio-5-fluoro-1,4-benzodioxine (Intermediate BF): To a solution of 3-fluorocatechol (2.0 g) in acetone (52 mL) were added potassium carbonate (6.6 g), followed by 1,2-dibromoethane-D$_4$ (1.43 mL). The reaction was heated at 60° C. for 18 h. The reaction was filtered over Celite and the filtrate was concentrated. The crude residue was purified by flash chromatography on silica gel (0-40% EtOAc/Hexanes) to afford the title compound (1.54 g). $^1$H NMR (400 MHz, CDCl$_3$) δ 6.76-6.70 (m, 1H), 6.69-6.64 (m, 2H).

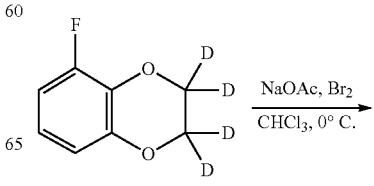

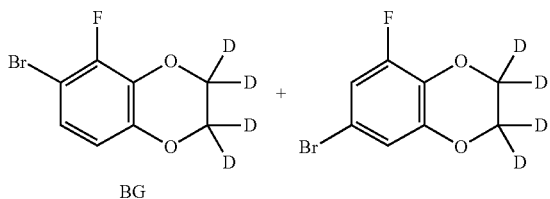

6-Bromo-2,2,3,3-tetradeuterio-5-fluoro-1,4-benzodioxine (Intermediate BG): To a solution of 2,2,3,3-tetradeuterio-5-fluoro-1,4-benzodioxine (500 mg) and sodium acetate (394 mg) in chloroform (5.3 mL) at 0° C. was added dropwise bromine (162 μL). The ice bath was removed and the reaction stirred at rt for 2 h. The reaction was treated with saturated $NaS_2O_5$, extracted with DCM (3×), passed through a phase separator, and concentrated. The crude residue was purified by flash chromatography on silica gel (0-20% EtOAc/Hexanes) to afford the title compound (660 mg; 3:1 mixture of regioisomers). Major regioisomer (Intermediate BG): $^1$H NMR (400 MHz, $CDCl_3$) δ 6.96 (dd, J=9.0, 7.0 Hz, 1H), 6.59 (dd, J=9.0, 2.0, 1H).

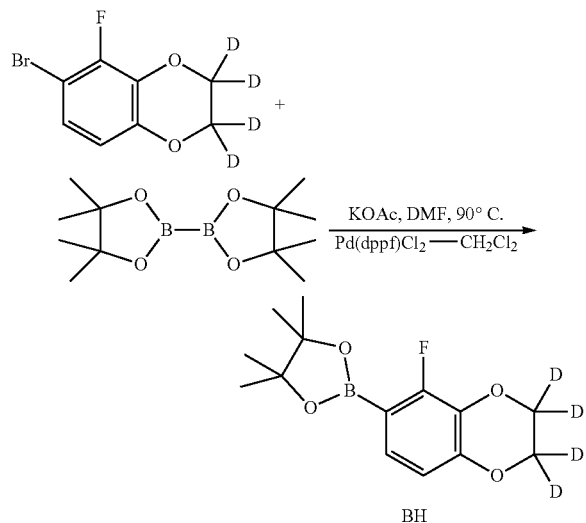

4,4,5,5-Tetramethyl-2-(2,2,3,3-tetradeuterio-5-fluoro-1,4-benzodioxin-6-yl)-1,3,2-dioxaborolane (Intermediate BH): To a vial were added bis(pinacolato)diboron (848 mg), 6-bromo-2,2,3,3-tetradeuterio-5-fluoro-1,4-benzodioxine (660 mg), dichloro[1,1'-bis(diphenylphosphino)-ferrocene] palladium(II) dichloromethane adduct (114 mg), and potassium acetate (820 mg) in DMF (9.3 mL). After the reaction was degassed, the reaction was heated to 90° C. for 18 h. The reaction was allowed to cool to room temperature and diluted with EtOAc, filtered through Celite and the filtrate was washed with water (3×), brine (2×), dried ($MgSO_4$), filtered, and concentrated. The crude residue was purified by flash chromatography on silica gel (0-40% EtOAc/Hexanes) to afford the title compound (494 mg). $^1$H NMR (400 MHz, $CDCl_3$) δ 7.16 (dd, J=8.4, 6.1 Hz, 1H), 6.64 (dd, J=8.3, 1.4 Hz, 1H), 1.33 (s, 12H); ES-MS [M+1]$^+$: 285.

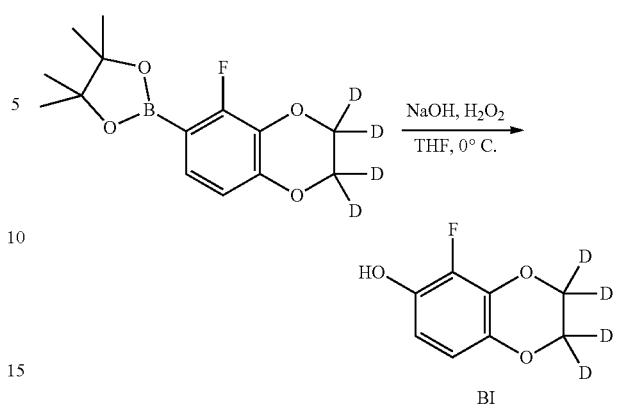

2,2,3,3-Tetradeuterio-5-fluoro-1,4-benzodioxin-6-ol (Intermediate BI): To a solution of 4,4,5,5-tetramethyl-2-(2,2,3,3-tetradeuterio-5-fluoro-1,4-benzodioxin-6-yl)-1,3,2-dioxaborolane (494 mg) in a mixture of sodium hydroxide solution (5.2 mL, 1M) and THF (6.7 mL) at 0° C. was added hydrogen peroxide (160 μL, 30% w/w). After the reaction stirred at room temperature for 1 h, the pH was adjusted to 3 with 1M HCl aqueous solution. The aqueous layer was extracted with EtOAc (3×) and the combined organic layers were washed with water, brine, dried ($MgSO_4$), filtered, and concentrated. The crude residue was purified by flash chromatography on silica gel (0-40% EtOAc/Hexanes) to afford the title compound (116 mg). $^1$H NMR (400 MHz, $CDCl_3$) δ 6.55 (dd, J=9.1, 2.1 Hz, 1H), 6.47 (t, J=8.8 Hz, 1H), 4.27 (s, 1H); ES-MS [M+1]$^+$: 175.

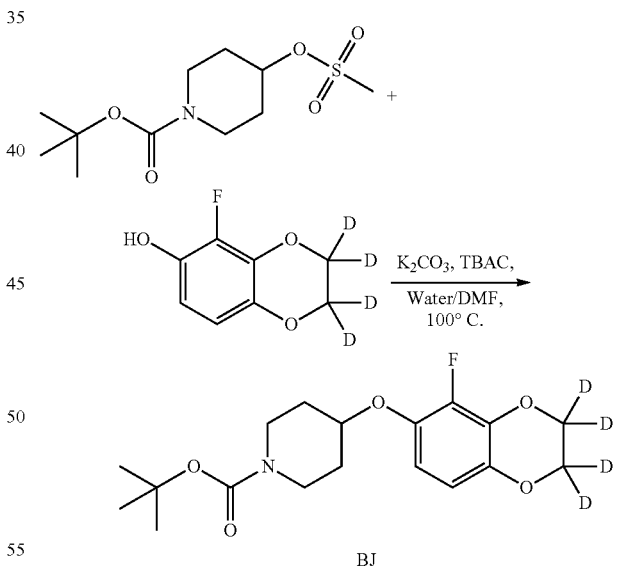

tert-Butyl 4-[(2,2,3,3-tetradeuterio-5-fluoro-1,4-benzodioxin-6-yl)oxy]piperidine-1-carboxylate (Intermediate BJ): To a vial were added tert-butyl 4-methylsulfonyloxypiperidine-1-carboxylate (369 mg), 2,2,3,3-tetradeuterio-5-fluoro-1,4-benzodioxin-6-ol (115 mg), potassium carbonate (278 mg), and tetrabutylammonium chloride (37 mg) in water (2.0 mL) and DMF (0.1 mL). The vial was sealed and heated at 100° C. for 18 h. The reaction was cooled, diluted with EtOAc and washed with water, saturated $NaHCO_3$ solution, brine (2×), and the organic layer was dried ($MgSO_4$), filtered, and concentrated. The crude residue was purified by flash chromatography on silica gel (0-40% EtOAc/Hexanes) to afford the title compound (124 mg). ¹H NMR (400 MHz, CDCl₃) δ 6.56 (dd, J=9.1, 1.9 Hz, 1H), 6.50 (dd, J=9.1, 7.9 Hz, 1H), 4.26 (m, 1H), 3.77-3.71 (m, 2H), 3.29-3.23 (m, 2H), 1.91-1.85 (m, 2H), 1.78-1.70 (m, 2H), 1.47 (s, 9H); ES-MS [M+1]⁺: 358.

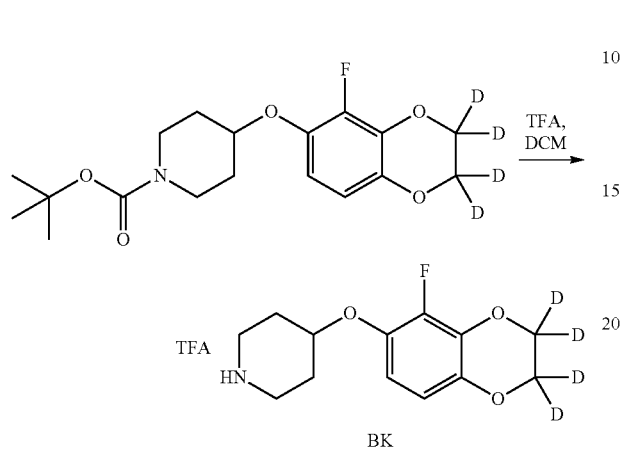

4-[(2,2,3,3-Tetradeuterio-5-fluoro-1,4-benzodioxin-6-yl) oxy]piperidine; 2,2,2-trifluoroacetic acid (Intermediate BK): To a vial were added tert-butyl 4-[(5-fluoro-2,3-dihydro-1, 4-benzodioxin-6-yl)oxy]piperidine-1-carboxylate (124 mg), trifluoroacetic acid (0.3 mL), and DCM (1.7 mL). After 1 h at rt, the reaction was concentrated in vacuo, and co-evaporated with with DCM (2×) to afford the title compound (158 mg). ¹H NMR (400 MHz, CD₃OD) δ 6.63 (dd, J=9.1, 7.8 Hz, 1H), 6.58 (dd, J=9.2, 1.6 Hz, 1H), 4.49-4.44 (m, 1H), 3.43-3.37 (m, 2H), 3.22-3.17 (m, 2H), 2.13-1.98 (m, 4H); ES-MS [M+1]⁺: 258.

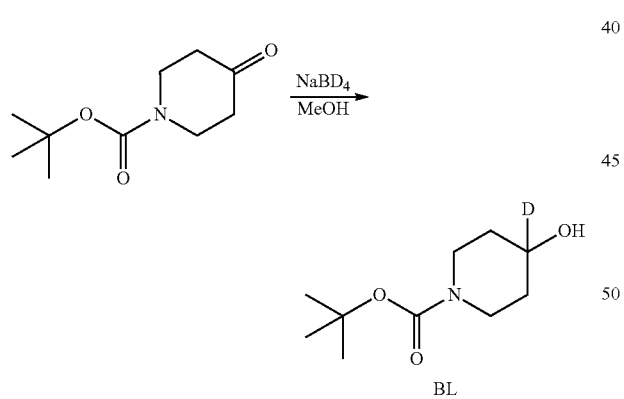

tert-Butyl 4-deuterio-4-hydroxy-piperidine-1-carboxylate (Intermediate BL): To a 0° C. solution of 1-tert-butyl-4-piperidone (10 g, 50 mmol) in methanol (250 mL) was added sodium borodeuteride (3.2 mL, 100 mmol). The resulting mixture was stirred for 4 h at room temperature. The reaction was quenched with saturated NH₄Cl (aq) and extracted with EtOAc (3×). The combined organic layers were dried (MgSO₄), filtered, and concentrated to afford the title compound 10 g (99%). ¹H NMR (400 MHz, CDCl₃) δ 3.85 (d, J=12.4 Hz, 2H), 3.06-3.00 (m, 2H), 1.87-1.82 (m, 2H), 1.48-1.42 (m, 2H), 1.46 (s, 9H).

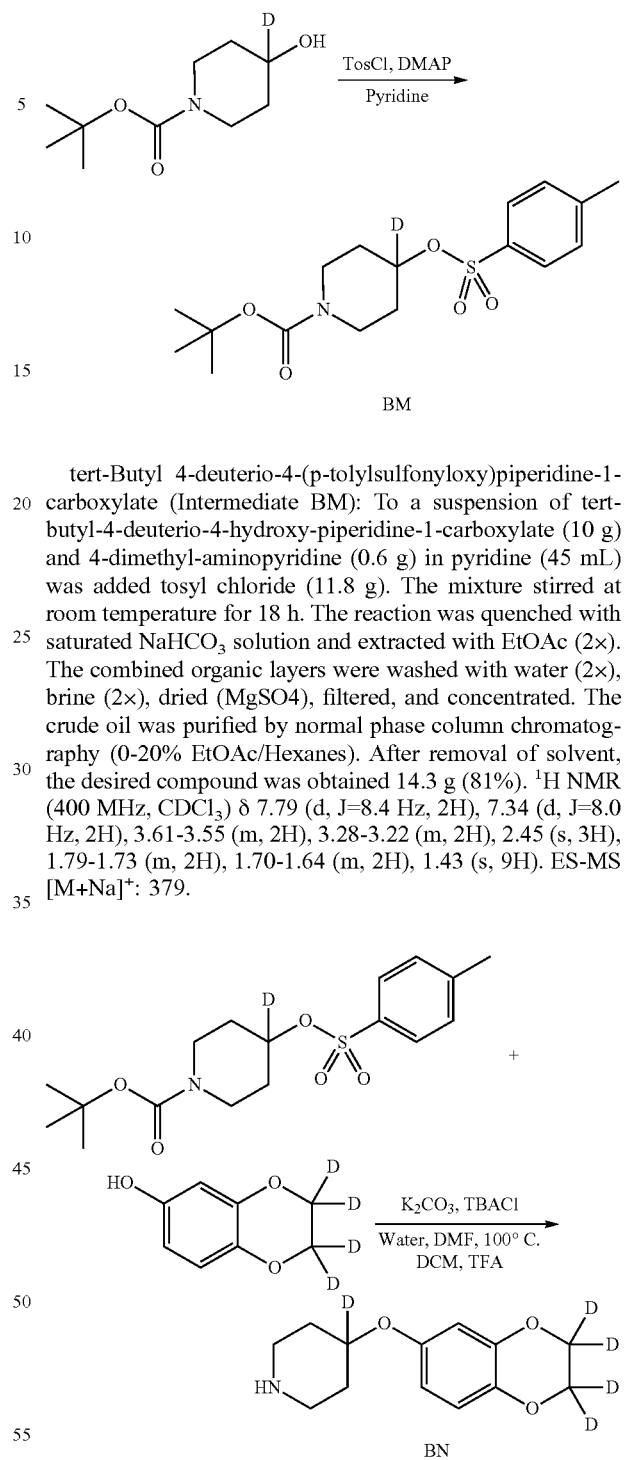

tert-Butyl 4-deuterio-4-(p-tolylsulfonyloxy)piperidine-1-carboxylate (Intermediate BM): To a suspension of tert-butyl-4-deuterio-4-hydroxy-piperidine-1-carboxylate (10 g) and 4-dimethyl-aminopyridine (0.6 g) in pyridine (45 mL) was added tosyl chloride (11.8 g). The mixture stirred at room temperature for 18 h. The reaction was quenched with saturated NaHCO₃ solution and extracted with EtOAc (2×). The combined organic layers were washed with water (2×), brine (2×), dried (MgSO4), filtered, and concentrated. The crude oil was purified by normal phase column chromatography (0-20% EtOAc/Hexanes). After removal of solvent, the desired compound was obtained 14.3 g (81%). ¹H NMR (400 MHz, CDCl₃) δ 7.79 (d, J=8.4 Hz, 2H), 7.34 (d, J=8.0 Hz, 2H), 3.61-3.55 (m, 2H), 3.28-3.22 (m, 2H), 2.45 (s, 3H), 1.79-1.73 (m, 2H), 1.70-1.64 (m, 2H), 1.43 (s, 9H). ES-MS [M+Na]⁺: 379.

4-Deuterio-4-[(2,2,3,3-tetradeuterio-1,4-benzodioxin-6-yl)oxy]piperidine (Intermediate BN): To a round bottom flask were added 2,2,3,3-tetradeuterio-1,4-benzodioxin-6-ol (1.0 g, 6.7 mmol), tert-butyl 4-deuterio-4-(p-tolylsulfonyloxy)piperidine-1-carboxylate (2.0 g, 5.6 mmol), potassium carbonate (2.4 g, 16.8 mmol), and tetrabutylammonium chloride (0.31 g, 1.1 mmol) in water (25 mL) and DMF (1.3 mL). The reaction was heated at reflux for 18 h. The reaction was diluted with 3:1 CHCl₃/IPA and the layers were separated. The aqueous was extracted with 3:1 CHCl₃/IPA (2×)

and the combined organic layers were washed with water, brine, then dried (MgSO₄), filtered, and concentrated. The crude oil was purified by normal phase column chromatography (0-20% EtOAc/Hexanes). After the removal of solvent, the oil was dissolved in DCM (9 mL) followed by addition of trifluoroacetic acid (2.1 mL, 28 mmol). After 1 h, the solvents were removed in vacuo. The residue was dissolved in MeOH and loaded onto SCX Cartridge. The cartridge was rinsed with MeOH and 7N NH₃/MeOH solution. The solvents were removed to afford the title compound 725 mg (53%). ¹H NMR (400 MHz, CDCl₃) δ 6.75 (d, J=8.7, 1H), 6.45 (d, J=2.8, 1H), 6.41 (dd, J=8.8, 2.9 Hz, 1H), 3.21-3.15 (m, 2H), 2.87-2.81 (m, 2H), 2.07-2.00 (m, 2H), 1.78-1.72 (m, 2H). ES-MS [M+1]⁺: 241.

(2R,4S)-4-((2,3-Dihydrobenzo[b][1,4]dioxin-6-yl-2,2,3,3-d₄)oxy)-2-methylpiperidine (Intermediate BP): To a solution of tert-butyl (2R,4S)-4-((2,3-dihydrobenzo[b][1,4]dioxin-6-yl-2,2,3,3-d₄)oxy)-2-methylpiperidine-1-carboxylate (3.7 g) in DCM (20 mL) was added TFA (4 mL) and the reaction was stirred at 20° C. for 3 hours. The reaction was quenched with sat. aq. Na₂CO₃ to pH 8~9 at 0° C. and extracted with DCM (20 mL×2). The combined organic layers were washed with brine (20 mL), dried over Na₂SO₄ and concentrated to give (2R,4S)-4-((2,3-dihydrobenzo[b][1,4]dioxin-6-yl-2,2,3,3-d₄)oxy)-2-methylpiperidine (2.6 g, crude). ES-MS [M+1]⁺: 254.2.

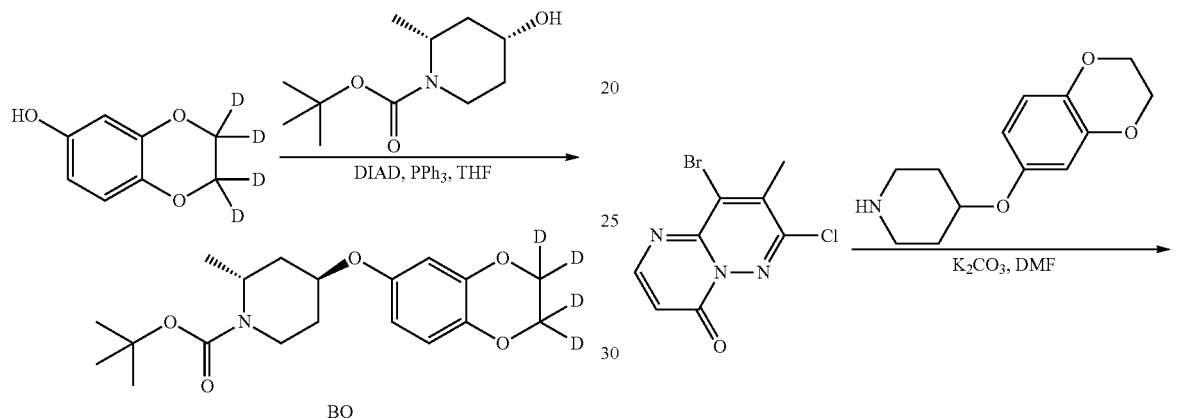

BO tert-butyl (2R,4S)-4-((2,3-Dihydrobenzo[b][1,4]dioxin-6-yl-2,2,3,3-d₄)oxy)-2-methylpiperidine-1-carboxylate (Intermediate BO): To a mixture of 2,3-dihydrobenzo[b][1,4]dioxin-2,2,3,3-d₄-6-ol (5 g, 32.02 mmol), (2R,4R)-tert-butyl 4-hydroxy-2-methylpiperidine-1-carboxylate (6.89 g) and PPh₃ (10.93 g) in THF (100 mL) was added slowly DIAD (8.1 mL) at 20° C. and the reaction was stirred at 20° C. for 16 hours. The reaction was concentrated and the residue was purified by Combi Flash (silica gel, from 0 to 30%, ethyl acetate in petroleum ether) to give tert-butyl (2R,4S)-4-((2,3-dihydrobenzo[b][1,4]dioxin-6-yl-2,2,3,3-d₄)oxy)-2-methylpiperidine-1-carboxylate (3.7 g). ¹H NMR (400 MHz, CDCl₃) δ 6.77 (d, J=8.8 Hz, 1H), 6.46 (s, 1H), 6.42 (dd, J=8.8 Hz, 1.6 Hz, 1H), 4.61-4.46 (m, 1H), 4.41-4.31 (m, 1H), 4.13-4.06 (m, 1H), 2.96-2.89 (m, 1H), 2.14-2.04 (m, 1H), 2.01-1.90 (m, 1H), 1.74-1.64 (m, 1H), 1.52-1.42 (s, 10H), 1.19 (d, J=7.2 Hz, 3H).

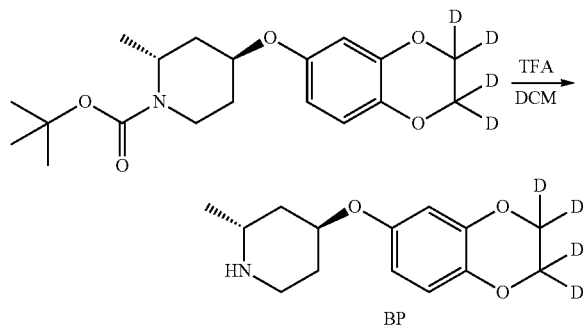

BP

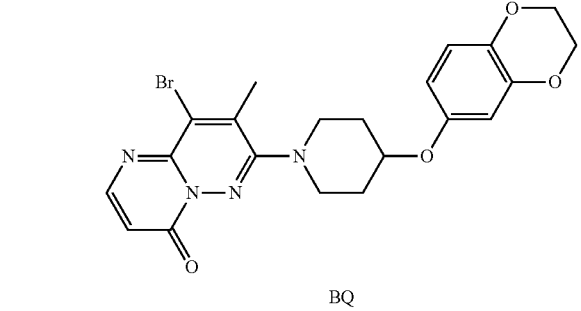

BQ

9-Bromo-7-(4-((2,3-dihydrobenzo[b][1,4]dioxin-6-yl)oxy)piperidin-1-yl)-8-methyl-4H-pyrimido[1,2-b]pyridazin-4-one (Intermediate BQ): To a solution of 9-bromo-7-chloro-8-methyl-4H-pyrimido[1,2-b]pyridazin-4-one (2.27 g) in DMF (30 mL) was added 4-((2,3-dihydrobenzo[b][1,4]dioxin-6-yl)oxy)piperidine (1.98 g) and K₂CO₃ (1.14 g). The mixture was stirred at 25° C. for 16 hours. The reaction mixture was concentrated and the residue was purified by flash silica gel chromatography (ISCO®; 220 g SepaFlash® Silica Flash Column, Eluent of 0~100% Ethyl acetate/Petroleum ether gradient @ 100 mL/min) to afford 9-bromo-7-(4-((2,3-dihydrobenzo[b][1,4]dioxin-6-yl)oxy)piperidin-1-yl)-8-methyl-4H-pyrimido[1,2-b]pyridazin-4-one (750 mg). ¹H NMR (400 MHz, CDCl₃) δ 8.22 (d, J=6.4 Hz, 1H), 6.79 (d, J=8.8 Hz, 1H), 6.60 (d, J=6.0 Hz, 1H), 6.51-6.44 (m, 2H), 4.43-4.39 (m, 1H), 4.28-4.20 (m, 4H), 3.64-3.54 (m, 2H), 3.30-3.20 (m, 2H), 2.56 (s, 3H), 2.20-2.09 (m, 2H), 2.04-1.93 (m, 2H).

b. Exemplified Compounds of the Invention

Example 1. 7-(4-((2,3-Dihydrobenzo[b][1,4]dioxin-6-yl-2,2,3,3-d4)oxy)piperidin-1-yl)-8-methyl-4H-pyrimido[1,2-b]pyridazin-4-one (Compound 1)

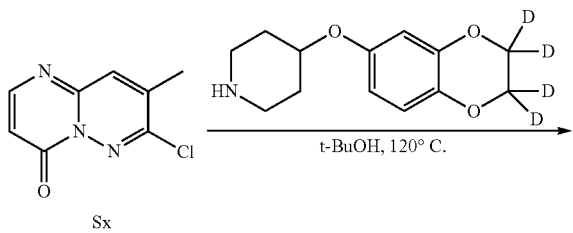

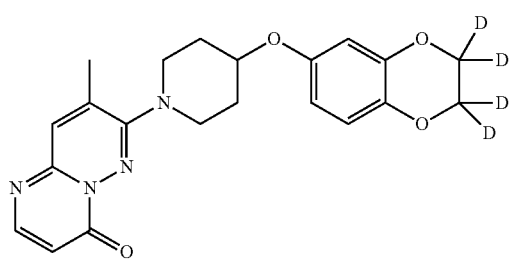

Compound 1

To a solution of 7-chloro-8-methyl-pyrimido[1,2-b]pyridazin-4-one (15 mg,) in t-butanol (1 mL) was added N,N-diisopropylethylamine (67 µL) and 4-((2,3-dihydrobenzo[b][1,4]dioxin-6-yl-2,2,3,3-d$_4$)oxy)piperidine (28 mg). The reaction mixture was heated to 120° C. for 18 hours. The crude product was dissolved in DMSO (1 mL) and purified by reverse-phase chromatography using Gilson HPLC (30×100 mm column, 10-55% ACN/0.05% aqueous NH$_4$OH, 8 min run). Fractions containing product were concentrated to give the title compound as a solid 15 mg.

$^1$H NMR (400 MHz, DMSO) δ 8.11 (d, J=6.3 Hz, 1H), 7.74 (q, J=1.2 Hz, 1H), 6.76 (d, J=8.8 Hz, 1H), 6.54 (d, J=2.8 Hz, 1H), 6.49 (dd, J=8.8, 2.9 Hz, 1H), 6.40 (d, J=6.3 Hz, 1H), 4.50 (hept, J=3.8 Hz, 1H), 3.64-3.46 (m, 2H), 3.21-3.10 (m, 2H), 2.42 (d, J=1.2 Hz, 3H), 2.10-2.01 (m, 2H), 1.84-1.71 (m, 2H). ES-MS [M+1]$^+$: 399.

Example 2. 7-(4-((2,3-Dihydrobenzo[b][1,4]dioxin-6-yl-2,2,3,3-d4)oxy)piperidin-1-yl)-8,9-dimethyl-4H-pyrimido[1,2-b]pyridazin-4-one (Compound 2)

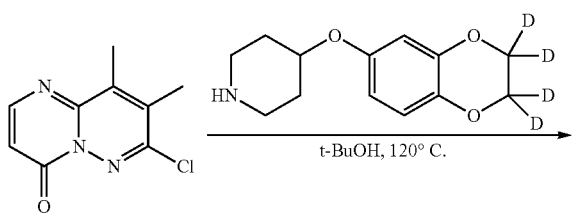

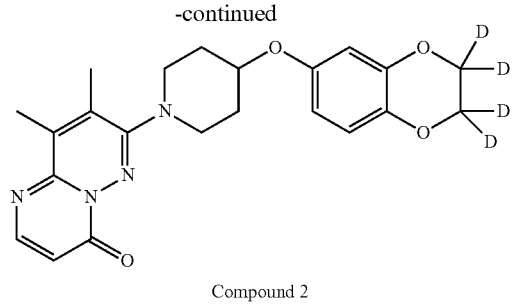

Compound 2

To a solution of 7-chloro-8,9-dimethyl-pyrimido[1,2-b]pyridazin-4-one (10 mg) and 4-[(2,2,3,3-tetradeuterio-1,4-benzodioxin-6-yl)oxy]piperidine (17 mg) in t-butanol (1 mL) was added N,N-diisopropylethylamine (42 µL). The mixture was heated to 120° C. for 18 hours. The solvent was removed and the crude product was dissolved in DMSO (2 mL) and purified by reverse-phase chromatography using Gilson HPLC (30×100 mm column, 25-60% ACN/0.05% aqueous NH$_4$OH, 8 min run). Fractions containing product were concentrated to give the title compound as a solid (11 mg; 53% yield). $^1$H NMR (400 MHz, CDCl$_3$) δ 8.15 (d, J=6.3 Hz, 1H), 6.78 (d, J=8.7 Hz, 1H), 6.55 (d, J=6.3 Hz, 1H), 6.49 (d, J=2.8 Hz, 1H), 6.45 (dd, J=8.7, 2.9 Hz, 1H), 4.38 (hept, J=3.7 Hz, 1H), 3.61-3.46 (m, 2H), 3.24-3.14 (m, 2H), 2.53 (d, J=0.5 Hz, 3H), 2.37 (d, J=0.5 Hz, 3H), 2.19-2.09 (m, 2H), 2.02-1.90 (m, 2H). ES-MS [M+1]$^+$: 413.

Example 3. 7-(4-((2,3-Dihydrobenzo[b][1,4]dioxin-6-yl-2,2,3,3-d4)oxy)piperidin-1-yl)-2,8-dimethyl-4H-pyrimido[1,2-b]pyridazin-4-one (Compound 3)

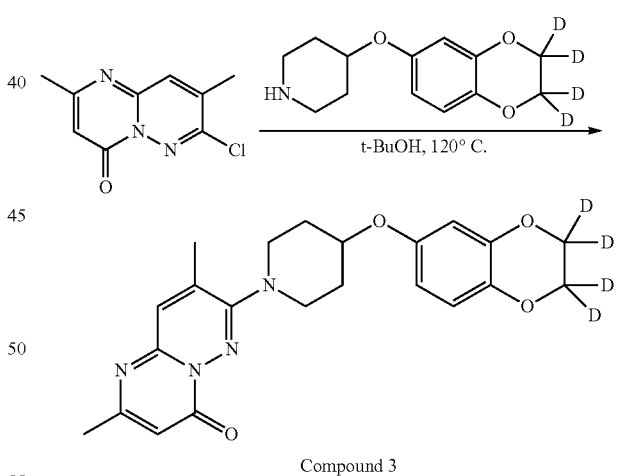

Compound 3

To a solution of 7-chloro-2,8-dimethyl-pyrimido[1,2-b]pyridazin-4-one (15 mg) and 4-[(2,2,3,3-tetradeuterio-1,4-benzodioxin-6-yl)oxy]piperidine (26 mg) t-butanol (1 mL) was added N,N-diisopropylethylamine (62 µL). The mixture was heated to 120° C. for 18 hours then cooled to room temperature and concentrated. The crude product was dissolved in DMSO (2 mL) and purified by reverse-phase chromatography using Gilson HPLC (30×100 mm column, 15-55% ACN/0.05% aqueous NH$_4$OH, 8 min run). Fractions containing product were concentrated to give the title compound as a solid (14 mg; 47% yield). $^1$H NMR (400 MHz, CDCl₃) δ 7.44 (q, J=1.0 Hz, 1H), 6.78 (d, J=8.7 Hz, 1H), 6.49 (d, J=2.8 Hz, 1H), 6.45 (dd, J=8.7, 2.9 Hz, 1H), 6.42 (s, 1H), 4.39 (hept, J=3.5 Hz, 1H), 3.66-3.55 (m, 2H), 3.30-3.19 (m, 2H), 2.43 (d, J=1.2 Hz, 3H), 2.39 (s, 3H), 2.17-2.03 (m, 2H), 2.03-1.89 (m, 2H). ES-MS [M+1]⁺: 413.

Example 4. 7-(4-((2,3-Dihydrobenzo[b][1,4]dioxin-6-yl-2,2,3,3-d4)oxy)piperidin-1-yl)-2,3,8-trimethyl-4H-pyrimido[1,2-b]pyridazin-4-one (Compound 4)

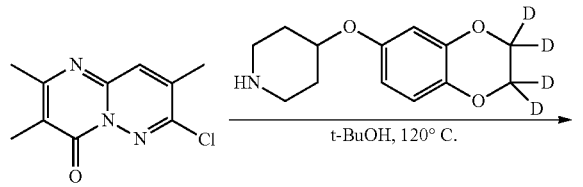

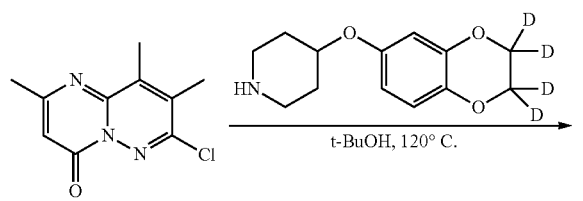

Compound 4

To a solution of 7-chloro-2,3,8-trimethyl-pyrimido[1,2-b]pyridazin-4-one (10 mg) and 4-[(2,2,3,3-tetradeuterio-1,4-benzodioxin-6-yl)oxy]piperidine (16 mg) in t-butanol (1 mL) was added N,N-diisopropylethylamine (40 μL). The mixture was heated to 120° C. for 18 hours then cooled to room temperature and concentrated. The crude product was dissolved in DMSO (2 mL) and purified by reverse-phase chromatography using Gilson HPLC (30×100 mm column, 20-60% ACN/0.05% aqueous NH₄OH, 8 min run). Fractions containing product were concentrated to give the title compound as a solid (11 mg; 56% yield). ¹H NMR (400 MHz, CDCl₃) δ 7.40 (q, J=1.2 Hz, 1H), 6.78 (d, J=8.7 Hz, 1H), 6.49 (d, J=2.8 Hz, 1H), 6.45 (dd, J=8.7, 2.8 Hz, 1H), 4.38 (hept, J=3.6 Hz, 1H), 3.65-3.55 (m, 2H), 3.29-3.18 (m, 2H), 2.42 (s, 3H), 2.40 (d, J=1.2 Hz, 3H), 2.23 (s, 3H), 2.18-2.07 (m, 2H), 2.01-1.88 (m, 2H). ES-MS [M+1]⁺: 427.

Example 5. 7-(4-((2,3-Dihydrobenzo[b][1,4]dioxin-6-yl-2,2,3,3-d4)oxy)piperidin-1-yl)-2,8,9-trimethyl-4H-pyrimido[1,2-b]pyridazin-4-one (Compound 5)

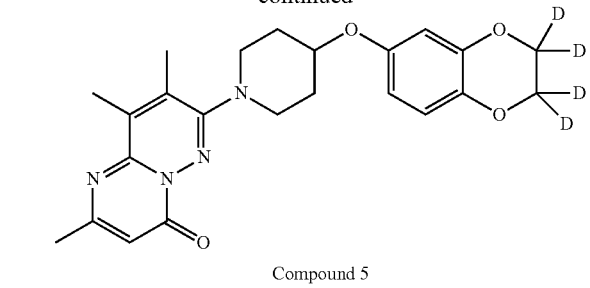

Compound 5

To a solution of 7-Chloro-2,8,9-trimethyl-pyrimido[1,2-b]pyridazin-4-one (10 mg) and 4-[(2,2,3,3-tetradeuterio-1,4-benzodioxin-6-yl)oxy]piperidine (16 mg) in t-butanol (1 mL) was added N,N-diisopropylethylamine (40 μL). The mixture was heated to 120° C. for 18 hours. Additional N,N-diisopropylethylamine (40 μL) and 4-[(2,2,3,3-tetradeuterio-1,4-benzodioxin-6-yl)oxy]piperidine (16 mg) were added and the reaction was stirred for an additional 18 hours at 120° C. The solvent was removed and the crude product was dissolved in DMSO (2 mL) and purified by reverse-phase chromatography using Gilson HPLC (30×100 mm column, 30-70% ACN/0.05% aqueous NH₄OH, 8 min run). Fractions containing product were concentrated to give the title compound as a solid (12 mg; 61% yield). ¹H NMR (400 MHz, CDCl₃) δ 6.78 (d, J=8.7 Hz, 1H), 6.49 (d, J=2.8 Hz, 1H), 6.45 (dd, J=8.7, 2.9 Hz, 1H), 6.42 (s, 1H), 4.37 (hept, J=3.7 Hz, 1H), 3.59-3.47 (m, 2H), 3.22-3.12 (m, 2H), 2.53 (s, 3H), 2.42 (s, 3H), 2.35 (s, 3H), 2.18-2.08 (m, 2H), 2.01-1.88 (m, 2H). ES-MS [M+1]⁺: 427.

Example 6. 7-(4-((2,3-Dihydrobenzo[b][1,4]dioxin-6-yl-2,2,3,3-d4)oxy)piperidin-1-yl)-8-methyl-2-(trifluoromethyl)-4H-pyrimido[1,2-b]pyridazin-4-one (Compound 6)

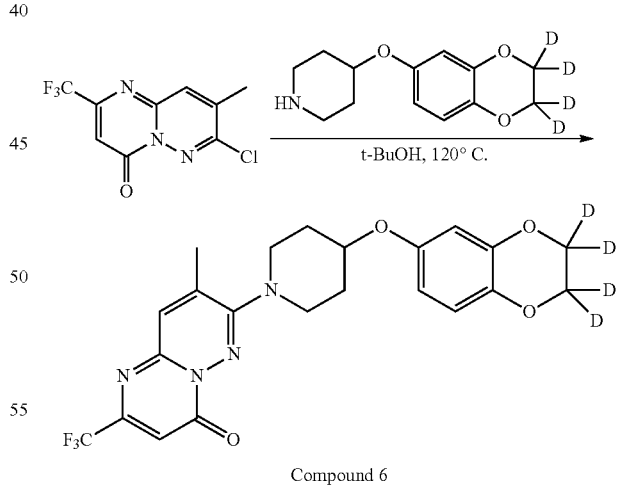

Compound 6

To a solution of 7-chloro-8-methyl-2-(trifluoromethyl)pyrimido[1,2-b]pyridazin-4-one (13 mg) and 4-[(2,2,3,3-tetradeuterio-1,4-benzodioxin-6-yl)oxy]piperidine (18 mg) in t-butanol (1 mL) was added N,N-diisopropylethylamine (43 μL). The mixture was heated to 120° C. for 18 hours then concentrated. The crude product was dissolved in DMSO (2 mL) and purified by reverse-phase chromatography using Gilson HPLC (30×100 mm column, 25-65% ACN/0.05% aqueous NH₄OH, 8 min run). Fractions containing product were concentrated to give the title compound as a solid (12 mg; 54% yield). ¹H NMR (400 MHz, CDCl₃) δ 7.62 (q, J=1.1 Hz, 1H), 6.88 (s, 1H), 6.78 (d, J=8.7 Hz, 1H), 6.49 (d, J=2.8 Hz, 1H), 6.45 (dd, J=8.7, 2.9 Hz, 1H), 4.42 (hept, J=3.4 Hz, 1H), 3.70-3.59 (m, 2H), 3.37-3.26 (m, 2H), 2.48 (d, J=1.2 Hz, 3H), 2.17-2.04 (m, 2H), 2.04-1.94 (m, 2H). ES-MS [M+1]⁺: 467.

Example 7. 7-(4-((2,3-Dihydrobenzo[b][1,4]dioxin-6-yl-2,2,3,3-d4)oxy)piperidin-1-yl)-8,9-dimethyl-2-(trifluoromethyl)-4H-pyrimido[1,2-b]pyridazin-4-one (Compound 7)

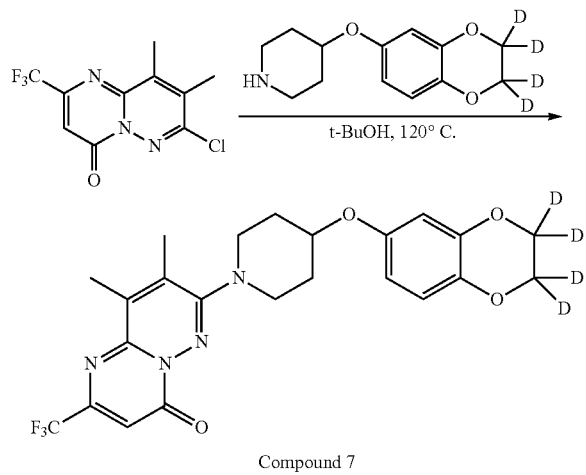

Compound 7

To a solution of 7-chloro-8,9-dimethyl-2-(trifluoromethyl)pyrimido[1,2-b]pyridazin-4-one (10 mg) and 4-[(2,2,3,3-tetradeuterio-1,4-benzodioxin-6-yl)oxy]piperidine (13 mg) in t-butanol (1 mL) was added N,N-diisopropylethylamine (32 μL). The mixture was heated to 120° C. for 18 hours. The solvent was removed and the crude product was dissolved in DMSO (2 mL) and purified by reverse-phase chromatography using Gilson HPLC (30×100 mm column, 25-65% ACN/0.05% aqueous NH₄OH, 8 min run). Fractions containing product were concentrated to give the title compound as a solid (15.5 mg; 90% yield). ¹H NMR (400 MHz, CDCl₃) δ 6.92 (s, 1H), 6.79 (d, J=8.7 Hz, 1H), 6.50 (d, J=2.8 Hz, 1H), 6.46 (dd, J=8.8, 2.9 Hz, 1H), 4.39 (hept, J=3.6 Hz, 1H), 3.51-3.37 (m, 2H), 3.14-3.03 (m, 2H), 2.48 (d, J=0.6 Hz, 3H), 2.34 (d, J=0.6 Hz, 3H), 2.15-2.03 (m, 2H), 2.01-1.88 (m, 2H). ES-MS [M+1]⁺: 481.

Example 8. 2-(Difluoromethyl)-7-(4-((2,3-dihydrobenzo[b][1,4]dioxin-6-yl-2,2,3,3-d4)oxy)piperidin-1-yl)-8-methyl-4H-pyrimido[1,2-b]pyridazin-4-one (Compound 8)

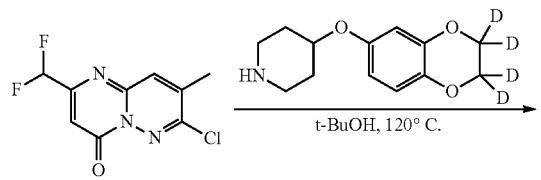

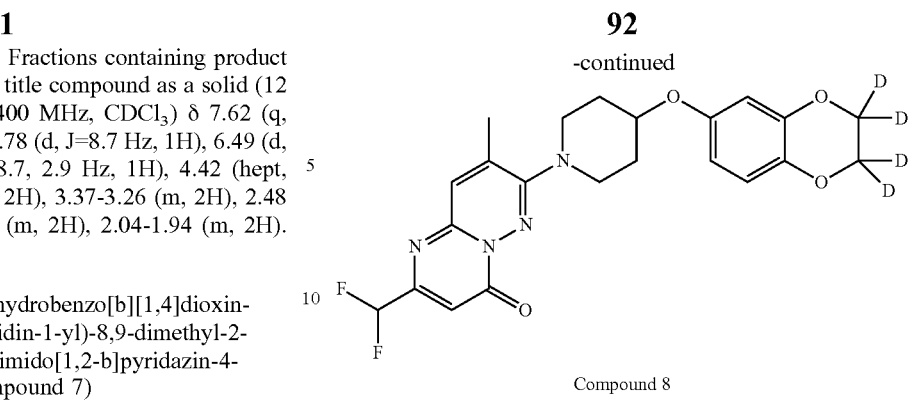

Compound 8

To a solution of 7-chloro-2-(difluoromethyl)-8-methylpyrimido[1,2-b]pyridazin-4-one (10 mg) and 4-[(2,2,3,3-tetradeuterio-1,4-benzodioxin-6-yl)oxy]piperidine (15 mg) in t-butanol (1 mL) was added N,N-diisopropylethylamine (36 μL). The mixture was heated to 120° C. for 18 hours. The solvent was removed and crude product was dissolved in DMSO (2 mL) and purified by reverse-phase chromatography using Gilson HPLC (30×100 mm column, 20-60% ACN/0.05% aqueous NH₄OH, 8 min run). Fractions containing product were concentrated to give the title compound as a solid (13 mg; 70% yield). ¹H NMR (400 MHz, CDCl₃) δ 7.56 (q, J=1.2 Hz, 1H), 6.80 (d, J=8.8 Hz, 1H), 6.78 (d, J=8.7 Hz, 1H), 6.49 (d, J=2.8 Hz, 1H), 6.45 (dd, J=8.8, 2.8 Hz, 1H), 6.44 (t, J=55.0 Hz, 1H), 4.41 (hept, J=3.5 Hz, 1H), 3.69-3.58 (m, 2H), 3.35-3.24 (m, 2H), 2.47 (d, J=1.2 Hz, 3H), 2.18-2.07 (m, 2H), 2.04-1.91 (m, 2H). ES-MS [M+1]⁺: 449.

Example 9. 2-(Difluoromethyl)-7-(4-((2,3-dihydrobenzo[b][1,4]dioxin-6-yl-2,2,3,3-d4)oxy)piperidin-1-yl)-8,9-dimethyl-4H-pyrimido[1,2-b]pyridazin-4-one (Compound 9)

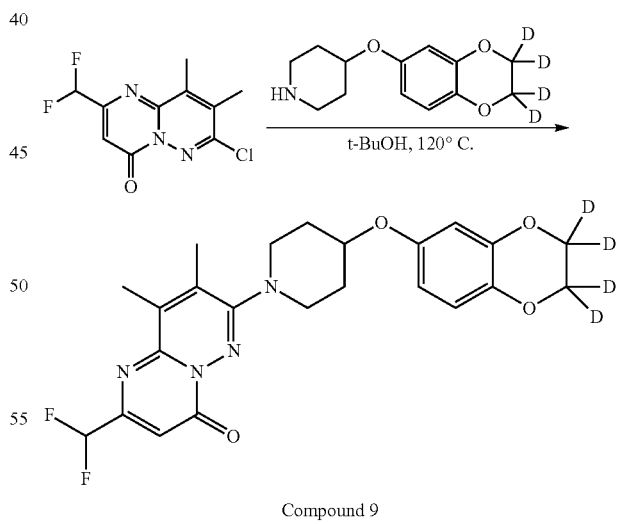

Compound 9

To a solution of 7-chloro-2-(difluoromethyl)-8,9-dimethyl-pyrimido[1,2-b]pyridazin-4-one (10 mg) and 4-[(2,2,3,3-tetradeuterio-1,4-benzodioxin-6-yl)oxy]piperidine (14 mg) in t-butanol (1 mL) was added N,N-diisopropylethylamine (34 μL). The mixture was heated to 120° C. for 18 hours. The solvent was removed and the crude product was dissolved in DMSO (2 mL) and purified by reverse-phase chromatography using Gilson HPLC (30×100 mm column, 30-70% ACN/0.05% aqueous NH₄OH, 8 min run). Fractions containing product were concentrated to give the title compound as a solid (14 mg; 76% yield). $^1$H NMR (400 MHz, CDCl$_3$) δ 6.82 (s, 1H), 6.78 (d, J=8.7 Hz, 1H), 6.53 (t, J=55.0 Hz, 1H), 6.49 (d, J=2.8 Hz, 1H), 6.45 (dd, J=8.7, 2.9 Hz, 1H), 4.39 (hept, J=3.5 Hz, 1H), 3.62-3.52 (m, 2H), 3.32-3.13 (m, 2H), 2.54 (s, 3H), 2.38 (s, 3H), 2.21-2.08 (m, 2H), 2.05-1.90 (m, 2H). ES-MS [M+1]$^+$: 463.

Example 10. 2-Cyclopropyl-7-(4-((2,3-dihydrobenzo[b][1,4]dioxin-6-yl-2,2,3,3-d4)oxy)piperidin-1-yl)-8-methyl-4H-pyrimido[1,2-b]pyridazin-4-one (Compound 10)

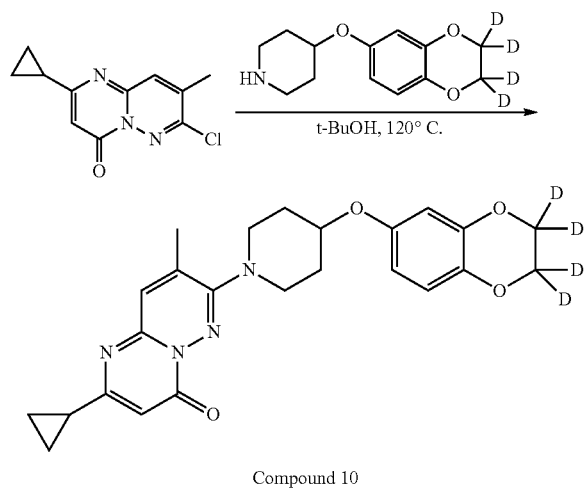

Compound 10

To a solution of 7-chloro-2-cyclopropyl-8-methyl-pyrimido[1,2-b]pyridazin-4-one (10 mg) and 4-[(2,2,3,3-tetradeuterio-1,4-benzodioxin-6-yl)oxy]piperidine (15 mg) in t-butanol (1 mL) was added N,N-diisopropylethylamine (37 μL). The mixture was heated to 120° C. for 18 hours. The solvent was removed and the crude product was dissolved in DMSO (2 mL) and purified by reverse-phase chromatography using Gilson HPLC (30×100 mm column, 25-65% ACN/0.05% aqueous NH₄OH, 8 min run). Fractions containing product were concentrated to give the title compound as a solid (8.4 mg; 45% yield). $^1$H NMR (400 MHz, CDCl$_3$) δ 7.39 (q, J=1.2 Hz, 1H), 6.78 (d, J=8.7 Hz, 1H), 6.49 (d, J=2.8 Hz, 1H), 6.45 (dd, J=8.7, 2.9 Hz, 1H), 6.41 (s, 1H), 4.37 (hept, J=3.7 Hz, 1H), 3.64-3.53 (m, 2H), 3.27-3.17 (m, 2H), 2.40 (d, J=1.2 Hz, 3H), 2.17-2.05 (m, 2H), 2.03-1.91 (m, 2H), 1.90-1.82 (m, 1H), 1.13-1.04 (m, 2H), 1.03-0.95 (m, 2H). ES-MS [M+1]$^+$: 439.

Example 11. 7-(4-((2,3-Dihydrobenzo[b][1,4]dioxin-6-yl-2,2,3,3-d4)oxy)piperidin-1-yl)-2-ethyl-8,9-dimethyl-4H-pyrimido[1,2-b]pyridazin-4-one (Compound 11)

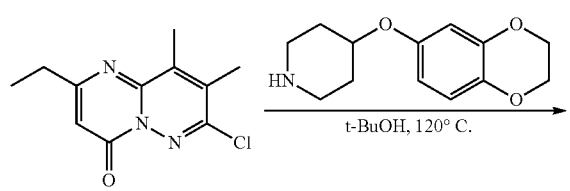

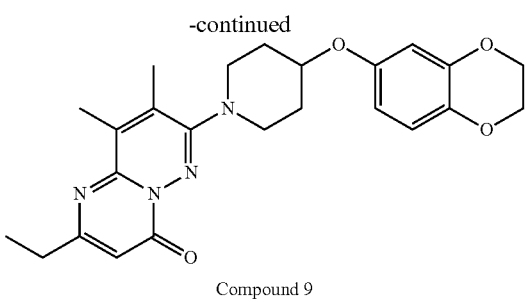

Compound 9

To a solution of 7-chloro-2-ethyl-8,9-dimethyl-pyrimido[1,2-b]pyridazin-4-one (15 mg) and 4-(2,3-dihydro-1,4-benzodioxin-6-yloxy)piperidine (28 mg) in t-butanol (0.5 mL) was added N,N-diisopropylethylamine (55 μL). The mixture was heated to 120° C. for 18 hours. The solvent was removed and the crude product was dissolved in DMSO (1 mL) and purified by reverse-phase chromatography using Gilson HPLC (30×100 mm column, 30-75% ACN/0.1% aqueous TFA, 8 min run). Fractions containing product were basified with saturated NaHCO₃, and extracted with 4:1 chloroform/IPA. The organic extracts were passed through a phase separator and concentrated to give the title compound as a solid (11 mg; 41% yield). $^1$H NMR (400 MHz, CDCl$_3$) δ 6.77 (d, J=8.7 Hz, 1H), 6.49 (d, J=2.8 Hz, 1H), 6.45 (dd, 1H), 6.44 (s, 1H), 4.36 (hept, J=3.7 Hz, 1H), 4.27-4.23 (m, 2H), 4.23-4.19 (m, 2H), 3.59-3.48 (m, 2H), 3.22-3.11 (m, 2H), 2.67 (q, J=7.5 Hz, 2H), 2.52 (s, 3H), 2.35 (s, 3H), 2.21-2.08 (m, 2H), 2.05-1.87 (m, 2H), 1.29 (t, J=7.6 Hz, 3H). ES-MS [M+1]$^+$: 437.

Example 12. 7-(4-((2,3-Dihydrobenzo[b][1,4]dioxin-6-yl)oxy)piperidin-1-yl)-2-isopropyl-8,9-dimethyl-4H-pyrimido[1,2-b]pyridazin-4-one (Compound 12)

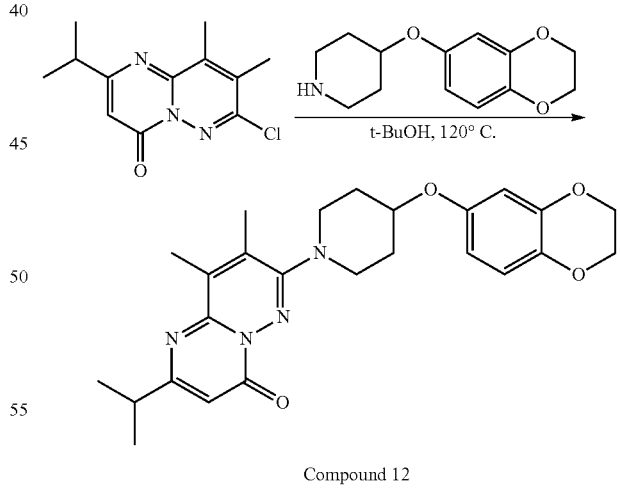

Compound 12

To a solution of 7-chloro-2-isopropyl-8,9-dimethyl-pyrimido[1,2-b]pyridazin-4-one (15 mg) and 4-(2,3-dihydro-1,4-benzodioxin-6-yloxy)piperidine (28 mg) in t-butanol (0.5 mL) was added N,N-diisopropylethylamine (52 μL). The mixture was heated to 120° C. for 18 hours. The solvent was removed and the crude product was dissolved in DMSO (1 mL) and purified by reverse-phase chromatography using Gilson HPLC (30×100 mm column, 20-65% ACN/0.1% aqueous TFA, 8 min run). Fractions containing product were basified with saturated NaHCO$_3$, and extracted with 4:1 chloroform/IPA. The organic extracts were passed through a phase separator and concentrated to give the title compound as a solid (21 mg; 79% yield). $^1$H NMR (400 MHz, CDCl$_3$) δ 6.79 (d, J=8.7 Hz, 1H), 6.50 (d, J=2.8 Hz, 1H), 6.46 (dd, 1H), 6.45 (s, 1H), 4.39 (tt, J=7.1, 3.6 Hz, 1H), 4.28-4.24 (m, 2H), 4.23-4.20 (m, 2H), 3.66 (hept, J=6.9 Hz, 1H), 3.43-3.32 (m, 2H), 3.10-2.97 (m, 2H), 2.49 (s, 3H), 2.32 (s, 3H), 2.24-2.06 (m, 2H), 2.04-1.90 (m, 2H), 1.31 (s, 3H), 1.29 (s, 3H). ES-MS [M+1]$^+$: 451.

Example 13. 7-(4-((2,3-Dihydrobenzo[b][1,4]dioxin-6-yl)oxy)piperidin-1-yl)-2-(methoxymethyl)-8,9-dimethyl-4H-pyrimido[1,2-b]pyridazin-4-one (Compound 13)

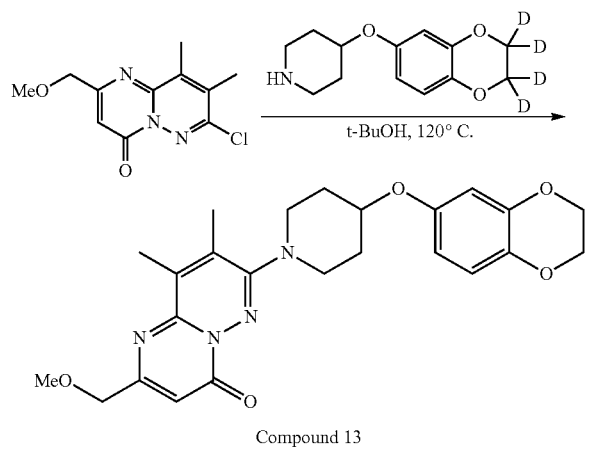

Compound 13

To a solution of 7-chloro-2-(methoxymethyl)-8,9-dimethyl-pyrimido[1,2-b]pyridazin-4-one (15 mg) and 4-(2,3-dihydro-1,4-benzodioxin-6-yloxy)piperidine (28 mg) in t-butanol (0.5 mL) was added N,N-diisopropylethylamine (52 μL). The mixture was heated to 120° C. for 18 hours. The solvent was removed and the crude product was dissolved in DMSO (1 mL) and purified by reverse-phase chromatography using Gilson HPLC (30×100 mm column, 25-65% ACN/0.05% aqueous NH$_4$OH, 8 min run). Fractions containing product were concentrated to give the title compound as a solid (20 mg; 75% yield). $^1$H NMR (400 MHz, CDCl$_3$) δ 6.78 (d, J=8.7 Hz, 1H), 6.69 (s, 1H), 6.49 (d, J=2.8 Hz, 1H), 6.45 (dd, J=8.7, 2.9 Hz, 1H), 4.43 (s, 2H), 4.37 (hept, J=3.8 Hz, 1H), 4.29-4.23 (m, 2H), 4.23-4.19 (m, 2H), 3.62-3.51 (m, 2H), 3.50 (s, 3H), 3.23-3.12 (m, 2H), 2.50 (s, 3H), 2.35 (s, 3H), 2.24-2.07 (m, 2H), 2.02-1.89 (m, 2H). ES-MS [M+1]$^+$: 453.

Example 14. 7-(4-((2,3-Dihydrobenzo[b][1,4]dioxin-6-yl-2,2,3,3-d4)oxy)piperidin-1-yl)-2-(methoxymethyl)-8-methyl-4H-pyrimido[1,2-b]pyridazin-4-one (Compound 14)

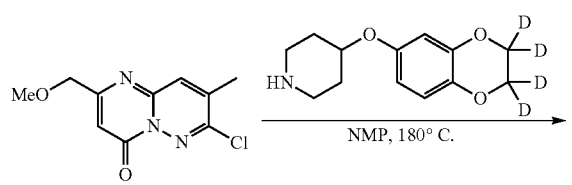

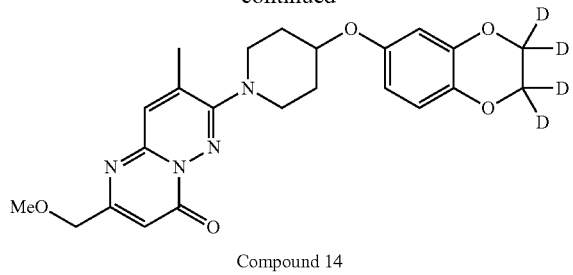

Compound 14

To a solution of 7-chloro-2-(methoxymethyl)-8-methyl-pyrimido[1,2-b]pyridazin-4-one (15 mg) and 4-[(2,2,3,3-tetradeuterio-1,4-benzodioxin-6-yl)oxy]piperidine (30 mg) in NMP (1 mL) was added N,N-diisopropylethylamine (55 μL). The mixture was heated to 180° C. for 18 hours. The crude product was dissolved in DMSO (1 mL) and purified by reverse-phase chromatography using Gilson HPLC (30× 100 mm column, 20-65% ACN/0.1% aqueous TFA, 10 min run). Fractions containing product were basified with saturated NaHCO$_3$, and extracted with 3:1 chloroform/IPA. The organic extracts were passed through a phase separator and concentrated to give the title compound as a solid (18 mg; 66% yield). $^1$H NMR (400 MHz, CDCl$_3$) δ 7.48 (q, J=1.2 Hz, 1H), 6.78 (d, J=8.7 Hz, 1H), 6.66 (t, J=0.9 Hz, 1H), 6.49 (d, J=2.8 Hz, 1H), 6.45 (dd, J=8.7, 2.9 Hz, 1H), 4.40 (d, J=0.9 Hz, 2H), 4.39 (hept, J=3.7 Hz, 1H), 3.66-3.56 (m, 2H), 3.49 (s, 3H), 3.31-3.20 (m, 2H), 2.43 (d, J=1.2 Hz, 3H), 2.18-2.05 (m, 2H), 2.02-1.89 (m, 2H). ES-MS [M+1]$^+$: 443.

Example 15. 7-(4-((2,3-Dihydrobenzo[b][1,4]dioxin-6-yl-2,2,3,3-d4)oxy)piperidin-1-yl)-3-fluoro-2,8-dimethyl-4H-pyrimido[1,2-b]pyridazin-4-one (Compound 15)

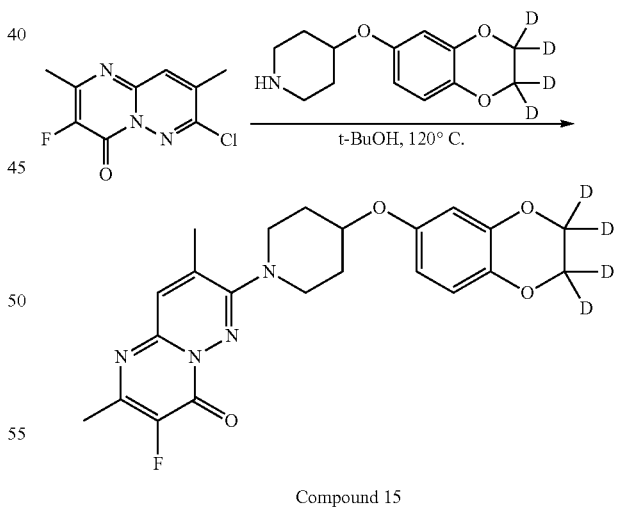

Compound 15

To a solution of 7-chloro-3-fluoro-2,8-dimethyl-pyrimido [1,2-b]pyridazin-4-one (10 mg) and 4-[(2,2,3,3-tetradeuterio-1,4-benzodioxin-6-yl)oxy]piperidine (16 mg) in t-butanol (0.5 mL) was added N,N-diisopropylethylamine (38 μL). The mixture was heated to 120° C. for 18 hours. The crude product was dissolved in DMSO (1 mL) and purified by reverse-phase chromatography using Gilson HPLC (30×100 mm column, 25-60% ACN/0.05% aqueous NH$_4$OH, 8 min run). Fractions containing product concentrated to give the title compound as a solid (10 mg; 54% yield). $^1$H NMR (400 MHz, CDCl$_3$) δ 7.38 (q, J=1.2 Hz, 1H), 6.72 (d, J=8.7 Hz, 1H), 6.43 (d, J=2.8 Hz, 1H), 6.39 (dd, J=8.7, 2.9 Hz, 1H), 4.34 (hept, J=3.6 Hz, 1H), 3.56 (ddd, J=12.0, 7.6, 3.5 Hz, 2H), 3.21 (ddd, J=12.5, 7.8, 3.4 Hz, 2H), 2.40 (d, J=3.5 Hz, 3H), 2.36 (s, 3H), 2.11-2.02 (m, 2H), 1.97-1.78 (m, 2H). ES-MS [M+1]$^+$: 431.

Example 16. 7-(4-((2,3-Dihydrobenzo[b][1,4]dioxin-6-yl-2,2,3,3-d4)oxy)piperidin-1-yl)-3-fluoro-2,8,9-trimethyl-4H-pyrimido[1,2-b]pyridazin-4-one (Compound 16)

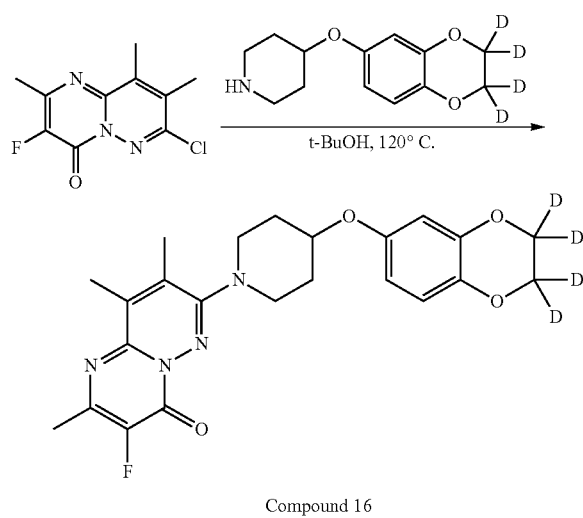

Compound 16

To a solution of 7-chloro-3-fluoro-2,8,9-trimethyl-pyrimido[1,2-b]pyridazin-4-one (10 mg) and 4-[(2,2,3,3-tetradeuterio-1,4-benzodioxin-6-yl)oxy]piperidine (15 mg) in t-butanol (0.5 mL) was added N,N-diisopropylethylamine (36 µL). The mixture was heated to 120° C. for 18 hours. The crude product was dissolved in DMSO (1 mL) and purified by reverse-phase chromatography using Gilson HPLC (30×100 mm column, 20-70% ACN/0.05% aqueous NH$_4$OH, 8 min run). Fractions containing product were concentrated to give the title compound as a solid (12 mg; 65% yield). $^1$H NMR (400 MHz, MeOD) δ 6.73 (d, J=8.8 Hz, 1H), 6.51 (d, J=2.7 Hz, 1H), 6.48 (dd, J=8.7, 2.8 Hz, 1H), 4.45 (dt, J=7.6, 3.9 Hz, 1H), 3.56 (ddd, J=11.7, 7.2, 3.5 Hz, 2H), 3.21 (ddd, J=12.5, 8.2, 3.3 Hz, 2H), 2.56 (d, J=0.6 Hz, 3H), 2.50 (d, J=3.5 Hz, 3H), 2.41 (s, 3H), 2.25-2.08 (m, 2H), 1.99-1.82 (m, 2H). ES-MS [M+1]$^+$: 445.

Example 17. 3-Chloro-7-(4-((2,3-dihydrobenzo[b][1,4]dioxin-6-yl-2,2,3,3-d4)oxy)piperidin-1-yl)-2,8-dimethyl-4H-pyrimido[1,2-b]pyridazin-4-one (Compound 17)

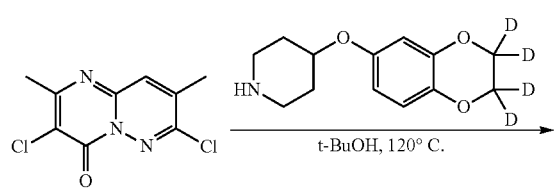

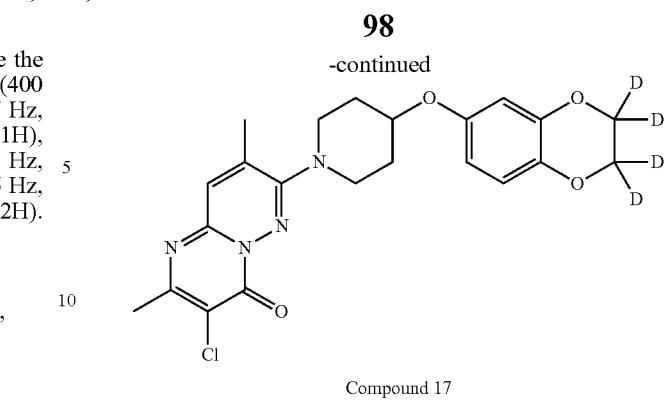

Compound 17

To a solution of 3,7-dichloro-2,8-dimethyl-pyrimido[1,2-b]pyridazin-4-one (10 mg) and 4-[(2,2,3,3-tetradeuterio-1,4-benzodioxin-6-yl)oxy]piperidine (15 mg) in tert-butanol (0.5 mL) was added N,N-diisopropylethylamine (36 µL). The mixture was heated to 120° C. for 18 hours. Crude product was dissolved in DMSO (1 mL) and purified by reverse-phase chromatography using Gilson HPLC (30×100 mm column, 25-65% ACN/0.05% aqueous NH$_4$OH, 8 min run). Fractions containing product concentrated to give the title compound as a solid (12.9 mg; 71% yield). $^1$H NMR (400 MHz, CDCl$_3$) δ 7.47 (d, J=0.6 Hz, 1H), 6.78 (d, J=8.7 Hz, 1H), 6.49 (d, J=2.8 Hz, 1H), 6.45 (dd, J=8.8, 2.9 Hz, 1H), 4.40 (hept, J=3.6 Hz, 1H), 3.74-3.57 (m, 2H), 3.33-3.22 (m, 2H), 2.56 (s, 3H), 2.44 (d, J=1.2 Hz, 3H), 2.18-2.07 (m, 2H), 2.02-1.89 (m, 2H). ES-MS [M+1]$^+$: 447.

Example 18. 7-(4-((2,3-Dihydrobenzo[b][1,4]dioxin-6-yl-2,2,3,3-d4)oxy)piperidin-1-yl)-8-(methoxymethyl)-9-methyl-4H-pyrimido[1,2-b]pyridazin-4-one (Compound 18)

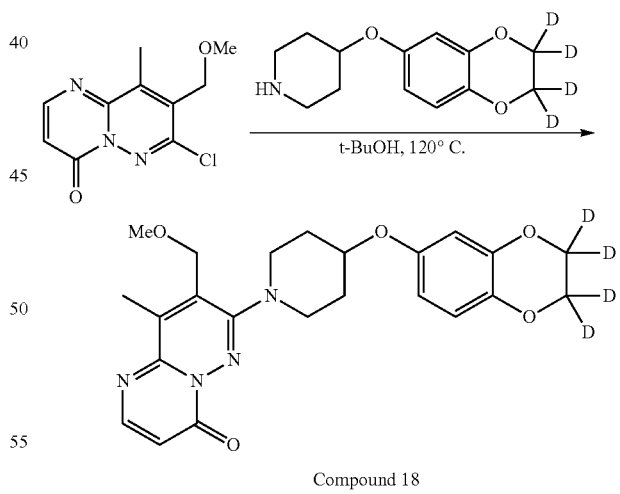

Compound 18

To a solution of 7-chloro-8-(methoxymethyl)-9-methyl-pyrimido[1,2-b]pyridazin-4-one (15 mg) and 4-[(2,2,3,3-tetradeuterio-1,4-benzodioxin-6-yl)oxy]piperidine (30 mg) in tert-butanol (1 mL) was added N,N-diisopropylethylamine (55 µL). The mixture was heated to 120° C. for 18 hours. The crude product was dissolved in DMSO (1 mL) and purified by reverse-phase chromatography using Gilson HPLC (30×100 mm column, 20-65% ACN/0.1% aqueous TFA, 8 min run). Fractions containing product were basified with saturated NaHCO₃, and extracted with 4:1 chloroform/IPA. The organic extracts were passed through a phase separator and concentrated to give the title compound as a solid (11.4 mg; 41% yield). ¹H NMR (400 MHz, CDCl₃) δ 8.15 (d, J=6.3 Hz, 1H), 6.78 (d, J=8.7 Hz, 1H), 6.58 (d, J=6.3 Hz, 1H), 6.49 (d, J=2.8 Hz, 1H), 6.45 (dd, J=8.7, 2.9 Hz, 1H), 4.42 (s, 2H), 4.37 (hept, J=3.7 Hz, 1H), 3.67 (ddd, J=11.3, 6.9, 3.6 Hz, 2H), 3.48 (s, 3H), 3.25 (ddd, J=12.6, 8.5, 3.2 Hz, 2H), 2.60 (s, 3H), 2.16 (ddt, J=13.4, 6.9, 3.5 Hz, 2H), 1.95 (dtd, J=12.4, 8.0, 3.5 Hz, 2H). ES-MS [M+1]⁺: 443.

Example 19. 7-(4-((2,3-Dihydrobenzo[b][1,4]di-oxin-6-yl-2,2,3,3-d4)oxy)piperidin-1-yl)-9-(methoxymethyl)-8-methyl-4H-pyrimido[1,2-b]pyridazin-4-one (Compound 19)

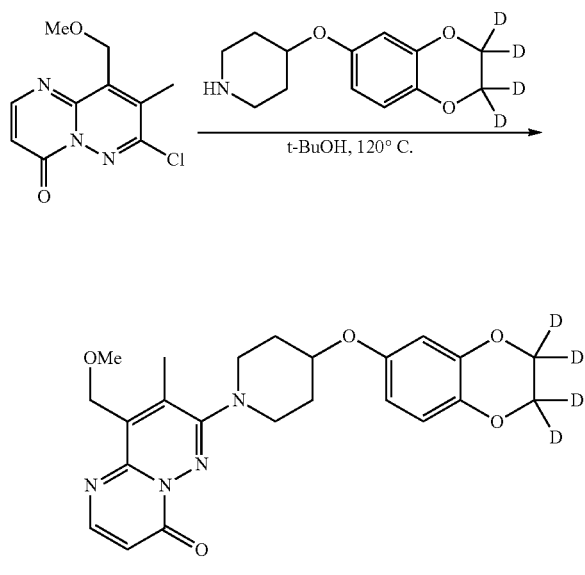

Compound 19

To a solution of 7-chloro-9-(methoxymethyl)-8-methyl-pyrimido[1,2-b]pyridazin-4-one (15 mg) and 4-[(2,2,3,3-tetradeuterio-1,4-benzodioxin-6-yl)oxy]piperidine (30 mg) in tert-butanol (1 mL) was added N,N-diisopropylethylamine (55 µL). The mixture was heated to 120° C. for 18 hours. The crude product was dissolved in DMSO (1 mL) and purified by reverse-phase chromatography using Gilson HPLC (30×100 mm column, 15-55% ACN/0.1% aqueous TFA, 8 min run). Fractions containing product were basified with saturated NaHCO₃, and extracted with 4:1 chloroform/IPA. The organic extracts were passed through a phase separator and concentrated to give the title compound as a solid (6 mg; 22% yield). ¹H NMR (400 MHz, CDCl₃) δ 8.14 (d, J=6.3 Hz, 1H), 6.78 (d, J=8.7 Hz, 1H), 6.54 (d, J=6.3 Hz, 1H), 6.49 (d, J=2.8 Hz, 1H), 6.45 (dd, J=8.7, 2.9 Hz, 1H), 4.91 (s, 2H), 4.38 (hept, J=3.7 Hz, 1H), 3.58 (ddd, J=11.8, 7.4, 3.5 Hz, 2H), 3.48 (s, 3H), 3.22 (ddd, J=12.4, 8.0, 3.3 Hz, 2H), 2.48 (s, 3H), 2.18-2.08 (m, 2H), 1.96 (dtd, J=11.2, 7.6, 3.4 Hz, 2H). ES-MS [M+1]⁺: 443.

Example 20. 9-Cyclopropyl-7-(4-((2,3-dihydrobenzo[b][1,4]dioxin-6-yl-2,2,3,3-d4)oxy)piperidin-1-yl)-8-methyl-4H-pyrimido[1,2-b]pyridazin-4-one (Compound 20)

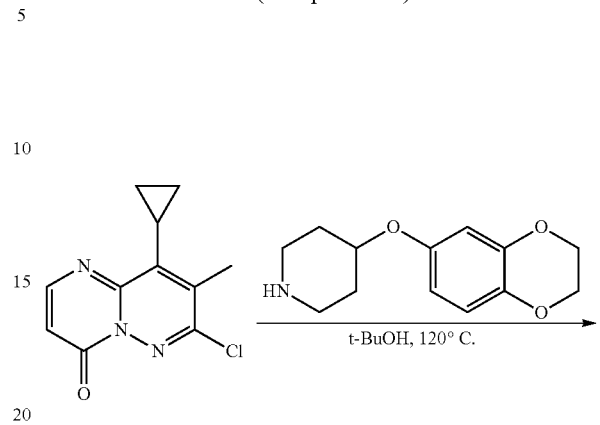

Compound 20

To a solution of 7-chloro-9-cyclopropyl-8-methyl-pyrimido[1,2-b]pyridazin-4-one (15 mg) and 4-(2,3-dihydro-1,4-benzodioxin-6-yloxy)piperidine (43 mg) in tert-butanol (0.5 mL) was added N,N-diisopropylethylamine (55 µL). The mixture was heated to 120° C. for 18 hours. The crude product was dissolved in DMSO (1 mL) and purified by reverse-phase chromatography using Gilson HPLC (30×100 mm column, 20-60% ACN/0.05% aqueous NH₄OH, 8 min run). Fractions containing product were concentrated to give the title compound as a solid (16 mg; 57% yield). ¹H NMR (400 MHz, CDCl₃) δ 8.14 (d, J=6.3 Hz, 1H), 6.78 (d, J=8.7 Hz, 1H), 6.52 (d, J=6.3 Hz, 1H), 6.49 (d, J=2.8 Hz, 1H), 6.45 (dd, J=8.7, 2.9 Hz, 1H), 4.37 (tt, J=3.8 Hz, 1H), 4.27-4.24 (m, 2H), 4.24-4.18 (m, 2H), 3.63-3.51 (m, 2H), 3.29-3.10 (m, 2H), 2.50 (s, 3H), 2.18-2.07 (m, 2H), 2.01-1.87 (m, 3H), 1.34-1.18 (m, 2H), 1.14-1.07 (m, 2H). ES-MS [M+1]⁺: 435.

Example 21. 8-cyclopropyl-7-(4-((2,3-dihydrobenzo[b][1,4]dioxin-6-yl-2,2,3,3-d4)oxy)piperidin-1-yl)-9-methyl-4H-pyrimido[1,2-b]pyridazin-4-one (Compound 21)

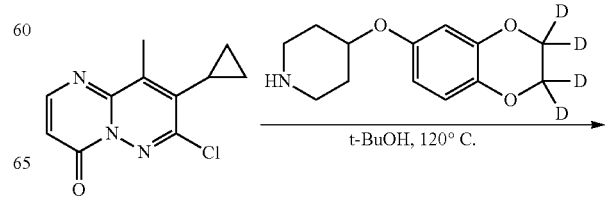

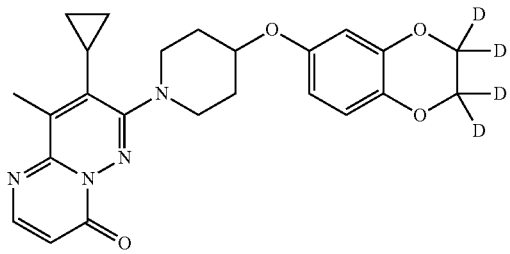

Compound 21

To a solution of 7-chloro-8-cyclopropyl-9-methyl-pyrimido[1,2-b]pyridazin-4-one (15 mg) and 4-[(2,2,3,3-tetradeuterio-1,4-benzodioxin-6-yl)oxy]piperidine (30 mg) in tert-butanol (0.5 mL) was added N,N-diisopropylethylamine (55 μL). The mixture was heated to 120° C. for 18 hours. The crude product was dissolved in DMSO (1 mL) and purified by reverse-phase chromatography using Gilson HPLC (30× 100 mm column, 25-65% ACN/0.05% aqueous NH$_4$OH, 8 min run). Fractions containing product were concentrated to give the title compound as a solid (1.8 mg; 7% yield). $^1$H NMR (400 MHz, CDCl$_3$) δ 8.13 (d, J=8.0 Hz, 1H), 6.78 (d, J=8.0 Hz, 1H), 6.53 (d, J=8.0 Hz, 1H), 6.49 (d, J=4.0 Hz, 1H), 6.45 (dd, J=8.0, 4.0 Hz, 1H), 4.38-4.35 (m, 1H), 3.85-3.79 (m, 2H), 3.40-3.31 (m, 2H), 2.66 (s, 3H), 2.20-2.12 (m, 2H), 2.01-1.93 (m, 2H), 1.88-1.84 (m, 1H), 1.30-1.17 (m, 2H), 0.81-0.73 (m, 2H). ES-MS [M+1]$^+$: 435.

Example 22. 7-((2R,4S)-4-((2,3-Dihydrobenzo[b][1,4]dioxin-6-yl)oxy)-2-methylpiperidin-1-yl)-8-methyl-4H-pyrimido[1,2-b]pyridazin-4-one (Compound 108)

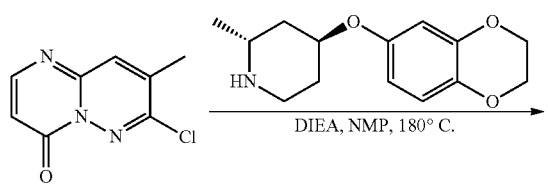

Compound 108

To a solution of (2S,4R)-4-((2,3-dihydrobenzo[b][1,4]dioxin-6-yl)oxy)-2-methylpiperidine (50 mg) in NMP (1 mL) was added 7-chloro-8-methyl-4H-pyrimido[1,2-b]pyridazin-4-one (43 mg) and DIEA (156 mg), The mixture was subjected to microwave irradiation at 180° C. for 2 hours. The reaction mixture was diluted with EtOAc (10 mL) and extracted with H$_2$O (10 mL×3). The combined organic layers were washed with brine (10 mL), dried over Na$_2$SO$_4$, filtered and concentrated. The residue was purified by basic preparative HPLC to give 7-((2S,4R)-4-((2,3-dihydrobenzo[b][1,4]dioxin-6-yl)oxy)-2-methylpiperidin-1-yl)-8-methyl-4H-pyrimido[1,2-b]pyridazin-4-one (16 mg). $^1$H NMR (400 MHz, CDCl$_3$) δ 8.11 (d, J=6.4 Hz, 1H), 7.51 (s, 1H), 6.78 (d, J=8.8 Hz, 1H), 6.54 (d, J=6.4 Hz, 1H), 6.51-6.42 (m, 2H), 4.62-4.47 (m, 1H), 4.29-4.20 (m, 4H), 4.19-4.11 (m, 1H), 3.62-3.56 (m, 1H), 3.40-3.33 (m, 1H), 2.45 (s, 3H), 2.18-2.15 (m, 1H), 2.07-1.99 (m, 2H), 1.95-1.82 (m, 1H), 1.27 (d, J=6.4 Hz, 3H); ES-MS [M+1]$^+$: 409.1.

Example 23. 7-(4-((2,3-Dihydrobenzo[b][1,4]dioxin-6-yl)oxy)piperidin-1-yl)-9-methoxy-8-methyl-4H-pyrimido[1,2-b]pyridazin-4-one (Compound 126)

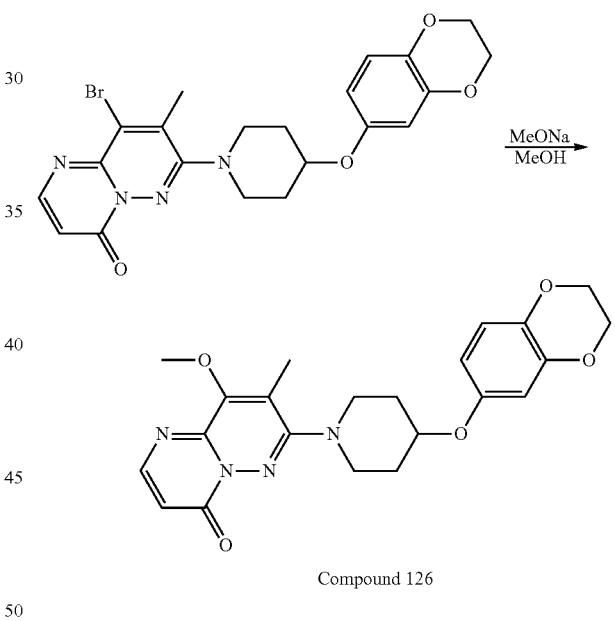

Compound 126

To a solution of 9-bromo-7-(4-((2,3-dihydrobenzo[b][1,4]dioxin-6-yl)oxy)piperidin-1-yl)-8-methyl-4H-pyrimido[1,2-b]pyridazin-4-one (300 mg) in MeOH (5 mL) was added NaOMe (137 mg) and the resulting mixture was stirred at 60° C. for 6 hours. H$_2$O (5 mL) was added to the reaction and extracted with EtOAc (5 mL×5). The combined organic layers were dried over Na$_2$SO$_4$, filtered and concentrated. The crude compound was purified by preparative thin layer chromatography (SiO$_2$, Ethyl acetate: Petroleum ether=1:0) to give 7-(4-((2,3-dihydrobenzo[b][1,4]dioxin-6-yl)oxy)piperidin-1-yl)-9-methoxy-8-methyl-4H-pyrimido[1,2-b]pyridazin-4-one (55 mg). $^1$H NMR (400 MHz, CDCl$_3$) δ8.15 (d, J=6.4 Hz, 1H), 6.79 (d, J=8.4 Hz, 1H), 6.57 (d, J=6.4 Hz, 1H), 6.50 (d, J=2.4 Hz, 1H), 6.46 (dd, J=2.8, 8.8 Hz, 1H), 4.41-3.36 (m, 1H), 4.28-4.25 (m, 2H), 4.24-4.21

(m, 2H), 4.18 (s, 3H), 3.64-3.55 (m, 2H), 3.27-3.18 (m, 2H), 2.33 (s, 3H), 2.18-2.09 (m, 2H), 2.01-1.91 (m, 2H). ES-MS [M+1]+: 425.2.

Example 24. 9-(Azetidin-1-yl)-7-(4-((2,3-dihydrobenzo[b][1,4]dioxin-6-yl)oxy)piperidin-1-yl)-8-methyl-4H-pyrimido[1,2-b]pyridazin-4-one (Compound 127)

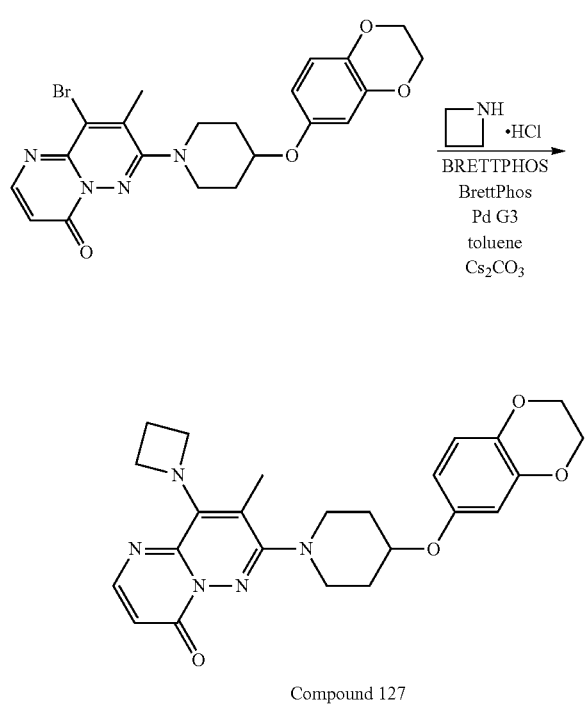

Compound 127

A mixture of 9-bromo-7-(4-((2,3-dihydrobenzo[b][1,4]dioxin-6-yl)oxy)piperidin-1-yl)-8-methyl-4H-pyrimido[1,2-b]pyridazin-4-one (200 mg), azetidine hydrochloride (198 mg), Cs$_2$CO$_3$ (1.1 g), BrettPhos Pd G3 (77 mg) and BRETTPHOS (45 mg) in toluene (5 mL) was degassed and purged with N$_2$ 3 times, and then the mixture was stirred at 100° C. for 16 hours under N$_2$ atmosphere. The reaction mixture was concentrated and the residue was purified by flash silica gel chromatography (ISCO®; 24 g SepaFlash® Silica Flash Column, Eluent of 0~100% Ethyl acetate/Petroleum ether gradient @ 30 mL/min) to give crude product. The crude product was purified by recrystallization from EtOAc (3 mL) at 80° C. Additional recrystallization with DCM (5 mL) and EtOAc (15 mL) provided 9-(azetidin-1-yl)-7-(4-((2,3-dihydrobenzo[b][1,4]dioxin-6-yl)oxy)piperidin-1-yl)-8-methyl-4H-pyrimido[1,2-b]pyridazin-4-one (50 mg). $^1$H NMR (400 MHz, CDCl$_3$) δ 7.98 (d, J=6.0 Hz, 1H), 6.78 (d, J=8.8 Hz, 1H), 6.50-6.44 (m, 3H), 4.68 (t, J=8.0 Hz, 4H), 4.39-4.29 (m, 1H), 4.28-4.24 (m, 2H), 4.24-4.18 (m, 2H), 3.62-3.52 (m, 2H), 3.21-3.12 (m, 2H), 2.40-2.32 (m, 2H), 2.20 (s, 3H), 2.15-2.06 (m, 2H), 1.96-1.85 (m, 2H). ES-MS [M+1]+: 450.0.

Example 25. 7-((2R,4S)-4-((2,3-Dihydrobenzo[b][1,4]dioxin-6-yl-2,2,3,3-d4)oxy)-2-methylpiperidin-1-yl)-8-methyl-4H-pyrimido[1,2-b]pyridazin-4-one (Compound 129)

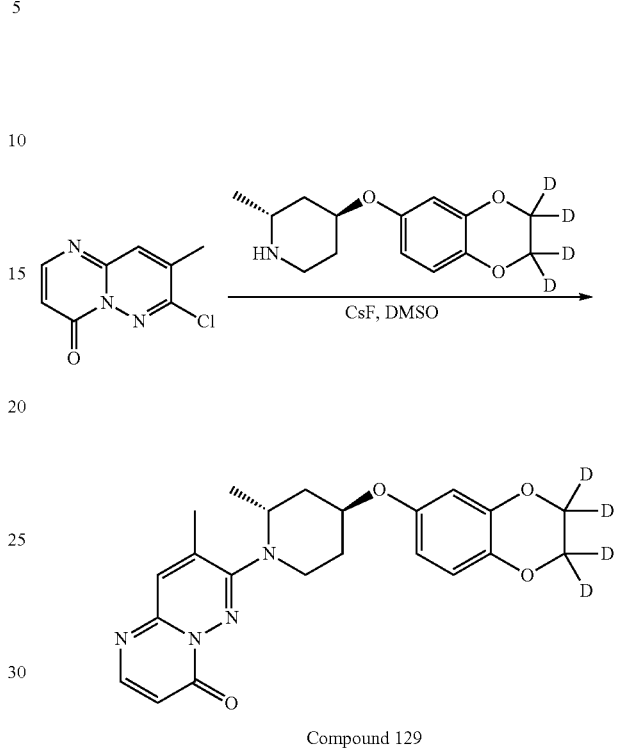

Compound 129

A mixture of 7-chloro-8-methyl-4H-pyrimido[1,2-b]pyridazin-4-one (2 g), (2R,4S)-4-((2,3-dihydrobenzo[b][1,4]dioxin-6-yl-2,2,3,3-d$_4$)oxy)-2-methylpiperidine (2.59 g) and CsF (1.86 g) in DMSO (20 mL) was stirred at 80° C. for 2 hours. The mixture was diluted with H$_2$O (20 mL) and extracted with EtOAc (40 mL×5). The combined organic layers were washed with brine (50 mL), dried over Na$_2$SO$_4$ and concentrated. The residue was purified by Combi Flash (silica gel, from 0 to 100%, Ethyl acetate in petroleum ether), followed by preparative HPLC (Instrument: Gilson GX-215 Liquid Handler, SHIMADZU LC-20AP, SHIMADZU SPD-20A; Column: Xtimate C18 150×40 mm×5 μm; Mobile Phase A: water (0.05% NH$_3$H$_2$O); Mobile phase B: MeCN; Gradient: B from 35% to 55% in 9 min then hold at 100% for 5 min; Flow Rate (ml/min): 60; Column temperature: 30° C.; Wavelength: 220 nm, 254 nm) to give 7-((2R,4S)-4-((2,3-dihydrobenzo[b][1,4]dioxin-6-yl-2,2,3,3-d$_4$)oxy)-2-methylpiperidin-1-yl)-8-methyl-4H-pyrimido[1,2-b]pyridazin-4-one (1.4 g). $^1$H NMR (400 MHz, CDCl$_3$) δ 8.10 (d, J=6.4 Hz, 1H), 7.50 (d, J=1.2 Hz, 1H), 6.77 (d, J=8.8 Hz, 1H), 6.53 (d, J=6.4 Hz, 1H), 6.48 (d, J=2.8 Hz, 1H), 6.44 (d, J=8.8 Hz, 2.8 Hz, 1H), 4.56-4.48 (m, 1H), 4.18-4.11 (m, 1H), 3.61-3.55 (m, 1H), 3.39-3.32 (m, 1H), 2.44 (s, 3H), 2.21-2.12 (m, 1H), 2.07-1.97 (m, 2H), 1.93-1.84 (m, 1H), 1.27 (d, J=6.8 Hz, 3H). ES-MS [M+1]+: 413.0. SFC: t$_R$=3.62 min, ee=99.8%, [α]$^{20}_D$=+104.0 (c=1.2 g/100 mL, DCM). SFC method: Instrument: Waters UPCC with PAD Detector; Column: Chiralcel OJ-3 100×4.6 mm I.D., 3 μm; Mobile phase: A: CO2 B: ethanol (0.05% DEA); Gradient: 5% to 40% of B in 4 min and hold 40% for 2.5 min, then 5% of B for 1.5 min; Flow rate: 2.8 mL/min; Column temp.: 35° C.; ABPR: 1500 psi; Run time: 8 min; Wavelength: 220 nm.

The compounds shown in Table 1 were prepared in an analogous manner with the appropriate starting materials.

TABLE 1

| Cpd. No | Name | Structure | ES-MS [M + 1]+ |
|---|---|---|---|
| 22 | 7-(4-((2,3-dihydrobenzo[b][1,4]dioxin-6-yl-2,2,3,3-d4)oxy)piperidin-1-yl)-9-methyl-4H-pyrimido[1,2-b]pyridazin-4-one | 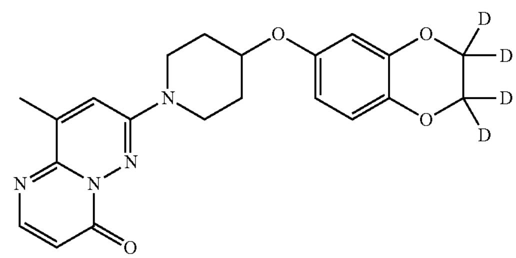 [SMILES: [2H]C1([2H])Oc2ccc(OC3CCN(c4cc(C)c5nccc(=O)n5n4)CC3)cc2OC1([2H])[2H]] | 399.2 |
| 23 | 3-chloro-7-(4-((2,3-dihydrobenzo[b][1,4]dioxin-6-yl-2,2,3,3-d4)oxy)piperidin-1-yl)-8-methyl-4H-pyrimido[1,2-b]pyridazin-4-one | 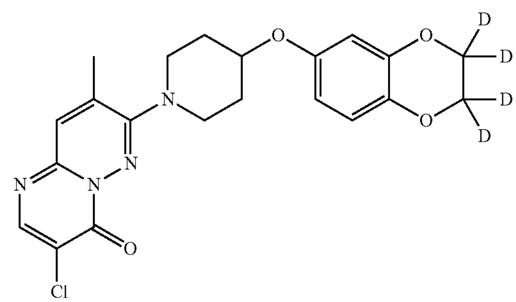 [SMILES: [2H]C1([2H])Oc2ccc(OC3CCN(c4nn5c(=O)c(Cl)cnc5cc4C)CC3)cc2OC1([2H])[2H]] | 433.2 |
| 24 | 8-methyl-7-(4-((6-methylpyridin-3-yl)oxy)piperidin-1-yl)-4H-pyrimido[1,2-b]pyridazin-4-one | 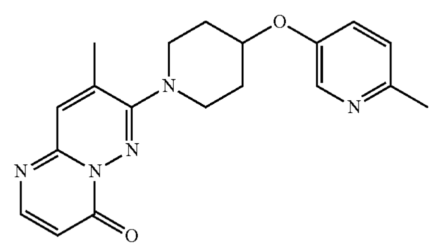 [SMILES: Cc1ccc(OC2CCN(c3nn4c(=O)ccnc4cc3C)CC2)cn1] | 352.4 |
| 25 | 7-(4-(4-fluorophenoxy)piperidin-1-yl)-8-methyl-4H-pyrimido[1,2-b]pyridazin-4-one | 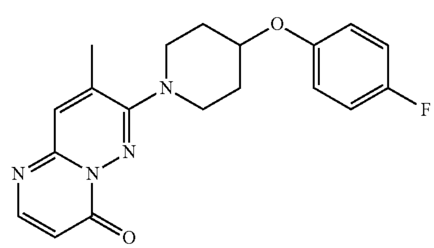 [SMILES: Cc1cc2nccc(=O)n2nc1N1CCC(Oc2ccc(F)cc2)CC1] | 355.4 |
| 26 | 7-(4-((2,3-dihydrobenzo[b][1,4]dioxin-6-yl)oxy)piperidin-1-yl)-8-methyl-4H-pyrimido[1,2-b]pyridazin-4-one | 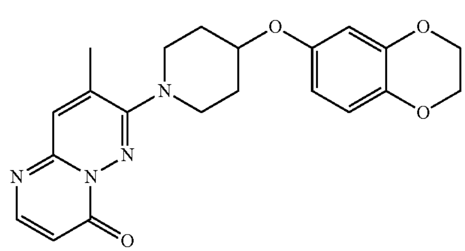 [SMILES: Cc1cc2nccc(=O)n2nc1N1CCC(Oc2ccc3c(c2)OCCO3)CC1] | 395.4 |

TABLE 1-continued

| Cpd. No | Name | Structure | ES-MS [M + 1]+ |
|---|---|---|---|
| 27 | 3-chloro-8-methyl-7-(4-((8-methyl-2,3-dihydrobenzo[b][1,4]dioxin-6-yl-2,2,3,3-d4)oxy)piperidin-1-yl)-4H-pyrimido[1,2-b]pyridazin-4-one | 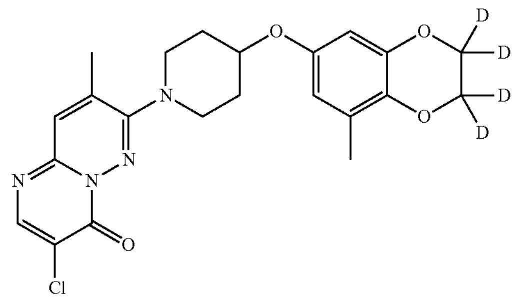 [SMILES: [2H]C1([2H])Oc2cc(OC3CCN(c4nn5c(=O)c(Cl)cnc5cc4C)CC3)cc(C)c2OC1([2H])[2H]] | 447.3 |
| 28 | 8-methyl-7-(4-((8-methyl-2,3-dihydrobenzo[b][1,4]dioxin-6-yl-2,2,3,3-d4)oxy)piperidin-1-yl)-4H-pyrimido[1,2-b]pyridazin-4-one | 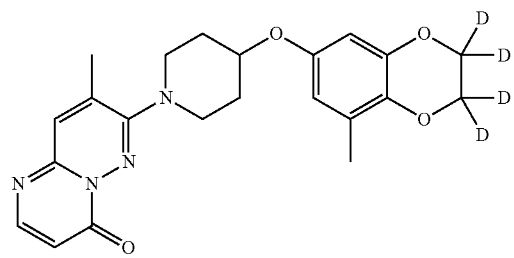 | 413.4 |
| 29 | 7-(4-((2,3-dihydrobenzo[b][1,4]dioxin-6-yl-2,2,3,3-d4)oxy)piperidin-1-yl)-3,8-dimethyl-4H-pyrimido[1,2-b]pyridazin-4-one | 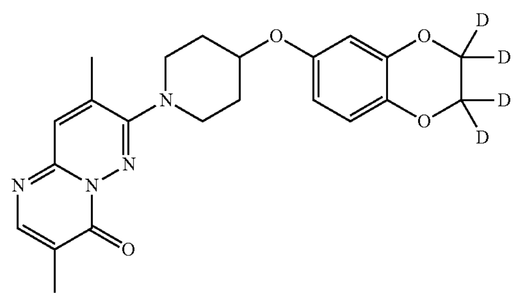 [SMILES: [2H]C1([2H])Oc2ccc(OC3CCN(c4nn5c(=O)c(C)cnc5cc4C)CC3)cc2OC1([2H])[2H]] | 413.2 |
| 30 | 3-cyclopropyl-7-(4-((2,3-dihydrobenzo[b][1,4]dioxin-6-yl-2,2,3,3-d4)oxy)piperidin-1-yl)-8-methyl-4H-pyrimido[1,2-b]pyridazin-4-one | 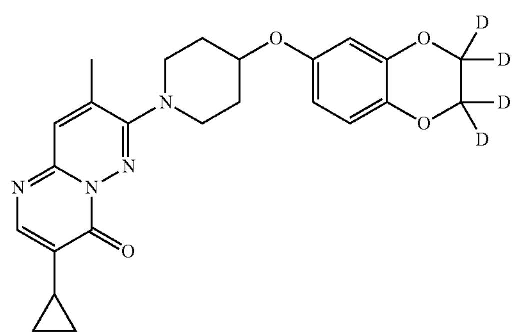 [SMILES: [2H]C1([2H])Oc2ccc(OC3CCN(c4nn5c(=O)c(C6CC6)cnc5cc4C)CC3)cc2OC1([2H])[2H]] | 439.2 |
| 31 | 3-chloro-7-(4-((2,3-dihydrobenzo[b][1,4]dioxin-6-yl)oxy)piperidin-1-yl)-8-methyl-4H-pyrimido[1,2-b]pyridazin-4-one | 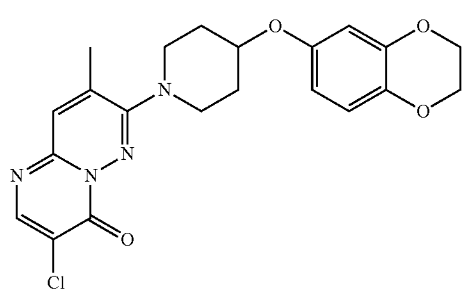 [SMILES: Cc1cc2ncc(Cl)c(=O)n2nc1N1CCC(Oc2ccc3c(c2)OCCO3)CC1] | 429.3 |

TABLE 1-continued

| Cpd. No | Name | Structure | ES-MS [M + 1]+ |
|---|---|---|---|
| 32 | 7-((3R,4R)-4-((2,3-dihydrobenzo[b][1,4]dioxin-6-yl)oxy)-3-fluoropiperidin-1-yl)-8-methyl-4H-pyrimido[1,2-b]pyridazin-4-one | Chiral | 413.4 |
| 33 | 7-((3S,4R)-4-((2,3-dihydrobenzo[b][1,4]dioxin-6-yl)oxy)-3-fluoropiperidin-1-yl)-2,8-dimethyl-4H-pyrimido[1,2-b]pyridazin-4-one | Chiral | 427.4 |
| 34 | 7-((3S,4R)-4-((2,3-dihydrobenzo[b][1,4]dioxin-6-yl)oxy)-3-fluoropiperidin-1-yl)-8-methyl-4H-pyrimido[1,2-b]pyridazin-4-one | Chiral | 413.4 |
| 35 | 3-(azetidin-1-yl)-7-(4-((2,3-dihydrobenzo[b][1,4]dioxin-6-yl-2,2,3,3-d4)oxy)piperidin-1-yl)-8-methyl-4H-pyrimido[1,2-b]pyridazin-4-one | 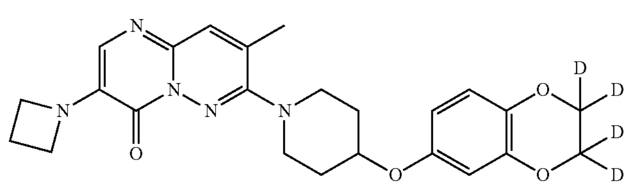 [SMILES: [2H]C1([2H])Oc2ccc(OC3CCN(c4nn5c(=O)c(N6CCC6)cnc5cc4C)CC3)cc2OC1([2H])[2H]] | 454.4 |
| 36 | 7-((3R,4R)-4-((2,3-dihydrobenzo[b][1,4]dioxin-6-yl)oxy)-3-fluoropiperidin-1-yl)-3-fluoro-2,8-dimethyl-4H-pyrimido[1,2-b]pyridazin-4-one | Chiral | 445.3 |

TABLE 1-continued

| Cpd. No | Name | Structure | ES-MS [M + 1]+ |
|---|---|---|---|
| 37 | 7-((3S,4S)-4-((2,3-dihydrobenzo[b][1,4]dioxin-6-yl)oxy)-3-fluoropiperidin-1-yl)-3-fluoro-2,8-dimethyl-4H-pyrimido[1,2-b]pyridazin-4-one | Chiral | 445.3 |
| 38 | 7-((3S,4S)-4-((2,3-dihydrobenzo[b][1,4]dioxin-6-yl-2,2,3,3-d4)oxy)-3-fluoropiperidin-1-yl)-3-fluoro-2,8-dimethyl-4H-pyrimido[1,2-b]pyridazin-4-one | Chiral | 449.4 |
| 39 | 7-(4-((2,3-dihydrobenzo[b][1,4]dioxin-6-yl-2,2,3,3-d4)oxy)piperidin-1-yl-4-d)-8-methyl-4H-pyrimido[1,2-b]pyridazin-4-one | 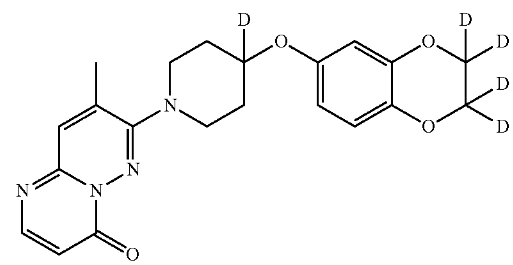 [SMILES: [2H]C1(Oc2ccc3c(c2)OC([2H])([2H])C([2H])([2H])O3)CCN(c2nn3c(=O)ccnc3cc2C)CC1] | 400.2 |
| 40 | 7-(4-((2,3-dihydrobenzo[b][1,4]dioxin-6-yl-2,2,3,3-d4)oxy)piperidin-1-yl-4-d)-2,8-dimethyl-4H-pyrimido[1,2-b]pyridazin-4-one | 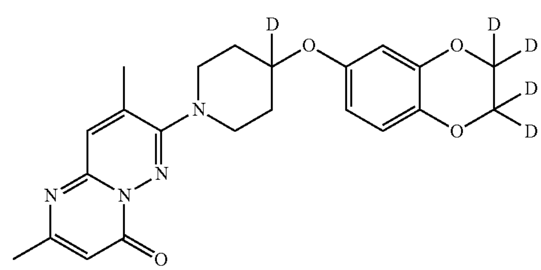 [SMILES: [2H]C1(Oc2ccc3c(c2)OC([2H])([2H])C([2H])([2H])O3)CCN(c2nn3c(=O)cc(C)nc3cc2C)CC1] | 414.2 |
| 41 | 7-((3R,4R)-4-((2,3-dihydrobenzo[b][1,4]dioxin-6-yl-2,2,3,3-d4)oxy)-3-fluoropiperidin-1-yl)-8-methyl-4H-pyrimido[1,2-b]pyridazin-4-one | Chiral | 417.2 |

TABLE 1-continued

| Cpd. No | Name | Structure | | ES-MS [M + 1]+ |
|---|---|---|---|---|
| 42 | 7-((3S,4S)-4-((2,3-dihydrobenzo[b][1,4]dioxin-6-yl-2,2,3,3-d4)oxy)-3-fluoropiperidin-1-yl)-8-methyl-4H-pyrimido[1,2-b]pyridazin-4-one | 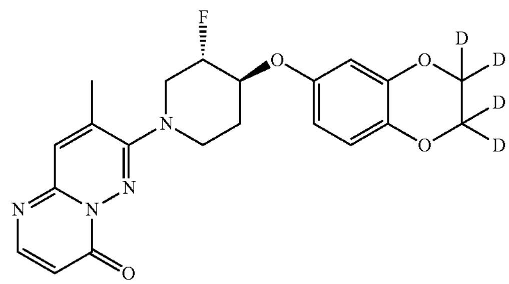 | Chiral | 417.2 |
| 43 | 7-((3R,4S)-4-((2,3-dihydrobenzo[b][1,4]dioxin-6-yl)oxy)-3-fluoropiperidin-1-yl)-8-methyl-4H-pyrimido[1,2-b]pyridazin-4-one | 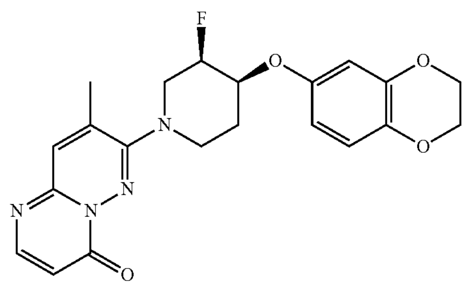 | Chiral | 413.2 |
| 44 | 7-((3R,4S)-4-((2,3-dihydrobenzo[b][1,4]dioxin-6-yl)oxy)-3-fluoropiperidin-1-yl)-2,8-dimethyl-4H-pyrimido[1,2-b]pyridazin-4-one | 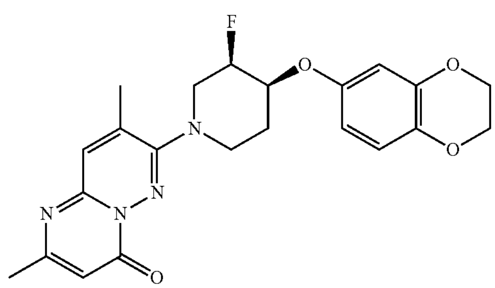 | Chiral | 427.4 |
| 45 | 7-(4-((2,3-dihydrobenzo[b][1,4]dioxin-6-yl-2,2,3,3-d4)oxy)piperidin-1-yl-4-d)-8-methyl-2-(trifluoromethyl)-4H-pyrimido[1,2-b]pyridazin-4-one | 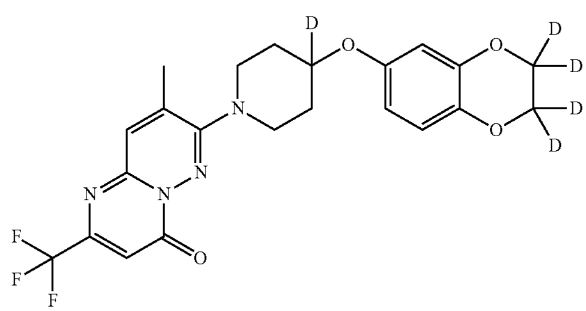 [SMILES: [2H]C1(Oc2ccc3c(c2)OC([2H])([2H])C([2H])([2H])O3)CCN(c2nn3c(=O)cc(C(F)(F)F)nc3cc2C)CC1] | | 468.2 |
| 46 | 7-(4-((2,3-dihydrobenzo[b][1,4]dioxin-6-yl-2,2,3,3-d4)oxy)piperidin-1-yl-4-d)-3-fluoro-2,8-dimethyl-4H-pyrimido[1,2-b]pyridazin-4-one | 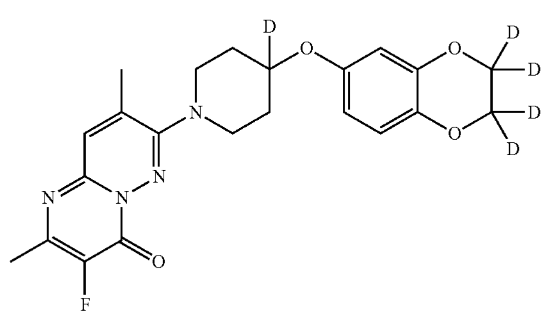 [SMILES: [2H]C1(Oc2ccc3c(c2)OC([2H])([2H])C([2H])([2H])O3)CCN(c2nn3c(=O)c(F)c(C)nc3cc2C)CC1] | | 432.2 |

TABLE 1-continued

| Cpd. No | Name | Structure | ES-MS [M + 1]+ |
|---|---|---|---|
| 47 | 7-(4-((2,3-dihydrobenzo[b][1,4]dioxin-6-yl-2,2,3,3-d4)oxy)piperidin-1-yl-4-d)-2,3,8-trimethyl-4H-pyrimido[1,2-b]pyridazin-4-one | 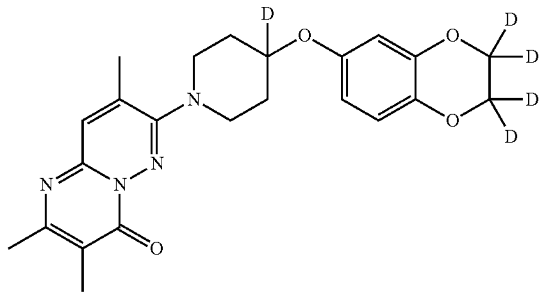 [SMILES: [2H]C1(Oc2ccc3c(c2)OC([2H])([2H])C([2H])([2H])O3)CCN(c2nn3c(=O)c(C)c(C)nc3cc2C)CC1] | 428.2 |
| 48 | 7-(4-((2,3-dihydrobenzo[b][1,4]dioxin-6-yl)oxy)piperidin-1-yl-4-d)-8-methyl-4H-pyrimido[1,2-b]pyridazin-4-one | 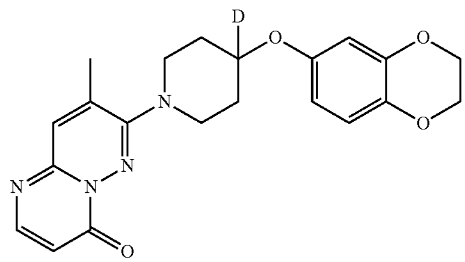 [SMILES: [2H]C1(Oc2ccc3c(c2)OCCO3)CCN(c2nn3c(=O)ccnc3cc2C)CC1] | 396.4 |
| 49 | 7-(4-((2,3-dihydrobenzo[b][1,4]dioxin-6-yl)oxy)piperidin-1-yl-4-d)-8-methyl-2-(trifluoromethyl)-4H-pyrimido[1,2-b]pyridazin-4-one | 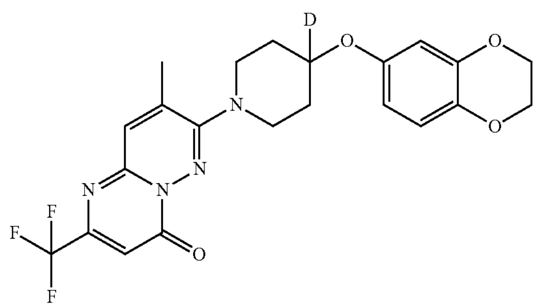 [SMILES: [2H]C1(Oc2ccc3c(c2)OCCO3)CCN(c2nn3c(=O)cc(C(F)(F)F)nc3cc2C)CC1] | 464.3 |
| 50 | 7-(4-((2,3-dihydrobenzo[b][1,4]dioxin-6-yl)oxy)piperidin-1-yl-4-d)-3-fluoro-2,8-dimethyl-4H-pyrimido[1,2-b]pyridazin-4-one | 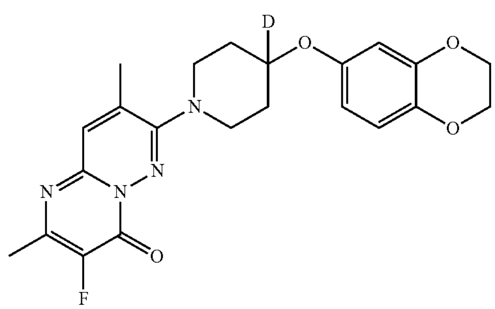 [SMILES: [2H]C1(Oc2ccc3c(c2)OCCO3)CCN(c2nn3c(=O)c(F)c(C)nc3cc2C)CC1] | 428.4 |
| 51 | 7-((3R,4R)-4-((2,3-dihydrobenzo[b][1,4]dioxin-6-yl-2,2,3,3-d4)oxy)-3-fluoropiperidin-1-yl)-2,8-dimethyl-4H-pyrimido[1,2-b]pyridazin-4-one | Chiral | 431.4 |

TABLE 1-continued

| Cpd. No | Name | Structure | ES-MS [M + 1]+ |
|---|---|---|---|
| 52 | 2,8-dimethyl-7-(4-((6-methylpyridin-3-yl)oxy)piperidin-1-yl)-4H-pyrimido[1,2-b]pyridazin-4-one | 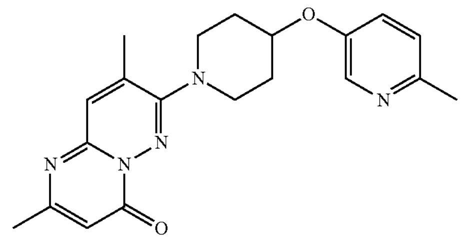 | 366.4 |
| 53 | 7-((3R,4R)-4-(benzo[d][1,3]dioxol-5-yloxy)-3-fluoropiperidin-1-yl)-8-methyl-4H-pyrimido[1,2-b]pyridazin-4-one | Chiral | 399.4 |
| 54 | 7-((3R,4R)-3-fluoro-4-(isochroman-6-yloxy)piperidin-1-yl)-8-methyl-4H-pyrimido[1,2-b]pyridazin-4-one | Chiral | 411.4 |
| 55 | 7-((3R,4R)-4-((3,4-dihydro-2H-benzo[b][1,4]dioxepin-7-yl)oxy)-3-fluoropiperidin-1-yl)-8-methyl-4H-pyrimido[1,2-b]pyridazin-4-one | Chiral | 427.4 |
| 56 | 7-((3R,4R)-4-((2,3-dihydrobenzofuran-5-yl)oxy)-3-fluoropiperidin-1-yl)-8-methyl-4H-pyrimido[1,2-b]pyridazin-4-one | Chiral | 397.4 |

TABLE 1-continued

| Cpd. No | Name | Structure | ES-MS [M + 1]+ |
|---|---|---|---|
| 57 | 7-((3R,4R)-4-(chroman-7-yloxy)-3-fluoropiperidin-1-yl)-8-methyl-4H-pyrimido[1,2-b]pyridazin-4-one | Chiral | 411.2 |
| 58 | 7-(4-(benzo[d][1,3]dioxol-5-yloxy)piperidin-1-yl-4-d)-2,8-dimethyl-4H-pyrimido[1,2-b]pyridazin-4-one | 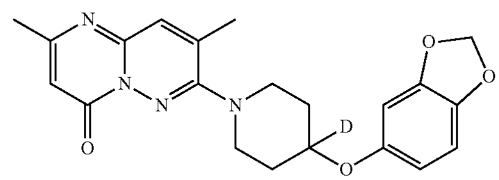 [SMILES: [2H]C1(Oc2ccc3c(c2)OCO3)CCN(c2nn3c(=O)cc(C)nc3cc2C)CC1] | 396.2 |
| 59 | 7-(4-((3,4-dihydro-2H-benzo[b][1,4]dioxepin-7-yl)oxy)piperidin-1-yl-4-d)-2,8-dimethyl-4H-pyrimido[1,2-b]pyridazin-4-one | 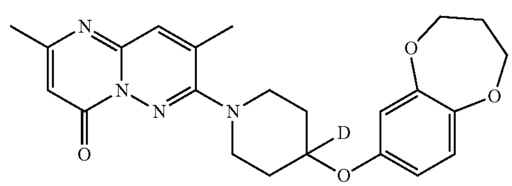 [SMILES: [2H]C1(Oc2ccc3c(c2)OCCCO3)CCN(c2nn3c(=O)cc(C)nc3cc2C)CC1] | 396.2 |
| 60 | 7-(4-((2,3-dihydrobenzo[b][1,4]dioxin-6-yl)oxy)piperidin-1-yl-4-d)-2,3,8-trimethyl-4H-pyrimido[1,2-b]pyridazin-4-one | 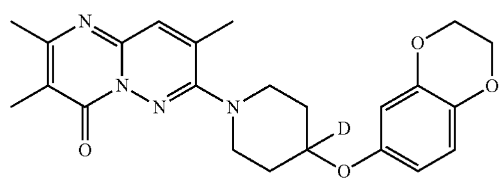 [SMILES: [2H]C1(Oc2ccc3c(c2)OCCO3)CCN(c2nn3c(=O)c(C)c(C)nc3cc2C)CC1] | 424.2 |
| 61 | 2-(difluoromethyl)-7-(4-((2,3-dihydrobenzo[b][1,4]dioxin-6-yl)oxy)piperidin-1-yl-4-d)-8-methyl-4H-pyrimido[1,2-b]pyridazin-4-one | 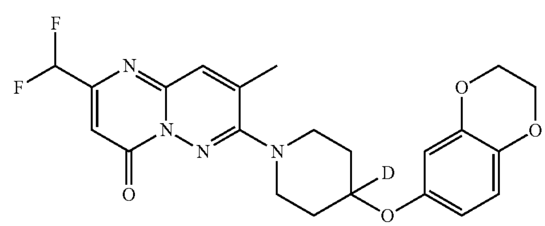 [SMILES: [2H]C1(Oc2ccc3c(c2)OCCO3)CCN(c2nn3c(=O)cc(C(F)F)nc3cc2C)CC1] | 446.2 |
| 62 | 7-(4-((2,3-dihydrobenzo[b][1,4]dioxin-6-yl)oxy)piperidin-1-yl-4-d)-2,8-dimethyl-4H-pyrimido[1,2-b]pyridazin-4-one | 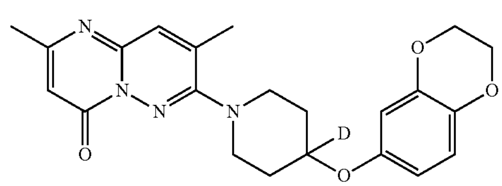 [SMILES: [2H]C1(Oc2ccc3c(c2)OCCO3)CCN(c2nn3c(=O)cc(C)nc3cc2C)CC1] | 410.4 |
| 63 | 7-(4-(benzo[d][1,3]dioxol-5-yloxy)piperidin-1-yl-4-d)-8-methyl-2-(trifluoromethyl)-4H-pyrimido[1,2-b]pyridazin-4-one | 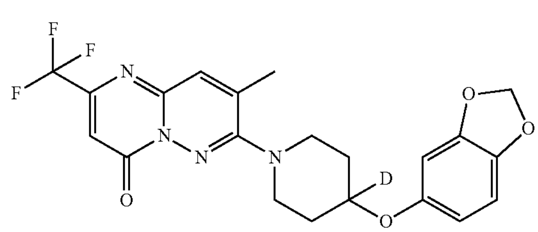 [SMILES: [2H]C1(Oc2ccc3c(c2)OCO3)CCN(c2nn3c(=O)cc(C(F)(F)F)nc3cc2C)CC1] | 450.4 |

TABLE 1-continued

| Cpd. No | Name | Structure | ES-MS [M + 1]+ |
|---|---|---|---|
| 64 | 7-(4-((3,4-dihydro-2H-benzo[b][1,4]dioxepin-7-yl)oxy)piperidin-1-yl-4-d)-8-methyl-2-(trifluoromethyl)-4H-pyrimido[1,2-b]pyridazin-4-one | 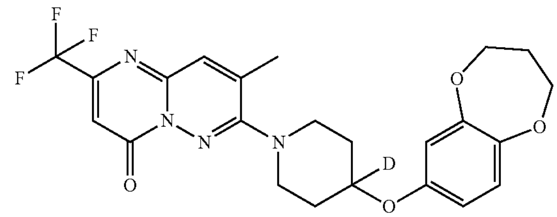 [SMILES: [2H]C1(Oc2ccc3c(c2)OCCCO3)CCN(c2nn3c(=O)cc(C(F)(F)F)nc3cc2C)CC1] | 478.4 |
| 65 | 2-(difluoromethyl)-7-(4-((2,3-dihydrobenzo[b][1,4]dioxin-6-yl-2,2,3,3-d4)oxy)piperidin-1-yl-4-d)-8-methyl-4H-pyrimido[1,2-b]pyridazin-4-one | 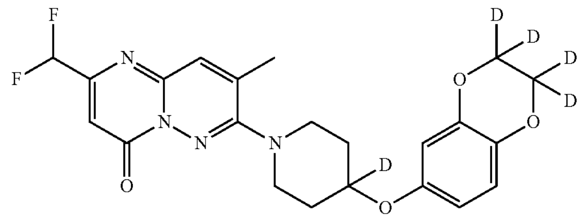 [SMILES: [2H]C1(Oc2ccc3c(c2)OC([2H])([2H])C([2H])([2H])O3)CCN(c2nn3c(=O)cc(C(F)F)nc3cc2C)CC1] | 450.4 |
| 66 | 7-(4-(benzo[d][1,3]dioxol-5-yloxy)piperidin-1-yl-4-d)-2-(difluoromethyl)-8-methyl-4H-pyrimido[1,2-b]pyridazin-4-one | 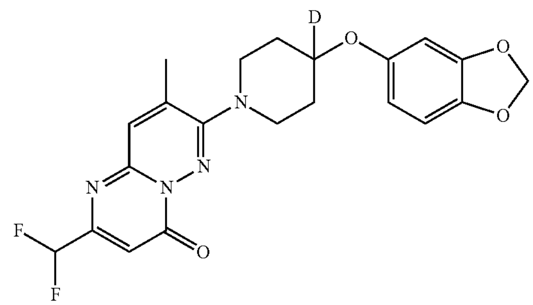 [SMILES: [2H]C1(Oc2ccc3c(c2)OCO3)CCN(c2nn3c(=O)cc(C(F)F)nc3cc2C)CC1] | 431.41 |
| 67 | 2-(difluoromethyl)-7-(4-((3,4-dihydro-2H-benzo[b][1,4]dioxepin-7-yl)oxy)piperidin-1-yl-4-d)-8-methyl-4H-pyrimido[1,2-b]pyridazin-4-one | 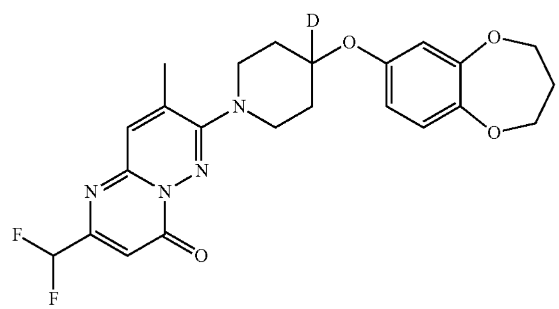 [SMILES: [2H]C1(Oc2ccc3c(c2)OCCCO3)CCN(c2nn3c(=O)cc(C(F)F)nc3cc2C)CC1] | 460.2 |
| 68 | 7-(4-(benzo[d][1,3]dioxol-5-yloxy)piperidin-1-yl-4-d)-8-methyl-4H-pyrimido[1,2-b]pyridazin-4-one | 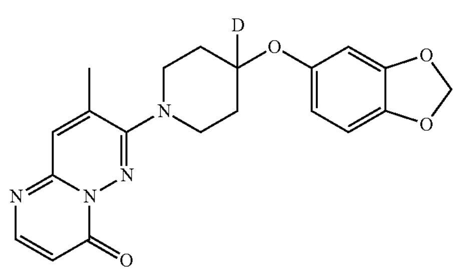 [SMILES: [2H]C1(Oc2ccc3c(c2)OCO3)CCN(c2nn3c(=O)ccnc3cc2C)CC1] | 382.4 |
| 69 | 7-(4-((2,3-dihydrobenzo[b][1,4]dioxin-6-yl-2,2,3,3-d4)oxy)piperidin-1-yl-4-d)-8,9-dimethyl-4H-pyrimido[1,2-b]pyridazin-4-one | 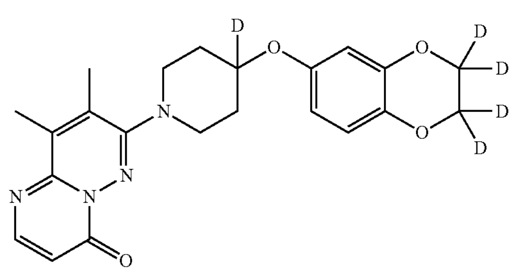 [SMILES: [2H]C1(Oc2ccc3c(c2)OC([2H])([2H])C([2H])([2H])O3)CCN(c2nn3c(=O)ccnc3c(C)c2C)CC1] | 414.4 |

TABLE 1-continued

| Cpd. No | Name | Structure | ES-MS [M + 1]+ |
|---|---|---|---|
| 70 | 7-(4-((2,3-dihydrobenzo[b][1,4]dioxin-6-yl)oxy)piperidin-1-yl-4-d)-8,9-dimethyl-4H-pyrimido[1,2-b]pyridazin-4-one | 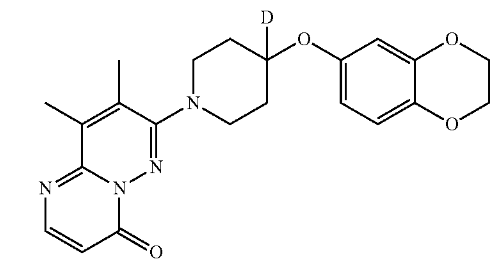 [SMILES: [2H]C1(Oc2ccc3c(c2)OCCO3)CCN(c2nn3c(=O)ccnc3c(C)c2C)CC1] | 410.4 |
| 71 | 7-(4-((2,3-dihydrobenzo[b][1,4]dioxin-6-yl)oxy)piperidin-1-yl)-8,9-dimethyl-4H-pyrimido[1,2-b]pyridazin-4-one | 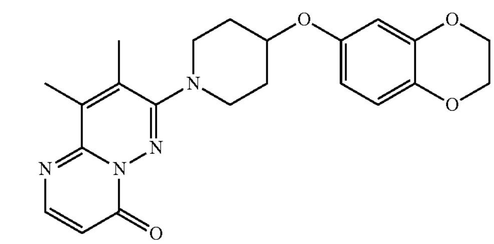 [SMILES: Cc1c(N2CCC(Oc3ccc4c(c3)OCCO4)CC2)nn2c(=O)ccnc2c1C] | 409.2 |
| 72 | 2,8-dimethyl-7-(4-((1-oxo-1,2,3,4-tetrahydroisoquinolin-7-yl)oxy)piperidin-1-yl)-4H-pyrimido[1,2-b]pyridazin-4-one | 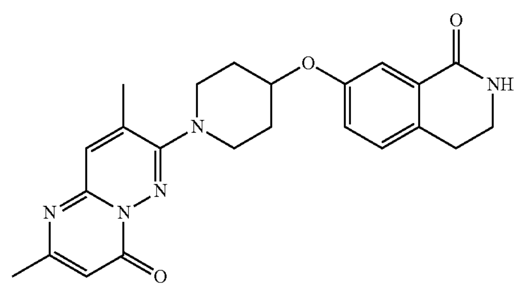 [SMILES: Cc1cc(=O)n2nc(N3CCC(Oc4ccc5c(c4)C(=O)NCC5)CC3)c(C)cc2n1] | 420.4 |
| 73 | 2,8-dimethyl-7-(4-((2-methyl-1-oxo-1,2,3,4-tetrahydroisoquinolin-7-yl)oxy)piperidin-1-yl)-4H-pyrimido[1,2-b]pyridazin-4-one | 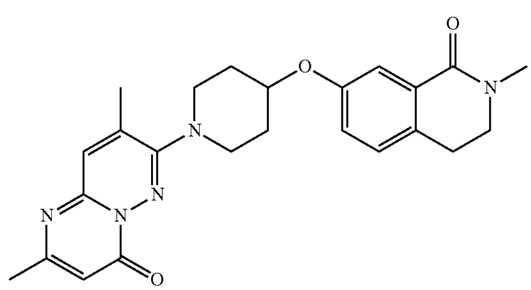 | 434.2 |
| 74 | 2,8-dimethyl-7-(4-((2-methyl-1-oxo-1,2,3,4-tetrahydroisoquinolin-6-yl)oxy)piperidin-1-yl)-4H-pyrimido[1,2-b]pyridazin-4-one | 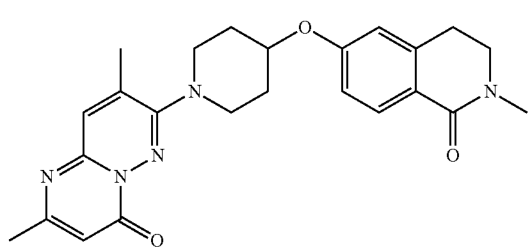 | 434.2 |
| 75 | 7-(4-((6-methoxy-5-methylpyridin-3-yl)oxy)piperidin-1-yl)-8-methyl-4H-pyrimido[1,2-b]pyridazin-4-one | 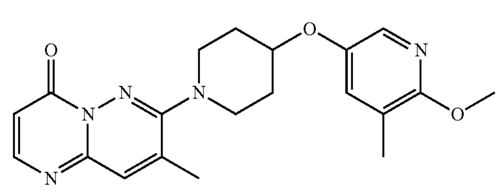 [SMILES: COc1ncc(OC2CCN(c3nn4c(=O)ccnc4cc3C)CC2)cc1C] | 382.2 |

TABLE 1-continued

| Cpd. No | Name | Structure | ES-MS [M + 1]+ |
|---|---|---|---|
| 76 | 7-(4-((6-(methoxymethyl)pyridin-3-yl)oxy)piperidin-1-yl)-8-methyl-4H-pyrimido[1,2-b]pyridazin-4-one | 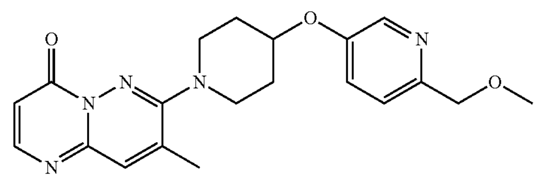 [SMILES: COCc1ccc(OC2CCN(c3nn4c(=O)ccnc4cc3C)CC2)cn1] | 382.1 |
| 77 | 8,9-dimethyl-7-(4-(p-tolyloxy)piperidin-1-yl)-4H-pyrimido[1,2-b]pyridazin-4-one | 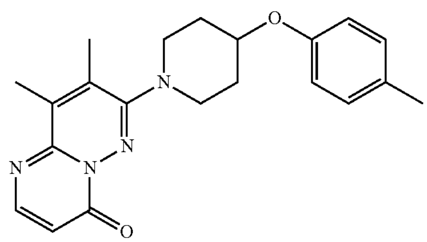 | 365.2 |
| 78 | 2-(difluoromethyl)-8,9-dimethyl-7-(4-((6-methylpyridin-3-yl)oxy)piperidin-1-yl)-4H-pyrimido[1,2-b]pyridazin-4-one | 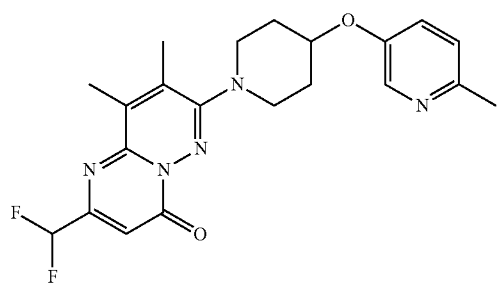 [SMILES: Cc1ccc(OC2CCN(c3nn4c(=O)cc(C(F)F)nc4c(C)c3C)CC2)cn1] | 416.2 |
| 79 | 7-(4-(4-chlorophenoxy)piperidin-1-yl)-2-(difluoromethyl)-8,9-dimethyl-4H-pyrimido[1,2-b]pyridazin-4-one | 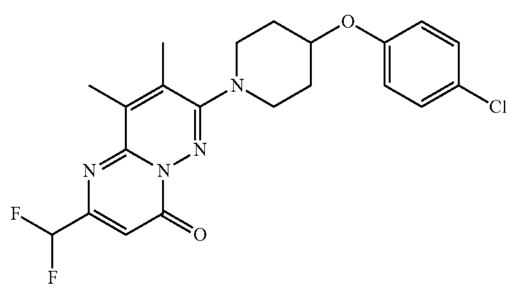 [SMILES: Cc1c(N2CCC(Oc3ccc(Cl)cc3)CC2)nn2c(=O)cc(C(F)F)nc2c1C] | 435.2 |
| 80 | 8,9-dimethyl-7-(4-(4-(trifluoromethyl)phenoxy)piperidin-1-yl)-4H-pyrimido[1,2-b]pyridazin-4-one | 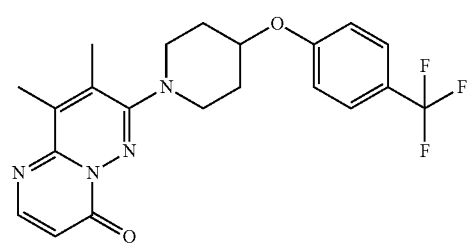 [SMILES: Cc1c(N2CCC(Oc3ccc(C(F)(F)F)cc3)CC2)nn2c(=O)ccnc2c1C] | 419.2 |
| 81 | 2-(difluoromethyl)-8,9-dimethyl-7-(4-(4-(trifluoromethyl)phenoxy)piperidin-1-yl)-4H-pyrimido[1,2-b]pyridazin-4-one | 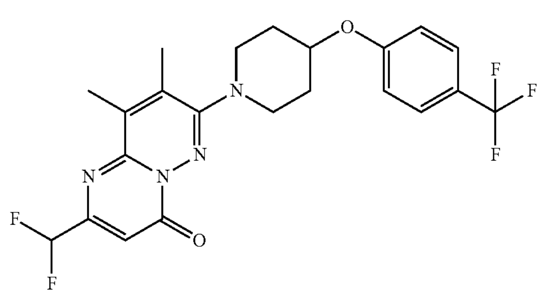 [SMILES: Cc1c(N2CCC(Oc3ccc(C(F)(F)F)cc3)CC2)nn2c(=O)cc(C(F)F)nc2c1C] | 469.2 |

TABLE 1-continued

| Cpd. No | Name | Structure | ES-MS [M + 1]+ |
|---|---|---|---|
| 82 | 2,8-dimethyl-7-(4-((1-oxo-1,2,3,4-tetrahydroisoquinolin-6-yl)oxy)piperidin-1-yl)-4H-pyrimido[1,2-b]pyridazin-4-one | 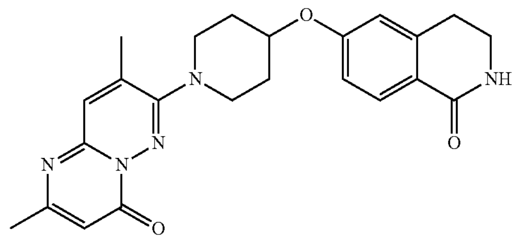 [SMILES: Cc1cc(=O)n2nc(N3CCC(Oc4ccc5c(c4)CCNC5=O)CC3)c(C)cc2n1] | 420.2 |
| 83 | 7-(4-(4-fluorophenoxy)piperidin-1-yl)-8,9-dimethyl-4H-pyrimido[1,2-b]pyridazin-4-one | 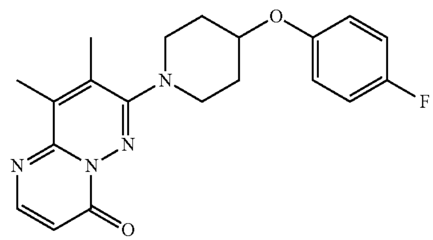 [SMILES: Cc1c(N2CCC(Oc3ccc(F)cc3)CC2)nn2c(=O)ccnc2c1C] | 369.2 |
| 84 | 2-(difluoromethyl)-7-(4-(4-fluorophenoxy)piperidin-1-yl)-8,9-dimethyl-4H-pyrimido[1,2-b]pyridazin-4-one | 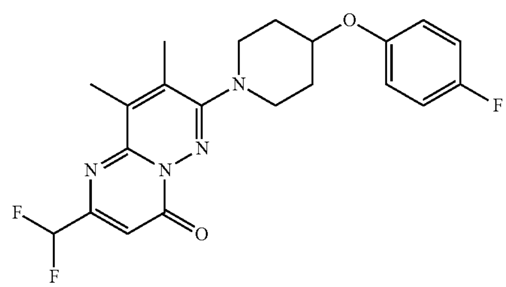 [SMILES: Cc1c(N2CCC(Oc3ccc(F)cc3)CC2)nn2c(=O)cc(C(F)F)nc2c1C] | 419.4 |
| 85 | 2-(difluoromethyl)-8,9-dimethyl-7-(4-(p-tolyloxy)piperidin-1-yl)-4H-pyrimido[1,2-b]pyridazin-4-one | 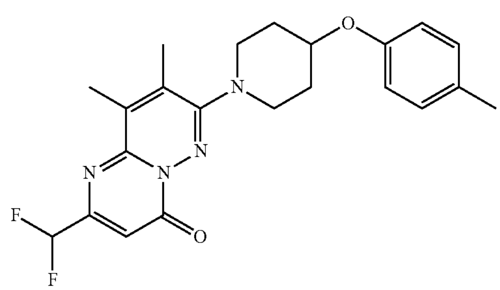 [SMILES: Cc1ccc(OC2CCN(c3nn4c(=O)cc(C(F)F)nc4c(C)c3C)CC2)cc1] | 415.4 |
| 86 | 8,9-dimethyl-7-(4-((6-methylpyridin-3-yl)oxy)piperidin-1-yl)-4H-pyrimido[1,2-b]pyridazin-4-one | 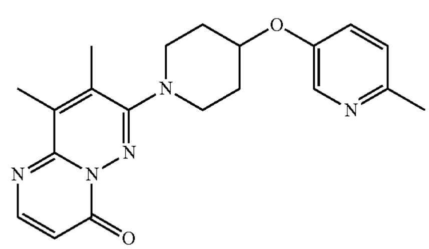 [SMILES: Cc1ccc(OC2CCN(c3nn4c(=O)ccnc4c(C)c3C)CC2)cn1] | 366.4 |
| 87 | 8,9-dimethyl-7-(4-((6-methylpyridin-3-yl)oxy)piperidin-1-yl)-4H-pyrimido[1,2-b]pyridazin-4-one | 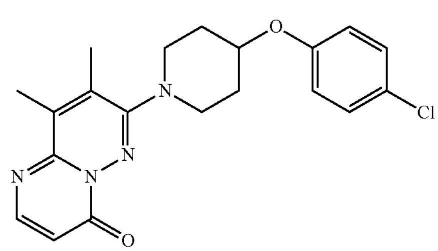 [SMILES: Cc1c(N2CCC(Oc3ccc(Cl)cc3)CC2)nn2c(=O)ccnc2c1C] | 385.4 |

TABLE 1-continued

| Cpd. No | Name | Structure | ES-MS [M + 1]+ |
|---|---|---|---|
| 88 | 7-(4-(3-fluoro-4-methylphenoxy)piperidin-1-yl)-8-methyl-4H-pyrimido[1,2-b]pyridazin-4-one | 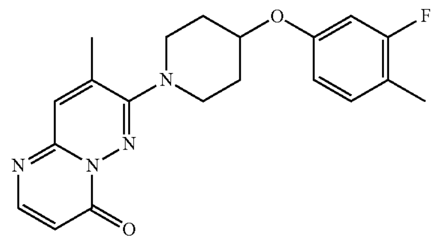 [SMILES: Cc1ccc(OC2CCN(c3nn4c(=O)ccnc4cc3C)CC2)cc1F] | 369.4 |
| 89 | 7-(4-(4-ethylphenoxy)piperidin-1-yl)-8-methyl-4H-pyrimido[1,2-b]pyridazin-4-one | 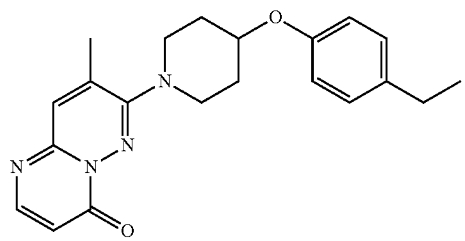 [SMILES: CCc1ccc(OC2CCN(c3nn4c(=O)ccnc4cc3C)CC2)cc1] | 365.4 |
| 90 | 7-(4-(4-isopropylphenoxy)piperidin-1-yl)-8-methyl-4H-pyrimido[1,2-b]pyridazin-4-one | 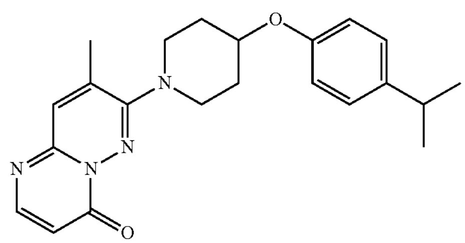 [SMILES: Cc1cc2nccc(=O)n2nc1N1CCC(Oc2ccc(C(C)C)cc2)CC1] | 379.2 |
| 91 | 8-methyl-7-(4-(4-propylphenoxy)piperidin-1-yl)-4H-pyrimido[1,2-b]pyridazin-4-one | 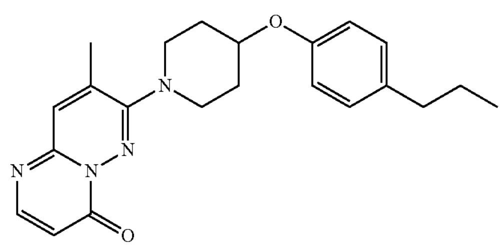 [SMILES: CCCc1ccc(OC2CCN(c3nn4c(=O)ccnc4cc3C)CC2)cc1] | 379.2 |
| 92 | 8-methyl-7-(4-(p-tolyloxy)piperidin-1-yl-4-d)-4H-pyrimido[1,2-b]pyridazin-4-one | 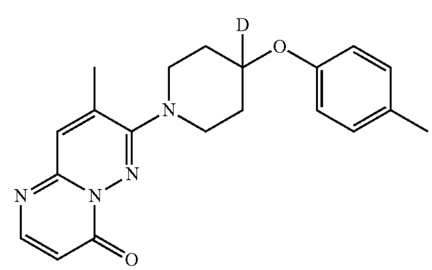 [SMILES: [2H]C1(Oc2ccc(C)cc2)CCN(c2nn3c(=O)ccnc3cc2C)CC1] | 352.2 |
| 93 | 7-(4-((6-(methoxymethyl)-5-methylpyridin-3-yl)oxy)piperidin-1-yl)-8-methyl-4H-pyrimido[1,2-b]pyridazin-4-one | 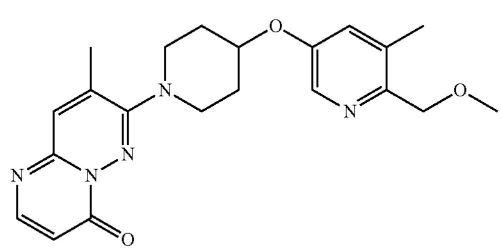 [SMILES: COCc1ncc(OC2CCN(c3nn4c(=O)ccnc4cc3C)CC2)cc1C] | 396.2 |

TABLE 1-continued

| Cpd. No | Name | Structure | ES-MS [M + 1]+ |
|---|---|---|---|
| 94 | 7-(4-((2,3-dihydrobenzo[b][1,4]dioxin-6-yl-2,2,3,3-d4)oxy)piperidin-1-yl-4-d)-2,8,9-trimethyl-4H-pyrimido[1,2-b]pyridazin-4-one | 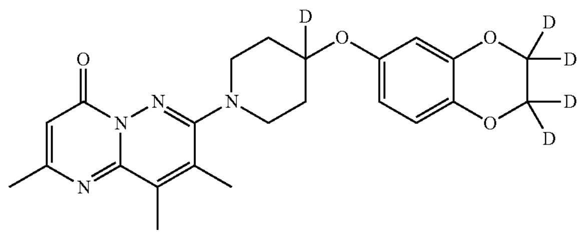 [SMILES: [2H]C1(Oc2ccc3c(c2)OC([2H])([2H])C([2H])([2H])O3)CCN(c2nn3c(=O)cc(C)nc3c(C)c2C)CC1] | 428.4 |
| 95 | 7-(4-((2,3-dihydrobenzo[b][1,4]dioxin-6-yl-2,2,3,3-d4)oxy)piperidin-1-yl-4-d)-8,9-dimethyl-2-(trifluoromethyl)-4H-pyrimido[1,2-b]pyridazin-4-one | 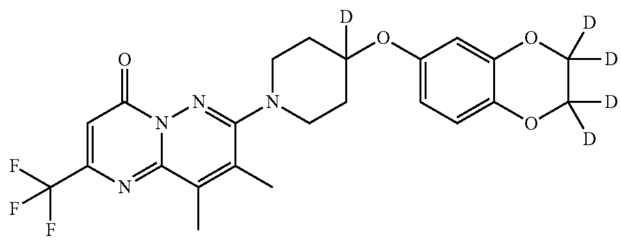 [SMILES: [2H]C1(Oc2ccc3c(c2)OC([2H])([2H])C([2H])([2H])O3)CCN(c2nn3c(=O)cc(C(F)(F)F)nc3c(C)c2C)CC1] | 482.3 |
| 96 | 7-(4-((2,3-dihydrobenzo[b][1,4]dioxin-6-yl-2,2,3,3-d4)oxy)piperidin-1-yl-4-d)-2-isopropyl-8,9-dimethyl-4H-pyrimido[1,2-b]pyridazin-4-one | 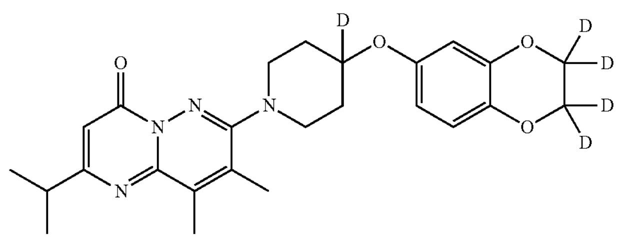 | 456.4 |
| 97 | 9-cyclopropyl-7-(4-((2,3-dihydrobenzo[b][1,4]dioxin-6-yl-2,2,3,3-d4)oxy)piperidin-1-yl-4-d)-8-methyl-4H-pyrimido[1,2-b]pyridazin-4-one | 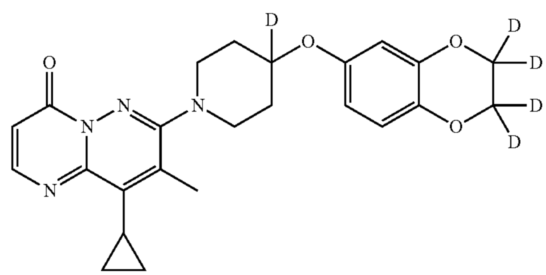 [SMILES: [2H]C1(Oc2ccc3c(c2)OC([2H])([2H])C([2H])([2H])O3)CCN(c2nn3c(=O)ccnc3c(C3CC3)c2C)CC1] | 440.3 |
| 98 | 7-(4-((2,3-dihydrobenzo[b][1,4]dioxin-6-yl-2,2,3,3-d4)oxy)piperidin-1-yl-4-d)-2-ethyl-8,9-dimethyl-4H-pyrimido[1,2-b]pyridazin-4-one | 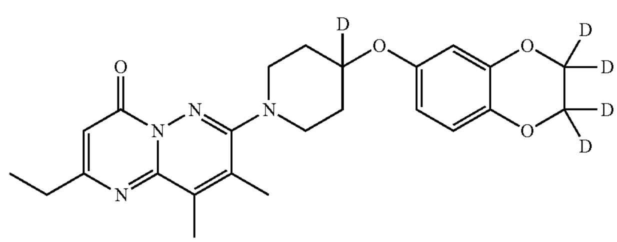 [SMILES: [2H]C1(Oc2ccc3c(c2)OC([2H])([2H])C([2H])([2H])O3)CCN(c2nn3c(=O)cc(CC)nc3c(C)c2C)CC1] | 442.4 |
| 99 | 7-(4-((2,3-dihydrobenzo[b][1,4]dioxin-6-yl-2,2,3,3-d4)oxy)piperidin-1-yl)-2-isopropyl-8,9-dimethyl-4H-pyrimido[1,2-b]pyridazin-4-one | 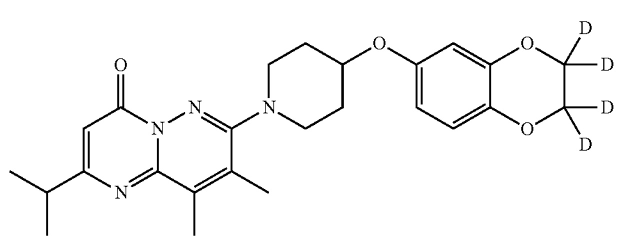 [SMILES: [2H]C1([2H])Oc2ccc(OC3CCN(c4nn5c(=O)cc(C(C)C)nc5c(C)c4C)CC3)cc2OC1([2H])[2H]] | 455.4 |

TABLE 1-continued

| Cpd. No | Name | Structure | ES-MS [M + 1]+ |
|---|---|---|---|
| 100 | 7-(4-((2,3-dihydrobenzo[b][1,4]dioxin-6-yl-2,2,3,3-d4)oxy)piperidin-1-yl)-2-ethyl-8,9-dimethyl-4H-pyrimido[1,2-b]pyridazin-4-one | 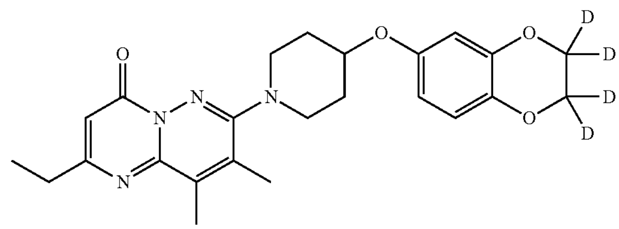 [SMILES: [2H]C1([2H])Oc2ccc(OC3CCN(c4nn5c(=O)cc(CC)nc5c(C)c4C)CC3)cc2OC1([2H])[2H]] | 441.4 |
| 101 | 2-(cyclopentylmethyl)-7-(4-((2,3-dihydrobenzo[b][1,4]dioxin-6-yl-2,2,3,3-d4)oxy)piperidin-1-yl-4-d)-8,9-dimethyl-4H-pyrimido[1,2-b]pyridazin-4-one | 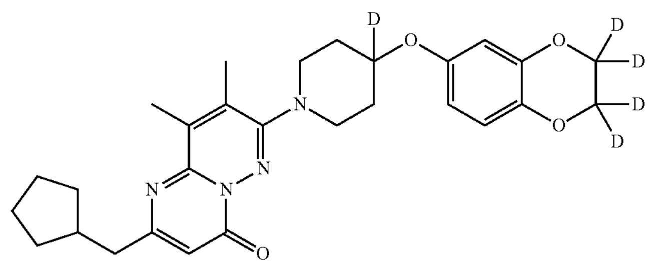 [SMILES: [2H]C1(Oc2ccc3c(c2)OC([2H])([2H])C([2H])([2H])O3)CCN(c2nn3c(=O)cc(CC4CCCC4)nc3c(C)c2C)CC1] | 496.4 |
| 102 | 7-(4-((2,3-dihydrobenzo[b][1,4]dioxin-6-yl-2,2,3,3-d4)oxy)piperidin-1-yl-4-d)-8-(methoxymethyl)-9-methyl-4H-pyrimido[1,2-b]pyridazin-4-one | 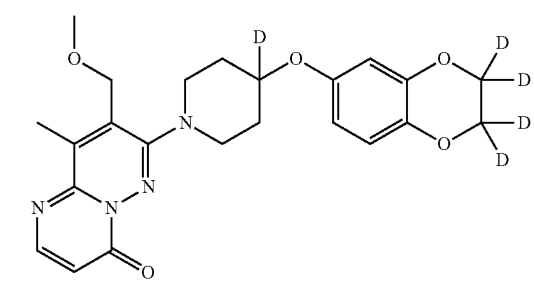 [SMILES: [2H]C1(Oc2ccc3c(c2)OC([2H])([2H])C([2H])([2H])O3)CCN(c2nn3c(=O)ccnc3c(C)c2COC)CC1] | 444.4 |
| 103 | 7-(4-((2,3-dihydrobenzo[b][1,4]dioxin-6-yl-2,2,3,3-d4)oxy)piperidin-1-yl-4-d)-9-(methoxymethyl)-8-methyl-4H-pyrimido[1,2-b]pyridazin-4-one | 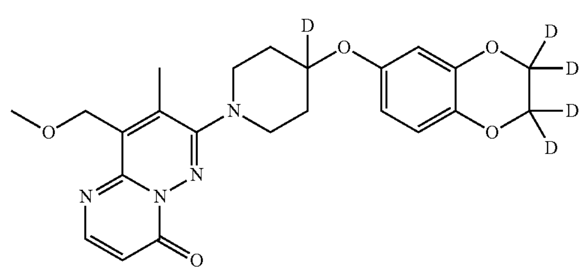 [SMILES: [2H]C1(Oc2ccc3c(c2)OC([2H])([2H])C([2H])([2H])O3)CCN(c2nn3c(=O)ccnc3c(COC)c2C)CC1] | 444.4 |
| 104 | 8-cyclopropyl-7-(4-((2,3-dihydrobenzo[b][1,4]dioxin-6-yl-2,2,3,3-d4)oxy)piperidin-1-yl-4-d)-9-methyl-4H-pyrimido[1,2-b]pyridazin-4-one | 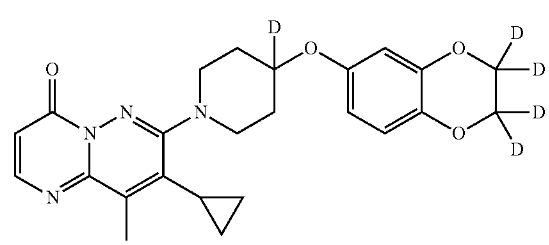 [SMILES: [2H]C1(Oc2ccc3c(c2)OC([2H])([2H])C([2H])([2H])O3)CCN(c2nn3c(=O)ccnc3c(C)c2C2CC2)CC1] | 440.4 |
| 105 | 8-cyclopropyl-7-(4-((2,3-dihydrobenzo[b][1,4]dioxin-6-yl-2,2,3,3-d4)oxy)piperidin-1-yl)-9-methyl-4H-pyrimido[1,2-b]pyridazin-4-one | 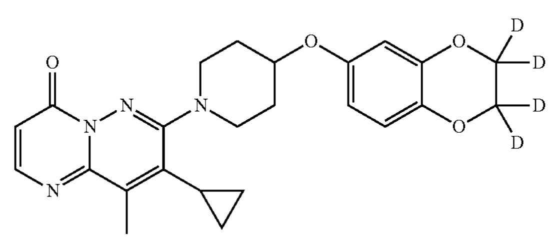 [SMILES: [2H]C1([2H])Oc2ccc(OC3CCN(c4nn5c(=O)ccnc5c(C)c4C4CC4)CC3)cc2OC1([2H])[2H]] | 439.4 |

TABLE 1-continued

| Cpd. No | Name | Structure | ES-MS [M + 1]+ |
|---|---|---|---|
| 106 | 7-((2R,4R)-4-((2,3-dihydrobenzo[b][1,4]dioxin-6-yl)oxy)-2-methylpiperidin-1-yl)-8-methyl-4H-pyrimido[1,2-b]pyridazin-4-one | 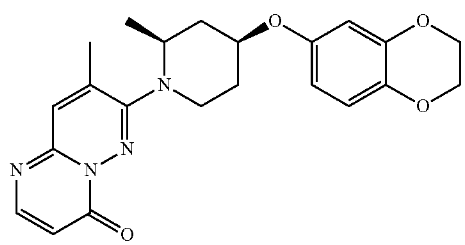 [SMILES: Cc1cc2nccc(=O)n2nc1N1CC[C@H](Oc2ccc3c(c2)OCCO3)C[C@@H]1C] | 409.1 |
| 107 | 7-((2R,4S)-4-((2,3-dihydrobenzo[b][1,4]dioxin-6-yl)oxy)-2-methylpiperidin-1-yl)-8-methyl-4H-pyrimido[1,2-b]pyridazin-4-one | 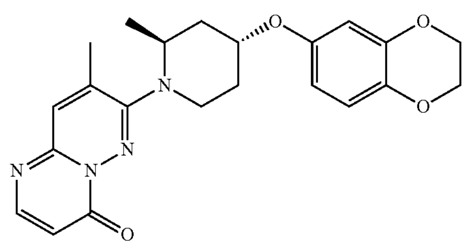 [SMILES: Cc1cc2nccc(=O)n2nc1N1CC[C@@H](Oc2ccc3c(c2)OCCO3)C[C@@H]1C] | 409.1 |
| 109 | 7-(4-((2,3-dihydrobenzo[b][1,4]dioxin-6-yl-2,2,3,3-d4)oxy)piperidin-1-yl-4-d)-2-(methoxymethyl)-8-methyl-4H-pyrimido[1,2-b]pyridazin-4-one | 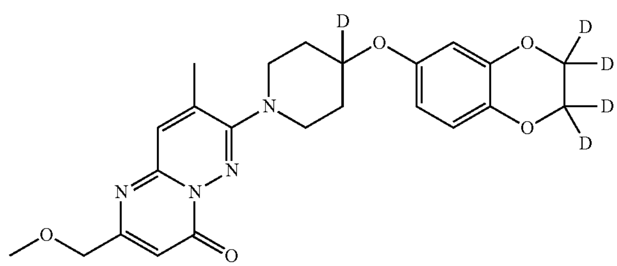 [SMILES: [2H]C1(Oc2ccc3c(c2)OC([2H])([2H])C([2H])([2H])O3)CCN(c2nn3c(=O)cc(COC)nc3cc2C)CC1] | 444.2 |
| 110 | 7-(4-((2,3-dihydrobenzo[b][1,4]dioxin-6-yl-2,2,3,3-d4)oxy)piperidin-1-yl-4-d)-2-(methoxymethyl)-8,9-dimethyl-4H-pyrimido[1,2-b]pyridazin-4-one | 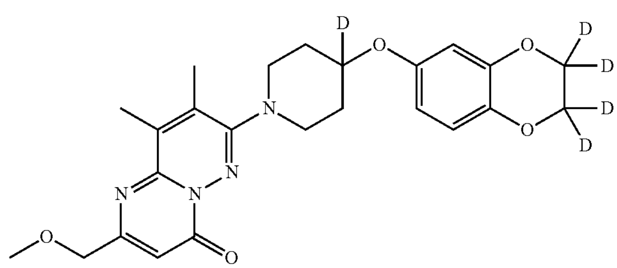 [SMILES: [2H]C1(Oc2ccc3c(c2)OC([2H])([2H])C([2H])([2H])O3)CCN(c2nn3c(=O)cc(COC)nc3c(C)c2C)CC1] | 458.2 |
| 111 | 7-((3S,4R)-4-((2,3-dihydrobenzo[b][1,4]dioxin-6-yl-2,2,3,3-d4)oxy)-3-fluoropiperidin-1-yl)-8-methyl-4H-pyrimido[1,2-b]pyridazin-4-one | 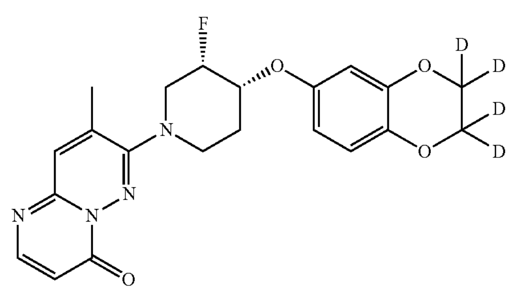 [SMILES: [2H]C1([2H])Oc2ccc(O[C@@H]3CCN(c4nn5c(=O)ccnc5cc4C)C[C@@H]3F)cc2OC1([2H])[2H]] | 417.3 |

TABLE 1-continued

| Cpd. No | Name | Structure | ES-MS [M + 1]+ |
|---|---|---|---|
| 112 | 7-((3R,4S)-4-((2,3-dihydrobenzo[b][1,4]dioxin-6-yl-2,2,3,3-d4)oxy)-3-fluoropiperidin-1-yl)-8-methyl-4H-pyrimido[1,2-b]pyridazin-4-one | 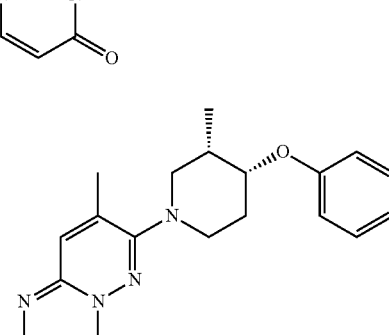 Chiral | 417.3 |
| 113 | 7-((3R,4S) or (3S,4R))-4-(2,3-dihydrobenzo[b][1,4]dioxin-6-yl)oxy)-3-methylpiperidin-1-yl)-8-methyl-4H-pyrimido[1,2-b]pyridazin-4-one | 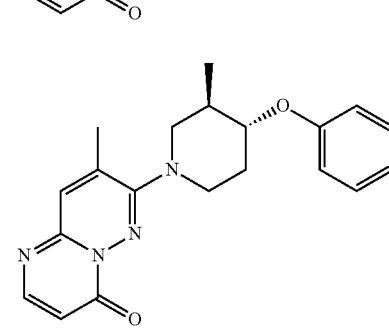 | 409.1 |
| 114 | 7-((3R,4R) or (3S,4S))-4-((2,3-dihydrobenzo[b][1,4]dioxin-6-yl)oxy)-3-methylpiperidin-1-yl)-8-methyl-4H-pyrimido[1,2-b]pyridazin-4-one | 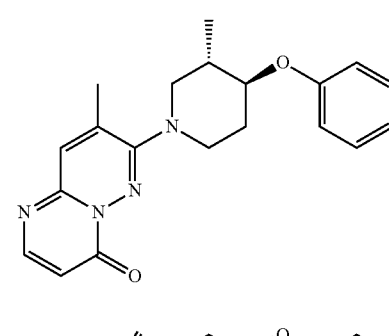 | 409.1 |
| 115 | 7-((3S,4S) or (3R, 4R))-4-((2,3-dihydrobenzo[b][1,4]dioxin-6-yl)oxy)-3-methylpiperidin-1-yl)-8-methyl-4H-pyrimido[1,2-b]pyridazin-4-one | 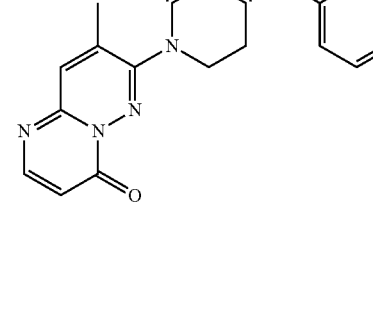 | 409.1 |
| 116 | 7-((2R,4R)-4-((2,3-dihydrobenzo[b][1,4]dioxin-6-yl)oxy)-2-methylpiperidin-1-yl)-8-methyl-4H-pyrimido[1,2-b]pyridazin-4-one | 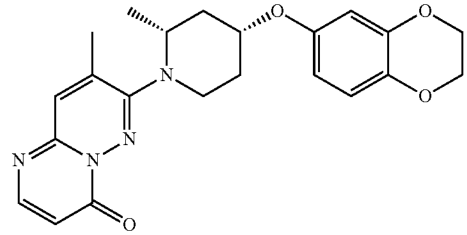 [SMILES: Cc1cc2nccc(=O)n2nc1N1CC[C@@H](Oc2ccc3c(c2)OCCO3)C[C@H]1C] | 409.1 |

TABLE 1-continued

| Cpd. No | Name | Structure | ES-MS [M + 1]+ |
|---|---|---|---|
| 117 | 7-((3S,4S)-4-((2,3-dihydrobenzo[b][1,4]dioxin-6-yl-2,2,3,3-d4)oxy)-3-fluoropiperidin-1-yl)-8,9-dimethyl-4H-pyrimido[1,2-b]pyridazin-4-one | 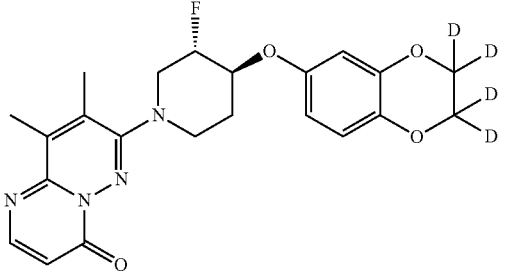 Chiral | 431.2 |
| 118 | 7-((3S,4R)-4-((2,3-dihydrobenzo[b][1,4]dioxin-6-yl-2,2,3,3-d4)oxy)-3-fluoropiperidin-1-yl)-8,9-dimethyl-4H-pyrimido[1,2-b]pyridazin-4-one | 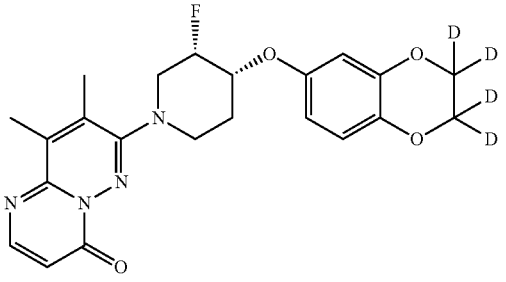 Chiral | 431.2 |
| 119 | 7-((3R,4S)-4-((2,3-dihydrobenzo[b][1,4]dioxin-6-yl-2,2,3,3-d4)oxy)-3-fluoropiperidin-1-yl)-8,9-dimethyl-4H-pyrimido[1,2-b]pyridazin-4-one | 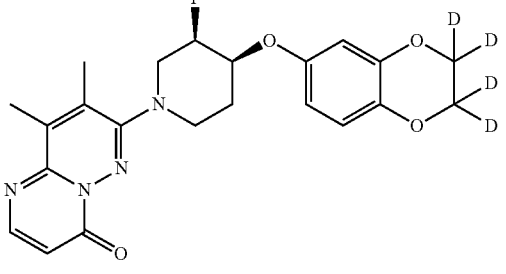 Chiral | 431.2 |
| 120 | 7-((3S,4S)-4-((2,3-dihydrobenzo[b][1,4]dioxin-6-yl-2,2,3,3-d4)oxy)-3-fluoropiperidin-1-yl)-2-(methoxymethyl)-8,9-dimethyl-4H-pyrimido[1,2-b]pyridazin-4-one | 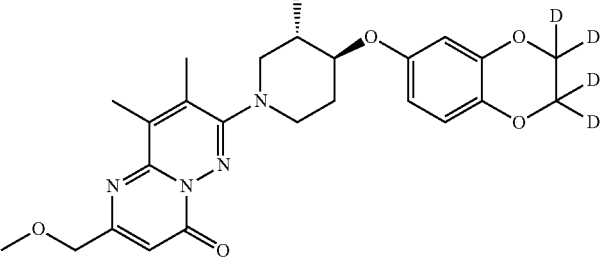 Chiral | 475.2 |

TABLE 1-continued

| Cpd. No | Name | Structure | | ES-MS [M + 1]+ |
|---|---|---|---|---|
| 121 | 7-((3S,4R)-4-((2,3-dihydrobenzo[b][1,4]dioxin-6-yl-2,2,3,3-d4)oxy)-3-fluoropiperidin-1-yl)-2-(methoxymethyl)-8,9-dimethyl-4H-pyrimido[1,2-b]pyridazin-4-one | 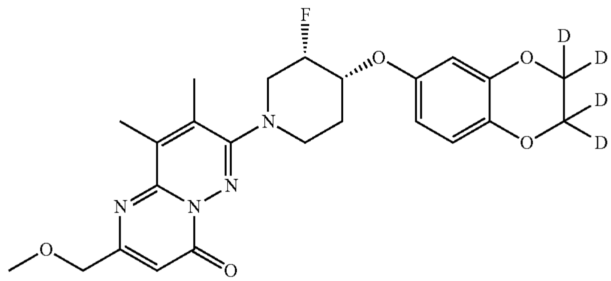 | Chiral | 475.2 |
| 122 | 7-((3R,4S)-4-((2,3-dihydrobenzo[b][1,4]dioxin-6-yl-2,2,3,3-d4)oxy)-3-fluoropiperidin-1-yl)-2-(methoxymethyl)-8,9-dimethyl-4H-pyrimido[1,2-b]pyridazin-4-one | 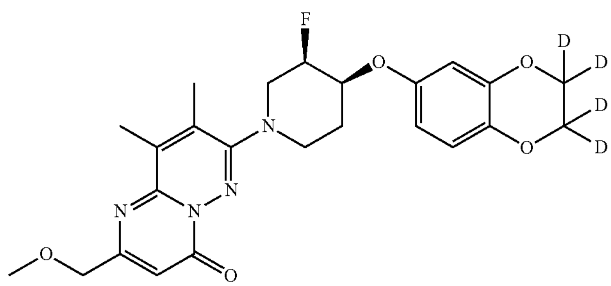 | Chiral | 475.2 |
| 123 | 7-(4-((2,3-dihydrobenzo[b][1,4]dioxin-6-yl)oxy)piperidin-1-yl)-8-methyl-9-(methylamino)-4H-pyrimido[1,2-b]pyridazin-4-one | 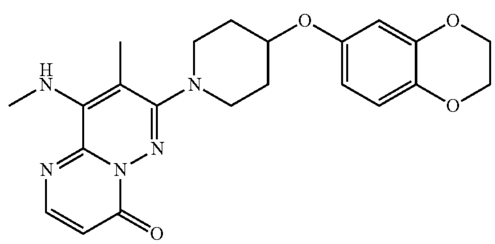 [SMILES: CNc1c(C)c(N2CCC(Oc3ccc4c(c3)OCCO4)CC2)nn2c(=O)ccnc12] | | 424.0 |
| 124 | 7-((3R,4R)-4-((2,3-dihydrobenzo[b][1,4]dioxin-6-yl-2,2,3,3-d4)oxy)-3-fluoropiperidin-1-yl)-2-(methoxymethyl)-8,9-dimethyl-4H-pyrimido[1,2-b]pyridazin-4-one | 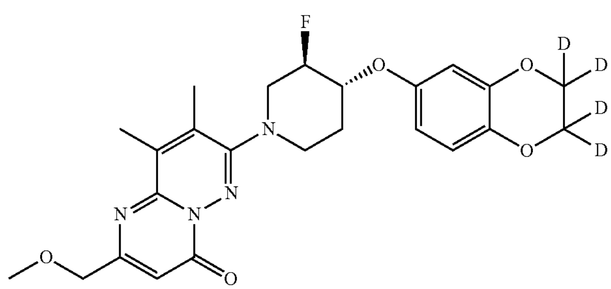 | Chiral | 475.2 |
| 125 | 7-((3R,4R)-4-((2,3-dihydrobenzo[b][1,4]dioxin-6-yl-2,2,3,3-d4)oxy)-3-fluoropiperidin-1-yl)-2-(methoxymethyl)-8-methyl-4H-pyrimido[1,2-b]pyridazin-4-one | 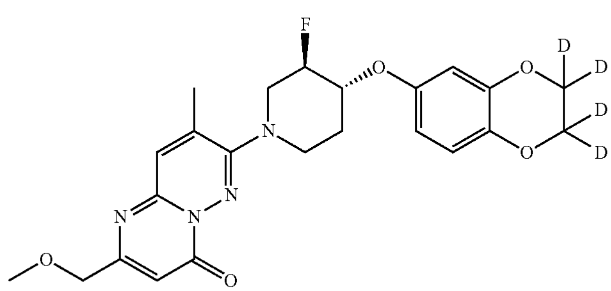 | Chiral | 461.2 |

TABLE 1-continued

| Cpd. No | Name | Structure | ES-MS [M + 1]+ |
|---|---|---|---|
| 126 | 7-(4-((2,3-dihydrobenzo[b][1,4]dioxin-6-yl)oxy)piperidin-1-yl)-9-methoxy-8-methyl-4H-pyrimido[1,2-b]pyridazin-4-one | 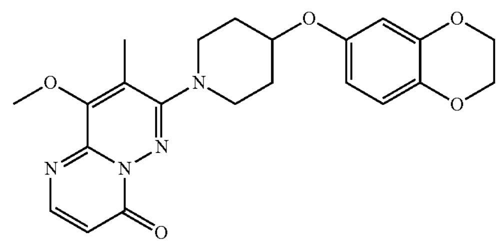 [SMILES: COc1c(C)c(N2CCC(Oc3ccc4c(c3)OCCO4)CC2)nn2c(=O)ccnc12] | 425.2 |
| 127 | 9-(azetidin-1-yl)-7-(4-((2,3-dihydrobenzo[b][1,4]dioxin-6-yl)oxy)piperidin-1-yl)-8-methyl-4H-pyrimido[1,2-b]pyridazin-4-one | 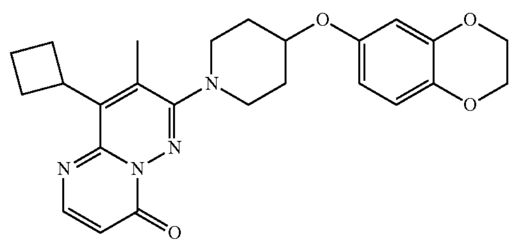 [SMILES: Cc1c(N2CCC(Oc3ccc4c(c3)OCCO4)CC2)nn2c(=O)ccnc2c1C1CCC1] | 450.0 |
| 128 | 7-((3R,4R)-4-((2,3-dihydrobenzo[b][1,4]dioxin-6-yl-2,2,3,3-d4)oxy)-3-fluoropiperidin-1-yl)-8,9-dimethyl-4H-pyrimido[1,2-b]pyridazin-4-one | Chiral | 431.3 |
| 130 | 7-((2R,4S)-4-((8-fluoro-2,3-dihydrobenzo[b][1,4]dioxin-6-yl-2,2,3,3-d4)oxy)-2-methylpiperidin-1-yl)-8-methyl-4H-pyrimido[1,2-b]pyridazin-4-one | 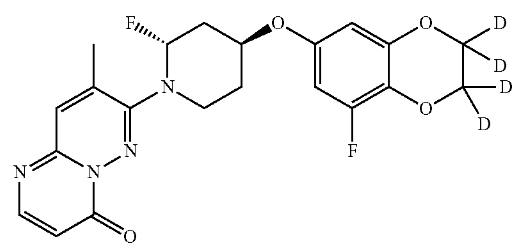 [SMILES: [2H]C1([2H])Oc2cc(O[C@H]3CCN(c4nn5c(=O)ccnc5cc4C)[C@H](F)C3)cc(F)c2OC1([2H])[2H]] | 431 |
| 131 | 7-((2R,4S)-4-((8-fluoro-2,3-dihydrobenzo[b][1,4]dioxin-6-yl)oxy)-2-methylpiperidin-1-yl)-8-methyl-4H-pyrimido[1,2-b]pyridazin-4-one | 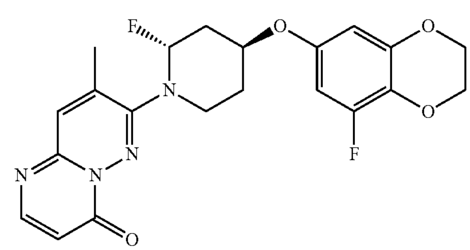 [SMILES: Cc1cc2nccc(=O)n2nc1N1CC[C@H](Oc2cc(F)c3c(c2)OCCO3)C[C@H]1F] | 427 |

TABLE 1-continued

| Cpd. No | Name | Structure | ES-MS [M + 1]+ |
|---|---|---|---|
| 132 | 7-((2R,4S)-4-((2,3-dihydrobenzo[b][1,4]dioxin-6-yl-2,2,3,3-d4)oxy)-2-methylpiperidin-1-yl)-8,9-dimethyl-4H-pyrimido[1,2-b]pyridazin-4-one | Chiral | 427.3 |
| 133 | 7-((2R,4S)-4-((2,3-dihydrobenzo[b][1,4]dioxin-6-yl-2,2,3,3-d4)oxy)-2-methylpiperidin-1-yl)-2-(methoxymethyl)-8,9-dimethyl-4H-pyrimido[1,2-b]pyridazin-4-one | Chiral | 471.4 |
| 134 | 7-((2R,4S)-4-((2,3-dihydrobenzo[b][1,4]dioxin-6-yl)oxy)-2-methylpiperidin-1-yl)-8,9-dimethyl-4H-pyrimido[1,2-b]pyridazin-4-one | Chiral | 423.2 |
| 135 | 7-(4-((8-fluoro-2,3-dihydrobenzo[b][1,4]dioxin-6-yl)oxy)piperidin-1-yl)-8-methyl-4H-pyrimido[1,2-b]pyridazin-4-one | 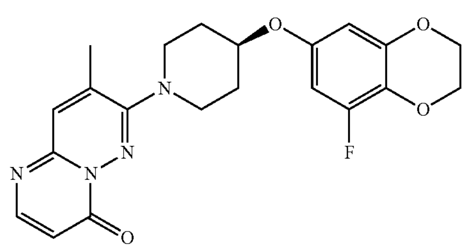 | 413.2 |
| 136 | 7-(4-((8-fluoro-2,3-dihydrobenzo[b][1,4]dioxin-6-yl-2,2,3,3-d4)oxy)piperidin-1-yl)-8-methyl-4H-pyrimido[1,2-b]pyridazin-4-one | 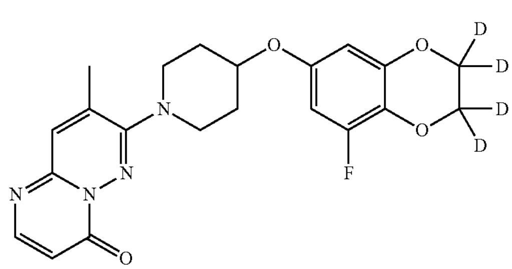 | 417.2 |

TABLE 1-continued

| Cpd. No | Name | Structure | ES-MS [M + 1]+ |
|---|---|---|---|
| 137 | 7-(4-((2,3-dihydrobenzo[b][1,4]dioxin-6-yl-2,2,3,3-d4)oxy)piperidin-1-yl-2,2,6,6-d4)-8-methyl-4H-pyrimido[1,2-b]pyridazin-4-one | | 403.4 | c. Biological Activity

A. Cell Lines Expressing Muscarinic Acetylcholine Receptors

Human and rat $M_4$ cDNAs, along with the chimeric G protein $G_{qi5}$, were transfected into Chinese hamster ovary (CHO-K1) cells purchased from the American Type Culture Collection using Lipofectamine2000. $hM_4$-$G_{qi5}$ cells were grown in Ham's F-12 medium containing 10% heat-inactivated fetal bovine serum (FBS), 20 mM HEPES, 50 µg/mL G418 sulfate, and 500 µg/mL Hygromycin B. $rM_4$-$G_{qi5}$ cells were grown in DMEM containing 10% heat-inactivated FBS, 20 mM HEPES, 400 µg/mL G418 sulfate, and 500 µg/mL Hygromycin B.

B. Cell-Based Functional Assay of Muscarinic Acetylcholine Receptor Activity

For high throughput measurement of agonist-evoked increases in intracellular calcium, CHO-K1 cells stably expressing muscarinic receptors were plated in growth medium lacking G418 and hygromycin at 15,000 cells/20 µL/well in Greiner 384-well black-walled, tissue culture (TC)-treated, clear-bottom plates (VWR). Cells were incubated overnight at 37° C. and 5% $CO_2$. The next day, cells were washed using an ELX 405 (BioTek) with assay buffer; the final volume was then aspirated to 20 µL. Next, 20 µL of a 2.3 µM stock of Fluo-4/acetoxymethyl ester (Invitrogen, Carlsbad, CA), prepared as a 2.3 mM stock in DMSO and mixed in a 1:1 ratio with 10% (w/v) Pluronic F-127 and diluted in assay buffer, was added to the wells and the cell plates were incubated for 50 min at 37° C. and 5% $CO_2$. Dye was removed by washing with the ELX 405 and the final volume was aspirated to 20 µL. Compound master plates were formatted in an 11 point concentration-response curve (CRC) format (1:3 dilutions) in 100% DMSO with a starting concentration of 10 mM using a BRAVO liquid handler (Agilent). Test compound CRCs were then transferred to daughter plates (240 nL) using the Echo acoustic plate reformatter (Labcyte, Sunnyvale, CA) and then diluted into assay buffer (40 µL) to a 2× stock using a Thermo Fisher Combi (Thermo Fisher Scientific, Waltham, MA).

Calcium flux was measured using the Functional Drug Screening System (FDSS) 6000 or 7000 (Hamamatsu Corporation, Tokyo, Japan) as an increase in the fluorescent static ratio. Compounds were applied to cells (20 µL, 2×) using the automated system of the FDSS at 2-4 seconds into the protocol and the data were collected at 1 Hz. At 144 seconds, 10 µL of an $EC_{20}$ concentration of the muscarinic receptor agonist acetylcholine was added (5×), followed by the addition of 12 µL of an $EC_{80}$ concentration of acetylcholine at the 230 second time point (5×). Agonist activity was analyzed as a concentration-dependent increase in calcium mobilization upon compound addition. Positive allosteric modulator activity was analyzed as a concentration-dependent increase in the $EC_{20}$ acetylcholine response. Antagonist activity was analyzed as a concentration-dependent decrease in the $EC_{80}$ acetylcholine response. Concentration-response curves were generated using a four-parameter logistical equation in XLFit curve fitting software (IDBS, Bridgewater, NJ) for Excel (Microsoft, Redmond, WA) or Prism (GraphPad Software, Inc., San Diego, CA).

The above described assay was also operated in a second mode where an appropriate fixed concentration of the present compounds were added to the cells after establishment of a fluorescence baseline for about 3 seconds, and the response in cells was measured. 140 s later, the appropriate concentration of agonist was added and the calcium response (maximum-local minima response) was measured. The $EC_{50}$ values for the agonist in the presence of test compound were determined by nonlinear curve fitting. A decrease in the $EC_{50}$ value of the agonist with increasing concentrations of the present compounds (a leftward shift of the agonist concentration-response curve) is an indication of the degree of muscarinic positive allosteric modulation at a given concentration of the present compound. An increase in the $EC_{50}$ value of the agonist with increasing concentrations of the present compounds (a rightward shift of the agonist concentration response curve) is an indication of the degree of muscarinic antagonism at a given concentration of the present compound. The second mode also indicates whether the present compounds also affect the maximum response of the muscarinic receptor to agonists.

d. Activity of Compounds in a mAChR $M_4$ Cell-Based Assay

Compounds were synthesized as described above. Activity ($EC_{50}$ and $E_{max}$) was determined in the mAChR $M_4$ cell-based functional assay as described above and the data are shown in Table 2. The compound number corresponds to the compound numbers used in Examples 1 to 11 and Tables 1.

TABLE 2

| No. | Human $M_4$ $EC_{50}$ (nM) | $E_{max}$ (%)* |
|---|---|---|
| 1 | 130 | 91 |
| 2 | 26 | 100 |
| 3 | 30 | 86 |
| 4 | 36 | 90 |
| 5 | 36 | 81 |
| 6 | 16 | 91 |
| 7 | 70 | 93 |
| 8 | 19 | 76 |
| 9 | 28 | 96 |

TABLE 2-continued

| No. | Human $M_4$ $EC_{50}$ (nM) | $E_{max}$ (%)* |
|---|---|---|
| 10 | 87 | 73 |
| 11 | 49 | 99 |
| 12 | 59 | 103 |
| 13 | 22 | 95 |
| 14 | 22 | 101 |
| 15 | 20 | 80 |
| 16 | 92 | 117 |
| 17 | 12 | 91 |
| 18 | 162 | 90 |
| 19 | 460 | 75 |
| 20 | 172 | 81 |
| 21 | 2070 | 82 |
| 22 | 1800 | 36 |
| 23 | 44 | 91 |
| 24 | 782 | 73 |
| 25 | 296 | 90 |
| 26 | 66 | 84 |
| 27 | 108 | 79 |
| 28 | 288 | 93 |
| 29 | 43 | 80 |
| 30 | 73 | 80 |
| 31 | 32 | 82 |
| 32 | 147 | 81 |
| 33 | 40 | 117 |
| 34 | 70 | 116 |
| 35 | 153 | 114 |
| 36 | 40 | 116 |
| 37 | 134 | 105 |
| 38 | 211 | 107 |
| 39 | 115 | 111 |
| 40 | 60 | 118 |
| 41 | 159 | 114 |
| 42 | 52 | 105 |
| 43 | 171 | 69 |
| 44 | 224 | 79 |
| 45 | 26 | 77 |
| 46 | 22 | 81 |
| 47 | 51 | 81 |
| 48 | 46 | 91 |
| 49 | 10 | 93 |
| 50 | 9 | 93 |
| 51 | 16 | 94 |
| 52 | 168 | 84 |
| 53 | 160 | 86 |
| 54 | 319 | 89 |
| 55 | 135 | 80 |
| 56 | 206 | 80 |
| 57 | 149 | 83 |
| 58 | 52 | 88 |
| 59 | 59 | 85 |
| 60 | 28 | 91 |
| 61 | 12 | 94 |
| 62 | 47 | 99 |
| 63 | 342 | 102 |
| 64 | 172 | 104 |
| 65 | 20 | 108 |
| 66 | 17 | 108 |
| 67 | 17 | 109 |
| 68 | 288 | 91 |
| 69 | 20 | 97 |
| 70 | 16 | 96 |
| 71 | 21 | 95 |
| 72 | 1540 | 74 |
| 73 | 2630 | 85 |
| 74 | 2360 | 84 |
| 75 | 1510 | 84 |
| 76 | >10,000 | 60 |
| 77 | 91 | 101 |
| 78 | 76 | 95 |
| 79 | 358 | 76 |
| 80 | 2180 | 76 |
| 81 | 2300 | 73 |
| 82 | 3340 | 74 |
| 83 | 186 | 89 |
| 84 | 141 | 86 |
| 85 | 385 | 101 |
| 86 | 341 | 101 |
| 87 | 268 | 93 |
| 88 | 383 | 77 |
| 89 | 503 | 76 |
| 90 | 1110 | 63 |
| 91 | 1070 | 70 |
| 92 | 632 | 89 |
| 93 | >10,000 | 70 |
| 94 | 30 | 84 |
| 95 | 73 | 87 |
| 96 | 99 | 85 |
| 97 | 424 | 78 |
| 98 | 64 | 90 |
| 99 | 131 | 90 |
| 100 | 52 | 89 |
| 101 | 1470 | 81 |
| 102 | 170 | 94 |
| 103 | 455 | 78 |
| 104 | 1410 | 87 |
| 105 | 1700 | 81 |
| 106 | 818 | 81 |
| 107 | 4070 | 55 |
| 108 | 73 | 99 |
| 109 | 19 | 97 |
| 110 | 44 | 80 |
| 111 | 67 | 106 |
| 112 | 75 | 108 |
| 113 | 110 | 96 |
| 114 | 160 | 102 |
| 115 | 1560 | 78 |
| 116 | 1330 | 71 |
| 117 | 326 | 93 |
| 118 | 34 | 115 |
| 119 | 51 | 114 |
| 120 | 162 | 106 |
| 121 | 42 | 111 |
| 122 | 94 | 111 |
| 123 | 556 | 89 |
| 124 | 101 | 109 |
| 125 | 87 | 108 |
| 126 | 421 | 109 |
| 127 | 1600 | 58 |
| 128 | 53 | 125 |
| 129 | 81 | 120 |
| 130 | 160 | 116 |
| 131 | 203 | 119 |
| 132 | 34 | 107 |
| 133 | 96 | 105 |
| 134 | 25 | 105 |
| 135 | 75 | 98 |
| 136 | 73 | 97 |
| 137 | 45 | 105 |

*% ACh maximum at 30 μM.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound of formula (Ib):

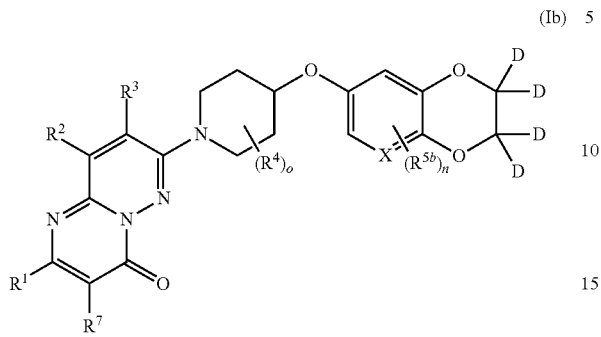

or a pharmaceutically acceptable salt or stereoisomer thereof,
wherein:
$R^1$ is H, $C_1$-$C_4$ alkyl, $C_1$-$C_4$ haloalkyl, $C_1$-$C_3$ alkylene-$OR^a$, $C_1$-$C_3$ alkylene-$C_3$-$C_6$ cycloalkyl, or $C_3$-$C_6$ cycloalkyl;
$R^a$ is $C_1$-$C_4$ alkyl, $C_1$-$C_4$ haloalkyl, or $C_3$-$C_6$ cycloalkyl;
$R^2$ is H, $C_1$-$C_4$ alkyl, $C_1$-$C_3$ alkylene-$OR^b$, $NHR^b$, $NR^bR^b$, $OR^b$, or $C_3$-$C_6$ cycloalkyl;
$R^7$ is H, halo, $C_1$-$C_4$ alkyl, $NR^bR^b$, or $C_3$-$C_6$ cycloalkyl;
each $R^3$ is independently $C_1$-$C_4$ alkyl, $C_1$-$C_4$ haloalkyl, or $C_3$-$C_6$ cycloalkyl; or
two $R^b$, taken together with the nitrogen heteroatom to which they are attached, form a monocyclic 4- to 7-membered heterocyclyl;
$R^3$ is H, $C_1$-$C_4$ alkyl, $C_1$-$C_3$ alkylene-$OR^c$, or $C_3$-$C_6$ cycloalkyl;
$R^c$ is $C_1$-$C_4$ alkyl, $C_1$-$C_4$ haloalkyl, or $C_3$-$C_6$ cycloalkyl;
$R^4$ is halo or $C_1$-$C_4$ alkyl;
X is $CR^{5a}$;
$R^{5a}$ is H, halo, or $C_1$-$C_4$ alkyl;
$R^{5b}$ is halo, CN, $C_1$-$C_2$ alkyl, $C_1$-$C_2$ fluoroalkyl, $OC_1$-$C_2$ alkyl, $OC_1$-$C_2$ fluoroalkyl, or $C_3$-$C_6$ cycloalkyl;
n is 0; and
o is 0 or 1.

2. The compound of claim 1, or a pharmaceutically acceptable salt or stereoisomer thereof, wherein $R^1$ is H.

3. The compound of claim 1, or a pharmaceutically acceptable salt or stereoisomer thereof, wherein $R^1$ is $C_1$-$C_4$ alkyl.

4. The compound of claim 1, or a pharmaceutically acceptable salt or stereoisomer thereof, wherein $R^1$ is $C_1$-$C_4$ fluoroalkyl.

5. The compound of claim 4, or a pharmaceutically acceptable salt or stereoisomer thereof, wherein $R^1$ is $CHF_2$.

6. The compound of claim 1, or a pharmaceutically acceptable salt or stereoisomer thereof, wherein $R^2$ is H.

7. The compound of claim 1, or a pharmaceutically acceptable salt or stereoisomer thereof, wherein $R^2$ is $CH_3$.

8. The compound of claim 1, or a pharmaceutically acceptable salt or stereoisomer thereof, wherein $R^7$ is H, F, Cl, $CH_3$, azetidin-1-yl, or cyclopropyl.

9. The compound of claim 8, or a pharmaceutically acceptable salt or stereoisomer thereof, wherein $R^7$ is H.

10. The compound of claim 1, or a pharmaceutically acceptable salt or stereoisomer thereof, wherein $R^3$ is $C_1$-$C_4$ alkyl.

11. The compound of claim 10, or a pharmaceutically acceptable salt or stereoisomer thereof, wherein $R^3$ is $CH_3$.

12. The compound of claim 1, wherein the compound is of formula (I-B):

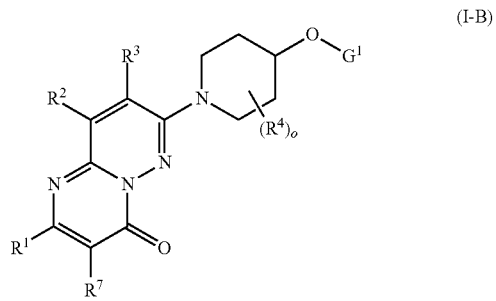

or a pharmaceutically acceptable salt or stereoisomer thereof,
wherein:
GI is

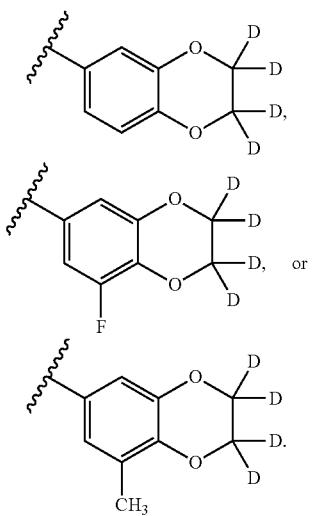

13. The compound of claim 1, or a pharmaceutically acceptable salt or stereoisomer thereof, wherein $R^{5a}$ is H.

14. The compound of claim 1, or a pharmaceutically acceptable salt or stereoisomer thereof, wherein 0.

15. The compound of claim 1, or a pharmaceutically acceptable salt or stereoisomer thereof, wherein o is 1.

16. The compound of claim 1, or a stereoisomer thereof, wherein the compound, or stereoisomer thereof, is selected from the group consisting of:

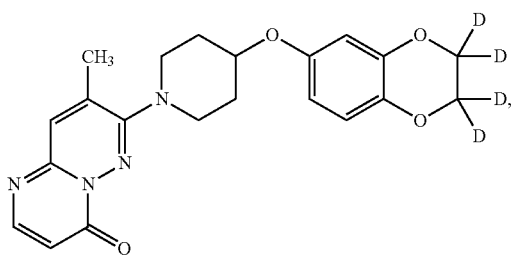

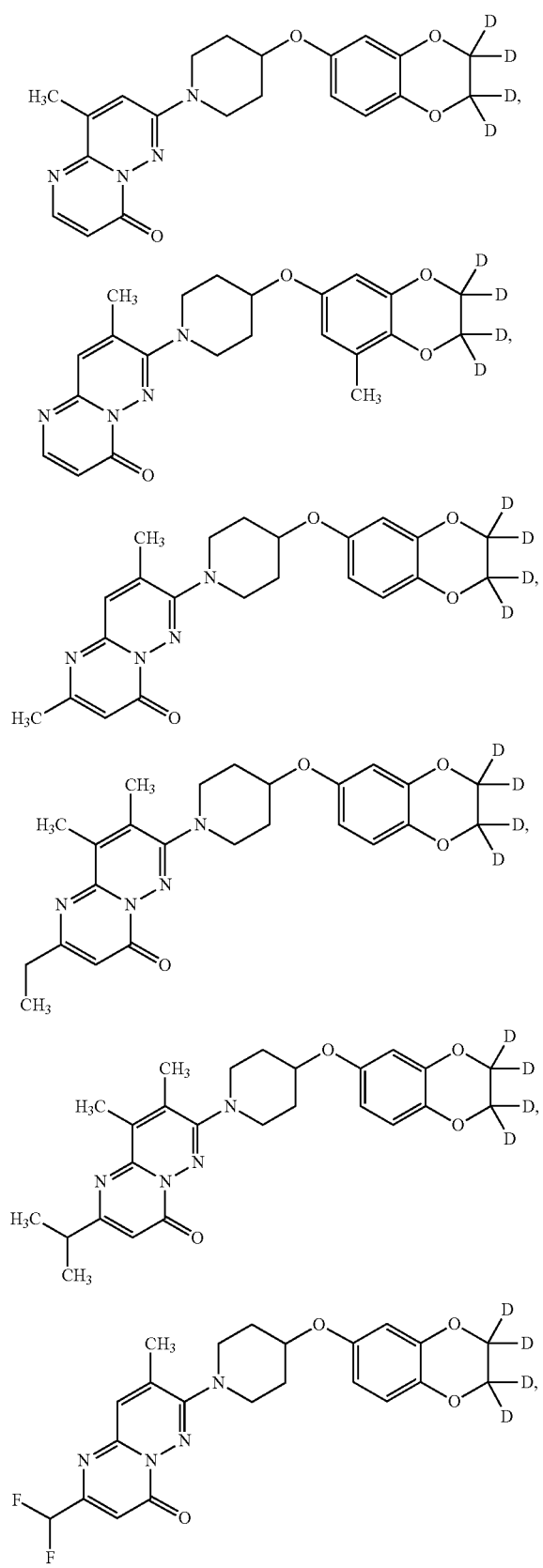
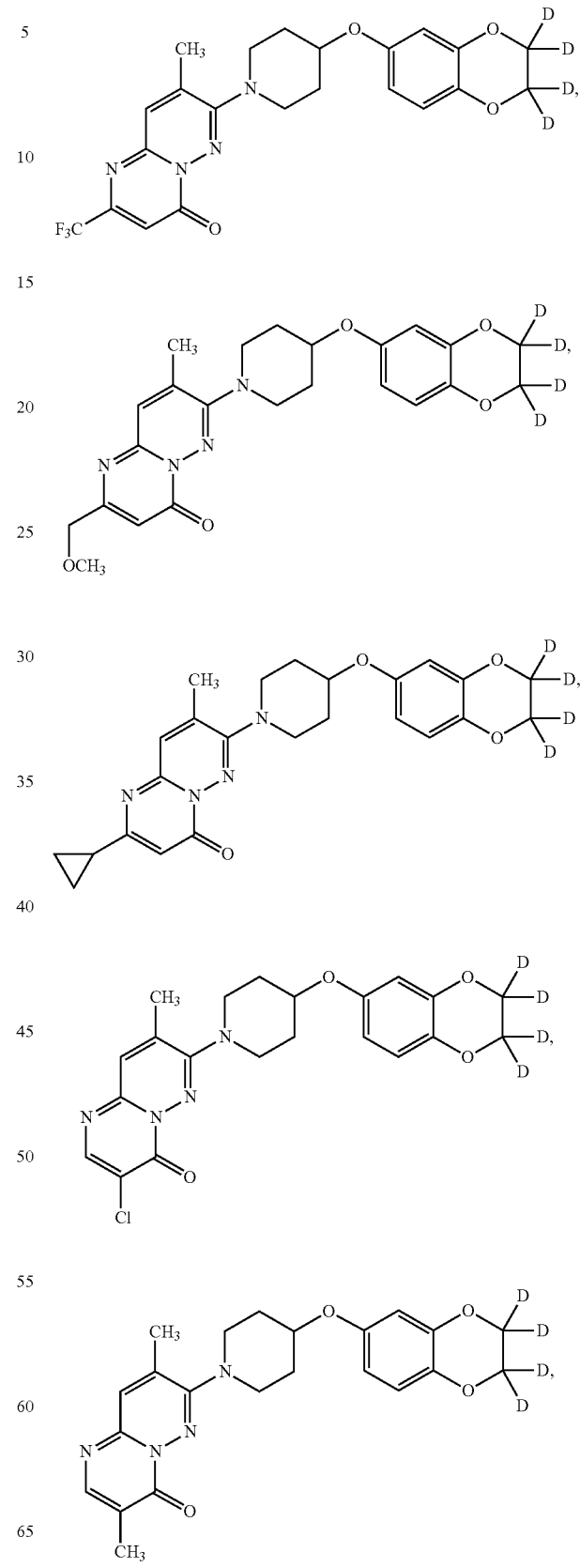

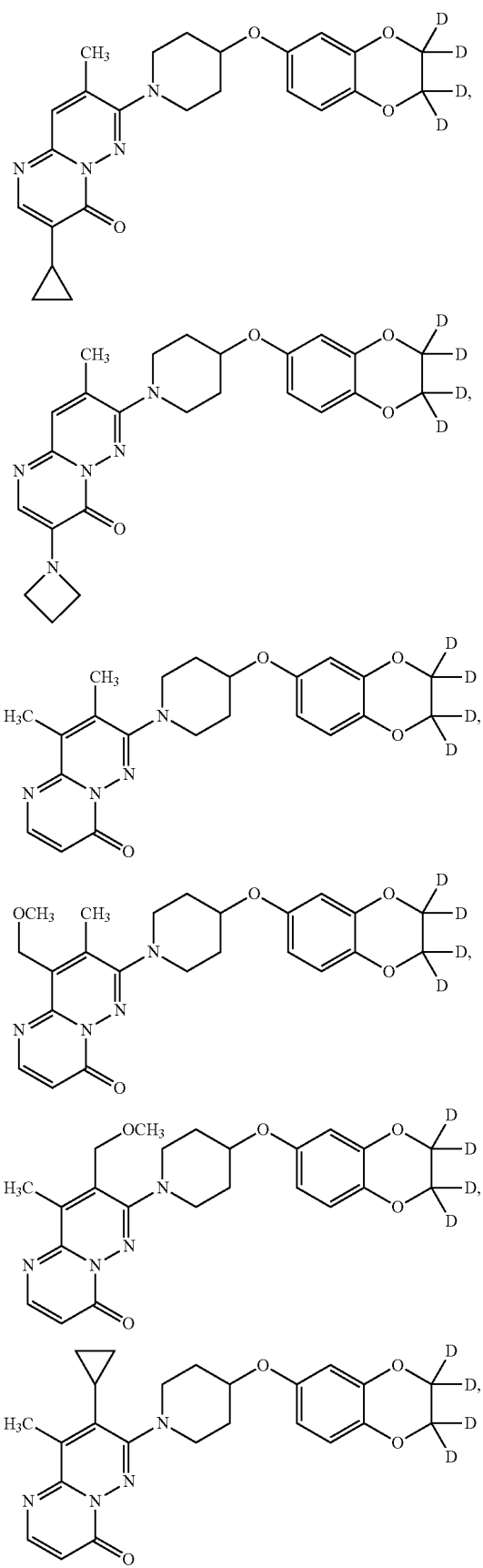
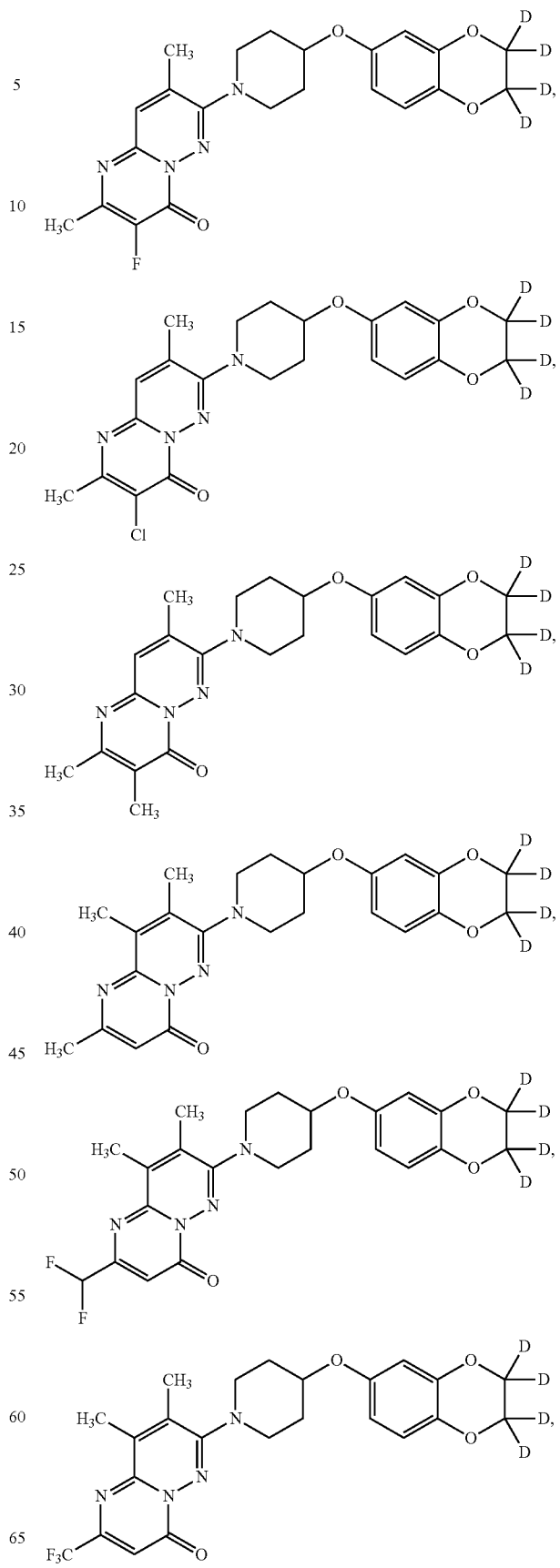

157
-continued
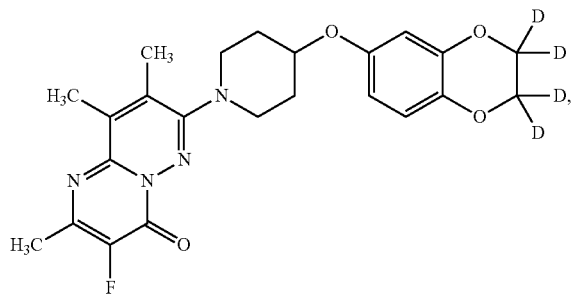
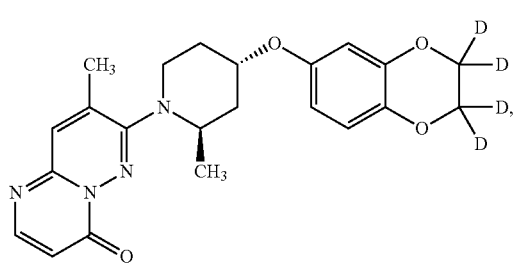
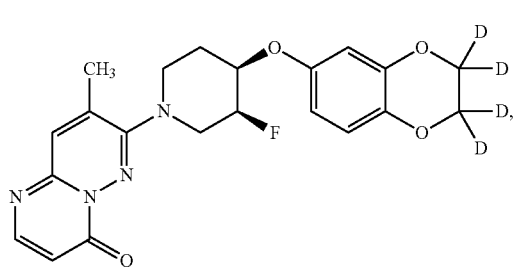
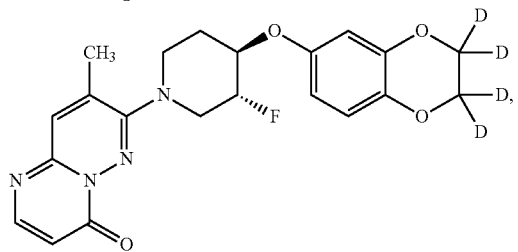
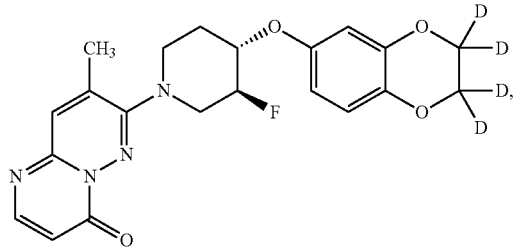
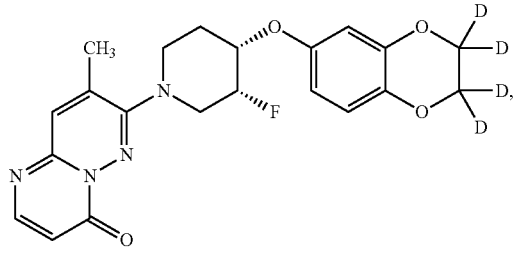
158
-continued
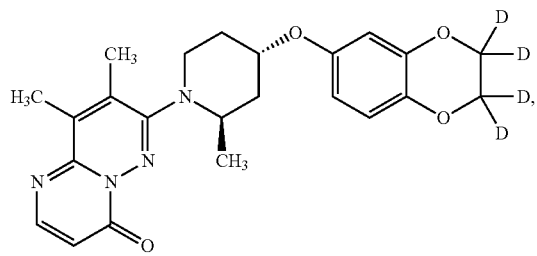
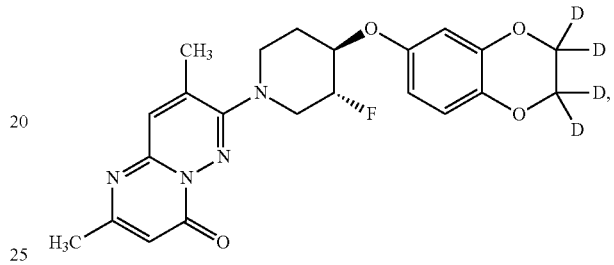
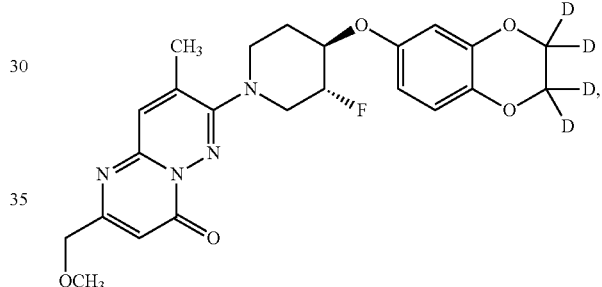
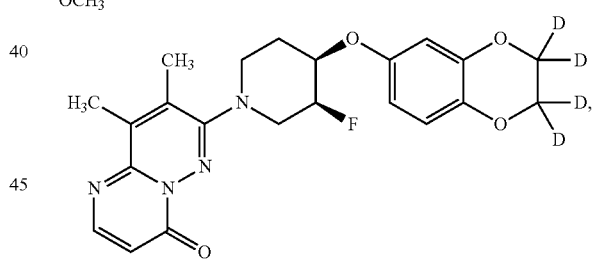
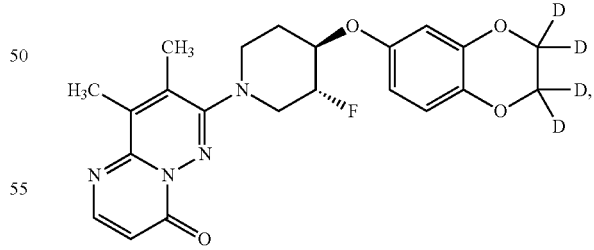
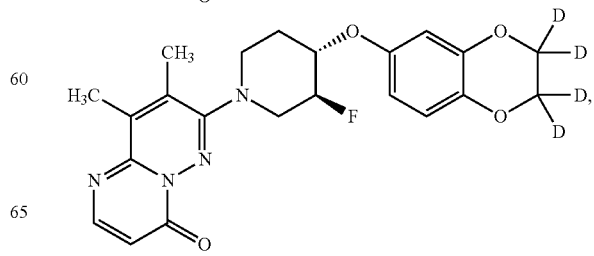

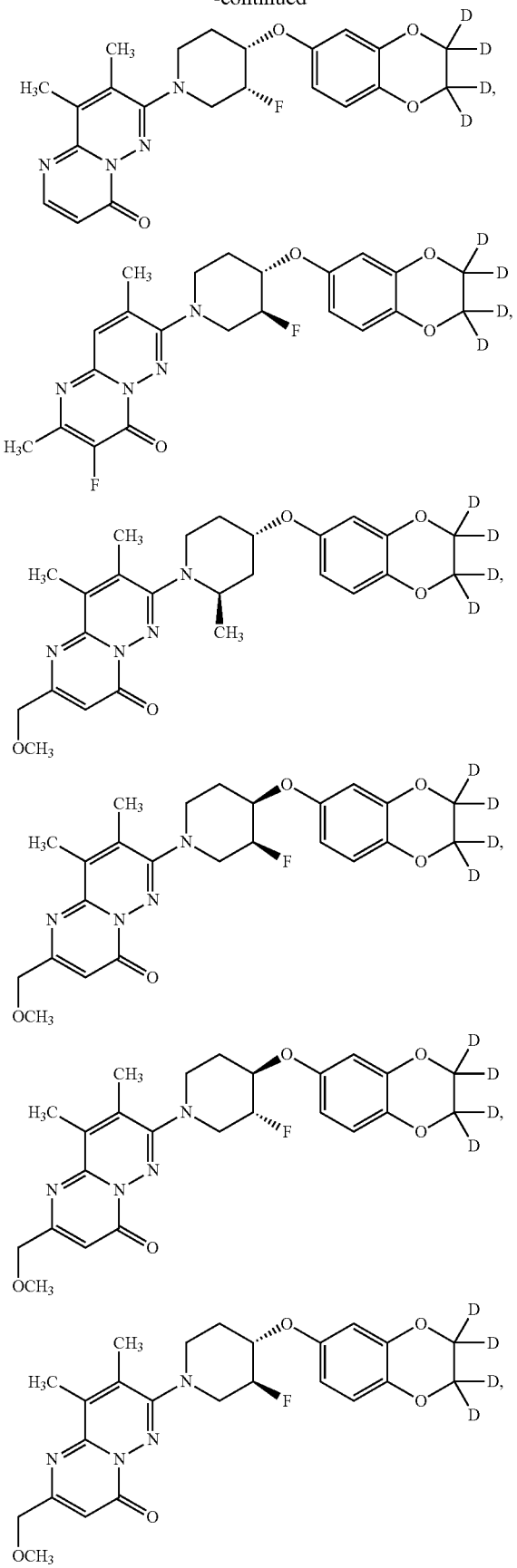
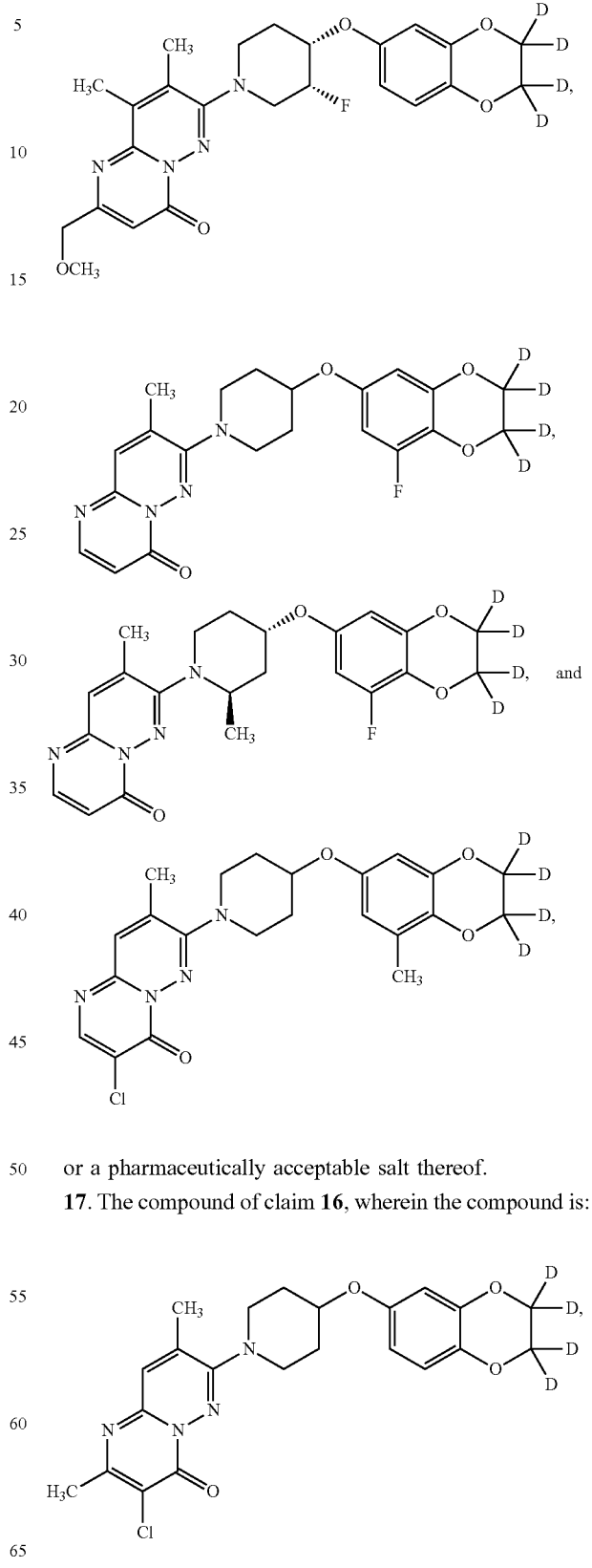
or a pharmaceutically acceptable salt thereof.
17. The compound of claim 16, wherein the compound is:
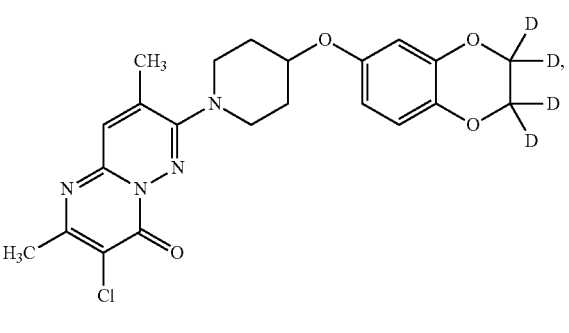
or a pharmaceutically acceptable salt thereof.

18. The compound of claim 16, wherein the compound is:

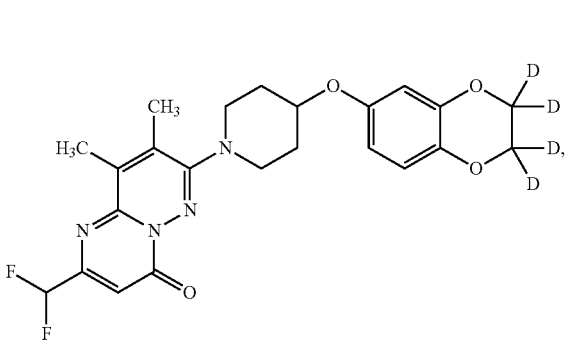

or a pharmaceutically acceptable salt thereof.

19. The compound of claim 16, or a stereoisomer thereof, wherein the compound, or stereoisomer thereof, is:

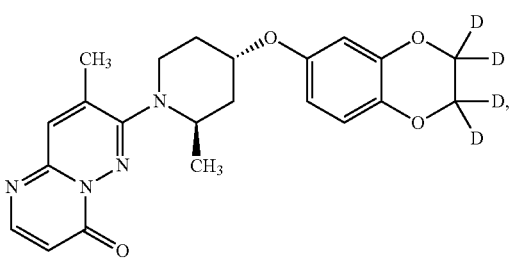

or a pharmaceutically acceptable salt thereof.

20. The compound of claim 16, or a stereoisomer thereof, wherein the compound, or stereoisomer thereof, is:

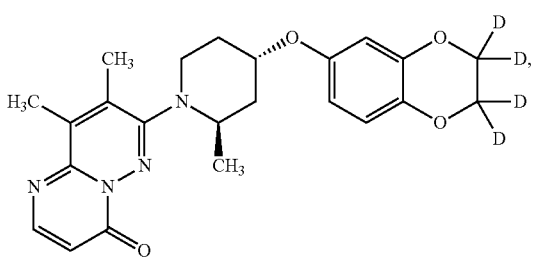

or a pharmaceutically acceptable salt thereof.

21. The compound of claim 16, or a stereoisomer thereof, wherein the compound, or stereoisomer thereof, is:

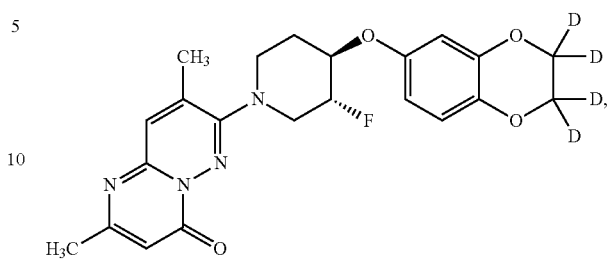

or a pharmaceutically acceptable salt thereof.

22. A pharmaceutical composition comprising a pharmaceutically acceptable carrier and a compound of claim 1, or a pharmaceutically acceptable salt or stereoisomer thereof.

23. A method for modulating muscarinic acetylcholine receptor (mAChR) $M_4$ activity in a patient in need thereof, wherein the method comprises administering to the patient a therapeutically effective amount of a compound of claim 1, or a pharmaceutically acceptable salt or stereoisomer thereof.

24. The method of claim 23 wherein the patient has a disorder selected from the group consisting of a neurological disorder and a psychiatric disorder.

25. The method of claim 24, wherein the neurological disorder or psychiatric disorder is selected from the group consisting of attention deficit hyperactivity disorder, an autistic disorder, a behavioral manifestation of mental retardation, a bipolar disorder, a cognitive disorder, a disruptive behavior disorder, a memory disorder, a movement disorder, and psychosis.

26. The method of claim 24, wherein the neurological disorder or psychiatric disorder is selected from the group consisting of Alzheimer's disease, bipolar disorder, borderline personality disorder, a cognitive disorder, Huntington's disease, a pain disorder, schizophrenia, a sleep disorder, tardive dyskinesia, and Tourette's syndrome.

27. The method of claim 24, wherein the neurological disorder or psychiatric disorder is selected from the group consisting of akinetic-rigid syndrome, a drug induced and neurodegeneration based dyskinesia, a movement disorder associated with Parkinson's disease, tardive dyskinesia, and Tourette's syndrome.

28. The method of claim 24, wherein the neurological disorder or psychiatric disorder is selected from the group consisting of anxiety associated with psychosis, a mood disorder associated with a psychotic disorder, a mood disorder associated with schizophrenia, a psychotic episode of anxiety, and schizophrenia.

29. The method of claim 24, wherein the neurological disorder or psychiatric disorder is selected from the group consisting of acute mania, conduct disorder, and depression associated with bipolar disorder.

30. The method of claim 24, wherein the neurological disorder or psychiatric disorder is dementia.

* * * * *